US007301022B2

(12) United States Patent
Bo et al.

(10) Patent No.: US 7,301,022 B2
(45) Date of Patent: *Nov. 27, 2007

(54) VANILLOID RECEPTOR LIGANDS AND THEIR USE IN TREATMENTS

(75) Inventors: Yunxin Y. Bo, Thousand Oaks, CA (US); Partha P. Chakrabarti, Simi Valley, CA (US); Ning Chen, Thousand Oaks, CA (US); Hongyu Liao, Thousand Oaks, CA (US); Mark H. Norman, Thousand Oaks, CA (US); Markian Stec, Fillmore, CA (US); Nuria Tamayo, Newbury Park, CA (US); Xianghong Wang, Moorpark, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/354,650

(22) Filed: Feb. 15, 2006

(65) Prior Publication Data

US 2006/0183745 A1 Aug. 17, 2006

Related U.S. Application Data

(60) Provisional application No. 60/671,794, filed on Apr. 15, 2005, provisional application No. 60/669,474, filed on Apr. 7, 2005, provisional application No. 60/653,294, filed on Feb. 15, 2005.

(51) Int. Cl.
| | |
|---|---|
| C07D 239/34 | (2006.01) |
| C07D 239/38 | (2006.01) |
| C07D 237/14 | (2006.01) |
| C07D 237/18 | (2006.01) |
| C07D 401/12 | (2006.01) |
| C07D 403/12 | (2006.01) |
| C07D 405/12 | (2006.01) |
| C07D 409/12 | (2006.01) |
| A61K 31/505 | (2006.01) |
| A61K 31/506 | (2006.01) |
| A61K 31/4427 | (2006.01) |
| A61P 19/02 | (2006.01) |
| A61P 35/00 | (2006.01) |

(52) U.S. Cl. ............... 544/239; 544/319; 514/252.01; 514/269; 514/345; 546/268.1

(58) Field of Classification Search ............... 544/239, 544/319; 546/268.1; 514/252.01, 345, 269
See application file for complete search history.

(56) References Cited

U.S. PATENT DOCUMENTS

| | | | |
|---|---|---|---|
| 5,272,167 A | 12/1993 | Girijavallabhan et al. |
| 5,459,144 A | 10/1995 | Girijavallabhan et al. |
| 5,750,532 A | 5/1998 | Girijavallabhan et al. |
| 5,916,887 A | 6/1999 | Singh et al. |
| 5,932,590 A | 8/1999 | Ciccarone et al. |
| 5,936,084 A | 8/1999 | Jirousek et al. |
| 5,959,123 A | 9/1999 | Singh et al. |
| 5,965,569 A | 10/1999 | Camps Garcia et al. |
| 5,969,140 A | 10/1999 | Ukita et al. |
| 6,093,737 A | 7/2000 | Anthony et al. |
| 6,153,619 A | 11/2000 | Wood et al. |
| 6,255,489 B1 | 7/2001 | Klintz et al. |
| 6,306,866 B1 | 10/2001 | Wood et al. |
| 6,407,111 B1 | 6/2002 | Bös et al. |
| 6,562,847 B1 | 5/2003 | Lee |
| 6,569,847 B1 | 5/2003 | Singh et al. |
| 6,593,330 B2 | 7/2003 | Nilsson |
| 6,596,773 B2 | 7/2003 | Bös et al. |
| 6,610,677 B2 | 8/2003 | Davies et al. |
| 6,613,776 B2 | 9/2003 | Knegtel et al. |
| 2002/0151712 A1 | 10/2002 | Lin et al. |
| 2004/0204386 A1 | 10/2004 | Bhatt et al. |

FOREIGN PATENT DOCUMENTS

EP 0 168 262 1/1986

(Continued)

OTHER PUBLICATIONS

West, Anthony R., Solid State Chemistry and its Applications, Wiley, New York, 1988, pp. 358 & 365.*

(Continued)

*Primary Examiner*—Venkataraman Balasubramanian
(74) *Attorney, Agent, or Firm*—Richard V. Person

(57) ABSTRACT

Compounds having the general structure

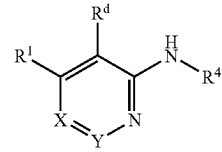

and compositions containing them, for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

11 Claims, No Drawings

FOREIGN PATENT DOCUMENTS

| | | |
|---|---|---|
| EP | 0 937 459 | 1/1999 |
| WO | WO 92/04333 | 3/1992 |
| WO | WO 96/02538 | 2/1996 |
| WO | WO 97/00612 | 1/1997 |
| WO | WO 97/13754 | 4/1997 |
| WO | WO 97/41127 | 11/1997 |
| WO | WO 98/12176 | 3/1998 |
| WO | WO 98/12210 | 3/1998 |
| WO | WO 98/23155 | 6/1998 |
| WO | WO 98/23156 | 6/1998 |
| WO | WO 98/28980 | 7/1998 |
| WO | WO 99/12911 | 3/1999 |
| WO | WO 99/28314 | 6/1999 |
| WO | WO 99/41248 | 8/1999 |
| WO | WO 99/51241 | 10/1999 |
| WO | WO 00/59881 | 10/2000 |
| WO | WO 01/05768 | 1/2001 |
| WO | WO 01/07032 | 2/2001 |
| WO | WO 01/07401 | 2/2001 |
| WO | WO 01/14331 | 3/2001 |
| WO | WO 01/19817 | 3/2001 |
| WO | WO 01/53263 | 7/2001 |
| WO | WO 01/54503 | 8/2001 |
| WO | WO 01/74331 | 10/2001 |
| WO | WO 01/76582 | 10/2001 |
| WO | WO 02/00651 | 1/2002 |
| WO | WO 02/16324 | 2/2002 |
| WO | WO 02/18339 | 3/2002 |
| WO | WO 02/26712 | 4/2002 |
| WO | WO 02/32872 | 4/2002 |
| WO | WO 02/36586 | 5/2002 |
| WO | WO 02/50052 | 6/2002 |
| WO | WO 02/079197 | 10/2002 |
| WO | WO 02/080853 | 10/2002 |
| WO | WO 02/088111 | 11/2002 |
| WO | WO 03/006471 | 1/2003 |
| WO | WO 03/028729 | 4/2003 |
| WO | WO 03/029210 | 4/2003 |
| WO | WO 03/041649 | 5/2003 |
| WO | WO 03/049702 | 6/2003 |
| WO | WO 03/093242 | 11/2003 |
| WO | WO 2004/005283 | 1/2004 |
| WO | WO 2004/014871 | 2/2004 |
| WO | WO 2004/046133 | 6/2004 |
| WO | WO 2004/065378 | 8/2004 |
| WO | WO 2004/089286 | 10/2004 |
| WO | WO 2005/047279 | 5/2005 |
| WO | WO 2005/077938 | 8/2005 |
| WO | WO 2005/077944 | 8/2005 |

OTHER PUBLICATIONS

Vippagunta et al., Advanced Drug Delivery Reviews 48: 3-26, 2001.*

Valenzano et al. Curr. Med. Chem. 3185-3202, 2004 (PubMed Abstract provided).*

Szallasi et al, Journal of Medicinal Chemistry 47(20): 2717-2723, 2004.*

Lee, et al.;J Med. Chem., N-(3-Acloxy-2-benzylpropyl)-N-[4-(methylsufonylamino)benzyl]thiourea Analogues: Novel Potent and High Affinity Antagonists and Partial Antagonists of the Vanilloid Receptor, 46: 3116-3126 (2003).

Matsuda, et al.; Bioorganic & Medicinal Chemistry Letters, *Synthesis and Bioactivities of Novel Pyridazine Derivatives: Inhibitors of Interleukin-1 Beta (IL-1β) Production*, 11: 2369-2372 (2001).

* cited by examiner

VANILLOID RECEPTOR LIGANDS AND THEIR USE IN TREATMENTS

This application claims the benefit of three (3) U.S. Provisional Applications No's. 60/653,294, filed Feb. 15, 2005; 60/669,474, filed Apr. 7, 2005; and 60/671,794, filed Apr. 15, 2005, which are hereby incorporated by reference.

BACKGROUND

The vanilloid receptor 1 (VR1) is the molecular target of capsaicin, the active ingredient in hot peppers. Julius et al. reported the molecular cloning of VR1 (Caterina et al., 1997). VR1 is a non-selective cation channel which is activated or sensitized by a series of different stimuli including capsaicin and resiniferatoxin (exogenous activators), heat & acid stimulation and products of lipid bilayer metabolism, anandamide (Premkumar et al., 2000, Szabo et al., 2000, Gauldie et al., 2001, Olah et al., 2001) and lipoxygenase metabolites (Hwang et al., 2000). VR1 is highly expressed in primary sensory neurons (Caterina et al., 1997) in rats, mice and humans (Onozawa et al., 2000, Mezey et al., 2000, Helliwell et al., 1998, Cortright et al., 2001). These sensory neurons innervate many visceral organs including the dermis, bones, bladder, gastrointestinal tract and lungs; VR1 is also expressed in other neuronal and non-neuronal tissues including but not limited to, CNS nuclei, kidney, stomach and T-cells (Nozawa et al., 2001, Yiangou et al., 2001, Birder et al., 2001). Presumably expression in these various cells and organs may contribute to their basic properties such as cellular signaling and cell division.

Prior to the molecular cloning of VR1, experimentation with capsaicin indicated the presence of a capsaicin sensitive receptor, which could increase the activity of sensory neurons in humans, rats and mice (Holzer, 1991; Dray, 1992, Szallasi and Blumberg 1996, 1999). The results of acute activation by capsaicin in humans was pain at injection site and in other species increased behavioral sensitivity to sensory stimuli (Szallasi and Blumberg, 1999). Capsaicin application to the skin in humans causes a painful reaction characterized not only by the perception of heat and pain at the site of administration but also by a wider area of hyperalgesia and allodynia, two characteristic symptoms of the human condition of neuropathic pain (Holzer, 1991). Taken together, it seems likely that increased activity of VR1 plays a significant role in the establishment and maintenance of pain conditions. Topical or intradermal injection of capsaicin has also been shown to produce localized vasodilation and edema production (Szallasi and Blumberg 1999, Singh et al., 2001). This evidence indicates that capsaicin through it's activation of VR1 can regulate afferent and efferent function of sensory nerves. Sensory nerve involvement in diseases could therefore be modified by molecules which effect the function of the vanilloid receptor to increase or decrease the activity of sensory nerves.

VR1 gene knockout mice have been shown to have reduced sensory sensitivity to thermal and acid stimuli (Caterina et al., 2000)). This supports the concept that VR1 contributes not only to generation of pain responses (i.e. via thermal, acid or capsaicin stimuli) but also to the maintenance of basal activity of sensory nerves. This evidence agrees with studies demonstrating capsaicin sensitive nerve involvement in disease. Primary sensory nerves in humans and other species can be made inactive by continued capsaicin stimulation. This paradigm causes receptor activation induced desensitization of the primary sensory nerve—such reduction in sensory nerve activity in vivo makes subjects less sensitive to subsequent painful stimuli. In this regard both capsaicin and resiniferatoxin (exogenous activators of VR1), produce desensitization and they have been used for many proof of concept studies in in vivo models of disease (Holzer, 1991, Dray 1992, Szallasi and Blumberg 1999).

BIBLIOGRAPHY

Birder-L A. Kanai-A J. de-Groat-W C. Kiss-S. Nealen-M L. Burke-N E. Dineley-K E. Watkins-S. Reynolds-I J. Caterina-M J. (2001) Vanilloid receptor expression suggests a sensory role for urinary bladder epithelial cells. PNAS 98: 23: 13396-13401.

Caterina, M. J, Schumacher, M. A., Tominaga, M., Rosen, T. A., Levine, J. D., and Julius, D, (1997). The capsaicin receptor: a heat-activated ion channel in the pain pathway. Nature 389: 816-824.

Caterina-M J. Leffler-A. Malmberg-A B. Martin-W J. Trafton-J. Petersen-Zeitz K R. Koltzenburg-M. Basbaum-A I. Julius-D (2000) Impaired nociception and pain sensation in mice lacking the capsaicin receptor. Science-(WASH-DC). 288: 5464: 306-313.

Cortright-D N. Crandall-M. Sanchez-J F. Zou-T. Krause-J E. White-G (2001) The tissue distribution and functional characterization of human VR1. Biochemical and Biophysical Research Communications 281: 5: 1183-1189

Dray, A., (1992). Therapeutic potential of capsaicin-like molecules. Life Sciences 51: 1759-1765.

Gauldie-S D. McQueen-D S. Pertwee-R. Chessell-I P. (2001) Anandamide activates peripheral nociceptors in normal and arthritic rat knee joints. British Journal of Pharmacology 132: 3: 617-621.

Helliwell-R J A. McLatchie-L M. Clarke-M. Winter-J. Bevan-S. McIntyre-P (1998) Capsaicin sensitivity is associated with expression of the vanilloid (capsaicin) receptor (VR1) mRNA in adult rat sensory ganglia. Neuroscience Lett. 250: 3: 177-180.

Holzer, P. (1991) Capsaicin: Cellular targets, Mechanisms of Action and selectivity for thin sensory neurons. Pharmacological reviews 43: 2: 143-201

Hwang-S W. Cho-H. Kwak-J. Lee-S Y. Kang-C J. Jung-J. Cho-S. Min-K H. Suh-Y G. Kim-D. Oh-U. (2000) Direct activation of capsaicin receptors by products of lipoxygenases: Endogenous capsaicin-like substances. PNAS 97: 11: 6155-6160.

Mezey-E. Toth-Z E. Cortright-D N. Arzubi-M K. Krause-J E. Elde-R. Guo-A. Blumberg-P M. Szallasi-A (2000) Distribution of mRNA for vanilloid receptor subtype 1 (VR1), and VR1-like immunoreactivity, in the central nervous system of the rat and human. PNAS 97: 7: 3655-3660.

Nozawa-Y. Nishihara-K. Yamamoto-A. Nakano-M. Ajioka-H. Matsuura-N. (2001) Distribution and characterization of vanilloid receptors in the rat stomach. Neuroscience Letters 309: 1: 33-36.

Olah-Z. Karai-L. Iadarola-M J. (2001) Anandamide activates vanilloid receptor 1 (VR1) at acidic pH in dorsal root ganglia neurons and cells ectopically expressing VR1. Journal of Biological Chemistry 276: 33, 31163-31170.

Onozawa-K. Nakamura-A. Tsutsumi-S. Yao-J. Ishikawa-R. Kohama-K. (2000) Tissue distribution of capsaicin receptor in the various organs of rats. Proc. Jpn. Acad. Ser. B, Phys.-Biol. Sci. 76: 5: 68-72.

Premkumar-L S. Ahern-G P. (2000) Induction of vanilloid receptor channel activity by protein kinase C. Nature (London) 408: 6815: 985-990.

Singh-L K. Pang-X. Alexacos-N. Letourneau-R. Theoharides-T C. (1999) Acute immobilization stress triggers skin mast cell degranulation via corticotropin releasing hormone, neurotensin, and substance P: A link to neurogenic skin disorders. Brain Behav. Immun. 13: 3: 225-239.

Szallasi, A. Blumberg-P M (1996) Vanilloid receptors: New insights enhance potential as a therapeutic target. Pain 68: 195-208

Szallasi-A. Blumberg-P M. (1999) Vanilloid (capsaicin) receptors and mechanisms. Pharmacol. Rev. 51: 2: 159-211.

Szabo-T. Wang-J. Gonzalez-A. Kedei-N. Lile-J. Treanor-J. Blumberg-P M. (2000) Pharmacological characterization of the human vanilloid receptor type-1 (hVR1). Society for Neuroscience Abstracts. 26:1-2: 634.18.

Tominaga, M., Caterina, M. J., Malmberg, A. B., Rosen, T. A., Gilbert, H., Skinner, K., Raumann, B. E., Basbaum, A. I., and Julius, D., (1998). The cloned capsaicin receptor integrates multiple pain-producing stimuli. Neuron 21: 531-543.

Yiangou-Y. Facer-P. Dyer-N H C. Chan-C L H. Knowles-C. Williams-N S. Anand-P. (2001) Vanilloid receptor 1 immunoreactivity in inflamed human bowel. Lancet (North American Edition) 357: 9265: 1338-1339.

Yiangou-Y. Facer-P. Ford-A. Brady-C. Wiseman-O. Fowler-C J. Anand-P. (2001) Capsaicin receptor VR1 and ATP-gated ion channel P2X3 in human urinary bladder. BJU International 87: 9: 774-779.

Wang-H. Bian-D. Zhu-D. Zajic-G. Loeloff-R. Lile-J. Wild-K. Treanor-J. Curran-E. (2000) Inflammation-induced upregulation of VR1 in rat spinal cord and DRG correlates with enhanced nociceptive processing. Society for Neuroscience Abstracts 26:1-2: 632.15.

SUMMARY

The present invention comprises a new class of compounds useful in the treatment of diseases, such as vanilloid-receptor-mediated diseases and other maladies, such as inflammatory or neuropathic pain and diseases involving sensory nerve function such as asthma, rheumatoid arthritis, osteoarthritis, inflammatory bowel disorders, depression, anxiety, urinary incontinence, migraine and psoriasis. In particular, the compounds of the invention are useful for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. Accordingly, the invention also comprises pharmaceutical compositions comprising the compounds, methods for the treatment of vanilloid-receptor-mediated diseases, such as inflammatory or neuropathic pain, asthma, rheumatoid arthritis, osteoarthritis, inflammatory bowel disorders, depression, anxiety, urinary incontinence, migraine and psoriasis diseases, using the compounds and compositions of the invention, and intermediates and processes useful for the preparation of the compounds of the invention.

The compounds of the invention are represented by the following general structure:

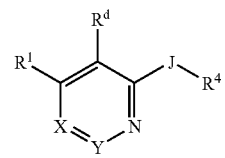

or a pharmaceutically acceptable salt thereof, wherein J, $R^1$, $R^4$, $R^d$, X and Y are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION

One aspect of the current invention relates to compounds having the general structure:

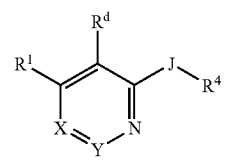

or any pharmaceutically-acceptable salt thereof, wherein:

J is O or S;

X is N or $C(R^2)$;

Y is N or $C(R^3)$, wherein at least one of X and Y is not N;

n is independently, at each instance, 0, 1 or 2;

$R^1$ is

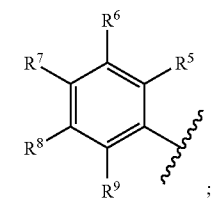

or $R^1$ is $R^b$ substituted by 1, 2 or 3 substituents selected from $R^e$, $R^h$, —$OR^e$, —$OR^h$, —$OC_{2-6}$alkylN$R^aR^e$, —$OC_{2-6}$alkylO$R^e$, —N$R^aR^e$, —N$R^aR^h$, —N$R^aC_{2-6}$alkylN$R^aR^e$, —N$R^aC_{2-6}$alkylO$R^e$, —$CO_2R^e$, —$OC(=O)R^e$, —$C(=O)R^e$, —$C(=O)NR^aR^e$, —$C(=O)NR^aR^h$, —$NR^aC(=O)R^e$, —$NR^aC(=O)R^h$, —$NR^aC(=O)NR^aR^e$, —$NR^aCO_2R^e$, —C$_{1-8}$alkylOR$^e$, —C$_{1-6}$alkylNR$^a$R$^e$, —S(=O)$_n$R$^e$, —S(=O)$_2$NR$^a$R$^e$, —NR$^a$S(=O)$_2$R$^e$, —OS(=O)$_2$R$^e$, —OC(=O)NR$^a$R$^e$, —OC$_{2-6}$alkylNR$^a$R$^h$, —OC$_{2-6}$alkylOR$^h$, —NR$^a$C$_{2-6}$alkylNR$^a$R$^h$, —NR$^a$C$_{2-6}$alkylOR$^h$, —NR$^h$C$_{2-6}$alkylNR$^a$R$^a$, —NR$^a$C$_{2-6}$alkylOR$^a$, —CO$_2$R$^h$, —OC(=O)R$^h$, —C(=O)R$^h$, —NR$^e$C(=O)R$^a$, —NR$^h$C(=O)R$^a$, —NR$^h$C(=O)NR$^a$R$^a$, —NR$^e$C(=O)NR$^a$R$^a$, —NR$^h$CO$_2$R$^a$, —NR$^e$CO$_2$R$^a$, —C$_{1-8}$alkylOR$^h$, —C$_{1-6}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^a$, —OS(=O)$_2$R$^h$ and —OC(=O)NR$^a$R$^h$, and additionally substituted by 0, 1, 2 or 3 substituents independently selected from halo, cyano, nitro, C$_{1-8}$alkyl, C$_{1-4}$haloalkyl, R$^i$, R$^k$, —OR$^a$, —NR$^a$R$^a$, —OC$_{2-6}$alkylNR$^a$R$^a$, —OC$_{2-6}$alkylOR$^a$, —NR$^a$C$_{2-6}$alkylNR$^a$R$^a$, —NR$^a$C$_{2-6}$alkylOR$^a$, —CO$_2$R$^a$, —OC(=O)R$^a$, —C(=O)(C$_{1-6}$alkyl), —C(=O)NR$^a$R$^a$, —NR$^a$C(=O)R$^a$, —NR$^a$C(=O)NR$^a$R$^a$, —NR$^a$CO$_2$R$^a$, —C$_{1-8}$alkylOR$^a$, —C$_{1-6}$alkylNR$^a$R$^a$, —S(=O)$_n$R$^a$, —S(=O)$_2$NR$^a$R$^a$, —NR$^a$S(=O)$_2$R$^a$, —OS(=O)$_2$R$^a$ and —OC(=O)NR$^a$R$^e$;

R$^2$ is selected from H, halo, cyano, nitro, R$^i$, R$^k$, —OH, —OR$^i$, —OR$^k$, —C(=O)R$^i$, —C(=O)R$^k$, —OC(=O)R$^i$, —OC(=O)R$^k$, —S(O)$_n$R$^i$, —S(O)$_n$R$^k$, —N(R$^a$)S(O)$_n$R$^i$, —N(R$^a$)S(O)$_n$R$^k$, —S(O)$_n$N(R$^a$)R$^i$, —S(O)$_n$N(R$^a$)R$^k$, —NH$_2$, —C(=O)NR$^a$R$^i$, —C(=O)NR$^a$R$^k$, —NR$^a$C(=O)R$^i$ and —NR$^a$C(=O)R$^k$, —NR$^a$R$^i$ and —NR$^a$R$^k$;

R$^3$ is selected from H, halo, cyano, nitro, R$^i$, R$^k$, —OH, —OR$^i$, —OR$^k$, —C(=O)R$^i$, —C(=O)R$^k$, —OC(=O)R$^i$, —OC(=O)R$^k$, —S(O)$_n$R$^i$, —S(O)$_n$R$^k$, —N(R$^a$)S(O)$_n$R$^i$, —N(R$^a$)S(O)$_n$R$^k$, —S(O)$_n$N(R$^a$)R$^i$, —S(O)$_n$N(R$^a$)R$^k$, —NH$_2$, —C(=O)NR$^a$R$^i$, —C(=O)NR$^a$R$^k$, —NR$^a$C(=O)R$^i$ and —NR$^a$C(=O)R$^k$, —NR$^a$R$^i$ and —NR$^a$R$^k$;

R$^4$ is independently at each instance

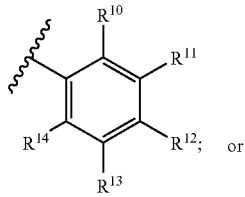

R$^4$ is independently at each instance a saturated, partially-saturated or unsaturated 5- or 6-membered ring heterocycle containing 1, 2 or 3 atoms selected from O, N and S that is optionally vicinally fused with a saturated, partially-saturated or unsaturated 3-, 4- or 5-atom bridge containing 0, 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from oxo, thioxo, R$^k$, C$_{1-4}$haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —C(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and wherein the heterocycle is additionally substituted by 0 or 1 groups independently selected from R$^i$ and additionally substituted by 0, 1, 2, 3, 4 or 5 substituents independently selected from Br, Cl, F and I; or R$^4$ is independently at each instance naphthyl substituted by 1, 2 or 3 substituents independently selected from R$^k$, C$_{1-4}$haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and wherein the naphthyl is additionally substituted by 0 or 1 groups independently selected from R$^i$ and additionally substituted by 0, 1, 2, 3, 4 or 5 substituents independently selected from Br, Cl, F and I;

R$^5$ is independently, at each instance, H, R$^k$, C$_{1-4}$haloalkyl, halo, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^6$ is independently, at each instance, H, R$^k$, C$_{1-4}$haloalkyl, halo, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^7$ is independently, at each instance, H, R$^k$, C$_{1-4}$haloalkyl, halo, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and A)
R$^8$ is independently, at each instance, H, R$^k$, C$_{1-4}$haloalkyl, halo, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$—S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and R$^9$ is independently, at each instance, R$^e$, R$^h$, —OR$^e$, —OR$^h$, —OC$_{2-6}$alkylNR$^a$R$^e$, —OC$_{2-6}$alkylOR$^e$, —NR$^a$R$^e$, —NR$^a$R$^h$, —NR$^a$C$_{2-6}$alkylNR$^a$R$^e$, —NR$^a$C$_{2-6}$alkylOR$^e$, —CO$_2$R$^e$, —OC(=O)R$^e$, —C(=O)R$^e$, —C(=O)NR$^a$R$^e$, —C(=O)NR$^a$R$^h$, —NR$^a$C(=O)R$^e$, —NR$^a$C(=O)R$^h$, —NR$^a$C(=O)NR$^a$R$^e$, —NR$^a$CO$_2$R$^e$, —C$_{1-8}$alkylOR$^e$, —C$_{1-6}$alkylNR$^a$R$^e$, —S(=O)$_n$R$^e$, —S(=O)$_2$NR$^a$R$^e$, —NR$^a$S(=O)$_2$R$^e$, —OS(=O)$_2$R$^e$, —OC(=O)NR$^a$R$^e$, —OR$^h$, —OC$_{2-6}$alkylNR$^a$R$^h$, —OC$_{2-6}$alkylOR$^h$, —NR$^a$C$_{2-6}$alkylNR$^a$R$^h$, —NR$^h$C$_{2-6}$alkylNR$^a$R$^a$, —NR$^h$C$_{2-6}$alkylOR$^a$, —NR$^a$C$_{2-6}$alkylOR$^h$, —CO$_2$R$^1$, —OC(=O)R$^h$, —C(=O)R$^h$, —C(=O)NR$^a$R$^h$, —NR$^e$C(=O)R$^a$, —NR$^h$C(=O)R$^a$, —NR$^h$C(=O)NR$^a$R$^a$, —NR$^e$C(=O)NR$^a$R$^a$, —NR$^h$CO$_2$R$^a$, NR$^e$CO$_2$R$^a$, —C$_{1-8}$alkylOR$^h$, —C$_{1-6}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^a$, —OS(=O)$_2$R$^h$ or —OC(=O)NR$^a$R$^h$; or

B)

R$^8$ is independently, at each instance, R$^e$, R$^h$, —OR$^e$, —OC$_{2-6}$alkylNR$^a$R$^e$, —OC$_{2-6}$alkylOR$^e$, —NR$^a$R$^e$, —NR$^a$R$^h$, —NR$^a$C$_{2-6}$alkylNR$^a$R$^e$, —NR$^a$C$_{2-6}$alkylOR$^e$, —CO$_2$R$^e$, —OC(=O)R$^e$, —C(=O)R$^e$, —C(=O)NR$^a$R$^h$, —NR$^a$C(=O)R$^e$, —NR$^a$C(=O)R$^h$, —NR$^a$C(=O)NR$^a$R$^e$, —NR$^a$CO$_2$R$^e$, —C$_{1-8}$alkylOR$^e$, —C$_{1-6}$alkylNR$^a$R$^e$, —S(=O)$_n$R$^e$, —S(=O)$_2$NR$^a$R$^e$, —NR$^a$S(=O)$_2$R$^e$, —OS(=O)$_2$R$^e$, —OC(=O)NR$^a$R$^e$, —OR$^h$, —OC$_{2-6}$alkylNR$^a$R$^h$, —OC$_{2-6}$alkylOR$^h$, —NR$^a$C$_{2-6}$alkylNR$^a$R$^h$, —NR$^h$C$_{2-6}$alkylNR$^a$R$^a$, —NR$^h$C$_{2-6}$alkylOR$^a$, —NR$^a$C$_{2-6}$alkylOR$^h$, —CO$_2$R$^h$, —OC(=O)R$^h$, —C(=O)NR$^a$R$^h$, —NR$^e$C(=O)R$^a$, —NR$^h$C(=O)R$^a$, —NR$^h$C(=O)NR$^a$R$^a$, —NR$^e$C(=O)NR$^a$R$^a$, —NR$^h$CO$_2$R$^a$, —NR$^e$CO$_2$R$^a$, —C$_{1-8}$alkylOR$^h$, —C$_{1-6}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^a$, —OS(=O)$_2$R$^h$ or —OC(=O)NR$^a$R$^h$; and R$^9$ is independently, at each instance, H, R$^k$, C$_{1-4}$haloalkyl, halo, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^{10}$ is independently, at each instance, selected from H, halo, C$_{1-8}$alkyl, C$_{1-4}$haloalkyl, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OH, —NH$_2$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{10}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, wherein the ring is substituted by 0, 1 or 2 oxo or thioxo groups, wherein the ring is substituted by 0, 1, 2 or 3 groups selected from R$^k$, halo, cyano, nitro, —OH, —NH$_2$, —SH, —C(O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{10}$ is C$_{1-4}$alkyl substituted by 0, 1, 2 or 3 groups selected from C$_{1-4}$haloalkyl, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$;

R$^{11}$ is independently, at each instance, selected from H, cyano, nitro, —OH, —NH$_2$, —SH, C$_{1-8}$alkyl, C$_{1-4}$haloalkyl, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)

S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^a$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{11}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from R$^k$, halo, cyano, nitro, —C(=O)R$^k$, —C(=O)OR$^k$, —C(=O)NR$^a$R$^k$, —C(=NR$^a$)NR$^a$R$^k$, —OH, —NH$_2$, —SH, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^i$R$^a$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{11}$ is C$_4$alkyl substituted by 0, 1, 2 or 3 groups selected from C$_{1-4}$haloalkyl, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{10}$ and R$^{11}$ together are a saturated, partially-saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^i$, R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{10}$ and R$^{11}$ together are a saturated or partially unsaturated 3-, 4- or 5-carbon bridge, wherein the bridge is substituted by 0, 1 or 2 substituents selected from oxo, thioxo, R$^i$, R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$;

R$^{12}$ is independently, at each instance, selected from H, C$_{1-8}$alkyl, C$_{1-4}$haloalkyl, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)

NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{12}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{12}$ is C$_{1-4}$alkyl substituted by 0, 1, 2 or 3 groups selected from C$_{1-4}$haloalkyl, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$ R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$, and additionally substituted by 0, 1 or 2 halo groups; or R$^{11}$ and R$^{12}$ together are a saturated, partially-saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^i$, R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{11}$ and R$^{12}$ together are a saturated or partially unsaturated 3-, 4- or 5-carbon bridge, wherein the bridge is substituted by 0, 1 or 2 substituents selected from oxo, thioxo, R$^i$, R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S (=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$;

R$^{13}$ is independently, at each instance, selected from H, halo, cyano, nitro, C$_{1-4}$haloalkyl, —OH, —NH$_2$, —SH, C$_{1-8}$alkyl, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^i$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{13}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from R$^k$, halo, cyano, nitro, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{13}$ is C$_{1-4}$alkyl substituted by 0, 1, 2 or 3 groups selected from C$_{1-4}$haloalkyl, cyano, nitro, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-1}$alkylOR$^k$ and —NR$^a$C$_{2-6}$alkylOR$^i$;

R$^{14}$ is independently, at each instance, selected from H, C$_{1-8}$alkyl, C$_{1-4}$haloalkyl, halo, cyano, nitro, —OH, —NH$_2$, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{14}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, wherein the ring is substituted by 0, 1 or 2 oxo or thioxo groups, wherein the ring is substituted by 0, 1, 2 or 3 groups selected from R$^k$, halo, cyano, nitro, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{14}$ is C$_{1-4}$alkyl substituted by 0, 1, 2 or 3 groups selected from C$_{1-4}$haloalkyl, halo, cyano, nitro, —C(=O)R$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^i$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^i$, —S(=O)$_2$N(R$^a$)C(=O)R$^i$, —S(=O)$_2$N(R$^i$)C(=O)OR$^i$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; wherein at least one of R$^{10}$, R$^{11}$, R$^{12}$, R$^{13}$ and R$^{14}$ is other than H;

R$^a$ is independently, at each instance, H, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl;

R$^b$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups;

R$^d$ is independently in each instance hydrogen or —CH$_3$;

R$^e$ is, independently, in each instance, C$_{1-9}$alkyl substituted by a group independently selected from R$^h$; and wherein the C$_{1-9}$alkyl is additionally substituted by 0, 1, 2 or 3 substituents selected from halo, C$_{1-4}$haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^h$ is, independently, in each instance, phenyl or a saturated, partially saturated or unsaturated 5-, 6- or 7-membered monocyclic or 6-, 7-, 8-, 9-, 10- or 11-membered bicyclic ring containing 1, 2 or 3 atoms selected from N, O and S, so long as the combination of O and S atoms is not greater than 2, wherein the ring is substituted by 0 or 1 oxo or thioxo groups, wherein the phenyl and monocycle are substituted by 1, 2 or 3 groups independently selected from C$_{1-9}$alkyl substituted by 0, 1, 2 or 3 substituents selected from halo, cyano, nitro, C$_{1-4}$haloalkyl, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and wherein the phenyl and monocycle are additionally substituted by 0, 1 or 2 substituents selected from C$_{1-9}$alkyl, halo, cyano, nitro, C$_{1-4}$haloalkyl, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^i$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the available carbon atoms of the ring are substituted by 0, 1 or 2 oxo or thioxo groups, wherein the ring is substituted by 0, 1, 2 or 3 substituents independently selected from C$_{1-9}$alkyl, halo, cyano, nitro, C$_{1-4}$haloalkyl, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$, —NR$^a$C$_{2-6}$alkylOR$^a$, and C$_{1-9}$alkyl substituted by 1, 2 or 3 substituents selected from halo, cyano, nitro, C$_{1-4}$haloalkyl, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and R$^k$ is, independently, in each instance, C$_{1-9}$alkyl or C$_{1-4}$alkyl(phenyl) wherein either is substituted by 0, 1, 2, 3 or 4 substituents selected from halo, C$_{1-4}$haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and wherein the C$_{1-9}$alkyl is additionally substituted by 0 or 1 groups independently selected from $R^i$ and additionally substituted by 0, 1, 2, 3, 4 or 5 substituents independently selected from Br, Cl, F and I.

In one embodiment, in conjunction with any one of the above and below embodiments, $R^b$ is a heterocycle selected from the group of thiophene, pyrrole, 1,3-oxazole, 1,3-thiazol-4-yl, 1,3,4-oxadiazole, 1,3,4-thiadiazole, 1,2,3-oxadiazole, 1,2,3-thiadiazole, 1H-1,2,3-triazole, isothiazole, 1,2,4-oxadiazole, 1,2,4-thiadiazole, 1,2,3,4-oxatriazole, 1,2,3,4-thiatriazole, 1H-1,2,3,4-tetraazole, 1,2,3,5-oxatriazole, 1,2,3,5-thiatriazole, furan, imidazol-2-yl, benzimidazole, 1,2,4-triazole, isoxazole, pyrazol-3-yl, pyrazol-4-yl, pyrazol-5-yl, thiolane, pyrrolidine, tetrahydrofuran, 4,5-dihydrothiophene, 2-pyrroline, 4,5-dihydrofuran, pyridazine, pyrimidine, pyrazine, 1,2,3-triazine, 1,2,4-triazine, 1,3,5-triazine, pyridine, 2H-3,4,5,6-tetrahydropyran, thiane, 1,2-diazaperhydroine, 1,3-diazaperhydroine, piperazine, 1,3-oxazaperhydroine, morpholine, 1,3-thiazaperhydroine, 1,4-thiazaperhydroine, piperidine, 2H-3,4-dihydropyran, 2,3-dihydro-4H-thiin, 1,4,5,6-tetrahydropyridine, 2H-5,6-dihydropyran, 2,3-dihydro-6H-thiin, 1,2,5,6-tetrahydropyridine, 3,4,5,6-tetrahydropyridine, 4H-pyran, 4H-thiin, 1,4-dihydropyridine, 1,4-dithiane, 1,4-dioxane, 1,4-oxathiane, 1,2-oxazolidine, 1,2-thiazolidine, pyrazolidine, 1,3-oxazolidine, 1,3-thiazolidine, imidazolidine, 1,2,4-oxadiazolidine, 1,3,4-oxadiazolidine, 1,2,4-thiadiazolidine, 1,3,4-thiadiazolidine, 1,2,4-triazolidine, 2-imidazolin-1-yl, 2-imidazolin-2-yl, 3-imidazoline, 2-pyrazoline, 4-imidazoline, 2,3-dihydroisothiazole, 4,5-dihydroisoxazole, 4,5-dihydroisothiazole, 2,5-dihydroisoxazole, 2,5-dihydroisothiazole, 2,3-dihydroisoxazole, 4,5-dihydrooxazole, 2,3-dihydrooxazole, 2,5-dihydrooxazole, 4,5-dihydrothiazole, 2,3-dihydrothiazole, 2,5-dihydrothiazole, 1,3,4-oxathiazolidine, 1,4,2-oxathiazolidine, 2,3-dihydro-1H-[1,2,3]triazole, 2,5-dihydro-1H-[1,2,3]triazole, 4,5-dihydro-1H-[1,2,3]triazol-1-yl, 4,5-dihydro-1H-[1,2,3]triazol-3-yl, 4,5-dihydro-1H-[1,2,3]triazol-5-yl, 2,3-dihydro-1H-[1,2,4]triazole, 4,5-dihydro-1H-[1,2,4]triazole, 2,3-dihydro-[1,2,4]oxadiazole, 2,5-dihydro-[1,2,4]oxadiazole, 4,5-dihydro-[1,2,4]thiadiazole, 2,3-dihydro-[1,2,4]thiadiazole, 2,5-dihydro-[1,2,4]thiadiazole, 4,5-dihydro-[1,2,4]thiadiazole, 2,5-dihydro-[1,2,4]oxadiazole, 2,3-dihydro-[1,2,4]oxadiazole, 4,5-dihydro-[1,2,4]oxadiazole, 2,5-dihydro-[1,2,4]thiadiazole, 2,3-dihydro-[1,2,4]thiadiazole, 4,5-dihydro-[1,2,4]thiadiazole, 2,3-dihydro-[1,3,4]oxadiazole, 2,3-dihydro-[1,3,4]thiadiazole, [1,4,2]oxathiazole, [1,3,4]oxathiazole, 1,3,5-triazaperhydroine, 1,2,4-triazaperhydroine, 1,4,2-dithiazaperhydroine, 1,4,2-dioxazaperhydroine, 1,3,5-oxadiazaperhydroine, 1,2,5-oxadiazaperhydroine, 1,3,4-thiadiazaperhydroine, 1,3,5-thiadiazaperhydroine, 1,2,5-thiadiazaperhydroine, 1,3,4-oxadiazaperhydroine, 1,4,3-oxathiazaperhydroine, 1,4,2-oxathiazaperhydroine, 1,4,5,6-tetrahydropyridazine, 1,2,3,4-tetrahydropyridazine, 1,2,3,6-tetrahydropyridazine, 1,2,5,6-tetrahydropyrimidine, 1,2,3,4-tetrahydropyrimidine, 1,4,5,6-tetrahydropyrimidine, 1,2,3,6-tetrahydropyrazine, 1,2,3,4-tetrahydropyrazine, 5,6-dihydro-4H-[1,2]oxazine, 5,6-dihydro-2H-[1,2]oxazine, 3,6-dihydro-2H-[1,2]oxazine, 3,4-dihydro-2H-[1,2]oxazine, 5,6-dihydro-4H-[1,2]thiazine, 5,6-dihydro-2H-[1,2]thiazine, 3,6-dihydro-2H-[1,2]thiazine, 3,4-dihydro-2H-[1,2]thiazine, 5,6-dihydro-2H-[1,3]oxazine, 5,6-dihydro-4H-[1,3]oxazine, 3,6-dihydro-2H-[1,3]oxazine, 3,4-dihydro-2H-[1,3]oxazine, 3,6-dihydro-2H-[1,4]oxazine, 3,4-dihydro-2H-[1,4]oxazine, 5,6-dihydro-2H-[1,3]thiazine, 5,6-dihydro-4H-[1,3]thiazine, 3,6-dihydro-2H-[1,3]thiazine, 3,4-dihydro-2H-[1,3]thiazine, 3,6-dihydro-2H-[1,4]thiazine, 3,4-dihydro-2H-[1,4]thiazine, 1,2,3,6-tetrahydro-[1,2,4]triazine, 1,2,3,4-tetrahydro-[1,2,4]triazine, 1,2,3,4-tetrahydro-[1,3,5]triazine, 2,3,4,5-tetrahydro-[1,2,4]triazine, 1,4,5,6-tetrahydro-[1,2,4]triazine, 5,6-dihydro-[1,4,2]dioxazine, 5,6-dihydro-[1,4,2]dithiazine, 2,3-dihydro-[1,4,2]dioxazine, 3,4-dihydro-2H-[1,3,4]oxadiazine, 3,6-dihydro-2H-[1,3,4]oxadiazine, 3,4-dihydro-2H-[1,3,5]oxadiazine, 3,6-dihydro-2H-[1,3,5]oxadiazine, 5,6-dihydro-2H-[1,2,5]oxadiazine, 5,6-dihydro-4H-[1,2,5]oxadiazine, 3,4-dihydro-2H-[1,3,4]thiadiazine, 3,6-dihydro-2H-[1,3,4]thiadiazine, 3,4-dihydro-2H-[1,3,5]thiadiazine, 3,6-dihydro-2H-[1,3,5]thiadiazine, 5,6-dihydro-2H-[1,2,5]thiadiazine, 5,6-dihydro-4H-[1,2,5]thiadiazine, 5,6-dihydro-2H-[1,2,3]oxadiazine, 3,6-dihydro-2H-[1,2,5]oxadiazine, 5,6-dihydro-4H-[1,3,4]oxadiazine, 3,4-dihydro-2H-[1,2,5]oxadiazine, 5,6-dihydro-2H-[1,2,3]thiadiazine, 3,6-dihydro-2H-[1,2,5]thiadiazine, 5,6-dihydro-4H-[1,3,4]thiadiazine, 3,4-dihydro-2H-[1,2,5]thiadiazine, 5,6-dihydro-[1,4,3]oxathiazine, 5,6-dihydro-[1,4,2]oxathiazine, 2,3-dihydro-[1,4,3]oxathiazine, 2,3-dihydro-[1,4,2]oxathiazine, 3,4-dihydropyridine, 1,2-dihydropyridine, 5,6-dihydropyridine, 2H-pyran, 2H-thiin, 3,6-dihydropyridine, 2,3-dihydropyridazine, 2,5-dihydropyridazine, 4,5-dihydropyridazine, 1,2-dihydropyridazine, 1,4-dihydropyrimidin-1-yl, 1,4-dihydropyrimidin-4-yl, 1,4-dihydropyrimidin-5-yl, 1,4-dihydropyrimidin-6-yl, 2,3-dihydropyrimidine, 2,5-dihydropyrimidine, 5,6-dihydropyrimidine, 3,6-dihydropyrimidine, 5,6-dihydropyrazine, 3,6-dihydropyrazine, 4,5-dihydropyrazine, 1,4-dihydropyrazine, 1,4-dithiin, 1,4-dioxin, 2H-1,2-oxazine, 6H-1,2-oxazine, 4H-1,2-oxazine, 2H-1,3-oxazine, 4H-1,3-oxazine, 6H-1,3-oxazine, 2H-1,4-oxazine, 4H-1,4-oxazine, 2H-1,3-thiazine, 2H-1,4-thiazine, 4H-1,2-thiazine, 6H-1,3-thiazine, 4H-1,4-thiazine, 2H-1,2-thiazine, 6H-1,2-thiazine, 1,4-oxathiin, 2H,5H-1,2,3-triazine, 1H,4H-1,2,3-triazine, 4,5-dihydro-1,2,3-triazine, 1H,6H-1,2,3-triazine, 1,2-dihydro-1,2,3-triazine, 2,3-dihydro-1,2,4-triazine, 3H,6H-1,2,4-triazine, 1H,6H-1,2,4-triazine, 3,4-dihydro-1,2,4-triazine, 1H,4H-1,2,4-triazine, 5,6-dihydro-1,2,4-triazine, 2H,5H-1,2,4-triazine, 4,5-dihydro-1,2,4-triazine, 1H,4H-1,3,5-triazine, 1,2-dihydro-1,3,5-triazine, 1,4,2-dithiazine, 1,4,2-dioxazine, 2H-1,3,4-oxadiazine, 2H-1,3,5-oxadiazine, 6H-1,2,5-oxadiazine, 4H-1,3,4-oxadiazine, 4H-1,3,5-oxadiazine, 4H-1,2,5-oxadiazine, 2H-1,3,5-thiadiazine, 6H-1,2,5-thiadiazine, 4H-1,3,4-thiadiazine, 4H-1,3,5-thiadiazine, 4H-1,2,5-thiadiazine, 2H-1,3,4-thiadiazine, 6H-1,3,4-thiadiazine, 6H-1,3,4-oxadiazine, and 1,4,2-oxathiazine, wherein the heterocycle is optionally vicinally fused with a saturated, partially-saturated or unsaturated 5-, 6- or 7-membered ring containing 0, 1 or 2 atoms independently selected from N, O and S.

In one embodiment, in conjunction with any one of the above and below embodiments, J is O.

In one embodiment, in conjunction with any one of the above and below embodiments, X is N or $C(R^2)$; Y is N or $C(R^3)$, wherein at least one of X and Y is not N.

In another embodiment, in conjunction with any one of the above and below embodiments, X is $C(R^2)$; Y is $C(R^3)$; and $R^3$ is halo, $—NH_2$, $—NHC_{1-3}alkyl$, $—N(C_{1-3}alkyl)C_{1-3}alkyl$, or $C_{1-3}alkyl$.

In another embodiment, in conjunction with any one of the above and below embodiments, X is $C(R^2)$; Y is $C(R^3)$; and $R^3$ is H;

In another embodiment, in conjunction with any one of the above and below embodiments, X is N; and Y is $C(R^3)$.

In another embodiment, in conjunction with any one of the above and below embodiments, X is $C(R^2)$; and Y is N.

Embodiment A: In another embodiment, in conjunction with any one of the above and below embodiments, $R^1$ is

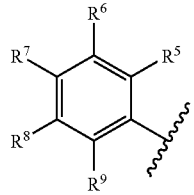

Embodiment B: In another embodiment, in conjunction with any one of the above and below embodiments, $R^1$ is $R^b$ substituted by 1, 2 or 3 substituents selected from $R^e$, $R^h$, —$OR^e$, —$OR^h$, —$OC_{2-6}$alkyl$NR^aR^e$, —$OC_{2-6}$alkyl$OR^e$, —$NR^aR^e$, —$NR^aR^h$, —$NR^aC_{2-6}$alkyl$NR^aC_{2-6}$alkyl$OR^e$, —$CO_2R^e$, —$OC(=O)R^e$, —$C(=O)R^e$, —$C(=O)NR^aR^e$, —$C(=O)NR^aR^h$, —$NR^aC(=O)R^e$, —$NR^aC(=O)R^h$, —$NR^aC(=O)NR^aR^e$, —$NR^aCO_2R^e$, —$C_{1-8}$alkyl$OR^e$, —$C_{1-6}$alkyl$NR^aR^e$, —$S(=O)_nR^e$, —$S(=O)_2NR^aR^e$, —$NR^aS(=O)_2R^e$, —$OS(=O)_2R^e$, —$OC(=O)NR^aR^e$, —$OC_{2-6}$alkyl$NR^aR^h$, —$OC_{2-6}$alkyl$OR^h$, —$NR^aC_{2-6}$alkyl$NR^aR^h$, —$NR^hC_{2-6}$alkyl$NR^aR^a$, —$NR^hC_{2-6}$alkyl$OR^a$, —$NR^aC_{2-6}$alkyl$OR^h$, —$CO_2R^h$, —$OC(=O)R^h$, —$NR^eC(=O)R^a$, —$NR^h(=O)R^a$, —$NR^hC(=O)NR^aR^a$, —$NR^eC(=O)NR^aR^a$, —$NR^hCO_2R^a$, —$NR^eCO_2R^a$, —$C_{1-8}$alkyl$NR^aR^h$, —$C_{1-6}$alkyl$NR^aR^h$, —$S(=O)_nR^h$, —$S(=O)_2NR^aR^h$, —$NR^aS(=O)_2R^h$, —$NR^hS(=O)_2R^a$, —$OS(=O)_2R^h$ and —$OC(=O)NR^aR^h$, and additionally substituted by 0, 1, 2 or 3 substituents independently selected from halo, cyano, nitro, $C_{1-8}$alkyl, $C_{1-4}$haloalkyl, $R^i$, $R^k$, —$OR^a$, —$NR^aR^a$, —$OC_{2-6}$alkyl$NR^aR^a$, —$OC_{2-6}$alkyl$OR^a$, —$NR^aC_{2-6}$alkyl$NR^aR^a$, —$NR^aC_{2-6}$alkyl$OR^a$, —$CO_2R^a$, —$OC(=O)R^a$, —$C(=O)(C_{1-6}$alkyl), —$C(=O)NR^aR^a$, —$NR^aC(=O)R^a$, —$NR^aC(=O)NR^aR^a$, —$NR^aCO_2R^a$, —$C_{1-8}$alkyl$OR^a$, —$C_{1-6}$alkyl$NR^aR^a$, —$S(=O)_nR^a$, —$S(=O)_2NR^aR^a$, —$NR^aS(=O)_2R^a$, —$OS(=O)_2R^a$ and —$OC(=O)NR^aR^e$.

Embodiment C: In another embodiment, in conjunction with any one of the above and below embodiments, $R^1$ is

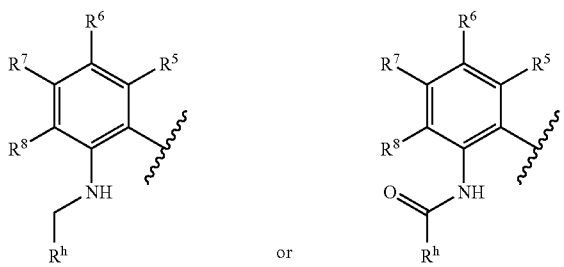

In another embodiment, in conjunction with any one of the above and below embodiments, $R^2$ is selected from H, halo, cyano, nitro, $R^i$, $R^k$, —OH, —$OR^i$, —$OR^k$, —$C(=O)OR^i$, —$C(=O)OR^k$, —$OC(=O)R^i$, —$OC(=O)R^k$, —$S(O)_nR^i$, —$S(O)R^k$, —$N(R^a)S(O)_nR^i$, —$N(R^a)S(O)_nR^k$, —$S(O)_nN(R^a)R^i$, —$S(O)_nN(R^a)R^k$, —$NH_2$, —$C(=O)NR^aR^i$, —$C(=O)NR^aR^k$, —$NR^aC(=O)R^i$ and —$NR^aC(=O)R^k$, —$NR^aR^i$ and —$NR^aR^k$.

In another embodiment, in conjunction with any one of the above and below embodiments, $R^2$ is H.

In another embodiment, in conjunction with any one of the above and below embodiments, $R^2$ is selected from H and halo.

In another embodiment, in conjunction with any one of the above and below embodiments, $R^2$ is selected from halo, cyano, nitro, $R^i$, $R^k$, —OH, —$OR^i$, —$OR^k$, —$C(=O)OR^i$, —$C(=O)OR^k$, —$OC(=O)R^i$, —$OC(=O)R^k$, —$S(O)_nR^i$, —$S(O)_nR^k$, —$N(R^a)S(O)_nR^i$, —$N(R^a)S(O)_nR^k$, —$S(O)_nN(R^a)R^i$, —$S(O)_nN(R^a)R^k$, —$NH_2$, —$C(=O)NR^aR^i$, —$C(=O)NR^aR^k$, —$NR^aC(=O)R^i$ and —$NR^aC(=O)R^k$, —$NR^aR^i$ and —$NR^aR^k$.

In another embodiment, in conjunction with any one of the above and below embodiments, $R^2$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the available carbon atoms of the ring are substituted by 0, 1 or 2 oxo or thioxo groups, wherein the ring is substituted by 0, 1, 2 or 3 substituents independently selected from $C_{1-9}$alkyl, halo, cyano, nitro, $C_{1-4}$haloalkyl, —$C(=O)R^a$, —$C(=O)OR^a$, —$C(=O)NR^aR^a$, —$C(=NR^a)NR^aR^a$, —$OR^a$, —$OC(=O)R^a$, —$OC(=O)NR^aR^a$, —$OC(=O)N(R^a)S(=O)_2R^a$, —$OC_{2-6}$alkyl$NR^aR^a$, —$OC_{2-6}$alkyl$OR^a$, —$SR^a$, —$S(=O)R^a$, —$S(=O)_2R^a$, —$S(=O)_2NR^aR^a$, —$S(=O)_2N(R^a)C(=O)R^a$, —$S(=O)_2N(R^a)C(=O)OR^a$, —$S(=O)_2N(R^a)C(=O)NR^aR^a$, —$NR^aR^a$, —$N(R^a)C(=O)R^a$, —$N(R^a)C(=O)OR^a$, —$N(R^a)C(=O)NR^aR^a$, —$N(R^a)C(=NR^a)NR^aR^a$, —$N(R^a)S(=O)_2R^a$, —$N(R^a)S(=O)_2NR^aR^a$, —$NR^aC_{2-6}$alkyl$NR^aR^a$, —$NR^aC_{2-6}$alkyl$OR^a$, and $C_{1-9}$alkyl substituted by 1, 2 or 3 substituents selected from halo, cyano, nitro, $C_{1-4}$haloalkyl, —$C(=O)R^a$, —$C(=O)OR^a$, —$C(=O)NR^aR^a$, —$C(=NR^a)NR^aR^a$, —$OR^a$, —$OC(=O)R^a$, —$OC(=O)NR^aR^a$, —$OC(=O)N(R^a)S(=O)_2R^a$, —$OC_{2-6}$alkyl$NR^aR^a$, —$OC_{2-6}$alkyl$OR^a$, —$SR^a$, —$S(=O)R^a$, —$S(=O)_2R^a$, —$S(=O)_2NR^aR^a$, —$S(=O)_2N(R^a)C(=O)R^a$, —$S(=O)_2N(R^a)C(=O)OR^a$, —$S(=O)_2N(R^a)C(=O)NR^aR^a$, —$NR^aR^a$, —$N(R^a)C(=O)R^a$, —$N(R^a)C(=O)OR^a$, —$N(R^a)C(=O)NR^aR^a$, —$N(R^a)C(=NR^a)NR^aR^a$, —$N(R^i)S(=O)_2R^i$, —$N(R^a)S(=O)_2NR^aR^a$, —$NR^aC_{2-6}$alkyl$NR^aR^a$ and —$NR^aC_{2-6}$alkyl$OR^a$.

In another embodiment, in conjunction with any one of the above and below embodiments, $R^2$ is $C_{1-9}$alkyl or $C_{1-4}$alkyl(phenyl) wherein either is substituted by 0, 1, 2, 3 or 4 substituents selected from halo, $C_{1-4}$haloalkyl, cyano, nitro, —$C(=O)R^a$, —$C(=O)OR^a$, —$C(=O)NR^aR^a$, —$C(=NR^a)NR^aR^a$, —$OR^a$, —$OC(=O)R^a$, —$OC(=O)NR^aR^a$, —$OC(=O)N(R^a)S(=O)_2R^a$, —$OC_{2-6}$alkyl$NR^aR^a$, —$OC_{2-6}$alkyl$OR^a$, —$SR^a$, —$S(=O)R^a$, —$S(=O)_2R^a$, —$S(=O)_2NR^aR^a$, —$S(=O)_2N(R^a)C(=O)R^a$, —$S(=O)_2N(R^a)C(=O)OR^a$, —$S(=O)_2N(R^a)C(=O)NR^aR^a$, —$NR^aR^a$, —$N(R^a)C(=O)R^a$, —$N(R^a)C(=O)OR^a$, —$N(R^a)C(=O)NR^aR^a$, —$N(R^a)C(=NR^a)NR^aR^a$, —$N(R^i)S(=O)_2R^i$, —$N(R^a)S(=O)_2NR^aR^a$, —$NR^aC_{2-6}$alkyl$NR^aR^a$ and —$NR^aC_{2-6}$alkyl$OR^a$; and wherein the $C_{1-9}$alkyl is additionally substituted by 0 or 1 groups independently selected from $R^i$ and additionally substituted by 0, 1, 2, 3, 4 or 5 substituents independently selected from Br, Cl, F and I.

In another embodiment, in conjunction with any one of the above and below embodiments, $R^3$ is selected from $R^3$ is selected from H, halo, cyano, nitro, $R^i$, $R^k$, —OH, —$OR^i$, —$OR^k$, —$C(=O)OR^i$, —$C(=O)OR^k$, —$OC(=O)R^i$, —$OC(=O)R^k$, —$S(O)_nR^i$, —$S(O)_nR^k$, —$N(R^a)S(O)_nR^i$, —$N(R^a)S(O)_nR^k$, —$S(O)_nN(R^a)R^i$, —$S(O)_nN(R^a)R^k$, —$NH_2$, —$C(=O)NR^aR^i$, —$C(=O)NR^aR^k$, —$NR^aC(=O)R^i$ and —$NR^aC(=O)R^k$, —$NR^aR^i$ and —$NR^aR^k$.

In another embodiment, in conjunction with any one of the above and below embodiments, $R^3$ is H.

In another embodiment, in conjunction with any one of the above and below embodiments, $R^3$ is selected from H and halo.

In another embodiment, in conjunction with any one of the above and below embodiments, $R^3$ is selected from $R^3$ is selected from halo, cyano, nitro, $R^i$, $R^k$, —OH, —$OR^i$, —$OR^k$, —C(=O)$OR^i$, —C(=O)$OR^k$, —OC(=O)$R^i$, —OC(=O)$R^k$, —S(O)$_n R^i$, —S(O)$_n R^k$, —N($R^a$)S(O)$_n R^i$, —N($R^a$)S(O)$_n R^k$, —S(O)$_n$N($R^a$)$R^i$, —S(O)$_n$N($R^a$)$R^k$, —NH$_2$, —C(=O)N$R^a R^i$, —C(=O)N$R^a R^k$, —$NR^a$C(=O)$R^i$ and —$NR^a$C(=O)$R^k$, —$NR^a R^i$ and —$NR^a R^k$.

In another embodiment, in conjunction with any one of the above and below embodiments, $R^3$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the available carbon atoms of the ring are substituted by 0, 1 or 2 oxo or thioxo groups, wherein the ring is substituted by 0, 1, 2 or 3 substituents independently selected from $C_{1-9}$alkyl, halo, cyano, nitro, $C_{1-4}$haloalkyl, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —O$C_{2-6}$alkylN$R^a R^a$, —O$C_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —$NR^a C_{2-6}$alkylN$R^a R^a$, —$NR^a C_{2-6}$alkylO$R^a$, and $C_{1-9}$alkyl substituted by 1, 2 or 3 substituents selected from halo, cyano, nitro, $C_{1-4}$haloalkyl, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —O$C_{2-6}$alkylN$R^a R^a$, —O$C_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —$NR^a C_{2-6}$alkylN$R^a R^a$ and —$NR^a C_{2-6}$alkylO$R^a$.

In another embodiment, in conjunction with any one of the above and below embodiments, $R^3$ is $C_{1-9}$alkyl or $C_{1-4}$alkyl(phenyl) wherein either is substituted by 0, 1, 2, 3 or 4 substituents selected from halo, $C_{1-4}$haloalkyl, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —O$C_{2-6}$alkylN$R^a R^a$, —O$C_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —$NR^a C_{2-6}$alkylN$R^a R^a$ and —$NR^a C_{2-6}$alkylO$R^a$; and wherein the $C_{1-9}$alkyl is additionally substituted by 0 or 1 groups independently selected from $R^i$ and additionally substituted by 0, 1, 2, 3, 4 or 5 substituents independently selected from Br, Cl, F and I.

Embodiment D: In another embodiment, in conjunction with any one of the above and below embodiments, $R^4$ is independently at each instance

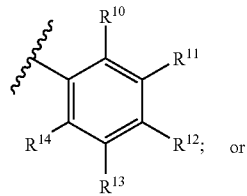

$R^4$ is independently at each instance a saturated, partially-saturated or unsaturated 5- or 6-membered ring heterocycle containing 1, 2 or 3 atoms selected from O, N and S that is optionally vicinally fused with a saturated, partially-saturated or unsaturated 3-, 4- or 5-atom bridge containing 0, 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from oxo, thioxo, $R^k$, $C_{1-4}$haloalkyl, cyano, nitro, —C(=O)$R^a$, —C(=O)O$R^a$, —C(=O)N$R^a R^a$, —C(=N$R^a$)N$R^a R^a$, —O$R^a$, —C(=O)$R^a$, —OC(=O)N$R^a R^a$, —OC(=O)N($R^a$)S(=O)$_2 R^a$, —O$C_{2-6}$alkylN$R^a R^a$, —O$C_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —$NR^a C_{2-6}$alkylN$R^a R^a$ and —$NR^a C_{2-6}$alkylO$R^a$; and wherein the heterocycle is additionally substituted by 0 or 1 groups independently selected from $R^i$ and additionally substituted by 0, 1, 2, 3, 4 or 5 substituents independently selected from Br, Cl, F and I; or $R^4$ is independently at each instance naphthyl substituted by 1, 2 or 3 substituents independently selected from $R^k$, $C_{1-4}$haloalkyl, cyano, nitro, —C(=)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —O$C_{2-6}$alkylN$R^a R^a$, —O$C_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —$NR^a C_{2-6}$alkylN$R^a R^a$ and —$NR^a C_{2-6}$alkylO$R^a$; and wherein the naphthyl is additionally substituted by 0 or 1 groups independently selected from $R^i$ and additionally substituted by 0, 1, 2, 3, 4 or 5 substituents independently selected from Br, Cl, F and I.

Embodiment E: In another embodiment, in conjunction with any one of the above and below embodiments, $R^4$ is independently at each instance

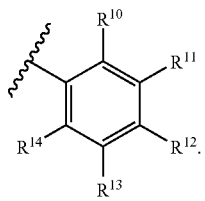

Embodiment F: In another embodiment, in conjunction with any one of the above and below embodiments, $R^4$ is independently at each instance a saturated, partially-saturated or unsaturated 5- or 6-membered ring heterocycle containing 1, 2 or 3 atoms selected from O, N and S that is optionally vicinally fused with a saturated, partially-saturated or unsaturated 3-, 4- or 5-atom bridge containing 0, 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from oxo, thioxo, $R^k$, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$; and wherein the heterocycle is additionally substituted by 0 or 1 groups independently selected from $R^i$ and additionally substituted by 0, 1, 2, 3, 4 or 5 substituents independently selected from Br, Cl, F and I; or $R^4$ is independently at each instance naphthyl substituted by 1, 2 or 3 substituents independently selected from $R^k$, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$; and wherein the naphthyl is additionally substituted by 0 or 1 groups independently selected from $R^i$ and additionally substituted by 0, 1, 2, 3, 4 or 5 substituents independently selected from Br, Cl, F and I.

Embodiment G: In another embodiment, in conjunction with any one of the above and below embodiments, $R^4$ is independently at each instance a saturated, partially-saturated or unsaturated 5- or 6-membered ring heterocycle containing 1, 2 or 3 atoms selected from O, N and S that is vicinally fused with a saturated, partially-saturated or unsaturated 3-, 4- or 5-atom bridge containing 0, 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from oxo, thioxo, $R^k$, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$; and wherein the heterocycle is additionally substituted by 0 or 1 groups independently selected from $R^i$ and additionally substituted by 0, 1, 2, 3, 4 or 5 substituents independently selected from Br, Cl, F and I.

In another embodiment, in conjunction with any one of the above and below embodiments, $R^4$ is independently at each instance naphthyl substituted by 1, 2 or 3 substituents independently selected from $R^k$, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$; and wherein the naphthyl is additionally substituted by 0 or 1 groups independently selected from $R^i$ and additionally substituted by 0, 1, 2, 3, 4 or 5 substituents independently selected from Br, Cl, F and I.

In another embodiment, in conjunction with any one of the above and below embodiments, $R^5$ is independently, at each instance, $R^k$, $C_{1-4}$haloalkyl, halo, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$.

In another embodiment, in conjunction with any one of the above and below embodiments, $R^5$ is H.

In another embodiment, in conjunction with any one of the above and below embodiments, $R^5$ is $R^k$.

In another embodiment, in conjunction with any one of the above and below embodiments, $R^5$ is independently, at each instance, H, $C_{1-4}$haloalkyl, halo, —O$R^a$, —OC(=O)$R^a$, —N$R^aR^a$ or —N($R^a$)C(=O)$R^a$.

In another embodiment, in conjunction with any one of the above and below embodiments, $R^6$ is independently, at each instance, $R^k$, $C_{1-4}$haloalkyl, halo, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$.

In another embodiment, in conjunction with any one of the above and below embodiments, $R^6$ is H.

In another embodiment, in conjunction with any one of the above and below embodiments, $R^6$ is $R^k$.

In another embodiment, in conjunction with any one of the above and below embodiments, $R^6$ is independently, at each instance, H, $C_{1-4}$haloalkyl, halo, —O$R^a$, —OC(=O)$R^a$, —N$R^aR^a$ or —N($R^a$)C(=O)$R^a$.

In another embodiment, in conjunction with any one of the above and below embodiments, $R^7$ is independently, at each instance, H, $C_{1-8}$alkyl, $C_{1-4}$haloalkyl, halo, cyano, —OC$_{1-6}$alkyl, —OC$_{1-4}$haloalkyl, —OC$_{2-6}$alkylN$R^aR^a$, —OC$_{2-6}$alkylO$R^a$, —N$R^aR^a$, —N$R^aC_{1-4}$haloalkyl, —N$R^aC_{2-6}$alkylN$R^aR^a$, —N$R^aC_{2-6}$alkylO$R^a$, —C$_{1-8}$alkylO$R^a$, —C$_{1-6}$alkylN$R^aR^a$, or —S(C$_{1-6}$alkyl); or $R^7$ is a saturated, partially-saturated or unsaturated 4- or 5-membered ring heterocycle containing a single nitrogen atom, wherein the ring is substituted with 0, 1 or 2 substituents independently selected from halo, $C_{1-2}$haloalkyl and $C_{1-3}$alkyl.

Embodiment H: In another embodiment, in conjunction with any one of the above and below embodiments, $R^7$ is independently, at each instance, $R^k$, $C_{1-4}$haloalkyl, halo, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$C$_{2-6}$alkylN$R^aR^a$ and —N$R^a$C$_{2-6}$alkylO$R^a$.

In another embodiment, in conjunction with any one of the above and below embodiments, $R^7$ is H.

In another embodiment, in conjunction with any one of the above and below embodiments, $R^7$ is $C_{1-5}$alkyl, $C_{1-4}$haloalkyl, halo.

Embodiment I: In another embodiment, in conjunction with any one of the above and below embodiments, $R^7$ is independently, at each instance, $C_{3-5}$alkyl or $C_{1-2}$haloalkyl.

In another embodiment, in conjunction with any one of the above and below embodiments, $R^7$ is $C_{3-5}$alkyl.

In another embodiment, in conjunction with any one of the above and below embodiments, $R^7$ is —C(CH$_3$)$_3$.

In another embodiment, in conjunction with any one of the above and below embodiments, $R^7$ is —CF$_3$.

Embodiment J: In another embodiment, in conjunction with any one of the above and below embodiments, $R^8$ is independently, at each instance, H, $R^k$, $C_{1-4}$haloalkyl, halo, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$C$_{2-6}$alkylN$R^aR^a$ and —N$R^a$C$_{2-6}$alkylO$R^a$; and $R^9$ is independently, at each instance, $R^e$, $R^h$, —O$R^e$, —O$R^h$, —OC$_{2-6}$alkylN$R^aR^e$, —OC$_{2-6}$alkylO$R^e$, —N$R^aR^e$, —N$R^aR^h$, —N$R^a$C$_{2-6}$alkylN$R^aR^e$, —N$R^a$C$_{2-6}$alkylO$R^e$, —CO$_2R^e$, —OC(=O)$R^e$, —C(=O)$R^e$, —C(=O)N$R^aR^e$, —C(=O)N$R^aR^h$, —N$R^a$C(=O)$R^e$, —N$R^a$C(=O)$R^h$, —N$R^a$C(=O)N$R^aR^e$, —N$R^a$CO$_2R^e$, —C$_{1-8}$alkylO$R^e$, —C$_{1-6}$alkylN$R^aR^e$, —S(=O)$_nR^e$, —S(=O)$_2$N$R^aR^e$, —N$R^a$S(=O)$_2R^e$, —OS(=O)$_2R^e$, —OC(=O)N$R^aR^e$, —O$R^h$, —OC$_{2-6}$alkylN$R^aR^h$, —OC$_{2-6}$alkylO$R^h$, —N$R^a$C$_{2-6}$alkylN$R^aR^h$, —N$R^h$C$_{2-6}$alkylN$R^aR^a$, —N$R^h$C$_{2-6}$alkylO$R^a$, —N$R^a$C$_{2-6}$alkylO$R^h$, —CO$_2R^h$, —OC(=O)$R^h$, —C(=O)$R^h$, —C(=O)N$R^aR^h$, —N$R^e$C(=O)$R^a$, —N$R^h$C(=O)$R^a$, —N$R^h$C(=O)N$R^aR^a$, —N$R^e$C(=O)N$R^aR^a$, —N$R^h$CO$_2R^a$, —N$R^e$CO$_2R^a$, —C$_{1-8}$alkylO$R^h$, —C$_{1-6}$alkylN$R^aR^h$, —S(=O)$_nR^h$, —S(=O)$_2$N$R^aR^h$, —N$R^a$S(=O)$_2R^h$, —N$R^h$S(=O)$_2R^a$, —OS(=O)$_2R^h$ or —OC(=O)N$R^aR^h$.

Embodiment K: In another embodiment, in conjunction with any one of the above and below embodiments, $R^8$ is H and $R^9$ is $R^e$, $R^h$, —O$R^e$, —O$R^h$, —OC$_{2-6}$alkylN$R^aR^e$, —OC$_{2-6}$alkylO$R^e$, —N$R^aR^e$, —N$R^aR^h$, —N$R^a$C$_{2-6}$alkylN$R^aR^e$, —N$R^a$C$_{2-6}$alkylO$R^e$, —CO$_2R^e$, —OC(=O)$R^e$, —C(=O)$R^e$, —C(=O)N$R^aR^e$, —C(=O)N$R^aR^h$, —N$R^a$C(=O)$R^e$, —N$R^a$C(=O)$R^h$, —N$R^a$C(=O)N$R^aR^e$, —N$R^a$CO$_2R^e$, —C$_{1-8}$alkylO$R^e$, —C$_{1-6}$alkylN$R^aR^e$, —S(=O)$_nR^e$, —S(=O)$_2$N$R^aR^e$, —N$R^a$S(=O)$_2R^e$, —OS(=O)$_2R^e$, —OC(=O)N$R^aR^e$, —O$R^h$, —OC$_{2-6}$alkylN$R^aR^h$, —OC$_{2-6}$alkylO$R^h$, —N$R^a$C$_{2-6}$alkylN$R^aR^h$, —N$R^h$C$_{2-6}$alkylN$R^aR^a$, —N$R^h$C$_{2-6}$alkylO$R^a$, —N$R^a$C$_{2-6}$alkylO$R^h$, —CO$_2R^h$, —OC(=O)$R^h$, —C(=O)$R^h$, —C(=O)N$R^aR^h$, —N$R^e$C(=O)$R^a$, —N$R^h$C(=O)$R^a$, —N$R^h$C(=O)N$R^aR^a$, —N$R^e$C(=O)N$R^aR^a$, —N$R^h$CO$_2R^a$, —N$R^e$CO$_2R^a$, —C$_{1-8}$alkylO$R^h$, —C$_{1-6}$alkylN$R^aR^h$, —S(=O)$_nR^h$, —S(=O)$_2$N$R^aR^h$, —N$R^a$S(=O)$_2R^h$, —N$R^h$S(=O)$_2R^a$, —OS(=O)$_2R^h$ or —OC(=O)N$R^aR^h$.

In another embodiment, in conjunction with any one of the above and below embodiments, $R^8$ is independently, at each instance, $R^k$, $C_{1-4}$haloalkyl, halo, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$C$_{2-6}$alkylN$R^aR^a$ and —N$R^a$C$_{2-6}$alkylO$R^a$; and $R^9$ is independently, at each instance, $R^e$, $R^h$, —O$R^e$, —O$R^h$, —OC$_{2-6}$alkylN$R^aR^e$, —OC$_{2-6}$alkylO$R^e$, —N$R^aR^e$, —N$R^aR^h$, —N$R^a$C$_{2-6}$alkylN$R^aR^e$, —N$R^a$C$_{2-6}$alkylO$R^e$, —CO$_2R^e$, —OC(=O)$R^e$, —C(=O)$R^e$, —C(=O)N$R^aR^e$, —C(=O)N$R^aR^h$, —N$R^a$C(=O)$R^e$, —N$R^a$C(=O)$R^h$, —N$R^a$C(=O)N$R^aR^e$, —N$R^a$CO$_2R^e$, —C$_{1-8}$alkylO$R^e$, —C$_{1-6}$alkylN$R^aR^e$, —S(=O)$_nR^e$, —S(=O)$_2$N$R^aR^e$, —N$R^a$S(=O)$_2R^e$, —OS(=O)$_2R^e$, —OC(=O)N$R^aR^e$, —O$R^h$, —OC$_{2-6}$alkylN$R^aR^h$, —OC$_{2-6}$alkylO$R^h$, —N$R^a$C$_{2-6}$alkylN$R^aR^h$, —N$R^h$C$_{2-6}$alkylN$R^aR^a$, —N$R^h$C$_{2-6}$alkylO$R^a$, —N$R^a$C$_{2-6}$alkylO$R^h$, —CO$_2R^h$, —OC(=O)$R^h$, —C(=O)$R^h$, —C(=O)N$R^aR^h$, —N$R^e$C(=O)$R^a$, —N$R^h$C(=O)$R^a$, —N$R^h$C(=O)N$R^aR^a$, —N$R^e$C(=O)N$R^aR^a$, —N$R^h$CO$_2R^a$, —N$R^e$CO$_2R^a$, —C$_{1-8}$alkylO$R^h$, —C$_{1-6}$alkylN$R^aR^h$, —S(=O)$_nR^h$, —S(=O)$_2$N$R^aR^h$, —N$R^a$S(=O)$_2R^h$, —N$R^h$S(=O)$_2R^a$, —OS(=O)$_2R^h$ or —OC(=O)N$R^aR^h$.

Embodiment L: In another embodiment, in conjunction with any one of the above and below embodiments, $R^8$ is independently, at each instance, $R^e$, $R^h$, —O$R^e$, —OC$_{2-6}$alkylN$R^aR^e$, —OC$_{2-6}$alkylO$R^e$, —N$R^aR^e$, —N$R^aR^h$, —N$R^a$C$_{2-6}$alkylN$R^aR^e$, —N$R^a$C$_{2-6}$alkylO$R^e$, —CO$_2R^e$, —OC(=O)$R^e$, —C(=O)$R^e$, —C(=O)N$R^aR^h$, —N$R^a$C(=O)$R^e$, —N$R^a$C(=O)$R^h$, —N$R^a$C(=O)N$R^aR^e$, —N$R^a$CO$_2R^e$, —C$_{1-8}$alkylO$R^e$, —C$_{1-6}$alkylN$R^aR^e$, —S(=O)$_nR^e$, —S(=O)$_2$N$R^aR^e$, —N$R^a$S(=O)$_2R^e$, —OS(=O)$_2R^e$, —OC(=O)N$R^aR^e$, —O$R^h$, —OC$_{2-6}$alkylN$R^aR^h$, —OC$_{2-6}$alkylO$R^h$, —N$R^a$C$_{2-6}$alkylN$R^aR^h$, —N$R^h$C$_{2-6}$alkylN$R^aR^a$, —N$R^h$C$_{2-6}$alkylO$R^a$, —N$R^a$C$_{2-6}$alkylO$R^h$, —CO$_2R^h$, —OC(=O)$R^h$, —C(=O)N$R^aR^h$, —N$R^e$C(=O)$R^a$, —N$R^h$C(=O)$R^a$, —N$R^h$C(=O)N$R^aR^a$, —N$R^e$C(=O)N$R^aR^a$, —N$R^h$CO$_2R^a$, —N$R^e$CO$_2R^a$, —C$_{1-8}$alkylO$R^h$, —C$_{1-6}$alkylN$R^aR^h$, —S(=O)$R^h$, —S(=O)$_2$N$R^aR^h$, —N$R^a$S(=O)$_2R^h$, —N$R^h$S(=O)$_2R^a$, —OS(=O)$_2R^h$ or —OC(=O)N$R^aR^h$; and $R^9$ is independently, at each instance, H, $R^k$, $C_{1-4}$haloalkyl, halo, cyano, nitro, —C(=O)$R^a$, —C(=O)O$R^a$, —C(=O)N$R^aR^a$, —C(=N$R^a$)N$R^aR^a$, —O$R^a$, —C(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$C$_{2-6}$alkylN$R^aR^a$ and —N$R^a$C$_{2-6}$alkylO$R^a$.

In another embodiment, in conjunction with any one of the above and below embodiments, $R^8$ is independently, at each instance, $R^e$, $R^h$, —$OR^e$, —$OC_{2-6}$alkyl$NR^aR^e$, —$OC_{2-6}$alkyl$OR^e$, —$NR^aR^e$, —$NR^aR^h$, —$NR^aC_{2-6}$alkyl$NR^aR^e$, —$NR^aC_{2-6}$alkyl$OR^e$, —$CO_2R^e$, —$OC(=O)R^e$, —$C(=O)R^e$, —$C(=O)NR^aR^h$, —$NR^aC(=O)R^e$, —$NR^aC(=O)R^h$, —$NR^aC(=O)NR^aR^e$, —$NR^aCO_2R^e$, —$C_{1-8}$alkyl$OR^e$, —$C_{1-6}$alkyl$NR^aR^e$, —$S(=O)_nR^e$, —$S(=O)_2NR^aR^e$, —$NR^aS(=O)_2R^e$, —$OS(=O)_2R^e$, —$OC(=O)NR^aR^e$, —$OR^h$, —$OC_{2-6}$alkyl$NR^aR^h$, —$OC_{2-6}$alkyl$OR^h$, —$NR^aC_{2-6}$alkyl$NR^aR^h$, —$NR^hC_{2-6}$alkyl$NR^aR^a$, —$NR^hC_{2-6}$alkyl$OR^a$, —$NR^aC_{2-6}$alkyl$OR^h$, —$CO_2R^h$, —$OC(=O)R^h$, —$C(=O)NR^aR^h$, —$NR^eC(=O)R^a$, —$NR^hC(=O)R^a$, —$NR^hC(=O)NR^aR^a$, —$NR^eC(=O)NR^aR^a$, —$NR^hCO_2R^a$, —$NR^eCO_2R^a$, —$C_{1-8}$alkyl$OR^h$, —$C_{1-6}$alkyl$NR^aR^h$, —$S(=O)_nR^h$, —$S(=O)_2NR^aR^h$, —$NR^aS(=O)_2R^h$, —$NR^hS(=O)_2R^a$, —$OS(=O)_2R^h$ or —$OC(=O)NR^aR^h$; and $R^9$ is H.

In another embodiment, in conjunction with any one of the above and below embodiments, $R^8$ is independently, at each instance, $R^e$, $R^h$, —$OR^e$, —$OC_{2-6}$alkyl$NR^aR^e$, —$OC_{2-6}$alkyl$OR^e$, —$NR^aR^e$, —$NR^aR^h$, —$NR^aC_{2-6}$alkyl$NR^aR^e$, —$NR^aC_{2-6}$alkyl$OR^e$, —$CO_2R^e$, —$OC(=O)R^e$, —$C(=O)R^e$, —$C(=O)NR^aR^h$, —$NR^aC(=O)R^e$, —$NR^aC(=O)R^h$, —$NR^aC(=O)NR^aR^e$, —$NR^aCO_2R^e$, —$C_{1-8}$alkyl$OR^e$, —$C_{1-6}$alkyl$NR^aR^e$, —$S(=O)_nR^e$, —$S(=O)_2NR^aR^e$, —$NR^aS(=O)_2R^e$, —$OS(=O)_2R^e$, —$OC(=O)NR^aR^e$, —$OR^h$, —$OC_{2-6}$alkyl$NR^aR^h$, —$OC_{2-6}$alkyl$OR^h$, —$NR^aC_{2-6}$alkyl$NR^aR^h$, —$NR^hC_{2-6}$alkyl$NR^aR^a$, —$NR^hC_{2-6}$alkyl$OR^a$, —$NR^aC_{2-6}$alkyl$OR^h$, —$CO_2R^h$, —$OC(=O)R^h$, —$C(=O)NR^aR^h$, —$NR^eC(=O)R^a$, —$NR^hC(=O)R^a$, —$NR^hC(=O)NR^aR^a$, —$NR^eC(=O)NR^aR^a$, —$NR^hCO_2R^a$, —$NR^eCO_2R^a$, —$C_{1-8}$alkyl$OR^h$, —$C_{1-6}$alkyl$NR^aR^h$, —$S(=O)_nR^h$, —$S(=O)_2NR^aR^h$, —$NR^aS(=O)_2R^h$, —$NR^hS(=O)_2R^a$, —$OS(=O)_2R^h$ or —$OC(=O)NR^aR^h$; and $R^9$ is $R^k$, $C_{1-4}$haloalkyl, halo, cyano, nitro, —$C(=O)R^a$, —$C(=O)OR^a$, —$C(=O)NR^aR^a$, —$C(=NR^a)NR^aR^a$, —$OR^a$, —$OC(=O)R^a$, —$C(=O)NR^aR^a$, —$OC(=O)N(R^a)S(=O)_2R^a$, —$OC_{2-6}$alkyl$NR^aR^a$, —$OC_{2-6}$alkyl$OR^a$, —$SR^a$, —$S(=O)R^a$, —$S(=O)_2R^a$, —$S(=O)_2NR^aR^a$, —$S(=O)_2N(R^a)C(=O)R^a$, —$S(=O)_2N(R^a)C(=O)OR^a$, —$S(=O)_2N(R^a)C(=O)NR^aR^a$, —$NR^aR^a$, —$N(R^a)C(=O)R^a$, —$N(R^a)C(=O)OR^a$, —$N(R^a)C(=O)NR^aR^a$, —$N(R^a)C(=NR^a)NR^aR^a$, —$N(R^a)S(=O)_2R^a$, —$N(R^a)S(=O)_2NR^aR^a$, —$NR^aC_{2-6}$alkyl$NR^aR^a$ and —$NR^aC_{2-6}$alkyl$OR^a$.

In another embodiment, in conjunction with any one of the above and below embodiments, at least one of $R^5$, $R^6$, $R^7$, $R^8$ and $R^9$ is tert-butyl or $CF_3$.

In another embodiment, in conjunction with any one of the above and below embodiments, $R^{10}$ is independently, at each instance, selected from H, halo, $C_{1-8}$alkyl, $C_{1-4}$haloalkyl, cyano, nitro, —OH, —$NH_2$, —SH, —$C(=O)R^k$, —$C(=O)OR^k$, —$C(=O)NR^aR^k$, —$C(=NR^a)NR^aR^k$, —OH, —$NH_2$, —$OR^k$, —$OC(=O)R^k$, —$OC(=O)NR^aR^k$, —$OC(=O)N(R^a)S(=O)_2R^k$, —$OC_{2-6}$alkyl$NR^aR^k$, —$OC_{2-6}$alkyl$OR^k$, —$SR^k$, —$S(=O)R^k$, —$S(=O)_2R^k$, —$S(=O)_2NR^aR^k$, —$S(=O)_2N(R^a)C(=O)R^k$, —$S(=O)_2N(R^a)C(=O)OR^k$, —$S(=O)_2N(R^a)C(=O)NR^aR^k$, —$NR^aR^k$, —$N(R^a)C(=O)R^k$, —$N(R^a)C(=O)OR^k$, —$N(R^a)C(=O)NR^aR^k$, —$N(R^a)C(=NR^a)NR^aR^k$, —$N(R^a)S(=O)_2R^k$, —$N(R^a)S(=O)_2NR^aR^k$, —$NR^aC_{2-6}$alkyl$NR^aR^k$, —$NR^aC_{2-6}$alkyl$OR^k$, —$C(=O)R^i$, —$C(=O)OR^i$, —$C(=O)NR^aR^i$, —$C(=NR^a)NR^aR^i$, —$OR^i$, —$OC(=O)R^i$, —$OC(=O)NR^aR^i$, —$OC(=O)N(R^a)S(=O)_2R^i$, —$OC(=O)N(R^i)S(=O)_2R^k$, —$OC_{2-6}$alkyl$NR^aR^i$, —$OC_{2-6}$alkyl$OR^i$, —$SR^i$, —$S(=O)R^i$, —$S(=O)_2R^i$, —$S(=O)_2NR^aR^i$, —$S(=O)_2N(R^i)C(=O)R^k$, —$S(=O)_2N(R^a)C(=O)R^i$, —$S(=O)_2N(R^i)C(=O)OR^k$, —$S(=O)_2N(R^a)C(=O)OR^i$, —$S(=O)_2N(R^i)C(=O)NR^aR^k$, —$S(=O)_2N(R^a)C(=O)NR^aR^i$, —$NR^aR^i$, —$N(R^i)C(=O)R^k$, —$N(R^a)C(=O)R^i$, —$N(R^i)C(=O)OR^k$, —$N(R^a)C(=O)OR^i$, —$N(R^i)C(=O)NR^aR^k$, —$N(R^a)C(=O)NR^aR^i$, —$N(R^i)C(=NR^a)NR^aR^k$, —$N(R^a)C(=NR^a)NR^aR^i$, —$N(R^i)S(=O)_2R^k$, —$N(R^a)S(=O)_2R^i$, —$N(R^i)S(=O)_2NR^aR^k$, —$N(R^a)S(=O)_2NR^aR^i$, —$NR^iC_{2-6}$alkyl$NR^aR^k$, —$NR^aC_{2-6}$alkyl$NR^aR^i$, —$NR^iC_{2-6}$alkyl$OR^k$ and —$NR^aC_{2-6}$alkyl$OR^i$; or $R^{10}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, wherein the ring is substituted by 0, 1 or 2 oxo or thioxo groups, wherein the ring is substituted by 0, 1, 2 or 3 groups selected from $R^k$, halo, cyano, nitro, —OH, —$NH_2$, —SH, —$C(=O)R^k$, —$C(=O)OR^k$, —$C(=O)NR^aR^k$, —$C(=NR^a)NR^aR^k$, —$OR^k$, —$OC(=O)R^k$, —$OC(=O)NR^aR^k$, —$OC(=O)N(R^a)S(=O)_2R^k$, —$OC_{2-6}$alkyl$NR^aR^k$, —$OC_{2-6}$alkyl$OR^k$, —$SR^k$, —$S(=O)R^k$, —$S(=O)_2R^k$, —$S(=O)_2NR^aR^k$, —$S(=O)_2N(R^a)C(=O)R^k$, —$S(=O)_2N(R^a)C(=O)OR^k$, —$S(=O)_2N(R^a)C(=O)NR^aR^k$, —$NR^aR^k$, —$N(R^a)C(=O)R^k$, —$N(R^a)C(=O)OR^k$, —$N(R^a)C(=O)NR^aR^k$, —$N(R^a)C(=NR^a)NR^aR^k$, —$N(R^a)S(=O)_2R^k$, —$N(R^a)S(=O)_2NR^aR^k$, —$NR^aC_{2-6}$alkyl$NR^aR^k$, —$NR^aC_{2-6}$alkyl$OR^k$, —$C(=O)R^i$, —$C(=O)OR^i$, —$C(=O)NR^aR^i$, —$C(=NR^a)NR^aR^i$, —$OR^i$, —$OC(=O)R^i$, —$OC(=O)NR^aR^i$, —$OC(=O)N(R^a)S(=O)_2R^i$, —$OC(=O)N(R^i)S(=O)_2R^k$, —$OC_{2-6}$alkyl$NR^aR^i$, —$OC_{2-6}$alkyl$OR^i$, —$SR^i$, —$S(=O)R^i$, —$S(=O)_2R^i$, —$S(=O)_2NR^aR^i$, —$S(=O)_2N(R^i)C(=O)R^k$, —$S(=O)_2N(R^a)C(=O)R^i$, —$S(=O)_2N(R^i)C(=O)OR^k$, —$S(=O)_2N(R^a)C(=O)OR^i$, —$S(=O)_2N(R^i)C(=O)NR^aR^k$, —$S(=O)_2N(R^a)C(=O)NR^aR^i$, —$NR^aR^i$, —$N(R^i)C(=O)R^k$, —$N(R^a)C(=O)R^i$, —$N(R^i)C(=O)OR^k$, —$N(R^a)C(=O)OR^i$, —$N(R^i)C(=O)NR^aR^k$, —$N(R^a)C(=O)NR^aR^i$, —$N(R^i)C(=NR^a)NR^aR^k$, —$N(R^a)C(=NR^a)NR^aR^i$, —$N(R^i)S(=O)_2R^k$, —$N(R^a)S(=O)_2R^i$, —$N(R^i)S(=O)_2NR^aR^k$, —$N(R^a)S(=O)_2NR^aR^i$, —$NR^iC_{2-6}$alkyl$NR^aR^k$, —$NR^aC_{2-6}$alkyl$NR^aR^i$, —$NR^iC_{2-6}$alkyl$OR^k$ and —$NR^aC_{2-6}$alkyl$OR^i$; or $R^{10}$ is $C_{1-4}$alkyl substituted by 0, 1, 2 or 3 groups selected from $C_{1-4}$haloalkyl, halo, cyano, nitro, —OH, —$NH_2$, —SH, —$C(=O)R^k$, —$C(=O)OR^k$, —$C(=O)NR^aR^k$, —$C(=NR^a)NR^aR^k$, —$OR^k$, —$OC(=O)R^k$, —$OC(=O)NR^aR^k$, —$OC(=O)N(R^a)S(=O)_2R^k$, —$OC_{2-6}$alkyl$NR^aR^k$, —$OC_{2-6}$alkyl$OR^k$, —$SR^k$, —$S(=O)R^k$, —$S(=O)_2R^k$, —$S(=O)_2NR^aR^k$, —$S(=O)_2N(R^a)C(=O)R^k$, —$S(=O)_2N(R^a)C(=O)OR^k$, —$S(=O)_2N(R^a)C(=O)NR^aR^k$, —$NR^aR^k$, —$N(R^a)C(=O)R^k$, —$N(R^a)C(=O)OR^k$, —$N(R^a)C(=O)NR^aR^k$, —$N(R^a)C(=NR^a)NR^aR^k$, —$N(R^a)S(=O)_2R^k$, —$N(R^a)S(=O)_2NR^aR^k$, —$NR^aC_{2-6}$alkyl$NR^aR^k$, —$NR^aC_{2-6}$alkyl$OR^k$, —$C(=O)R^i$, —$C(=O)OR^i$, —$C(=O)NR^aR^i$, —$C(=NR^a)NR^aR^i$, —$OR^i$, —$OC(=O)R^i$, —$OC(=O)NR^aR^i$, —$OC(=O)N(R^a)S(=O)_2R^i$, —$OC(=O)N(R^i)S(=O)_2R^k$, —$OC_{2-6}$alkyl$NR^aR^i$, —$OC_{2-6}$alkyl$OR^i$, —$SR^i$, —$S(=O)R^i$, —$S(=O)_2R^i$, —$S(=O)_2NR^aR^i$, —$S(=O)_2N(R^i)C(=O)R^k$, —$S(=O)_2N(R^a)C(=O)R^i$, —$S(=O)_2N(R^i)C(=O)OR^k$, —$S(=O)_2N(R^a)C(=O)OR^i$, —$S(=O)_2N(R^i)C(=O)NR^aR^k$, —$S(=O)_2N(R^a)C(=O)NR^aR^i$, —$NR^aR^i$, —$N(R^i)C(=O)R^k$, —$N(R^a)C(=O)R^i$, —$N(R^i)C(=O)OR^k$, —$N(R^a)C(=O)OR^i$, —$N(R^i)C(=O)NR^aR^k$, —$N(R^a)C(=O)NR^aR^i$, —$N(R^i)C(=NR^a)NR^aR^k$, —$N(R^a)C(=NR^a)NR^aR^i$, —$N(R^i)S(=O)_2R^k$, —$N(R^a)S(=O)_2R^i$, —$N(R^i)S(=O)_2NR^aR^k$, —$N(R^a)S(=O)_2NR^aR^i$, —$NR^iC_{2-6}$alkyl$NR^aR^k$, —$NR^aC_{2-6}$alkyl$NR^aR^i$, —$NR^iC_{2-6}$alkyl$OR^k$ and —$NR^aC_{2-6}$alkyl$OR^i$.

In another embodiment, in conjunction with any one of the above and below embodiments, $R^{10}$ is H.

In another embodiment, in conjunction with any one of the above and below embodiments, $R^{10}$ is independently, at each instance, selected from halo, $C_{1-8}$alkyl, $C_{1-4}$haloalkyl, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OH, —NH$_2$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or $R^{10}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, wherein the ring is substituted by 0, 1 or 2 oxo or thioxo groups, wherein the ring is substituted by 0, 1, 2 or 3 groups selected from R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —C(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or $R^{10}$ is $C_{1-4}$alkyl substituted by 0, 1, 2 or 3 groups selected from $C_{1-4}$haloalkyl, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$) S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$.

In another embodiment, in conjunction with any one of the above and below embodiments, $R^{11}$ is independently, at each instance, selected from H, cyano, nitro, —OH, —NH$_2$, —SH, $C_{1-8}$alkyl, $C_{1-4}$haloalkyl, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or $R^{11}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from R$^k$, halo, cyano, nitro —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^a$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{11}$ is C$_{1-4}$alkyl substituted by 0, 1, 2 or 3 groups selected from C$_{1-4}$haloalkyl, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^i$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{10}$ and R$^{11}$ together are a saturated, partially-saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^i$, R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^i$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{10}$ and R$^{11}$ together are a saturated or partially unsaturated 3-, 4- or 5-carbon bridge, wherein the bridge is substituted by 0, 1 or 2 substituents selected from oxo, thioxo, R$^i$, R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$.

In another embodiment, in conjunction with any one of the above and below embodiments, R$^{11}$ is independently, at each instance, selected from cyano, nitro, —OH, —NH$_2$, —SH, C$_{1-8}$alkyl, C$_{1-4}$haloalkyl, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{11}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)

$R^k$, —N($R^a$)C(=O)O$R^k$, —N($R^a$)C(=O)NR$^a$R$^k$, —N($R^a$)C(=NR$^a$)NR$^a$R$^k$, —N($R^a$)S(=O)$_2$R$^k$, —N($R^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^i$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or $R^{11}$ is C$_{1-4}$alkyl substituted by 0, 1, 2 or 3 groups selected from C$_{1-4}$haloalkyl, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^i$, —N(R$^a$)S(=O)$_2$R$^i$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or $R^{10}$ and $R^{11}$ together are a saturated, partially-saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^i$, R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$W, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$.

In another embodiment, in conjunction with any one of the above and below embodiments, $R^{11}$ is independently, at each instance, selected from cyano, nitro, —OH, —NH$_2$, —SH, C$_{1-8}$alkyl, C$_{1-4}$haloalkyl, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$.

In another embodiment, in conjunction with any one of the above and below embodiments, $R^{11}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from $R^k$, halo, cyano, nitro, —$NH_2$, —SH, —C(=O)$R^k$, —C(=O)O$R^k$, —C(=O)N$R^aR^k$, —C(=N$R^a$)N$R^aR^k$, —O$R^k$, —OC(=O)$R^k$, —OC(=O)N$R^aR^k$, —OC(=O)N($R^a$)S(=O)$_2R^k$, —O$C_{2-6}$alkylN$R^aR^k$, —O$C_{2-6}$alkylO$R^k$, —S$R^k$, —S(=O)$R^k$, —S(=O)$_2R^k$, —S(=O)$_2$N$R^aR^k$, —S(=O)$_2$N($R^a$)C(=O)$R^k$, —S(=O)$_2$N($R^a$)C(=O)O$R^k$, —S(=O)$_2$N($R^a$)C(=O)N$R^aR^k$, —N$R^aR^k$, —N($R^a$)C(=O)$R^k$, —N($R^a$)C(=O)O$R^k$, —N($R^a$)C(=O)N$R^aR^k$, —N($R^a$)C(=N$R^a$)N$R^aR^k$, —N($R^a$)S(=O)$_2R^k$, —N($R^a$)S(=O)$_2$N$R^aR^k$, —N$R^aC_{2-6}$alkylN$R^aR^k$, —N$R^aC_{2-6}$alkylO$R^k$, —C(=O)$R^i$, —C(=O)O$R^i$, —C(=O)N$R^aR^i$, —C(=N$R^a$)N$R^aR^i$, —O$R^i$, —OC(=O)$R^i$, —OC(=O)N$R^aR^i$, —OC(=O)N($R^a$)S(=O)$_2R^i$, —OC(=O)N($R^i$)S(=O)$_2R^k$, —O$C_{2-6}$alkylN$R^aR^i$, —O$C_{2-6}$alkylO$R^i$, —S$R^i$, —S(=O)$R^i$, —S(=O)$_2R^i$, —S(=O)$_2$N$R^aR^i$, —S(=O)$_2$N($R^i$)C(=O)$R^k$, —S(=O)$_2$N($R^a$)C(=O)$R^i$, —S(=O)$_2$N($R^i$)C(=O)O$R^k$, —S(=O)$_2$N($R^a$)C(=O)O$R^i$, —S(=O)$_2$N($R^i$)C(=O)N$R^aR^k$, —S(=O)$_2$N($R^a$)C(=O)N$R^aR^i$, —N$R^aR^i$, —N($R^i$)C(=O)$R^k$, —N($R^a$)C(=O)$R^i$, —N($R^i$)C(=O)O$R^k$, —N($R^a$)C(=O)O$R^i$, —N($R^i$)C(=O)N$R^aR^k$, —N($R^a$)C(=O)N$R^aR^i$, —N($R^i$)C(=N$R^a$)N$R^aR^k$, —N($R^a$)C(=N$R^a$)N$R^aR^i$, —N($R^i$)S(=O)$_2R^k$, —N($R^a$)S(=O)$_2R^i$, —N($R^i$)S(=O)$_2$N$R^aR^k$, —N($R^a$)S(=O)$_2$N$R^aR^i$, —N$R^iC_{2-6}$alkylN$R^aR^k$, —N$R^aC_{2-6}$alkylN$R^aR^i$, —N$R^iC_{2-6}$alkylO$R^k$ and —N$R^aC_{2-6}$alkylO$R^i$.

In another embodiment, in conjunction with any one of the above and below embodiments, $R^{11}$ is $C_{1-4}$alkyl substituted by 0, 1, 2 or 3 groups selected from $C_{1-4}$haloalkyl, cyano, nitro, —OH, —$NH_2$, —SH, —C(=O)$R^k$, —C(=O)O$R^k$, —C(=O)N$R^aR^k$, —C(=N$R^a$)N$R^aR^k$, —O$R^k$, —OC(=O)$R^k$, —OC(=O)N$R^aR^k$, —OC(=O)N($R^a$)S(=O)$_2R^k$, —O$C_{2-6}$alkylN$R^aR^k$, —O$C_{2-6}$alkylO$R^k$, —S$R^k$, —S(=O)$R^k$, —S(=O)$_2R^k$, —S(=O)$_2$N$R^aR^k$, —S(=O)$_2$N($R^a$)C(=O)$R^k$, —S(=O)$_2$N($R^a$)C(=O)O$R^k$, —S(=O)$_2$N($R^a$)C(=O)N$R^aR^k$, —N$R^aR^k$, —N($R^a$)C(=O)$R^k$, —N($R^a$)C(=O)O$R^k$, —N($R^a$)C(=O)N$R^aR^k$, —N($R^a$)C(=N$R^a$)N$R^aR^k$, —N($R^a$)S(=O)$_2R^k$, —N($R^a$)S(=O)$_2$N$R^aR^k$, —N$R^aC_{2-6}$alkylN$R^aR^k$, —N$R^aC_{2-6}$alkylO$R^k$, —C(=O)$R^i$, —C(=O)O$R^i$, —C(=O)N$R^aR^i$, —C(=N$R^a$)N$R^aR^i$, —O$R^i$, —OC(=O)$R^i$, —OC(=O)N$R^aR^i$, —OC(=O)N($R^a$)S(=O)$_2R^i$, —OC(=O)N($R^i$)S(=O)$_2R^k$, —O$C_{2-6}$alkylN$R^aR^i$, —O$C_{2-6}$alkylO$R^i$, —S$R^i$, —S(=O)$R^i$, —S(=O)$_2R^i$, —S(=O)$_2$N$R^aR^i$, —S(=O)$_2$N($R^i$)C(=O)$R^k$, —S(=O)$_2$N($R^a$)C(=O)$R^i$, —S(=O)$_2$N($R^i$)C(=O)O$R^k$, —S(=O)$_2$N($R^a$)C(=O)O$R^i$, —S(=O)$_2$N($R^i$)C(=O)N$R^aR^k$, —S(=O)$_2$N($R^a$)C(=O)N$R^aR^i$, —N$R^aR^i$, —N($R^i$)C(=O)$R^k$, —N($R^a$)C(=O)$R^i$, —N($R^i$)C(=O)O$R^k$, —N($R^a$)C(=O)O$R^i$, —N($R^i$)C(=O)N$R^aR^k$, —N($R^a$)C(=O)N$R^aR^i$, —N($R^i$)C(=N$R^a$)N$R^aR^k$, —N($R^a$)C(=N$R^a$)N$R^aR^i$, —N($R^i$)S(=O)$_2R^k$, —N($R^a$)S(=O)$_2R^i$, —N($R^i$)S(=O)$_2$N$R^aR^k$, —N($R^a$)S(=O)$_2$N$R^aR^i$, —N$R^iC_{2-6}$alkylN$R^aR^k$, —N$R^aC_{2-6}$alkylN$R^aR^i$, —N$R^iC_{2-6}$alkylO$R^k$ and —N$R^aC_{2-6}$alkylO$R^i$.

Embodiment N: In another embodiment, in conjunction with any one of the above and below embodiments, $R^{10}$ and $R^{11}$ together are a saturated, partially-saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, $R^i$, $R^k$, halo, cyano, nitro, —OH, —$NH_2$, —SH, —C(=O)$R^k$, —C(=O)O$R^k$, —C(=O)N$R^aR^k$, —C(=N$R^a$)N$R^aR^k$, —O$R^k$, —OC(=O)$R^k$, —OC(=O)N$R^aR^k$, —OC(=O)N($R^a$)S(=O)$_2R^k$, —O$C_{2-6}$alkylN$R^aR^k$, —O$C_{2-6}$alkylO$R^k$, —S$R^k$, —S(=O)$R^k$, —S(=O)$_2R^k$, —S(=O)$_2$N$R^aR^k$, —S(=O)$_2$N($R^a$)C(=O)$R^k$, —S(=O)$_2$N($R^a$)C(=O)O$R^k$, —S(=O)$_2$N($R^a$)C(=O)N$R^aR^k$, —N$R^aR^k$, —N($R^a$)C(=O)$R^k$, —N($R^a$)C(=O)O$R^k$, —N($R^a$)C(=O)N$R^aR^k$, —N($R^a$)C(=N$R^a$)N$R^aR^k$, —N($R^a$)S(=O)$_2R^k$, —N($R^a$)S(=O)$_2$N$R^aR^k$, —N$R^aC_{2-6}$alkylN$R^aR^k$, —N$R^aC_{2-6}$alkylO$R^k$, —C(=O)$R^i$, —C(=O)O$R^i$, —C(=O)N$R^aR^i$, —C(=N$R^a$)N$R^aR^i$, —O$R^i$, —OC(=O)$R^i$, —OC(=O)N$R^aR^i$, —OC(=O)N($R^a$)S(=O)$_2R^i$, —OC(=O)N($R^i$)S(=O)$_2R^k$, —O$C_{2-6}$alkylN$R^aR^i$, —O$C_{2-6}$alkylO$R^i$, —S$R^i$, —S(=O)$R^i$, —S(=O)$_2R^i$, —S(=O)$_2$N$R^aR^i$, —S(=O)$_2$N($R^i$)C(=O)$R^k$, —S(=O)$_2$N($R^a$)C(=O)$R^i$, —S(=O)$_2$N($R^i$)C(=O)O$R^k$, —S(=O)$_2$N($R^a$)C(=O)O$R^i$, —S(=O)$_2$N($R^i$)C(=O)N$R^aR^k$, —S(=O)$_2$N($R^a$)C(=O)N$R^aR^i$, —N$R^aR^i$, —N($R^i$)C(=O)$R^k$, —N($R^a$)C(=O)$R^i$, —N($R^i$)C(=O)O$R^k$, —N($R^a$)C(=O)O$R^i$, —N($R^i$)C(=O)N$R^aR^k$, —N($R^a$)C(=O)N$R^aR^i$, —N($R^i$)C(=N$R^a$)N$R^aR^k$, —N($R^a$)C(=N$R^a$)N$R^aR^i$, —N($R^i$)S(=O)$_2R^k$, —N($R^a$)S(=O)$_2R^i$, —N($R^i$)S(=O)$_2$N$R^aR^k$, —N($R^a$)S(=O)$_2$N$R^aR^i$, —N$R^iC_{2-6}$alkylN$R^aR^k$, —N$R^aC_{2-6}$alkylN$R^aR^i$, —N$R^iC_{2-6}$alkylO$R^k$ and —N$R^aC_{2-6}$alkylO$R^i$.

In another embodiment, in conjunction with any one of the above and below embodiments, $R^{10}$ and $R^{11}$ together are a saturated, partially-saturated or unsaturated 3-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, $R^i$, $R^k$, halo, cyano, nitro, —OH, —$NH_2$, —SH, —C(=O)$R^k$, —C(=O)O$R^k$, —C(=O)N$R^aR^k$, —C(=N$R^a$)N$R^aR^k$, —O$R^k$, —OC(=O)$R^k$, —OC(=O)N$R^aR^k$, —OC(=O)N($R^a$)S(=O)$_2R^k$, —O$C_{2-6}$alkylN$R^aR^k$, —O$C_{2-6}$alkylO$R^k$, —S$R^k$, —S(=O)$R^k$, —S(=O)$_2R^k$, —S(=O)$_2$N$R^aR^k$, —S(=O)$_2$N($R^a$)C(=O)$R^k$, —S(=O)$_2$N($R^a$)C(=O)O$R^k$, —S(=O)$_2$N($R^a$)C(=O)N$R^aR^k$, —N$R^aR^k$, —N($R^a$)C(=O)$R^k$, —N($R^a$)C(=O)O$R^k$, —N($R^a$)C(=O)N$R^aR^k$, —N($R^a$)C(=N$R^a$)N$R^aR^k$, —N($R^a$)S(=O)$_2R^k$, —N($R^a$)S(=O)$_2$N$R^aR^k$, —N$R^aC_{2-6}$alkylN$R^aR^k$, —N$R^aC_{2-6}$alkylO$R^k$, —C(=O)$R^i$, —C(=O)O$R^i$, —C(=O)N$R^aR^i$, —C(=N$R^a$)N$R^aR^i$, —O$R^i$, —OC(=O)$R^i$, —OC(=O)N$R^aR^i$, —OC(=O)N($R^a$)S(=O)$_2R^i$, —OC(=O)N($R^i$)S(=O)$_2R^k$, —O$C_{2-6}$alkylN$R^aR^i$, —O$C_{2-6}$alkylO$R^i$, —S$R^i$, —S(=O)$R^i$, —S(=O)$_2R^i$, —S(=O)$_2$N$R^aR^i$, —S(=O)$_2$N($R^i$)C(=O)$R^k$, —S(=O)$_2$N($R^a$)C(=O)$R^i$, —S(=O)$_2$N($R^i$)C(=O)O$R^k$, —S(=O)$_2$N($R^a$)C(=O)O$R^i$, —S(=O)$_2$N($R^i$)C(=O)N$R^aR^k$, —S(=O)$_2$N($R^a$)C(=O)N$R^aR^i$, —N$R^aR^i$, —N($R^i$)C(=O)$R^k$, —N($R^a$)C(=O)$R^i$, —N($R^i$)C(=O)O$R^k$, —N($R^a$)C(=O)O$R^i$, —N($R^i$)C(=O)N$R^aR^k$, —N($R^a$)C(=O)N$R^aR^i$, —N($R^i$)C(=N$R^a$)N$R^aR^k$, —N($R^a$)C(=N$R^a$)N$R^aR^i$, —N($R^i$)S(=O)$_2R^k$, —N($R^a$)S(=O)$_2R^i$, —N($R^i$)S(=O)$_2$N$R^aR^k$, —N($R^a$)S(=O)$_2$N$R^aR^i$, —N$R^iC_{2-6}$alkylN$R^aR^k$, —N$R^aC_{2-6}$alkylN$R^aR^i$, —N$R^iC_{2-6}$alkylO$R^k$ and —N$R^aC_{2-6}$alkylO$R^i$.

In another embodiment, in conjunction with any one of the above and below embodiments, $R^{10}$ and $R^{11}$ together are a saturated, partially-saturated or unsaturated 4-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, $R^i$, $R^k$, halo, cyano, nitro, —OH, —$NH_2$, —SH, —C(=O)$R^k$, —C(=O)O$R^k$, —C(=O)N$R^aR^k$, —C(=N$R^a$)N$R^aR^k$, —O$R^k$, —OC(=O)$R^k$, —OC(=O)N$R^aR^k$, —OC(=O)N($R^a$)S(=O)$_2R^k$, —O$C_{2-6}$alkylN$R^aR^k$, —O$C_{2-6}$alkylO$R^k$, —S$R^k$, —S(=O)$R^k$, —S(=O)$_2R^k$, —S(=O)$_2$N$R^aR^k$, —S(=O)$_2$N($R^a$)C(=O)$R^k$, —S(=O)$_2$N $(R^a)C(=O)OR^k$, —$S(=O)_2N(R^a)C(=O)NR^aR^k$, —$NR^aR^k$, —$N(R^a)C(=O)R^k$, —$N(R^a)C(=O)OR^k$, —$N(R^a)C(=O)NR^aR^i$, —$N(R^a)C(=NR^a)NR^aR^i$, —$N(R^a)S(=O)_2R^k$, —$N(R^a)S(=O)_2NR^aR^k$, —$NR^aC_{2-6}alkylN-R^aR^k$, —$NR^aC_{2-6}alkylOR^k$, —$C(=O)R^i$, —$C(=O)OR^i$, —$C(=O)NR^aR^i$, —$C(=NR^a)NR^aR^i$, —$OR^i$, —$OC(=O)R^i$, —$OC(=O)NR^aR^i$, —$OC(=O)N(R^a)S(=O)_2R^i$, —$OC(=O)N(R^i)S(=O)_2R^k$, —$OC_{2-6}alkylNR^aR^i$, —$OC_{2-6}alkylOR^i$, —$SR^i$, —$S(=O)R^i$, —$S(=O)_2R^i$, —$S(=O)_2NR^aR^i$, —$S(=O)_2N(R^i)C(=O)R^k$, —$S(=O)_2N(R^a)C(=O)R^i$, —$S(=O)_2N(R^i)C(=O)OR^k$, —$S(=O)_2N(R^a)C(=O)OR^i$, —$S(=O)_2N(R^i)C(=O)NR^aR^k$, —$S(=O)_2N(R^a)C(=O)NR^aR^i$, —$NR^aR^i$, —$N(R^i)C(=O)R^k$, —$N(R^a)C(=O)R^i$, —$N(R^i)C(=O)OR^k$, —$N(R^a)C(=O)OR^i$, —$N(R^i)C(=O)NR^aR^k$, —$N(R^a)C(=O)NR^aR^i$, —$N(R^i)C(=NR^a)NR^aR^k$, —$N(R^a)C(=NR^a)NR^aR^i$, —$N(R^i)S(=O)_2R^k$, —$N(R^a)S(=O)_2R^i$, —$N(R^i)S(=O)_2NR^aR^k$, —$N(R^a)S(=O)_2NR^aR^i$, —$NR^iC_{2-6}alkylNR^aR^k$, —$NR^aC_{2-6}alkylNR^aR^i$, —$NR^iC_{2-6}alkylOR^k$ and —$NR^aC_{2-6}alkylOR^i$.

In another embodiment, in conjunction with any one of the above and below embodiments, $R^{10}$ and $R^{11}$ together are a saturated, partially-saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 1 or 2 substituents selected from oxo, thioxo, $R^i$, $R^k$, halo, cyano, nitro, —OH, —$NH_2$, —SH, —$C(=O)R^k$, —$C(=O)OR^k$, —$C(=O)NR^aR^k$, —$C(=NR^a)NR^aR^k$, —$OR^k$, —$OC(=O)R^k$, —$OC(=O)NR^aR^k$, —$OC(=O)N(R^a)S(=O)_2R^k$, —$OC_{2-6}alkylNR^aR^k$, —$OC_{2-6}alkylOR^k$, —$SR^k$, —$S(=O)R^k$, —$S(=O)_2R^k$, —$S(=O)_2NR^aR^k$, —$S(=O)_2N(R^a)C(=O)R^k$, —$S(=O)_2N(R^a)C(=O)OR^k$, —$S(=O)_2N(R^a)C(=O)NR^aR^k$, —$NR^aR^k$, —$N(R^a)C(=O)R^k$, —$N(R^a)C(=O)OR^k$, —$N(R^a)C(=O)NR^aR^k$, —$N(R^a)C(=NR^a)NR^aR^k$, —$N(R^a)S(=O)_2R^k$, —$N(R^a)S(=O)_2NR^aR^k$, —$NR^aC_{2-6}alkylNR^aR^k$, —$NR^aC_{2-6}alkylOR^k$, —$C(=O)R^i$, —$C(=O)OR^i$, —$C(=O)NR^aR^i$, —$C(=NR^a)NR^aR^i$, —$OR^i$, —$OC(=O)R^i$, —$OC(=O)NR^aR^i$, —$OC(=O)N(R^a)S(=O)_2R^i$, —$OC(=O)N(R^i)S(=O)_2R^k$, —$OC_{2-6}alkylNR^aR^i$, —$OC_{2-6}alkylOR^i$, —$SR^i$, —$S(=O)R^i$, —$S(=O)_2R^i$, —$S(=O)_2NR^aR^i$, —$S(=O)_2N(R^i)C(=O)R^k$, —$S(=O)_2N(R^a)C(=O)R^i$, —$S(=O)_2N(R^i)C(=O)OR^k$, —$S(=O)_2N(R^a)C(=O)OR^i$, —$S(=O)_2N(R^i)C(=O)NR^aR^k$, —$S(=O)_2N(R^a)C(=O)NR^aR^i$, —$NR^aR^i$, —$N(R^i)C(=O)R^k$, —$N(R^a)C(=O)R^i$, —$N(R^i)C(=O)OR^k$, —$N(R^a)C(=O)OR^i$, —$N(R^i)C(=O)NR^aR^k$, —$N(R^a)C(=O)NR^aR^i$, —$N(R^i)C(=NR^a)NR^aR^k$, —$N(R^a)C(=NR^a)NR^aR^i$, —$N(R^i)S(=O)_2R^k$, —$N(R^a)S(=O)_2R^i$, —$N(R^i)S(=O)_2NR^aR^k$, —$N(R^a)S(=O)_2NR^aR^i$, —$NR^iC_{2-6}alkylNR^aR^k$, —$NR^aC_{2-6}alkylNR^aR^i$, —$NR^iC_{2-6}alkylOR^k$ and —$NR^aC_{2-6}alkylOR^i$.

Embodiment O: In another embodiment, in conjunction with any one of the above and below embodiments, $R^{10}$ and $R^{11}$ together are a saturated, partially-saturated or unsaturated 3-atom bridge containing 1, 2 or 3 atoms selected from O, N and S with the remaining atoms being carbon, so long as the combination of 0 and S atoms is not greater than 2, wherein the bridge is substituted by 1 or 2 substituents selected from oxo, thioxo, $R^i$, $R^k$, halo, cyano, nitro, —OH, —$NH_2$, —SH, —$C(=O)R^k$, —$C(=O)OR^k$, —$C(=O)NR^aR^k$, —$C(=NR^a)NR^aR^k$, —$OR^k$, —$OC(=O)R^k$, —$OC(=O)NR^aR^k$, —$OC(=O)N(R^a)S(=O)_2R^k$, —$OC_{2-6}alkylNR^aR^k$, —$OC_{2-6}alkylOR^k$, —$SR^k$, —$S(=O)R^i$, —$S(=O)_2R^k$, —$S(=O)_2NR^aR^k$, —$S(=O)_2N(R^a)C(=O)R^k$, —$S(=O)_2N(R^a)C(=O)OR^k$, —$S(=O)_2N(R^a)C(=O)NR^aR^k$, —$NR^aR^k$, —$N(R^a)C(=O)R^k$, —$N(R^a)C(=O)OR^k$, —$N(R^a)C(=O)NR^aR^k$, —$N(R^a)C(=NR^a)NR^aR^k$, —$N(R^a)S(=O)_2R^k$, —$N(R^a)S(=O)_2NR^aR^k$, —$NR^aC_{2-6}alkylN-R^aR^k$, —$NR^aC_{2-6}alkylOR^k$, —$C(=O)R^i$, —$C(=O)OR^i$, —$C(=O)NR^aR^i$, —$C(=NR^a)NR^aR^i$, —$OR^i$, —$OC(=O)R^i$, —$OC(=O)NR^aR^i$, —$OC(=O)N(R^a)S(=O)_2R^i$, —$OC(=O)N(R^i)S(=O)_2R^k$, —$OC_{2-6}alkylNR^aR^i$, —$OC_{2-6}alkylOR^i$, —$SR^i$, —$S(=O)R^i$, —$S(=O)_2R^i$, —$S(=O)_2NR^aR^i$, —$S(=O)_2N(R^i)C(=O)R^k$, —$S(=O)_2N(R^a)C(=O)R^i$, —$S(=O)_2N(R^i)C(=O)OR^k$, —$S(=O)_2N(R^a)C(=O)OR^i$, —$S(=O)_2N(R^i)C(=O)NR^aR^k$, —$S(=O)_2N(R^a)C(=O)NR^aR^i$, —$NR^aR^i$, —$N(R^i)C(=O)R^k$, —$N(R^a)C(=O)R^i$, —$N(R^i)C(=O)OR^k$, —$N(R^a)C(=O)OR^i$, —$N(R^i)C(=O)NR^aR^k$, —$N(R^a)C(=O)NR^aR^i$, —$N(R^i)C(=NR^a)NR^aR^k$, —$N(R^a)C(=NR^a)NR^aR^i$, —$N(R^i)S(=O)_2R^k$, —$N(R^a)S(=O)_2R^i$, —$N(R^i)S(=O)_2NR^aR^k$, —$N(R^a)S(=O)_2NR^aR^i$, —$NR^iC_{2-6}alkylNR^aR^k$, —$NR^aC_{2-6}alkylNR^aR^i$, —$NR^iC_{2-6}alkylOR^k$ and —$NR^aC_{2-6}alkylOR^i$.

Embodiment P: In another embodiment, in conjunction with any one of the above and below embodiments, $R^{10}$ and $R^{11}$ together are a saturated, partially-saturated or unsaturated 3-atom bridge containing 1, 2 or 3 atoms selected from O, N and S with the remaining atoms being carbon, so long as the combination of O and S atoms is not greater than 2, wherein the bridge is substituted by a substituent selected from —OH, —$NH_2$, —SH, $R^i$, $R^k$, —$C(=O)R^k$, —$C(=O)OR^k$, —$C(=O)NR^aR^k$, —$C(=NR^a)NR^aR^k$, —$OR^k$, —$OC(=O)R^k$, —$OC(=O)NR^aR^k$, —$OC(=O)N(R^a)S(=O)_2R^k$, —$OC_{2-6}alkylNR^aR^k$, —$OC_{2-6}alkylOR^k$, —$SR^k$, —$S(=O)R^k$, —$S(=O)_2R^k$, —$S(=O)_2NR^aR^k$, —$S(=O)_2N(R^a)C(=O)R^k$, —$S(=O)_2N(R^a)C(=O)OR^k$, —$S(=O)_2N(R^a)C(=O)NR^aR^k$, —$NR^aR^k$, —$N(R^a)C(=O)R^k$, —$N(R^a)C(=O)OR^k$, —$N(R^a)C(=O)NR^aR^k$, —$N(R^a)C(=NR^a)NR^aR^k$, —$N(R^a)S(=O)_2R^k$, —$N(R^a)S(=O)_2NR^aR^k$, —$NR^aC_{2-6}alkylNR^aR^k$, —$NR^aC_{2-6}alkylOR^k$, —$C(=O)R^i$, —$C(=O)OR^i$, —$C(=O)NR^aR^i$, —$C(=NR^a)NR^aR^i$, —$OR^i$, —$OC(=O)R^i$, —$OC(=O)NR^aR^i$, —$OC(=O)N(R^a)S(=O)_2R^i$, —$OC(=O)N(R^i)S(=O)_2R^k$, —$OC_{2-6}alkylNR^aR^i$, —$OC_{2-6}alkylOR^i$, —$SR^i$, —$S(=O)R^i$, —$S(=O)_2R^i$, —$S(=O)_2NR^aR^i$, —$S(=O)_2N(R^i)C(=O)R^k$, —$S(=O)_2N(R^a)C(=O)R^i$, —$S(=O)_2N(R^i)C(=O)OR^k$, —$S(=O)_2N(R^a)C(=O)OR^i$, —$S(=O)_2N(R^i)C(=O)NR^aR^k$, —$S(=O)_2N(R^a)C(=O)NR^aR^i$, —$NR^aR^i$, —$N(R^i)C(=O)R^k$, —$N(R^a)C(=O)R^i$, —$N(R^i)C(=O)OR^k$, —$N(R^a)C(=O)OR^i$, —$N(R^i)C(=O)NR^aR^k$, —$N(R^a)C(=O)NR^aR^i$, —$N(R^i)C(=NR^a)NR^aR^k$, —$N(R^a)C(=NR^a)NR^aR^i$, —$N(R^i)S(=O)_2R^k$, —$N(R^a)S(=O)_2R^i$, —$N(R^i)S(=O)_2NR^aR^k$, —$N(R^a)S(=O)_2NR^aR^i$, —$NR^iC_{2-6}alkylNR^aR^k$, —$NR^aC_{2-6}alkylNR^aR^i$, —$NR^iC_{2-6}alkylOR^k$ and —$NR^aC_{2-6}alkylOR^i$.

In another embodiment, in conjunction with any one of the above and below embodiments, $R^{10}$ and $R^{11}$ together are a saturated or partially unsaturated 3-, 4- or 5-carbon bridge, wherein the bridge is substituted by 0, 1 or 2 substituents selected from oxo, thioxo, $R^i$, $R^k$, halo, cyano, nitro, —OH, —$NH_2$, —SH, —$C(=O)R^k$, —$C(=O)OR^k$, —$C(=O)NR^aR^k$, —$C(=NR^a)NR^aR^k$, —$OR^k$, —$OC(=O)R^k$, —$OC(=O)NR^aR^k$, —$OC(=O)N(R^a)S(=O)_2R^k$, —$OC_{2-6}alkylNR^aR^k$, —$OC_{2-6}alkylOR^k$, —$SR^k$, —$S(=O)R^k$, —$S(=O)_2R^k$, —$S(=O)_2NR^aR^k$, —$S(=O)_2N(R^a)C(=O)R^k$, —$S(=O)_2N(R^a)C(=O)OR^k$, —$S(=O)_2N(R^a)C(=O)NR^aR^k$, —$NR^aR^k$, —$N(R^a)C(=O)R^k$, —$N(R^a)C(=O)OR^k$, —$N(R^a)C(=O)NR^aR^k$, —$N(R^a)C(=NR^a)NR^aR^k$, —$N(R^a)S(=O)_2R^k$, —$N(R^a)S(=O)_2NR^aR^k$, —$NR^aC_{2-6}a\ NR^aR^k$, —$NR^aC_{2-6}alkylOR^k$, —$C(=O)R^i$, —$C(=O)OR^i$, —$C(=O)NR^aR^i$, —$C(=NR^a)NR^aR^i$, —$OR^i$, —$OC(=O)R^i$, —$OC(=O)NR^aR^i$, —$OC(=O)N(R^a)S(=O)_2R^i$, —$OC(=O)N(R^i)S(=O)_2R^k$, —$OC_{2-6}alkylNR^aR^i$, —$OC_{2-6}alkylOR^i$, —$SR^i$, —$S(=O)R^i$, —$S(=O)_2R^i$, —$S(=O)_2NR^aR^i$, —S(=O)₂N(Rⁱ)C(=O)Rᵏ, —S(=O)₂N(Rᵃ)C(=O)Rⁱ, —S(=O)₂N(Rⁱ)C(=O)ORᵏ, —S(=O)₂N(Rᵃ)C(=O)ORⁱ, —S(=O)₂N(Rⁱ)C(=O)NRᵃRᵏ, —S(=O)₂N(Rᵃ)C(=O)NRᵃRⁱ, —NRᵃRᵏ, —N(Rⁱ)C(=O)Rᵏ, —N(Rᵃ)C(=O)Rⁱ, —N(Rⁱ)C(=O)ORᵏ, —N(Rᵃ)C(=O)ORⁱ, —N(Rⁱ)C(=O)NRᵃRᵏ, —N(Rᵃ)C(=O)NRᵃRⁱ, —N(Rⁱ)C(=NRᵃ)NRᵃRᵏ, —N(Rᵃ)C(=NRᵃ)NRᵃRⁱ, —N(Rⁱ)S(=O)₂Rᵏ, —N(Rᵃ)S(=O)₂Rⁱ, —N(Rⁱ)S(=O)₂NRᵃRᵏ, —N(Rᵃ)S(=O)₂NRᵃRⁱ, —NRⁱC₂₋₆alkylNRᵃRᵏ, —NRᵃC₂₋₆alkylNRᵃRⁱ, —NRⁱC₂₋₆alkylORᵏ and —NRᵃC₂₋₆alkylORⁱ.

In another embodiment, in conjunction with any one of the above and below embodiments, R¹⁰ and R¹¹ together are a saturated or partially unsaturated 3-, 4- or 5-carbon bridge, wherein the bridge is substituted by 1 or 2 substituents selected from oxo, thioxo, Rⁱ, Rᵏ, halo, cyano, nitro, —OH, —NH₂, —SH, —C(=O)Rᵏ, —C(=O)ORᵏ, —C(=O)NRᵃRᵏ, —C(=NRᵃ)NRᵃRᵏ, —ORᵏ, —OC(=O)Rᵏ, —OC(=O)NRᵃRᵏ, —OC(=O)N(Rᵃ)S(=O)₂Rᵏ, —OC₂₋₆alkylNRᵃRᵏ, —OC₂₋₆alkylORᵏ, —SRᵏ, —S(=O)Rᵏ, —S(=O)₂Rᵏ, —S(=O)₂NRᵃRᵏ, —S(=O)₂N(Rⁱ)C(=O)Rᵏ, —S(=O)₂N(Rᵃ)C(=O)Rⁱ, —S(=O)₂N(Rⁱ)C(=O)ORᵏ, —S(=O)₂N(Rᵃ)C(=O)ORⁱ, —S(=O)₂N(Rⁱ)C(=O)NRᵃRᵏ, —S(=O)₂N(Rᵃ)C(=O)NRᵃRⁱ, —NRᵃRᵏ, —N(Rᵃ)C(=O)Rᵏ, —N(Rᵃ)C(=O)ORᵏ, —N(Rᵃ)C(=O)NRᵃRᵏ, —N(Rᵃ)C(=NRᵃ)NRᵃRᵏ, —N(Rᵃ)S(=O)₂Rᵏ, —N(Rᵃ)S(=O)₂NRᵃRᵏ, —NRᵃC₂₋₆alkylNRᵃRᵏ, —NRᵃC₂₋₆alkylORᵏ, —C(=O)Rⁱ, —C(=O)ORⁱ, —C(=O)NRᵃRⁱ, —C(=NRᵃ)NRᵃRⁱ, —ORⁱ, —OC(=O)Rⁱ, —OC(=O)NRᵃRⁱ, —OC(=O)N(Rᵃ)S(=O)₂Rⁱ, —OC(=O)N(Rⁱ)S(=O)₂Rᵏ, —OC₂₋₆alkylNRᵃRⁱ, —OC₂₋₆alkylORⁱ, —SRⁱ, —S(=O)Rⁱ, —S(=O)₂Rⁱ, —S(=O)₂NRᵃRⁱ, —S(=O)₂N(Rⁱ)C(=O)Rᵏ, —S(=O)₂N(Rᵃ)C(=O)Rⁱ, —S(=O)₂N(Rⁱ)C(=O)ORᵏ, —S(=O)₂N(Rᵃ)C(=O)ORⁱ, —S(=O)₂N(Rⁱ)C(=O)NRᵃRᵏ, —S(=O)₂N(Rᵃ)C(=O)NRᵃRⁱ, —NRᵃRⁱ, —N(Rⁱ)C(=O)Rᵏ, —N(Rᵃ)C(=O)Rⁱ, —N(Rⁱ)C(=O)ORᵏ, —N(Rᵃ)C(=O)ORⁱ, —N(Rⁱ)C(=O)NRᵃRᵏ, —N(Rᵃ)C(=O)NRᵃRⁱ, —N(Rⁱ)C(=NRᵃ)NRᵃRᵏ, —N(Rᵃ)C(=NRᵃ)NRᵃRⁱ, —N(Rⁱ)S(=O)₂Rᵏ, —N(Rᵃ)S(=O)₂Rⁱ, —N(Rⁱ)S(=O)₂NRᵃRᵏ, —N(Rᵃ)S(=O)₂NRᵃRⁱ, —NRⁱC₂₋₆alkylNRᵃRᵏ, —NRᵃC₂₋₆alkylNRᵃRⁱ, —NRⁱC₂₋₆alkylORᵏ and —NRᵃC₂₋₆alkylORⁱ.

In another embodiment, in conjunction with any one of the above and below embodiments, R¹² is independently, at each instance, selected from H, C₁₋₈alkyl, C₁₋₄haloalkyl, halo, cyano, nitro, —OH, —NH₂, —SH, —C(=O)Rᵏ, —C(=O)ORᵏ, —C(=O)NRᵃRᵏ, —C(=NRᵃ)NRᵃRᵏ, —ORᵏ, —OC(=O)Rᵏ, —OC(=O)NRᵃRᵏ, —OC(=O)N(Rᵃ)S(=O)₂Rᵏ, —OC₂₋₆alkylNRᵃRᵏ, —OC₂₋₆alkylORᵏ, —SRᵏ, —S(=O)Rᵏ, —S(=O)₂Rᵏ, —S(=O)₂NRᵃRᵏ, —S(=O)₂N(Rᵃ)C(=O)Rᵏ, —S(=O)₂N(Rᵃ)C(=O)ORᵏ, —S(=O)₂N(Rᵃ)C(=O)NRᵃRᵏ, —NRᵃRᵏ, —N(Rᵃ)C(=O)Rᵏ, —N(Rᵃ)C(=O)ORᵏ, —N(Rᵃ)C(=O)NRᵃRᵏ, —N(Rᵃ)C(=NRᵃ)NRᵃRᵏ, —N(Rᵃ)S(=O)₂Rᵏ, —N(Rᵃ)S(=O)₂NRᵃRᵏ, —NRᵃC₂₋₆alkylNRᵃRᵏ, —NRᵃC₂₋₆alkylORᵏ, —C(=O)Rⁱ, —C(=O)ORⁱ, —C(=O)NRᵃRⁱ, —C(=NRᵃ)NRᵃRⁱ, —ORⁱ, —OC(=O)Rⁱ, —OC(=O)NRᵃRⁱ, —OC(=O)N(Rᵃ)S(=O)₂Rⁱ, —OC(=O)N(Rⁱ)S(=O)₂Rᵏ, —OC₂₋₆alkylNRᵃRⁱ, —OC₂₋₆alkylORⁱ, —SRⁱ, —S(=O)Rⁱ, —S(=O)₂Rⁱ, —S(=O)₂NRᵃRⁱ, —S(=O)₂N(Rⁱ)C(=O)Rᵏ, —S(=O)₂N(Rᵃ)C(=O)Rⁱ, —S(=O)₂N(Rⁱ)C(=O)ORᵏ, —S(=O)₂N(Rᵃ)C(=O)ORⁱ, —S(=O)₂N(Rⁱ)C(=O)NRᵃRᵏ, —S(=O)₂N(Rᵃ)C(=O)NRᵃRⁱ, —NRᵃRⁱ, —N(Rⁱ)C(=O)Rᵏ, —N(Rᵃ)C(=O)Rⁱ, —N(Rⁱ)C(=O)ORᵏ, —N(Rᵃ)C(=O)ORⁱ, —N(Rⁱ)C(=O)NRᵃRᵏ, —N(Rᵃ)C(=O)NRᵃRⁱ, —N(Rⁱ)C(=NRᵃ)NRᵃRᵏ, —N(Rᵃ)C(=NRᵃ)NRᵃRⁱ, —N(Rⁱ)S(=O)₂Rᵏ, —N(Rᵃ)S(=O)₂Rⁱ, —N(Rⁱ)S(=O)₂NRᵃRᵏ, —N(Rᵃ)S(=O)₂NRᵃRⁱ, —NRⁱC₂₋₆—NRᵃC₂₋₆alkylNRᵃRᵏ, —NRⁱC₂₋₆alkylORᵏ and —NRᵃC₂₋₆alkylORⁱ; or R¹² is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from Rᵏ, halo, cyano, nitro, —OH, —NH₂, —SH, —C(=O)Rᵏ, —C(=O)ORᵏ, —C(=O)NRᵃRᵏ, —C(=NRᵃ)NRᵃRᵏ, —ORᵏ, —OC(=O)Rᵏ, —OC(=O)NRᵃRᵏ, —OC(=O)N(Rᵃ)S(=O)₂Rᵏ, —OC₂₋₆alkylNRᵃRᵏ, —OC₂₋₆alkylORᵏ, —SRᵏ, —S(=O)Rᵏ, —S(=O)₂Rᵏ, —S(=O)₂NRᵃRᵏ, —S(=O)₂N(Rᵃ)C(=O)Rᵏ, —S(=O)₂N(Rᵃ)C(=O)ORᵏ, —S(=O)₂N(Rᵃ)C(=O)NRᵃRᵏ, —NRᵃRᵏ, —N(Rᵃ)C(=O)Rᵏ, —N(Rᵃ)C(=O)ORᵏ, —N(Rᵃ)C(=O)NRᵃRᵏ, —N(Rᵃ)C(=NRᵃ)NRᵃRᵏ, —N(Rᵃ)S(=O)₂Rᵏ, —N(Rᵃ)S(=O)₂NRᵃRᵏ, —NRᵃC₂₋₆alkylNRᵃRᵏ, —NRᵃC₂₋₆alkylORᵏ, —C(=O)Rⁱ, —C(=O)ORⁱ, —C(=O)NRᵃRⁱ, —C(=NRᵃ)NRᵃRⁱ, —ORⁱ, —OC(=O)Rⁱ, —OC(=O)NRᵃRⁱ, —OC(=O)N(Rᵃ)S(=O)₂Rⁱ, —OC(=O)N(Rⁱ)S(=O)₂Rᵏ, —OC₂₋₆alkylNRᵃRⁱ, —OC₂₋₆alkylORⁱ, —SRⁱ, —S(=O)Rⁱ, —S(=O)₂Rⁱ, —S(=O)₂NRᵃRⁱ, —S(=O)₂N(Rⁱ)C(=O)Rᵏ, —S(=O)₂N(Rᵃ)C(=O)Rⁱ, —S(=O)₂N(Rⁱ)C(=O)ORᵏ, —S(=O)₂N(Rᵃ)C(=O)ORⁱ, —S(=O)₂N(Rⁱ)C(=O)NRᵃRᵏ, —S(=O)₂N(Rᵃ)C(=O)NRᵃRⁱ, —NRᵃRⁱ, —N(Rⁱ)C(=O)Rᵏ, —N(Rᵃ)C(=O)Rⁱ, —N(Rⁱ)C(=O)ORᵏ, —N(Rᵃ)C(=O)ORⁱ, —N(Rⁱ)C(=O)NRᵃRᵏ, —N(Rᵃ)C(=O)NRᵃRⁱ, —N(Rⁱ)C(=NRᵃ)NRᵃRᵏ, —N(Rᵃ)C(=NRᵃ)NRᵃRⁱ, —N(Rⁱ)S(=O)₂Rᵏ, —N(Rᵃ)S(=O)₂Rⁱ, —N(Rⁱ)S(=O)₂NRᵃRᵏ, —N(Rᵃ)S(=O)₂NRᵃRⁱ, —NRⁱC₂₋₆alkylNRᵃRᵏ, —NRᵃC₂₋₆alkylNRᵃRⁱ, —NRⁱC₂₋₆alkylORᵏ and —NRᵃC₂₋₆alkylORⁱ; or R¹² is C₁₋₄alkyl substituted by 0, 1, 2 or 3 groups selected from C₁₋₄haloalkyl, cyano, nitro, —OH, —NH₂, —SH, —C(=O)Rᵏ, —C(=O)ORᵏ, —C(=O)NRᵃRᵏ, —C(=NRᵃ)NRᵃRᵏ, —ORᵏ, —OC(=O)Rᵏ, —OC(=O)NRᵃRᵏ, —OC(=O)N(Rᵃ)S(=O)₂Rᵏ, —OC₂₋₆alkylNRᵃRᵏ, —OC₂₋₆alkylORᵏ, —SRᵏ, —S(=O)Rᵏ, —S(=O)₂Rᵏ, —S(=O)₂NRᵃRᵏ, —S(=O)₂N(Rᵃ)C(=O)Rᵏ, —S(=O)₂N(Rᵃ)C(=O)ORᵏ, —S(=O)₂N(Rᵃ)C(=O)NRᵃRᵏ, —NRᵃRᵏ, —N(Rᵃ)C(=O)Rᵏ, —N(Rᵃ)C(=O)ORᵏ, —N(Rᵃ)C(=O)NRᵃRᵏ, —N(Rᵃ)C(=NRᵃ)NRᵃRᵏ, —N(Rᵃ)S(=O)₂Rᵏ, —N(Rᵃ)S(=O)₂NRᵃRᵏ, —NRᵃC₂₋₆alkylNRᵃRᵏ, —NRᵃC₂₋₆alkylORᵏ, —C(=O)Rⁱ, —C(=O)ORⁱ, —C(=O)NRᵃRⁱ, —C(=NRᵃ)NRᵃRⁱ, —ORⁱ, —OC(=O)Rⁱ, —OC(=O)NRᵃRⁱ, —OC(=O)N(Rᵃ)S(=O)₂Rⁱ, —OC(=O)N(Rⁱ)S(=O)₂Rᵏ, —OC₂₋₆alkylNRᵃRⁱ, —OC₂₋₆alkylORⁱ, —SRⁱ, —S(=O)Rⁱ, —S(=O)₂Rⁱ, —S(=O)₂NRᵃRⁱ, —S(=O)₂N(Rⁱ)C(=O)Rᵏ, —S(=O)₂N(Rᵃ)C(=O)Rⁱ, —S(=O)₂N(Rⁱ)C(=O)ORᵏ, —S(=O)₂N(Rᵃ)C(=O)ORⁱ, —S(=O)₂N(Rⁱ)C(=O)NRᵃRᵏ, —S(=O)₂N(Rᵃ)C(=O)NRᵃRⁱ, —NRᵃRⁱ, —N(Rⁱ)C(=O)Rᵏ, —N(Rᵃ)C(=O)Rⁱ, —N(Rⁱ)C(=O)ORᵏ, —N(Rᵃ)C(=O)ORⁱ, —N(Rⁱ)C(=O)NRᵃRᵏ, —N(Rᵃ)C(=O)NRᵃRⁱ, —N(Rⁱ)C(=NRᵃ)NRᵃRᵏ, —N(Rᵃ)C(=NRᵃ)NRᵃRⁱ, —N(Rⁱ)S(=O)₂Rᵏ, —N(Rᵃ)S(=O)₂Rⁱ, —N(Rⁱ)S(=O)₂NRᵃRᵏ, —N(Rᵃ)S(=O)₂NRᵃRⁱ, —NRⁱC₂₋₆alkylNRᵃRᵏ, —NRᵃC₂₋₆alkylNRᵃRⁱ, —NRⁱC₂₋₆alkylORᵏ and —NRᵃC₂₋₆alkylORⁱ, and additionally substituted by 0, 1 or 2 halo groups; or R¹¹ and R¹² together are a saturated, partially-saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, Rⁱ, Rᵏ, halo, cyano, nitro, —OH, —NH₂, —SH, —C(=O)Rᵏ, —C(=O)ORᵏ, —C(=O)NRᵃRᵏ, —C(=NRᵃ)NRᵃRᵏ, —ORᵏ, —OC(=O)Rᵏ, —OC(=O)NRᵃRᵏ, —OC(=O)N(Rᵃ)S(=O)₂Rᵏ, —OC₂₋₆alkylNRᵃRᵏ, —OC₂₋₆alkylORᵏ, —SRᵏ, —S(=O)Rᵏ, —S(=O)₂Rᵏ, —S(=O)₂NRᵃRᵏ, —S(=O)₂N(Rᵃ)C(=O)Rᵏ, —S(=O)₂N(Rᵃ)C(=O)ORᵏ, —S(=O)₂N(Rᵃ)C(=O)

NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^k$, —SR$^i$, —S(=O)R$^i$, —S(=O)$_2$R$^k$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{11}$ and R$^{12}$ together are a saturated or partially unsaturated 3-, 4- or 5-carbon bridge, wherein the bridge is substituted by 0, 1 or 2 substituents selected from oxo, thioxo, R$^i$, R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^i$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$.

Embodiment Q: In another embodiment, in conjunction with any one of the above and below embodiments, R$^{12}$ is H.

In another embodiment, in conjunction with any one of the above and below embodiments, R$^{12}$ is independently, at each instance, selected from C$_{1-8}$alkyl, C$_{1-4}$haloalkyl, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —C(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$, and additionally substituted by 0, 1 or 2 halo groups; or R$^{12}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^a$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{12}$ is C$_{1-4}$alkyl substituted by 0, 1, 2 or 3 groups selected from C$_{1-4}$haloalkyl, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^i$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$, and additionally substituted by 0, 1 or 2 halo groups; or R$^{11}$ and R$^{12}$ together are a saturated, partially-saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, $R^i$, $R^k$, halo, cyano, nitro, —OH, —NH$_2$, —SH, —C(=O)$R^k$, —C(=O)O$R^k$, —C(=O)N$R^aR^k$, —C(=N$R^a$)N$R^aR^k$, —O$R^k$, —OC(=O)$R^k$, —OC(=O)N$R^aR^k$, —OC(=O)N($R^a$)S(=O)$_2R^k$, —OC$_{2-6}$alkylN$R^aR^k$, —OC$_{2-6}$alkylO$R^k$, —S$R^k$, —S(=O)$R^k$, —S(=O)$_2R^k$, —S(=O)$_2$N$R^aR^k$, —S(=O)$_2$N($R^a$)C(=O)$R^k$, —S(=O)$_2$N($R^a$)C(=O)O$R^k$, —S(=O)$_2$N($R^a$)C(=O)N$R^aR^k$, —N$R^aR^k$, —N($R^a$)C(=O)$R^k$, —N($R^a$)C(=O)O$R^k$, —N($R^a$)C(=O)N$R^aR^k$, —N($R^a$)C(=N$R^a$)N$R^aR^k$, —N($R^a$)S(=O)$_2R^k$, —N($R^a$)S(=O)$_2$N$R^aR^k$, —N$R^aC_{2-6}$alkylN$R^aR^k$, —N$R^aC_{2-6}$alkylO$R^k$, —C(=O)$R^i$, —C(=O)O$R^i$, —C(=O)N$R^aR^i$, —C(=N$R^a$)N$R^aR^i$, —O$R^i$, —OC(=O)$R^i$, —OC(=O)N$R^aR^i$, —OC(=O)N($R^a$)S(=O)$_2R^i$, —OC(=O)N($R^i$)S(=O)$_2R^k$, —OC$_{2-6}$alkylN$R^aR^i$, —OC$_{2-6}$alkylO$R^i$, —S$R^i$, —S(=O)$R^i$, —S(=O)$_2R^i$, —S(=O)$_2$N$R^aR^i$, —S(=O)$_2$N($R^i$)C(=O)$R^k$, —S(=O)$_2$N($R^a$)C(=O)$R^i$, —S(=O)$_2$N($R^i$)C(=O)O$R^k$, —S(=O)$_2$N($R^a$)C(=O)O$R^i$, —S(=O)$_2$N($R^i$)C(=O)N$R^aR^k$, —S(=O)$_2$N($R^a$)C(=O)N$R^aR^i$, —N$R^aR^i$, —N($R^i$)C(=O)$R^k$, —N($R^a$)C(=O)$R^i$, —N($R^i$)C(=O)O$R^k$, —N($R^a$)C(=O)O$R^i$, —N($R^i$)C(=O)N$R^aR^k$, —N($R^a$)C(=O)N$R^aR^i$, —N($R^i$)C(=N$R^a$)N$R^aR^k$, —N($R^a$)C(=N$R^a$)N$R^aR^i$, —N($R^i$)S(=O)$_2R^k$, —N($R^a$)S(=O)$_2R^i$, —N($R^i$)S(=O)$_2$N$R^aR^k$, —N($R^a$)S(=O)$_2$N$R^aR^i$, —N$R^iC_{2-6}$alkylN$R^aR^k$, —N$R^aC_{2-6}$alkylN$R^aR^i$, —N$R^iC_{2-6}$alkylO$R^k$ and —N$R^aC_{2-6}$alkylO$R^i$; or $R^{11}$ and $R^{12}$ together are a saturated or partially unsaturated 3-, 4- or 5-carbon bridge, wherein the bridge is substituted by 0, 1 or 2 substituents selected from oxo, thioxo, $R^i$, $R^k$, halo, cyano, nitro, —OH, —NH$_2$, —SH, —C(=O)$R^k$, —C(=O)O$R^k$, —C(=O)N$R^aR^k$, —C(=N$R^a$)N$R^aR^k$, —O$R^k$, —OC(=O)$R^k$, —OC(=O)N$R^aR^k$, —OC(=O)N($R^a$)S(=O)$_2R^k$, —OC$_{2-6}$alkylN$R^aR^k$, —OC$_{2-6}$alkylO$R^k$, —S$R^k$, —S(=O)$R^k$, —S(=O)$_2R^k$, —S(=O)$_2$N$R^aR^k$, —S(=O)$_2$N($R^a$)C(=O)$R^k$, —S(=O)$_2$N($R^a$)C(=O)O$R^k$, —S(=O)$_2$N($R^a$)C(=O)N$R^aR^k$, —N$R^aR^k$, —N($R^a$)C(=O)$R^k$, —N($R^a$)C(=O)O$R^k$, —N($R^a$)C(=O)N$R^aR^k$, —N($R^a$)C(=N$R^a$)N$R^aR^k$, —N($R^a$)S(=O)$_2R^k$, —N($R^a$)S(=O)$_2$N$R^aR^k$, —N$R^aC_{2-6}$alkylN$R^aR^k$, —N$R^aC_{2-6}$alkylO$R^k$, —C(=O)$R^i$, —C(=O)O$R^i$, —C(=O)N$R^aR^i$, —C(=N$R^a$)N$R^aR^i$, —O$R^i$, —OC(=O)$R^i$, —OC(=O)N$R^aR^i$, —OC(=O)N($R^a$)S(=O)$_2R^i$, —OC(=O)N($R^i$)S(=O)$_2R^k$, —OC$_{2-6}$alkylN$R^aR^i$, —OC$_{2-6}$alkylO$R^i$, —S$R^i$, —S(=O)$R^i$, —S(=O)$_2R^i$, —S(=O)$_2$N$R^aR^i$, —S(=O)$_2$N($R^i$)C(=O)$R^k$, —S(=O)$_2$N($R^a$)C(=O)$R^i$, —S(=O)$_2$N($R^i$)C(=O)O$R^k$, —S(=O)$_2$N($R^a$)C(=O)O$R^i$, —S(=O)$_2$N($R^i$)C(=O)N$R^aR^k$, —S(=O)$_2$N($R^a$)C(=O)N$R^aR^i$, —N$R^aR^i$, —N($R^i$)C(=O)$R^k$, —N($R^a$)C(=O)$R^i$, —N($R^i$)C(=O)O$R^k$, —N($R^a$)C(=O)O$R^i$, —N($R^i$)C(=O)N$R^aR^k$, —N($R^a$)C(=O)N$R^aR^i$, —N($R^i$)C(=N$R^a$)N$R^aR^k$, —N($R^a$)C(=N$R^a$)N$R^aR^i$, —N($R^i$)S(=O)$_2R^k$, —N($R^a$)S(=O)$_2R^i$, —N($R^i$)S(=O)$_2$N$R^aR^k$, —N($R^a$)S(=O)$_2$N$R^aR^i$, —N$R^iC_{2-6}$alkylN$R^aR^k$, —N$R^aC_{2-6}$alkylN$R^aR^i$, —N$R^iC_{2-6}$alkylO$R^k$ and —N$R^aC_{2-6}$alkylO$R^i$.

In another embodiment, in conjunction with any one of the above and below embodiments, $R^{12}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from $R^k$, halo, cyano, nitro, —OH, —NH$_2$, —SH, —C(=O)$R^k$, —C(=O)O$R^k$, —C(=O)N$R^aR^k$, —C(=N$R^a$)N$R^aR^k$, —O$R^k$, —OC(=O)$R^k$, —OC(=O)N$R^aR^k$, —OC(=O)N($R^a$)S(=O)$_2R^k$, —OC$_{2-6}$alkylN$R^aR^k$, —OC$_{2-6}$alkylO$R^k$, —S$R^k$, —S(=O)$R^k$, —S(=O)$_2R^k$, —S(=O)$_2$N$R^aR^k$, —S(=O)$_2$N($R^a$)C(=O)$R^k$, —S(=O)$_2$N($R^a$)C(=O)O$R^k$, —S(=O)$_2$N($R^a$)C(=O)N$R^aR^k$, —N$R^aR^k$, —N($R^a$)C(=O)$R^k$, —N($R^a$)C(=O)O$R^k$, —N($R^a$)C(=O)N$R^aR^k$, —N($R^a$)C(=N$R^a$)N$R^aR^k$, —N($R^a$)S(=O)$_2R^k$, —N($R^a$)S(=O)$_2$N$R^aR^k$, —N$R^aC_{2-6}$alkylN$R^aR^k$, —N$R^aC_{2-6}$alkylO$R^k$, —C(=O)$R^i$, —C(=O)O$R^i$, —C(=O)N$R^aR^i$, —C(=N$R^a$)N$R^aR^i$, —O$R^i$, —OC(=O)$R^i$, —OC(=O)N$R^aR^i$, —OC(=O)N($R^a$)S(=O)$_2R^i$, —OC(=O)N($R^i$)S(=O)$_2R^k$, —OC$_{2-6}$alkylN$R^aR^i$, —OC$_{2-6}$alkylO$R^i$, —S$R^i$, —S(=O)$R^i$, —S(=O)$_2R^i$, —S(=O)$_2$N$R^aR^i$, —S(=O)$_2$N($R^i$)C(=O)$R^k$, —S(=O)$_2$N($R^a$)C(=O)$R^i$, —S(=O)$_2$N($R^i$)C(=O)O$R^k$, —S(=O)$_2$N($R^a$)C(=O)O$R^i$, —S(=O)$_2$N($R^i$)C(=O)N$R^aR^k$, —S(=O)$_2$N($R^a$)C(=O)N$R^aR^i$, —N$R^aR^i$, —N($R^i$)C(=O)$R^k$, —N($R^a$)C(=O)$R^i$, —N($R^i$)C(=O)O$R^k$, —N($R^a$)C(=O)O$R^i$, —N($R^i$)C(=O)N$R^aR^k$, —N($R^a$)C(=O)N$R^aR^i$, —N($R^i$)C(=N$R^a$)N$R^aR^k$, —N($R^a$)C(=N$R^a$)N$R^aR^i$, —N($R^i$)S(=O)$_2R^k$, —N($R^a$)S(=O)$_2R^i$, —N($R^i$)S(=O)$_2$N$R^aR^k$, —N($R^a$)S(=O)$_2$N$R^aR^i$, —N$R^iC_{2-6}$alkylN$R^aR^k$, —N$R^aC_{2-6}$alkylN$R^aR^i$, —N$R^iC_{2-6}$alkylO$R^k$, and —N$R^aC_{2-6}$alkylO$R^i$.

In another embodiment, in conjunction with any one of the above and below embodiments, $R^{12}$ is $C_{1-4}$alkyl substituted by 0, 1, 2 or 3 groups selected from $C_{1-4}$haloalkyl, cyano, nitro, —OH, —NH$_2$, —SH, —C(=O)$R^k$, —C(=O)O$R^k$, —C(=O)N$R^aR^k$, —C(=N$R^a$)N$R^aR^k$, —O$R^k$, —C(=O)$R^k$, —C(=O)N$R^aR^k$, —OC(=O)N($R^a$)S(=O)$_2R^k$, —OC$_{2-6}$alkylN$R^aR^k$, —OC$_{2-6}$alkylO$R^k$, —S$R^k$, —S(=O)$R^k$, —S(=O)$_2R^k$, —S(=O)$_2$N$R^aR^k$, —S(=O)$_2$N($R^a$)C(=O)$R^k$, —S(=O)$_2$N($R^a$)C(=O)O$R^k$, —S(=O)$_2$N($R^a$)C(=O)N$R^aR^k$, —N$R^aR^k$, —N($R^a$)C(=O)$R^k$, —N($R^a$)C(=O)O$R^k$, —N($R^a$)C(=O)N$R^aR^k$, —N($R^a$)C(=N$R^a$)N$R^aR^k$, —N($R^a$)S(=O)$_2R^k$, —N($R^a$)S(=O)$_2$N$R^aR^k$, —N$R^aC_{2-6}$alkylN$R^aR^k$, —N$R^aC_{2-6}$alkylO$R^k$, —C(=O)$R^i$, —C(=O)O$R^i$, —C(=O)N$R^aR^i$, —C(=N$R^a$)N$R^aR^i$, —O$R^i$, —OC(=O)$R^i$, —OC(=O)N$R^aR^i$, —OC(=O)N($R^a$)S(=O)$_2R^i$, —OC(=O)N($R^i$)S(=O)$_2R^k$, —OC$_{2-6}$alkylN$R^aR^i$, —OC$_{2-6}$alkylO$R^i$, —S$R^i$, —S(=O)$R^i$, —S(=O)$_2R^i$, —S(=O)$_2$N$R^aR^i$, —S(=O)$_2$N($R^i$)C(=O)$R^k$, —S(=O)$_2$N($R^a$)C(=O)$R^i$, —S(=O)$_2$N($R^i$)C(=O)O$R^k$, —S(=O)$_2$N($R^a$)C(=O)O$R^i$, —S(=O)$_2$N($R^i$)C(=O)N$R^aR^k$, —S(=O)$_2$N($R^a$)C(=O)N$R^aR^i$, —N$R^aR^i$, —N($R^i$)C(=O)$R^k$, —N($R^a$)C(=O)$R^i$, —N($R^i$)C(=O)O$R^k$, —N($R^a$)C(=O)O$R^i$, —N($R^i$)C(=O)N$R^aR^k$, —N($R^a$)C(=O)N$R^aR^i$, —N($R^i$)C(=N$R^a$)N$R^aR^k$, —N($R^a$)C(=N$R^a$)N$R^aR^i$, —N($R^i$)S(=O)$_2R^k$, —N($R^a$)S(=O)$_2R^i$, —N($R^i$)S(=O)$_2$N$R^aR^k$, —N($R^a$)S(=O)$_2$N$R^aR^i$, —N$R^iC_{2-6}$alkylN$R^aR^k$, —N$R^aC_{2-6}$alkylN$R^aR^i$, —N$R^iC_{2-6}$alkylO$R^k$ and —N$R^aC_{2-6}$alkylO$R^i$, and additionally substituted by 0, 1 or 2 halo groups. $R^{11}$ and $R^{12}$ together are a saturated, partially-saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, $R^i$, $R^k$, halo, cyano, nitro, —OH, —NH$_2$, —SH, —C(=O)$R^k$, —C(=O)O$R^k$, —C(=O)N$R^aR^k$, —C(=N$R^a$)N$R^aR^k$, —O$R^k$, —OC(=O)$R^k$, —OC(=O)N$R^aR^k$, —OC(=O)N($R^a$)S(=O)$_2R^k$, —OC$_{2-6}$alkylN$R^aR^k$, —OC$_{2-6}$alkylO$R^k$, —S$R^k$, —S(=O)$R^k$, —S(=O)$_2R^k$, —S(=O)$_2$N$R^aR^k$, —S(=O)$_2$N($R^a$)C(=O)$R^k$, —S(=O)$_2$N($R^a$)C(=O)O$R^k$, —S(=O)$_2$N($R^a$)C(=O)N$R^aR^k$, —N$R^aR^k$, —N($R^a$)C(=O)$R^k$, —N($R^a$)C(=O)O$R^k$, —N($R^a$)C(=O)N$R^aR^k$, —N($R^a$)C(=N$R^a$)N$R^aR^k$, —N($R^a$) S(=O)$_2R^k$, —N($R^a$)S(=O)$_2$N$R^aR^k$, —N$R^aC_{2-6}$alkylN$R^aR^k$, —N$R^aC_{2-6}$alkylO$R^k$, —C(=O)$R^i$, —C(=O)O$R^i$, —C(=O)N$R^aR^i$, —C(=N$R^a$)N$R^aR^i$, —O$R^i$, —OC(=O)

$R^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^k$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$.

Embodiment R: In another embodiment, in conjunction with any one of the above and below embodiments, $R^{11}$ and $R^{12}$ together are a saturated, partially-saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, $R^i$, $R^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$.

Embodiment S: In another embodiment, in conjunction with any one of the above and below embodiments, $R^{11}$ and $R^{12}$ together are a saturated, partially-saturated or unsaturated 3-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, $R^i$, $R^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O) NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$—OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$NR$^a$R$^i$, —NR$^i$C$_{2-6}$alkylOR$^k$ and —NR$^a$C$_{2-6}$alkylOR$^i$.

In another embodiment, in conjunction with any one of the above and below embodiments, $R^{11}$ and $R^{12}$ together are a saturated, partially-saturated or unsaturated 3-atom bridge containing 1, 2 or 3 atoms selected from O, N and S with the remaining atoms being carbon, so long as the combination of O and S atoms is not greater than 2, wherein the bridge is substituted by a group selected from oxo, thioxo, $R^i$, $R^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)

NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$.

In another embodiment, in conjunction with any one of the above and below embodiments, R$^{11}$ and R$^{12}$ together are a saturated, partially-saturated or unsaturated 4-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^i$, R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{1-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$.

Embodiment T: In another embodiment, in conjunction with any one of the above and below embodiments, R$^{11}$ and R$^{12}$ together form a —R$^{11}$-R$^{12}$— bridge selected from —O—C—C—O—, —N—C—C—C— and —N=C—C=C—, wherein the bridge is substituted by 0, 1 or 2 substituents selected from oxo, thioxo, R$^i$, R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$.

R$^{11}$ and R$^{12}$ together form a —R$^{11}$-R$^{12}$— bridge selected from —O—C—C—O—, —N—C—C—C— and —N=C—C=C—, wherein the bridge is substituted by 1 or 2 substituents selected from oxo, thioxo, R$^i$, R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$.

In another embodiment, in conjunction with any one of the above and below embodiments, or R$^{11}$ and R$^{12}$ together are a saturated or partially unsaturated 3-, 4- or 5-carbon bridge, wherein the bridge is substituted by 0, 1 or 2 substituents selected from oxo, thioxo, R$^i$, R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —C(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$.

In another embodiment, in conjunction with any one of the above and below embodiments, or R$^{11}$ and R$^{12}$ together are a saturated or partially unsaturated 3-, 4- or 5-carbon bridge, wherein the bridge is substituted by 1 or 2 substituents selected from oxo, thioxo, $R^i$, $R^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$.

In another embodiment, in conjunction with any one of the above and below embodiments, $R^{13}$ is independently, at each instance, selected from H, halo, cyano, nitro, C$_{1-4}$haloalkyl, —OH, —NH$_2$, —SH, C$_{1-8}$alkyl, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or $R^{13}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from $R^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$) C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or $R^{13}$ is C$_{1-4}$alkyl substituted by 0, 1, 2 or 3 groups selected from C$_{1-4}$haloalkyl, cyano, nitro, —OH, —NH$_2$, —SH, —C(=O)R$^k$, —OC(=O)OR$^k$, —C(=O)NR$^a$R$^k$, —C(=NR$^a$)NR$^a$R$^k$, —OR$^k$, —C(=O)R$^k$, —C(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^i$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$.

In another embodiment, in conjunction with any one of the above and below embodiments, $R^{13}$ is H.

In another embodiment, in conjunction with any one of the above and below embodiments, $R^{13}$ is independently, at each instance, selected from halo, cyano, nitro, C$_{1-4}$haloalkyl, —OH, —NH$_2$, —SH, C$_{1-8}$alkyl, —C(=O)R$^k$, —C(=O)OR$^k$, —C(=O)NR$^a$R$^k$, —C(=NR$^a$)NR$^a$R$^k$, —OR$^k$, —OC(=O)R$^k$, —C(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N($R^a$)C(=O)O$R^i$, —N($R^i$)C(=O)N$R^aR^k$, —N($R^a$)C(=O)N$R^aR^i$, —N($R^i$)C(=N$R^a$)N$R^aR^k$, —N($R^a$)C(=N$R^a$)N$R^aR^i$, —N($R^i$)S(=O)$_2R^k$, —N($R^a$)S(=O)$_2R^i$, —N($R^i$)S(=O)$_2$N$R^aR^k$, —N($R^a$)S(=O)$_2$N$R^aR^i$, —N$R^iC_{2-6}$alkylN$R^aR^k$, —N$R^aC_{2-6}$alkylN$R^aR^i$, —N$R^iC_{2-6}$alkylO$R^k$ and —N$R^aC_{2-6}$alkylO$R^i$; or $R^{13}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from $R^k$, halo, cyano, nitro, —OH, —NH$_2$, —SH, —C(=O)$R^k$, —C(=O)O$R^k$, —C(=O)N$R^aR^k$, —C(=N$R^a$)N$R^aR^k$, —O$R^k$, —OC(=O)$R^k$, —OC(=O)N$R^aR^k$, —OC(=O)N($R^a$)S(=O)$_2R^k$, —OC$_{2-6}$alkylN$R^aR^k$, —OC$_{2-6}$alkylO$R^k$, —S$R^k$, —S(=O)$R^k$, —S(=O)$_2R^k$, —S(=O)$_2$N$R^aR^k$, —S(=O)$_2$N($R^a$)C(=O)$R^k$, —S(=O)$_2$N($R^a$)C(=O)O$R^k$, —S(=O)$_2$N($R^a$)C(=O)N$R^aR^k$, —N$R^aR^k$, —N($R^a$)C(=O)$R^k$, —N($R^a$)C(=O)O$R^k$, —N($R^a$)C(=O)N$R^aR^k$, —N($R^a$)C(=N$R^a$)N$R^aR^k$, —N($R^a$)S(=O)$_2R^k$, —N($R^a$)S(=O)$_2$N$R^aR^k$, —N$R^aC_{2-6}$alkylN$R^aR^k$, —N$R^aC_{2-6}$alkylO$R^k$, —C(=O)$R^i$, —C(=O)O$R^i$, —C(=O)N$R^aR^i$, —C(=N$R^a$)N$R^aR^i$, —O$R^i$, —OC(=O)$R^i$, —OC(=O)N$R^aR^i$, —OC(=O)N($R^i$)S(=O)$_2R^k$, —OC(=O)N($R^a$)S(=O)$_2R^i$, —OC(=O)N($R^i$)S(=O)$_2R^k$, —OC$_{2-6}$alkylN$R^aR^i$, —OC$_{2-6}$alkylO$R^i$, —S$R^i$, —S(=O)$R^i$, —S(=O)$_2R^i$, —S(=O)$_2$N$R^aR^i$, —S(=O)$_2$N($R^i$)C(=O)$R^k$, —S(=O)$_2$N($R^a$)C(=O)$R^i$, —S(=O)$_2$N($R^i$)C(=O)O$R^k$, —S(=O)$_2$N($R^a$)C(=O)O$R^i$, —S(=O)$_2$N($R^i$)C(=O)N$R^aR^k$, —S(=O)$_2$N($R^a$)C(=O)N$R^aR^i$, —N$R^aR^i$, —N($R^i$)C(=O)$R^k$, —N($R^a$)C(=O)$R^i$, —N($R^i$)C(=O)O$R^k$, —N($R^a$)C(=O)O$R^i$, —N($R^i$)C(=O)N$R^aR^k$, —N($R^a$)C(=O)N$R^aR^i$, —N($R^i$)C(=N$R^a$)N$R^aR^k$, —N($R^a$)C(=N$R^a$)N$R^aR^i$, —N($R^i$)S(=O)$_2R^k$, —N($R^a$)S(=O)$_2R^i$, —N($R^i$)S(=O)$_2$N$R^aR^k$, —N($R^a$)S(=O)$_2$N$R^aR^i$, —N$R^iC_{2-6}$alkylN$R^aR^k$, —N$R^aC_{2-6}$alkylN$R^aR^i$, —N$R^iC_{2-6}$alkylO$R^k$ and —N$R^aC_{2-6}$alkylO$R^i$; or $R^{13}$ is $C_{1-4}$alkyl substituted by 0, 1, 2 or 3 groups selected from $C_{1-4}$haloalkyl, cyano, nitro, —OH, —NH$_2$, —SH, —C(=O)$R^k$, —C(=O)O$R^k$, —C(=O)N$R^aR^k$, —C(=N$R^a$)N$R^aR^k$, —O$R^k$, —OC(=O)$R^k$, —OC(=O)N$R^aR^k$, —OC(=O)N($R^a$)S(=O)$_2R^k$, —OC$_{2-6}$alkylN$R^aR^k$, —OC$_{2-6}$alkylO$R^k$, —S$R^k$, —S(=O)$R^k$, —S(=O)$_2R^k$, —S(=O)$_2$N$R^aR^k$, —S(=O)$_2$N($R^a$)C(=O)$R^k$, —S(=O)$_2$N($R^a$)C(=O)O$R^k$, —S(=O)$_2$N($R^a$)C(=O)N$R^aR^k$, —N$R^aR^k$, —N($R^a$)C(=O)$R^k$, —N($R^a$)C(=O)O$R^k$, —N($R^a$)C(=O)N$R^aR^k$, —N($R^a$)C(=N$R^a$)N$R^aR^k$, —N($R^a$)S(=O)$_2R^i$, —N($R^a$)S(=O)$_2$N$R^aR^k$, —N$R^aC_{2-6}$alkylN$R^aR^k$, —N$R^aC_{2-6}$alkylO$R^k$, —C(=O)$R^i$, —C(=O)O$R^i$, —C(=O)N$R^aR^i$, —C(=N$R^a$)N$R^aR^i$, —O$R^i$, —OC(=O)$R^i$, —OC(=O)N$R^aR^i$, —OC(=O)N($R^a$)S(=O)$_2R^i$, —OC(=O)N($R^i$)S(=O)$_2R^k$, —OC$_{2-6}$alkylN$R^aR^i$, —OC$_{2-6}$alkylO$R^i$, —S$R^i$, —S(=O)$R^i$, —S(=O)$_2R^i$, —S(=O)$_2$N$R^aR^i$, —S(=O)$_2$N($R^i$)C(=O)$R^k$, —S(=O)$_2$N($R^a$)C(=O)$R^i$, —S(=O)$_2$N($R^i$)C(=O)O$R^k$, —S(=O)$_2$N($R^a$)C(=O)O$R^i$, —S(=O)$_2$N($R^i$)C(=O)N$R^aR^k$, —S(=O)$_2$N($R^a$)C(=O)N$R^aR^i$, —N$R^aR^i$, —N($R^i$)C(=O)$R^k$, —N($R^a$)C(=O)$R^i$, —N($R^i$)C(=O)O$R^k$, —N($R^a$)C(=O)O$R^i$, —N($R^i$)C(=O)N$R^aR^k$, —N($R^a$)C(=O)N$R^aR^i$, —N($R^i$)C(=N$R^a$)N$R^aR^k$, —N($R^a$)C(=N$R^a$)N$R^aR^i$, —N($R^i$)S(=O)$_2R^k$, —N($R^a$)S(=O)$_2R^i$, —N($R^i$)S(=O)$_2$N$R^aR^k$, —N($R^a$)S(=O)$_2$N$R^aR^i$, —N$R^iC_{2-6}$alkylN$R^aR^k$, —N$R^aC_{2-6}$alkylN$R^aR^i$, —N$R^iC_{2-6}$alkylO$R^k$ and —N$R^aC_{2-6}$alkylO$R^i$.

In another embodiment, in conjunction with any one of the above and below embodiments, $R^{13}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from $R^k$, halo, cyano, nitro, —OH, —NH$_2$, —SH, —C(=O)$R^k$, —C(=O)O$R^k$, —C(=O)N$R^aR^k$, —C(=N$R^a$)N$R^aR^k$, —O$R^k$, —OC(=O)$R^k$, —OC(=O)N$R^aR^k$, —OC(=O)N($R^a$)S(=O)$_2R^k$, —OC$_{2-6}$alkylN$R^aR^k$, —OC$_{2-6}$alkylO$R^k$, —S$R^k$, —S(=O)$R^k$, —S(=O)$_2R^k$, —S(=O)$_2$N$R^aR^k$, —S(=O)$_2$N($R^a$)C(=O)$R^k$, —S(=O)$_2$N($R^a$)C(=O)O$R^k$, —S(=O)$_2$N($R^a$)C(=O)N$R^aR^k$, —N$R^aR^k$, —N($R^a$)C(=O)$R^k$, —N($R^a$)C(=O)O$R^k$, —N($R^a$)C(=O)N$R^aR^k$, —N($R^a$)C(=N$R^a$)N$R^aR^k$, —N($R^a$)S(=O)$_2R^k$, —N($R^a$)S(=O)$_2$N$R^aR^k$, —N$R^aC_{2-6}$alkylN$R^aR^k$, —N$R^aC_{2-6}$alkylO$R^k$, —C(=O)$R^i$, —C(=O)O$R^i$, —C(=O)N$R^aR^i$, —C(=N$R^a$)N$R^aR^i$, —O$R^i$, —OC(=O)$R^i$, —OC(=O)N$R^aR^i$, —OC(=O)N($R^a$)S(=O)$_2R^i$, —OC(=O)N($R^i$)S(=O)$_2R^k$, —OC$_{2-6}$alkylN$R^aR^i$, —OC$_{2-6}$alkylO$R^i$, —S$R^i$, —S(=O)$R^i$, —S(=O)$_2R^i$, —S(=O)$_2$N$R^aR^i$, —S(=O)$_2$N($R^i$)C(=O)$R^k$, —S(=O)$_2$N($R^a$)C(=O)$R^i$, —S(=O)$_2$N($R^i$)C(=O)O$R^k$, —S(=O)$_2$N($R^a$)C(=O)O$R^i$, —S(=O)$_2$N($R^i$)C(=O)N$R^aR^k$, —S(=O)$_2$N($R^a$)C(=O)N$R^aR^i$, —N$R^aR^i$, —N($R^i$)C(=O)$R^k$, —N($R^a$)C(=O)$R^i$, —N($R^i$)C(=O)O$R^k$, —N($R^a$)C(=O)O$R^i$, —N($R^i$)C(=O)N$R^aR^k$, —N($R^a$)C(=O)N$R^aR^i$, —N($R^i$)C(=N$R^a$)N$R^aR^k$, —N($R^a$)C(=N$R^a$)N$R^aR^i$, —N($R^i$)S(=O)$_2R^k$, —N($R^a$)S(=O)$_2R^i$, —N($R^i$)S(=O)$_2$N$R^aR^k$, —N($R^a$)S(=O)$_2$N$R^aR^i$, —N$R^iC_{2-6}$alkylN$R^aR^k$, —N$R^aC_{2-6}$alkylN$R^aR^i$, —N$R^iC_{2-6}$alkylO$R^k$ and —N$R^aC_{2-6}$alkylO$R^i$.

In another embodiment, in conjunction with any one of the above and below embodiments, $R^{13}$ is $C_{1-4}$alkyl substituted by 0, 1, 2 or 3 groups selected from $C_{1-4}$haloalkyl, cyano, nitro, —OH, —NH$_2$, —SH, —C(=O)$R^k$, —C(=O)O$R^k$, —C(=O)N$R^aR^k$, —C(=N$R^a$)N$R^aR^k$, —O$R^k$, —OC(=O)$R^k$, —OC(=O)N$R^aR^k$, —OC(=O)N($R^a$)S(=O)$_2R^k$, —OC$_{2-6}$alkylN$R^aR^k$, —OC$_{2-6}$alkylO$R^k$, —S$R^k$, —S(=O)$R^k$, —S(=O)$_2R^k$, —S(=O)$_2$N$R^aR^k$, —S(=O)$_2$N($R^a$)C(=O)$R^k$, —S(=O)$_2$N($R^a$)C(=O)O$R^k$, —S(=O)$_2$N($R^a$)C(=O)N$R^aR^k$, —N$R^aR^k$, —N($R^a$)C(=O)$R^k$, —N($R^a$)C(=O)O$R^k$, —N($R^a$)C(=O)N$R^aR^k$, —N($R^a$)C(=N$R^a$)N$R^aR^k$, —N($R^a$)S(=O)$_2R^i$, —N($R^a$)S(=O)$_2$N$R^aR^k$, —N$R^aC_{2-6}$alkylN$R^aR^k$, —N$R^aC_{2-6}$alkylO$R^k$, —C(=O)$R^i$, —C(=O)O$R^i$, —C(=O)N$R^aR^i$, —C(=N$R^a$)N$R^aR^i$, —O$R^i$, —OC(=O)$R^i$, —OC(=O)N$R^aR^i$, —OC(=O)N($R^a$)S(=O)$_2R^i$, —OC(=O)N($R^i$)S(=O)$_2R^k$, —OC$_{2-6}$alkylN$R^aR^i$, —OC$_{2-6}$alkylO$R^i$, —S$R^i$, —S(=O)$R^i$, —S(=O)$_2R^i$, —S(=O)$_2$N$R^aR^i$, —S(=O)$_2$N($R^i$)C(=O)$R^k$, —S(=O)$_2$N($R^a$)C(=O)$R^i$, —S(=O)$_2$N($R^i$)C(=O)O$R^k$, —S(=O)$_2$N($R^a$)C(=O)O$R^i$, —S(=O)$_2$N($R^i$)C(=O)N$R^aR^k$, —S(=O)$_2$N($R^a$)C(=O)N$R^aR^i$, —N$R^aR^i$, —N($R^i$)C(=O)$R^k$, —N($R^a$)C(=O)$R^i$, —N($R^i$)C(=O)O$R^k$, —N($R^a$)C(=O)O$R^i$, —N($R^i$)C(=O)N$R^aR^k$, —N($R^a$)C(=O)N$R^aR^i$, —N($R^i$)C(=N$R^a$)N$R^aR^k$, —N($R^a$)C(=N$R^a$)N$R^aR^i$, —N($R^i$)S(=O)$_2R^k$, —N($R^a$)S(=O)$_2R^i$, —N($R^i$)S(=O)$_2$N$R^aR^k$, —N($R^a$)S(=O)$_2$N$R^aR^i$, —N$R^iC_{2-6}$alkylN$R^aR^k$, —N$R^aC_{2-6}$alkylN$R^aR^i$, —N$R^iC_{2-6}$alkylO$R^k$ and —N$R^aC_{2-6}$alkylO$R^i$.

In another embodiment, in conjunction with any one of the above and below embodiments, $R^{14}$ is independently, at each instance, selected from H, $C_{1-8}$alkyl, $C_{1-4}$haloalkyl, halo, cyano, nitro, —OH, —NH$_2$, —SH, —C(=O)$R^k$, —C(=O)O$R^k$, —C(=O)N$R^aR^k$, —C(=N$R^a$)N$R^aR^k$, —O$R^k$, —OC(=O)$R^k$, —OC(=O)N$R^aR^k$, —OC(=O)N($R^a$)S(=O)$_2R^k$, —OC$_{2-6}$alkylN$R^aR^k$, —OC$_{2-6}$alkylO$R^k$, —S$R^k$, —S(=O)$R^k$, —S(=O)$_2R^k$, —S(=O)$_2$N$R^aR^k$, —S(=O)$_2$N($R^a$)C(=O)$R^k$, —S(=O)$_2$N($R^a$)C(=O)O$R^k$, —S(=O)$_2$N($R^a$)C(=O)N$R^aR^k$, —N$R^aR^k$, —N($R^a$)C(=O)$R^k$, —N($R^a$)C(=O)O$R^k$, —N($R^a$)C(=O)N$R^aR^k$, —N($R^a$)C(=N$R^a$)N$R^aR^k$, —N($R^a$)S(=O)$_2R^k$, —N($R^a$)S(=O)$_2$ NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{14}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, wherein the ring is substituted by 0, 1 or 2 oxo or thioxo groups, wherein the ring is substituted by 0, 1, 2 or 3 groups selected from R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^i$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{14}$ is C$_{1-4}$alkyl substituted by 0, 1, 2 or 3 groups selected from C$_{1-4}$haloalkyl, halo, cyano, nitro, —OH, —NH$_2$, —SH, —C(=O)R$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$ and —NR$^a$C$_{2-6}$alkylOR$^i$.

In another embodiment, in conjunction with any one of the above and below embodiments, R$^{14}$ is H.

In another embodiment, in conjunction with any one of the above and below embodiments, R$^{14}$ is independently, at each instance, selected from C$_{1-8}$alkyl, C$_{1-4}$haloalkyl, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^i$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^i$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{14}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, wherein the ring is substituted by 0, 1 or 2 oxo or thioxo groups, wherein the ring is substituted by 0, 1, 2 or 3 groups selected from R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{14}$ is C$_{1-4}$alkyl substituted by 0, 1, 2 or 3 groups selected from C$_{1-4}$haloalkyl, halo, cyano, nitro, —OH, —NH$_2$, —SH, —C(=O)R$^k$, —C(=O)NR$^a$R$^k$, —C(=NR$^a$)NR$^a$R$^k$, —OR$^k$, —C(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_n$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$.

In another embodiment, in conjunction with any one of the above and below embodiments, at least one of R$^{10}$, R$^{11}$, R$^{12}$, R$^{13}$ and R$^{14}$ is other than H.

In another embodiment, in conjunction with any one of the above and below embodiments, at least two of R$^{10}$, R$^{11}$, R$^{12}$, R$^{13}$ and R$^{14}$ is other than H.

As stated above, the above embodiments may be used in conjuction with other embodiments listed. The following table is a non-exclusive, non-limiting list of some of the combinations of embodiments. Although the following embodiment sets are meant to be used with any of the above embodiments, they are also considered wherein R$^5$, R$^6$, R$^{13}$ and R$^{14}$ are all H.

Where X is N and Y is CH:

| Emb. # | R$^1$ | R$^4$ | R$^7$ | R$^8$ & R$^9$ | R$^{10}$ | R$^{11}$ | R$^{12}$ |
|---|---|---|---|---|---|---|---|
| 1001 | C | E | — | — | N | N | Q |
| 1002 | C | E | — | — | O | O | Q |
| 1003 | C | E | — | — | P | P | Q |
| 1004 | C | E | — | — | M | R | R |
| 1005 | C | E | — | — | M | S | S |
| 1006 | C | E | — | — | M | T | T |
| 1007 | C | D | — | — | — | — | — |
| 1008 | C | F | — | — | — | — | — |
| 1009 | C | G | — | — | — | — | — |
| 1010 | A | E | H | J | N | N | Q |
| 1011 | A | E | H | J | O | O | Q |
| 1012 | A | E | H | J | P | P | Q |
| 1013 | A | E | H | J | M | R | R |
| 1014 | A | E | H | J | M | S | S |
| 1015 | A | E | H | J | M | T | T |
| 1016 | A | D | H | J | — | — | — |
| 1017 | A | F | H | J | — | — | — |
| 1018 | A | G | H | J | — | — | — |
| 1019 | A | E | H | K | N | N | Q |
| 1020 | A | E | H | K | O | O | Q |
| 1021 | A | E | H | K | P | P | Q |
| 1022 | A | E | H | K | M | R | R |
| 1023 | A | E | H | K | M | S | S |
| 1024 | A | E | H | K | M | T | T |
| 1025 | A | D | H | K | — | — | — |
| 1026 | A | F | H | K | — | — | — |
| 1027 | A | G | H | K | — | — | — |
| 1028 | A | E | H | L | N | N | Q |
| 1029 | A | E | H | L | O | O | Q |
| 1030 | A | E | H | L | P | P | Q |
| 1031 | A | E | H | L | M | R | R |
| 1032 | A | E | H | L | M | S | S |
| 1033 | A | E | H | L | M | T | T |
| 1034 | A | D | H | L | — | — | — |
| 1035 | A | F | H | L | — | — | — |
| 1036 | A | G | H | L | — | — | — |
| 1037 | A | E | I | J | N | N | Q |
| 1038 | A | E | I | J | O | O | Q |
| 1039 | A | E | I | J | P | P | Q |
| 1040 | A | E | I | J | M | R | R |
| 1041 | A | E | I | J | M | S | S |
| 1042 | A | E | I | J | M | T | T |
| 1043 | A | D | I | J | — | — | — |
| 1044 | A | F | I | J | — | — | — |
| 1045 | A | G | I | J | — | — | — |
| 1046 | A | E | I | K | N | N | Q |
| 1047 | A | E | I | K | O | O | Q |
| 1048 | A | E | I | K | P | P | Q |
| 1049 | A | E | I | K | M | R | R |
| 1050 | A | E | I | K | M | S | S |
| 1051 | A | E | I | K | M | T | T |
| 1052 | A | D | I | K | — | — | — |
| 1053 | A | F | I | K | — | — | — |
| 1054 | A | G | I | K | — | — | — |
| 1055 | A | E | I | L | N | N | Q |
| 1056 | A | E | I | L | O | O | Q |
| 1057 | A | E | I | L | P | P | Q |
| 1058 | A | E | I | L | M | R | R |
| 1059 | A | E | I | L | M | S | S |
| 1060 | A | E | I | L | M | T | T |
| 1061 | A | D | I | L | — | — | — |
| 1062 | A | F | I | L | — | — | — |
| 1063 | A | G | I | L | — | — | — |
| 1064 | B | E | H | J | N | N | Q |
| 1065 | B | E | H | J | O | O | Q |
| 1066 | B | E | H | J | P | P | Q |
| 1067 | B | E | H | J | M | R | R |
| 1068 | B | E | H | J | M | S | S |
| 1069 | B | E | H | J | M | T | T |
| 1070 | B | D | H | J | — | — | — |
| 1071 | B | F | H | J | — | — | — |
| 1072 | B | G | H | J | — | — | — |
| 1073 | B | E | H | K | N | N | Q |
| 1074 | B | E | H | K | O | O | Q |
| 1075 | B | E | H | K | P | P | Q |
| 1076 | B | E | H | K | M | R | R |
| 1077 | B | E | H | K | M | S | S |
| 1078 | B | E | H | K | M | T | T |
| 1079 | B | D | H | K | — | — | — |
| 1080 | B | F | H | K | — | — | — |
| 1081 | B | G | H | K | — | — | — |
| 1082 | B | E | H | L | N | N | Q |
| 1083 | B | E | H | L | O | O | Q |
| 1084 | B | E | H | L | P | P | Q |
| 1085 | B | E | H | L | M | R | R |
| 1086 | B | E | H | L | M | S | S |
| 1087 | B | E | H | L | M | T | T |
| 1088 | B | D | H | L | — | — | — |
| 1089 | B | F | H | L | — | — | — |
| 1090 | B | G | H | L | — | — | — |
| 1091 | B | E | I | J | N | N | Q |
| 1092 | B | E | I | J | O | O | Q |
| 1093 | B | E | I | J | P | P | Q |
| 1094 | B | E | I | J | M | R | R |
| 1095 | B | E | I | J | M | S | S |
| 1096 | B | E | I | J | M | T | T |
| 1097 | B | D | I | J | — | — | — |
| 1098 | B | F | I | J | — | — | — |
| 1099 | B | G | I | J | — | — | — |
| 1100 | B | E | I | K | N | N | Q |
| 1101 | B | E | I | K | O | O | Q |
| 1102 | B | E | I | K | P | P | Q |
| 1103 | B | E | I | K | M | R | R |
| 1104 | B | E | I | K | M | S | S |
| 1105 | B | E | I | K | M | T | T |

-continued

| Emb. # | R¹ | R⁴ | R⁷ | R⁸ & R⁹ | R¹⁰ | R¹¹ | R¹² |
|---|---|---|---|---|---|---|---|
| 1106 | B | D | I | K | — | — | — |
| 1107 | B | F | I | K | — | — | — |
| 1108 | B | G | I | K | — | — | — |
| 1109 | B | E | I | L | N | N | Q |
| 1110 | B | E | I | L | O | O | Q |
| 1111 | B | E | I | L | P | P | Q |
| 1112 | B | E | I | L | M | R | R |
| 1113 | B | E | I | L | M | S | S |
| 1114 | B | E | I | L | M | T | T |
| 1115 | B | D | I | L | — | — | — |
| 1116 | B | F | I | L | — | — | — |
| 1117 | B | G | I | L | — | — | — |

Where W is CH and Y is N:

| Emb. # | R¹ | R⁴ | R⁷ | R⁹ | R¹⁰ | R¹¹ | R¹² |
|---|---|---|---|---|---|---|---|
| 2001 | C | E | — | — | N | N | Q |
| 2002 | C | E | — | — | O | O | Q |
| 2003 | C | E | — | — | P | P | Q |
| 2004 | C | E | — | — | M | R | R |
| 2005 | C | E | — | — | M | S | S |
| 2006 | C | E | — | — | M | T | T |
| 2007 | C | D | — | — | — | — | — |
| 2008 | C | F | — | — | — | — | — |
| 2009 | C | G | — | — | — | — | — |
| 2010 | A | E | H | J | N | N | Q |
| 2011 | A | E | H | J | O | O | Q |
| 2012 | A | E | H | J | P | P | Q |
| 2013 | A | E | H | J | M | R | R |
| 2014 | A | E | H | J | M | S | S |
| 2015 | A | E | H | J | M | T | T |
| 2016 | A | D | H | J | — | — | — |
| 2017 | A | F | H | J | — | — | — |
| 2018 | A | G | H | J | — | — | — |
| 2019 | A | E | H | K | N | N | Q |
| 2020 | A | E | H | K | O | O | Q |
| 2021 | A | E | H | K | P | P | Q |
| 2022 | A | E | H | K | M | R | R |
| 2023 | A | E | H | K | M | S | S |
| 2024 | A | E | H | K | M | T | T |
| 2025 | A | D | H | K | — | — | — |
| 2026 | A | F | H | K | — | — | — |
| 2027 | A | G | H | K | — | — | — |
| 2028 | A | E | H | L | N | N | Q |
| 2029 | A | E | H | L | O | O | Q |
| 2030 | A | E | H | L | P | P | Q |
| 2031 | A | E | H | L | M | R | R |
| 2032 | A | E | H | L | M | S | S |
| 2033 | A | E | H | L | M | T | T |
| 2034 | A | D | H | L | — | — | — |
| 2035 | A | F | H | L | — | — | — |
| 2036 | A | G | H | L | — | — | — |
| 2037 | A | E | I | J | N | N | Q |
| 2038 | A | E | I | J | O | O | Q |
| 2039 | A | E | I | J | P | P | Q |
| 2040 | A | E | I | J | M | R | R |
| 2041 | A | E | I | J | M | S | S |
| 2042 | A | E | I | J | M | T | T |
| 2043 | A | D | I | J | — | — | — |
| 2044 | A | F | I | J | — | — | — |
| 2045 | A | G | I | J | — | — | — |
| 2046 | A | E | I | K | N | N | Q |
| 2047 | A | E | I | K | O | O | Q |
| 2048 | A | E | I | K | P | P | Q |
| 2049 | A | E | I | K | M | R | R |
| 2050 | A | E | I | K | M | S | S |
| 2051 | A | E | I | K | M | T | T |
| 2052 | A | D | I | K | — | — | — |
| 2053 | A | F | I | K | — | — | — |
| 2054 | A | G | I | K | — | — | — |
| 2055 | A | E | I | L | N | N | Q |
| 2056 | A | E | I | L | O | O | Q |
| 2057 | A | E | I | L | P | P | Q |
| 2058 | A | E | I | L | M | R | R |
| 2059 | A | E | I | L | M | S | S |
| 2060 | A | E | I | L | M | T | T |
| 2061 | A | D | I | L | — | — | — |
| 2062 | A | F | I | L | — | — | — |
| 2063 | A | G | I | L | — | — | — |
| 2064 | B | E | H | J | N | N | Q |
| 2065 | B | E | H | J | O | O | Q |
| 2066 | B | E | H | J | P | P | Q |
| 2067 | B | E | H | J | M | R | R |
| 2068 | B | E | H | J | M | S | S |
| 2069 | B | E | H | J | M | T | T |
| 2070 | B | D | H | J | — | — | — |
| 2071 | B | F | H | J | — | — | — |
| 2072 | B | G | H | J | — | — | — |
| 2073 | B | E | H | K | N | N | Q |
| 2074 | B | E | H | K | O | O | Q |
| 2075 | B | E | H | K | P | P | Q |
| 2076 | B | E | H | K | M | R | R |
| 2077 | B | E | H | K | M | S | S |
| 2078 | B | E | H | K | M | T | T |
| 2079 | B | D | H | K | — | — | — |
| 2080 | B | F | H | K | — | — | — |
| 2081 | B | G | H | K | — | — | — |
| 2082 | B | E | H | L | N | N | Q |
| 2083 | B | E | H | L | O | O | Q |
| 2084 | B | E | H | L | P | P | Q |
| 2085 | B | E | H | L | M | R | R |
| 2086 | B | E | H | L | M | S | S |
| 2087 | B | E | H | L | M | T | T |
| 2088 | B | D | H | L | — | — | — |
| 2089 | B | F | H | L | — | — | — |
| 2090 | B | G | H | L | — | — | — |
| 2091 | B | E | I | J | N | N | Q |
| 2092 | B | E | I | J | O | O | Q |
| 2093 | B | E | I | J | P | P | Q |
| 2094 | B | E | I | J | M | R | R |
| 2095 | B | E | I | J | M | S | S |
| 2096 | B | E | I | J | M | T | T |
| 2097 | B | D | I | J | — | — | — |
| 2098 | B | F | I | J | — | — | — |
| 2099 | B | G | I | J | — | — | — |
| 2100 | B | E | I | K | N | N | Q |
| 2101 | B | E | I | K | O | O | Q |
| 2102 | B | E | I | K | P | P | Q |
| 2103 | B | E | I | K | M | R | R |
| 2104 | B | E | I | K | M | S | S |
| 2105 | B | E | I | K | M | T | T |
| 2106 | B | D | I | K | — | — | — |
| 2107 | B | F | I | K | — | — | — |
| 2108 | B | G | I | K | — | — | — |
| 2109 | B | E | I | L | N | N | Q |
| 2110 | B | E | I | L | O | O | Q |
| 2111 | B | E | I | L | P | P | Q |
| 2112 | B | E | I | L | M | R | R |
| 2113 | B | E | I | L | M | S | S |
| 2114 | B | E | I | L | M | T | T |
| 2115 | B | D | I | L | — | — | — |
| 2116 | B | F | I | L | — | — | — |
| 2117 | B | G | I | L | — | — | — |

Another aspect of the invention relates to a method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to any of the above embodiments.

Another aspect of the invention relates to a pharmaceutical composition comprising a compound according to any of the above embodiments and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

Another aspect of the invention relates to a method of making a compound according to the above embodiments, comprising the step of:

reacting

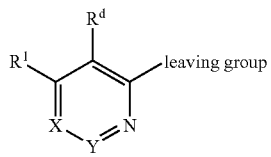

with $R^4JH$ to form

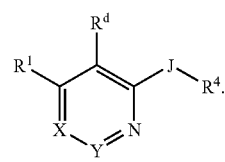

The compounds of this invention may have in general several asymmetric centers and are typically depicted in the form of racemic mixtures. This invention is intended to encompass racemic mixtures, partially racemic mixtures and separate enantiomers and diastereomers.

Unless otherwise specified, the following definitions apply to terms found in the specification and claims:

"$C_{\alpha-\beta}$alkyl" means an alkyl group comprising a minimum of $\alpha$ and a maximum of $\beta$ carbon atoms in a branched, cyclical or linear relationship or any combination of the three, wherein $\alpha$ and $\beta$ represent integers. The alkyl groups described in this section may also contain one or two double or triple bonds. Examples of $C_{1-6}$alkyl include, but are not limited to the following:

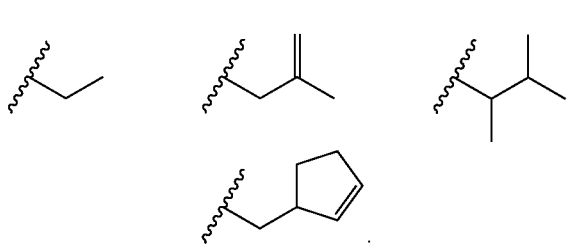

"Benzo group", alone or in combination, means the divalent radical $C_4H_4$=, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

"Halo" or "halogen" means a halogen atoms selected from F, Cl, Br and I.

"$C_{V-W}$haloalkyl" means an alkyl group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Examples of heterocycles that may be found in the claims include, but are not limited to, the following:

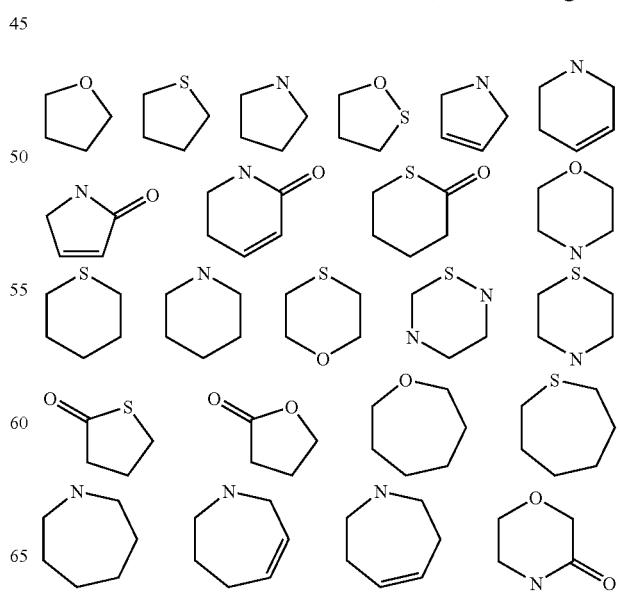

-continued

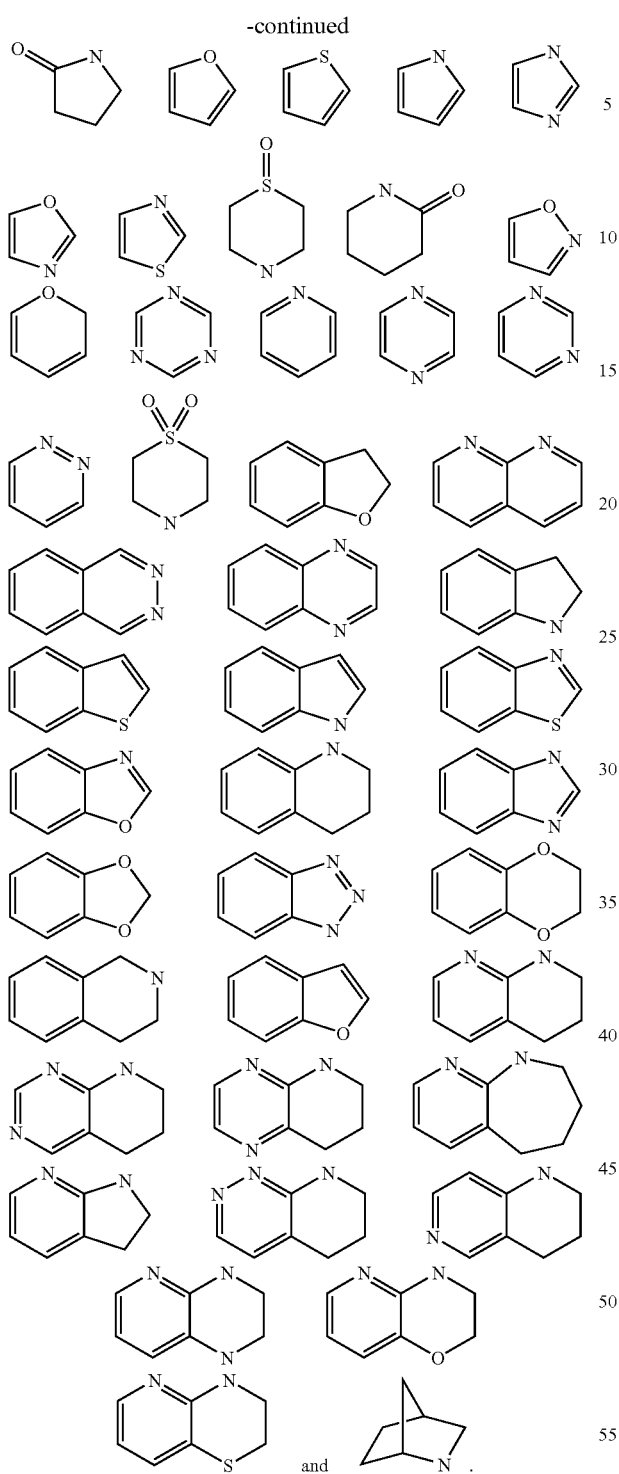

"Available nitrogen atoms" are those nitrogen atoms that are part of a heterocycle and are joined by two single bonds (e.g. piperidine), leaving an external bond available for substitution by, for example, H or CH$_3$.

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, alkyl, substituted alkyl, acyl, alkoxycarbonyl, aralkoxycarbonyl, silyl and the like. Examples of aralkyl include, but are not limited to, benzyl, orthomethylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

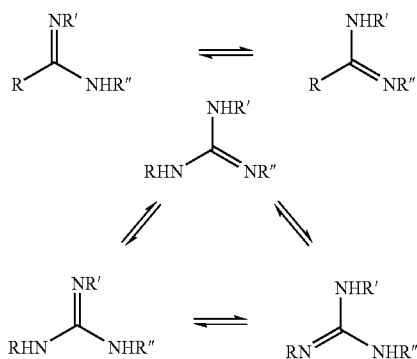

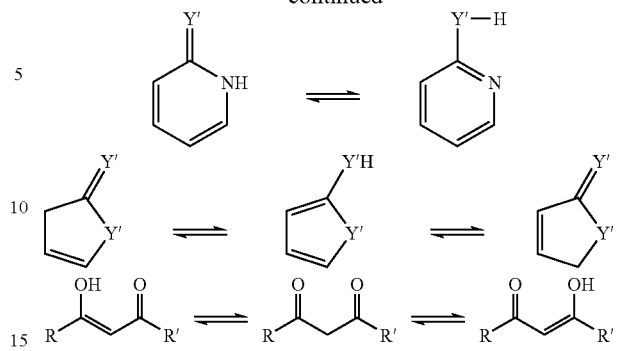

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives, which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Experimental

Unless otherwise noted, all materials were obtained from commercial suppliers and used without further purification. All parts are by weight and temperatures are in degrees centigrade unless otherwise indicated. All microwave-assisted reactions were conducted with a Smith Synthesizer from Personal Chemistry, Uppsala, Sweden. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography (HPLC). Unless otherwise stated, reactions were run at room temperature.

The following abbreviations are used:
DMSO—dimethyl sulfoxide
DMF—N,N-dimethylformamide
THF—tetrahydrofuran
Et$_2$O—diethyl ether
EtOAc—ethyl acetate
MeOH—methyl alcohol
EtOH—ethyl alcohol
MeCN—acetonitrile
MeI—iodomethane
NMP—1-methyl-2-pyrrolidinone
DCM—dichloromethane
DCE—1,2-dichloroethane
TFA—trifuoroacetic acid
MP-carbonate—macroporous polystyrene anion-exchange resin that is a resin bound equivalent of tetraalkylammonium carbonate.
sat.—saturated
h—hour
min—minutes

EXAMPLE 1

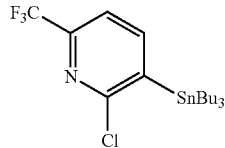

(a) 2-Chloro-3-tributylstannyl-6-trifluoromethyl-pyridine. To a solution of diisopropylamine (5.5 mL, 39 mmol, Aldrich,) in THF (30 mL) was added n-BuLi (15.6 mL, 2.5 M in hexanes, 39 mmol, Aldrich) with stirring at −78° C. The mixture was stirred at −78° C. for 30 min and at room temperature for 15 min. The reaction mixture was cooled again to −78° C. and a solution of 2-chloro-6-trifluoromethylpyridine (5.0 g, 27.5 mmol, Lancaster) in THF (20 mL) was added. The mixture was stirred at −78° C. for 1 h, tributyltin chloride (9 mL, 33 mmol, Aldrich) was added via a syringe, and stirring was continued for 2 h. The reaction mixture was allowed to reach 0° C., quenched with a sat. aqueous solution of NH$_4$Cl, and extracted with Et$_2$O (3×). The combined organic extracts were dried over MgSO$_4$, filtered, and concentrated under reduced pressure. Purification of the residue by flash silica gel chromatography (gradient: 0-1% EtOAc/hexane) afforded the title compound as colorless oil. MS (ESI, pos. ion.) m/z: 471 (M+1).

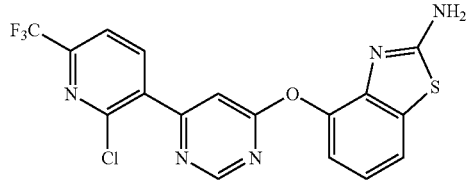

(b) 4-(6-(2-Chloro-6-(trifluoromethylpyridin-3-yl)pyrimidin-4-yloxy)benzo[d]thiazol-2-amine. To a mixture of 4-(6-iodo-pyrimidin-4-yloxy)-benzothiazol-2-ylamine (3.5 g, 9.46 mmol, prepared as described in WO04014871), Pd(PPh$_3$)$_4$ (1.09 g, 0.95 mmol, Strem) and copper iodide (0.36 g, 1.90 mmol, Aldrich) was added a solution of 2-chloro-3-tributylstannyl-6-trifluoromethyl-pyridine from step (a) above (6.0 g, 12.77 mmol) in DMF (40 mL) under an argon atmosphere. The mixture was heated at 90° C. with stirring for 16 h, cooled to room temperature, quenched with a sat. aqueous solution of NH$_4$Cl, and extracted with EtOAc (3×). The combined organic extracts were washed with sat. NaHCO$_3$, H$_2$O and brine, dried over Na$_2$SO$_4$, filtered, and concentrated under reduced pressure. Purification of the residue by silica gel column chromatography (gradient: 50-100% EtOAc/hexane) afforded the title compound as an off-white solid. MS (ESI, pos. ion.) m/z: 424 (M+1).

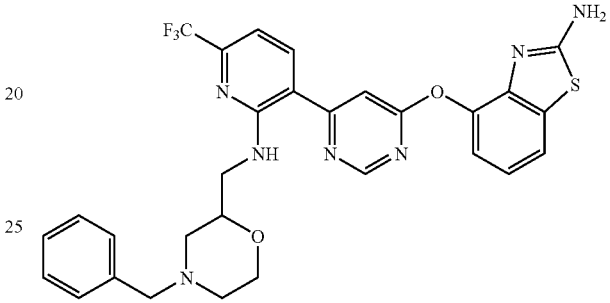

(c) 4-(6-(2((4-Benzylmorpholin-2-yl)methylamino)-6-(trifluoromethyl)-pyridin-3-yl)pyrimidin-4-yloxy)benzo[d]thiazol-2-amine. A mixture of 4-(6-(2-chloro-6-(trifluoromethyl)pyridin-3-yl)pyrimidin-4-yloxy)benzo[d]thiazol-2-amine from step (b) above (400 mg, 0.95 mmol) and 4-benzyl-1,4-oxazinan-2-yl)-methyl amine (800 mg, 3.88 mmol, Maybridge) in CH$_3$CN (0.5 mL) was heated in a microwave synthesizer at 120° C. for 15 min. The reaction mixture was evaporated in vacuo and the residue was purified by silica gel column chromatography [5% (2N NH$_3$ in MeOH)/DCM] to give the title compound as a yellow solid. MS (ESI, pos. ion.) m/z: 594 (M+1).

EXAMPLE 2

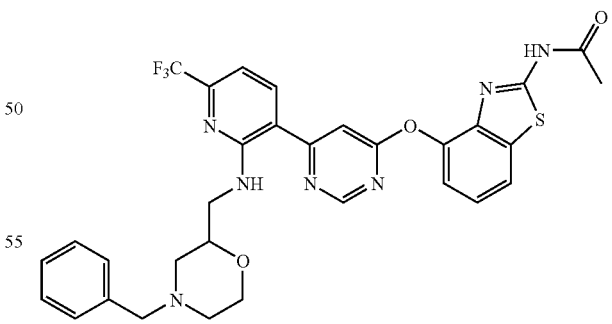

N-(4-(6-(2((4-Benzylmorpholin-2-yl)methylamino)-6-(trifluoromethyl)-pyridin-3-yl)pyrimidin-4-yloxy)benzo[d]thiazol-2-yl)acetamide. To a solution of 4-(6-(2((4-benzylmorpholin-2-yl)methylamino)-6-(trifluoromethyl)pyridin-3-yl)pyrimidin-4-yloxy)benzo[d]thiazol-2-amine, Example 1(c), (110 mg, 0.18 mmol) and DMAP (10 mg, 0.08 mmol, Aldrich) in DCM (8 mL) was added acetic anhydride (90 μL, 0.9 mmol, Aldrich). The mixture was stirred at room temperature for 18 h and evaporated under reduced pressure. The residue was dissolved in EtOAc and the solution was washed with a sat. aqueous solution of NaHCO₃, H₂O and brine, dried over Na₂SO₄, and filtered. The filtrate was evaporated in vacuo and the residue was purified by silica gel column chromatography [2% (2N NH₃ in MeOH)/DCM] to give the title compound as a light-yellow solid. MS (ESI, pos. ion.) m/z: 636 (M+1).

EXAMPLE 3

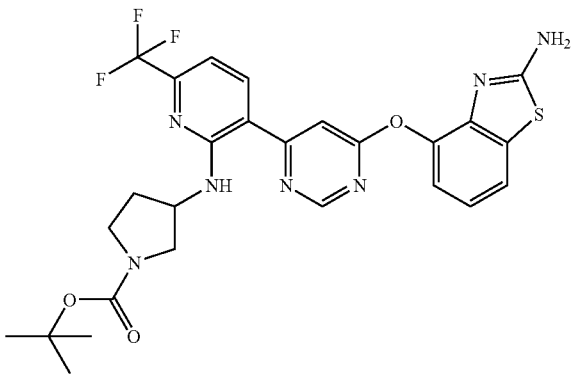

(a) tert-Butyl 3-(3-(6-(2-aminobenzo[d]thiazol-4-yloxy) pyrimidin-4-yl)-6-(trifluoromethyl)pyridin-2-ylamino)pyrrolidine-1-carboxylate. A mixture of 4-(6-(2-chloro-6-(trifluoromethyl)pyridin-3-yl)pyrimidin-4-yloxy)-benzo[d]thiazol-2-amine, Example 1(b), (250 mg, 0.58 mmol), tert-butyl 3-aminopyrrolidine-1-carboxylate (400 mg, 2.15 mmol, Astatech) and CsF (20 mg, 0.13 mmol, Aldrich) in CH₃CN (0.2 mL) was heated in a microwave synthesizer at 120° C. for 20 min. The reaction mixture was evaporated in vacuo and the residue was purified by silica gel column chromatography (gradient: 20-30% EtOAc/hexane) to give the title compound as a yellow solid. MS (ESI, pos. ion.) m/z: 574 (M+1).

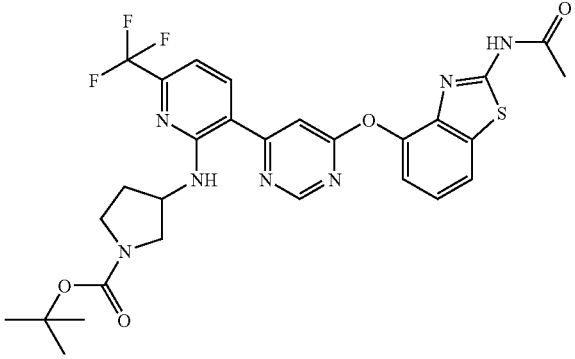

(b) tert-Butyl 3-(3-(6-(2-acetamidobenzo[d]thiazol-4-yloxy)pyrimidin-4-yl)-6-(trifluoromethyl)pyridin-2-ylamino)pyrrolidine-1-carboxylate. tert-Butyl 3-(3-(6-(2-aminobenzo[d]thiazol-4-yloxy)pyrimidin-4-yl)-6-(trifluoromethyl)-pyridin-2-ylamino)pyrrolidine-1-carboxylate from step (a) above (200 mg, 0.35 mmol) was reacted with acetic anhydride (100 μL, 1.06 mmol, Aldrich) under the conditions of Example 2 to give the title compound as a light-yellow solid. MS (ESI, pos. ion.) m/z: 616 (M+1).

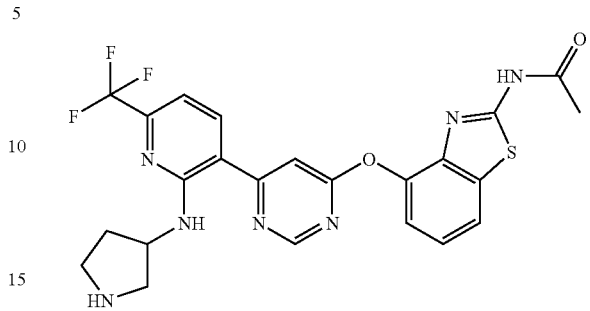

(c) N-(4-(6-(2-(Pyrrolidin-3-ylamino)-6-(trifluoromethyl) pyridin-3-yl)-pyrimidin-4-yloxy)benzo[d]thiazol-2-yl)acetamide. A mixture of tert-butyl 3-(3-(6-(2-acetamidobenzo [d]thiazol-4-yloxy)pyrimidin-4-yl)-6-(trifluoromethyl)-pyridin-2-ylamino)pyrrolidine-1-carboxylate from step (b) above (120 mg, 0.19 mmol) and 1:1 mixture of DCM/TFA (5 mL) was stirred at room temperature for 30 min. The reaction mixture was evaporated in vacuo and the residue was dissolved in EtOAc. The solution was washed with a sat. aqueous solution of NaHCO₃, water and brine, dried over Na₂SO₄, and filtered. The filtrate was evaporated in vacuo to provide the title compound as a yellow solid. MS (ESI, pos. ion.) m/z: 516 (M+1).

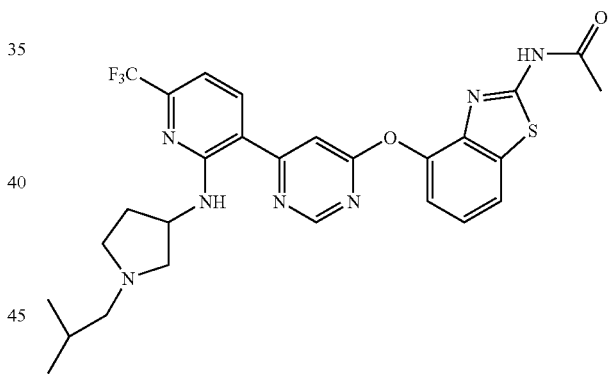

(d) N-(4-(6-(2-(1-Isobutylpyrrolidin-3-ylamino)-6-(trifluoromethyl)pyridin-3-yl)pyrimidin-4-yloxy)benzo[d]thiazol-2-yl)acetamide. To a solution of N-(4-(6-(2-(pyrrolidin-3-ylamino)-6-(trifluoromethyl)pyridin-3-yl)pyrimidin-4-yloxy)-benzo[d]thiazol-2-yl)acetamide from step (c) above (30 mg, 0.06 mmol) in DCE (5 mL) was added isobutyraldehyde (20 mg, 0.20 mmol, Aldrich). The mixture was stirred at room temperature for 10 min, sodium triacetoxy borohydride (25 mg, 0.12 mmol, Aldrich) was added, and the stirring was continued for 1 h. The reaction mixture was evaporated in vacuo and the residue was dissolved in EtOAc. The solution was washed with sat. aqueous solution of NaHCO₃, H₂O and brine, dried over Na₂SO₄, filtered, and evaporated under reduced pressure. Purification of the residue by silica gel column chromatography [gradient: 0-2% (2N NH₃ in MeOH)/DCM] afforded the title compound as a yellow solid. MS (ESI, pos. ion.) m/z: 572 (M+1). Mp: 138-139° C.

EXAMPLE 4

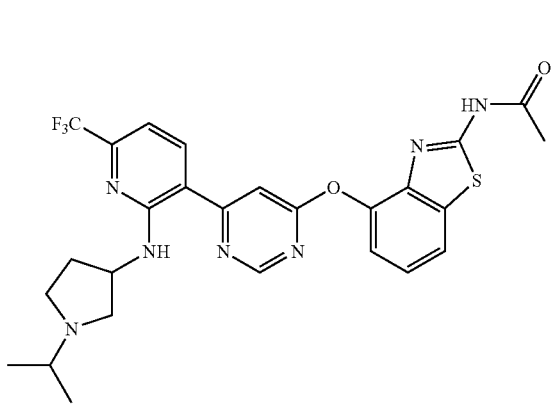

N-(4-(6-(2-(1-Isopropylpyrrolidin-3-ylamino)-6-(trifluoromethyl)pyridin-3-yl)pyrimidin-4-yloxy)benzo[d]thiazol-2-yl)acetamide. N-(4-(6-(2-(Pyrrolidin-3-ylamino)-6-(trifluoromethyl)pyridin-3-yl)pyrimidin-4-yloxy)benzo[d]thiazol-2-yl)acetamide, Example 3(c), (30 mg, 0.06 mmol) was reacted with acetone (1 mL, 136 mmol, Aldrich) under the conditions of Example 3(d) to give the title compound as a yellow solid. MS (ESI, pos. ion.) m/z: 558 (M+1). Mp: 140-141° C.

EXAMPLE 5

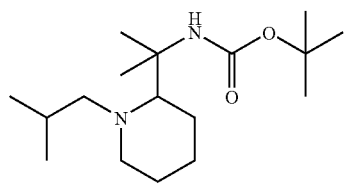

(a) tert-Butyl 2-(1-isobutylpiperidin-2-yl)propan-2-ylcarbamate. tert-Butyl 2-(piperidin-2-yl)propan-2-yl carbamate (2.0 g, 8.3 mmol, CarboGen) was reacted with isobutyraldehyde (1.2 g, 16.5 mmol, Aldrich) under the conditions of Example 3(d) to give the title compound as a yellow oil. MS (ESI, pos. ion.) m/z: 299 (M+1).

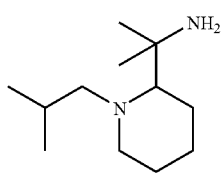

(b) 2-(1-Isobutylpiperidin-2-yl)propan-2-amine. tert-Butyl 2-(1-isobutylpiperidin-2-yl)propan-2-ylcarbamate, (2.2 g, 7.3 mmol) was reacted with 1:1 mixture of DCM/TFA (40 mL) under the conditions of Example 3(c) to give the title compound as TFA salt. The salt was diluted with DCM (20 mL) and MP-carbonate resin (4 g, 10.9 mmol, 2.7 mmol/g, Argonaut) was added. The mixture was stirred at room temperature for 16 h and filtered. The filtrate was evaporated and the residue was dried under vacuo to yield the title compound as a yellow oil. MS (ESI, pos. ion.) m/z: 199 (M+1).

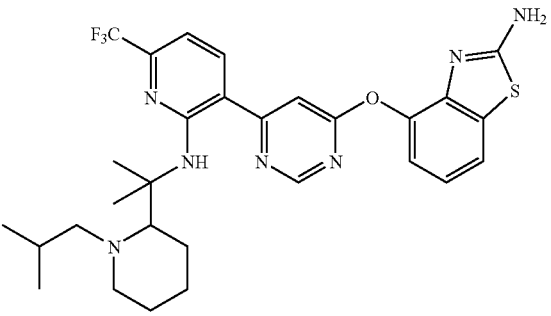

(c) 4-(6-(2-(2-(1-Isobutylpiperidin-2-yl)propan-2-ylamino)-6-(trifluoromethyl)pyridin-3-yl)pyrimidin-4-yloxy)benzo[d]thiazol-2-amine. A mixture of 4-(6-(2-chloro-6-(trifluoromethyl)pyridin-3-yl)pyrimidin-4-yloxy) benzo[d]thiazol-2-amine, Example 1(b), (200 mg, 0.47 mmol) and 2-(1-isobutylpiperidin-2-yl)-propan-2-amine from step (b) above (200 mg, 1.0 mmol) in DMSO (1 mL) was heated in a microwave synthesizer at 160° C. for 15 min. The reaction mixture was partitioned between EtOAc and H₂O. The organic phase was separated, washed with H₂O and brine, dried over Na₂SO₄, and filtered. The filtrate was evaporated under reduced pressure and the residue was purified by silica gel column chromatography [5% (2N NH₃ in MeOH)/DCM] to give the title compound as a yellow solid. MS (ESI, pos. ion.) m/z: 586 (M+1). Mp: 166-170° C.

EXAMPLE 6

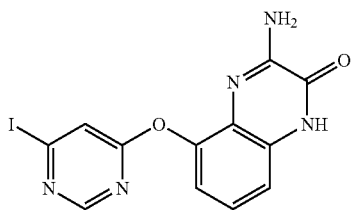

(a) 3-Amino-5-(6-iodopyrimidin-4-yloxy)quinoxalin-2(1H)-one. A mixture of 3-amino-5-hydroxyquinoxalin-2(1H)-one hydrobromide (3.8 g, 15 mmol, prepared as described in WO04014871), 4,6-diiodopyrimidine (4.9 g, 15 mmol, prepared as described in WO04014871) and Cs₂CO₃ (9.6 g, 29 mmol, Aldrich) in DMF (30 mL) was heated at 70° C. with stirring for 4 h. The reaction mixture was allowed to reach room temperature, diluted with EtOAc (100 mL) and water (100 mL), and filtered. The filter cake was washed with water and dried under vacuo to give the title compound as an off-white solid. MS (ESI, pos. ion.) m/z: 382 (M+1).

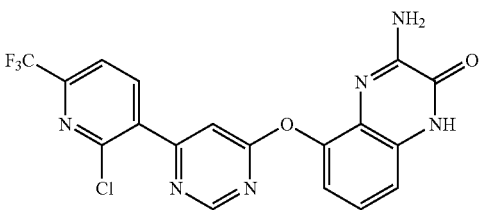

(b) 3-Amino-5-(6-(2-chloro-6-(trifluoromethyl)pyridin-3-yl)pyrimidin-4-yloxy)quinoxalin-2(1H)-one. 3-Amino-5-(6-iodopyrimidin-4-yloxy)quinoxalin-2(1H)-one from step (a) above (3.68 g, 9.66 mmol) was reacted with 2-chloro-3-(tributylstannyl)-6-(trifluoromethyl)pyridine, Example 1(a), (5.45 g, 11.6 mmol) under the conditions of Example 1(b) to give the title compound as a brown solid. MS (ESI, pos. ion.) m/z: 435 (M+1).

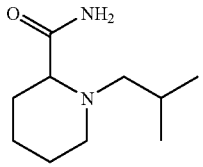

(c) 1-Isobutylpiperidine-2-carboxamide. Piperidine-2-carboxamide (4.52 g, 35 mmol, Bionet-Inter) was reacted with isobutyraldehyde (9.6 mL, 106 mmol, Aldrich) under the conditions of Example 3(d) to give the title compound as yellow oil. (ESI, pos. ion.) m/z: 185 (M+1).

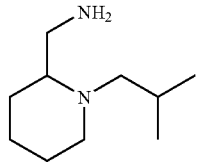

(d) (1-Isobutylpiperidin-2-yl)methanamine. To a solution of 1-isobutylpiperidine-2-carboxamide from step (a) above (5 g, 27.2 mmol) in THF (70 mL) was added LiAlH$_4$ (1 M in THF, 53 mL, 0.053 mmol, Aldrich) dropwise with stirring at 0° C. After the addition was complete, the reaction mixture was allowed to warm to room temperature and the stirring was continued for 20 h. The reaction mixture was quenched with MeOH (3 mL) and 20% aqueous KOH (30 ml), and filtered through Celite®. The filtrate was extracted with Et$_2$O (2×250 mL) and the combined organic extracts were concentrated under reduced pressure. The residue was purified by silica gel column chromatography [5% (2N NH$_3$ in MeOH)-/DCM] to give the title compound as pale-yellow oil. MS (ESI, pos. ion.) m/z: 171 (M+1).

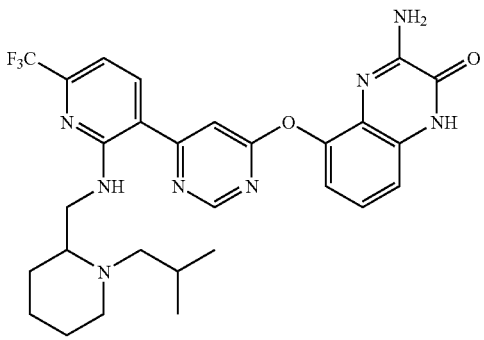

(e) 3-Amino-5-(6-(2-((1-isobutylpiperidin-2-ylmethylamino)-6-(trifluoromethyl)pyridin-3-yl)pyrimidin-4-yloxy)quinoxalin-2(1H)-one. A mixture of 3-amino-5-(6-(2-chloro-6-(trifluoromethyl)pyridin-3-yl)pyrimidin-4-yloxy)-quinoxalin-2(1H)-one from step (b) above (300 mg, 0.70 mmol) and 1-(1-isobutylpiperidin-2-yl)ethanamine from step (d) above (200 mg, 1.2 mmol) in DMSO (2.5 mL) was heated in a microwave synthesizer at 120° C. for 25 min. The reaction mixture was partitioned between EtOAc and H$_2$O. The organic phase was separated, washed with H$_2$O and brine, dried over Na$_2$SO$_4$, filtered and evaporated under reduced pressure. Purification of the residue by silica gel column chromatography [gradient: 0-5% (2N NH$_3$ in MeOH)/DCM] afforded the title compound as a yellow solid. MS (ESI, pos. ion.) m/z: 569 (M+1). Mp: 228-229° C.

EXAMPLE 7

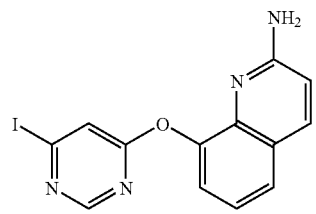

(a) 8-(6-Iodopyrimidin-4-yloxy)quinolin-2-amine. To a solution of 2-amino-quinolin-8-ol (5 g, 31.25 mmol, Fluka) and 4,6-diiodopyrimidine (3.9 g, 12 mmol, prepared as described in WO04014871) in DMF (40 mL) was added NaH (60%, 1.5 g, 37.5 mmol, Aldrich) in small portions with stirring at room temperature. The reaction mixture was stirred at room temperature for 16 h and quenched with sat. aqueous solution of NaHCO$_3$. The mixture was extracted with EtOAc (3×) and the combined organic extracts were washed with brine, dried over Na$_2$SO$_4$ and filtered. The filtrate was evaporated under reduced pressure and the residue was purified by flash silica gel column chromatography (gradient: 0-65% EtOAc/hexane) to give the title compound as a brown solid. MS (ESI, pos. ion.) m/z: 365 (M+1).

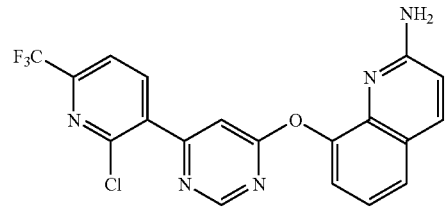

(b) 8-(6-(2-Chloro-6-(trifluoromethyl)pyridin-3-yl)pyrimidin-4-yloxy)-quinolin-2-amine. 8-(6-Iodopyrimidin-4-yloxy)quinolin-2-amine from step (a) above (1 g, 2.7 mmol) was reacted with 2-chloro-3-(tributylstannyl)-6-(trifluoromethyl)pyridine, Example 1(a), (1.6 g, 3.4 mmol) under the condition of Example 1(b) to give the title compound as a yellow solid. MS (ESI, pos. ion.) m/z: 418 (M+1).

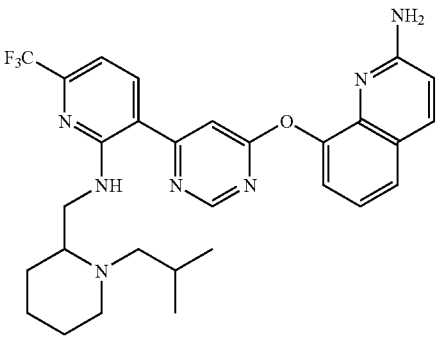

(c) 8-(6-(2-((1-Isobutylpiperidin-2-yl)methylamino)-6-(trifluoromethyl)-pyridin-3-yl)pyrimidin-4-yloxy)quinolin-2-amine. 8-(6-(2-Chloro-6-(trifluoromethyl)pyridin-3-yl)pyrimidin-4-yloxy)quinolin-2-amine from step (b) above (120 mg, 0.28 mmol) was reacted with 1-(1-isobutylpiperidin-2-yl)methanamine, Example 6(d), (150 mg, 0.88 mmol) under the conditions of Example 6(e) to give the title compound as a yellow solid. MS (ESI, pos. ion.) m/z: 552 (M+1).

EXAMPLE 8

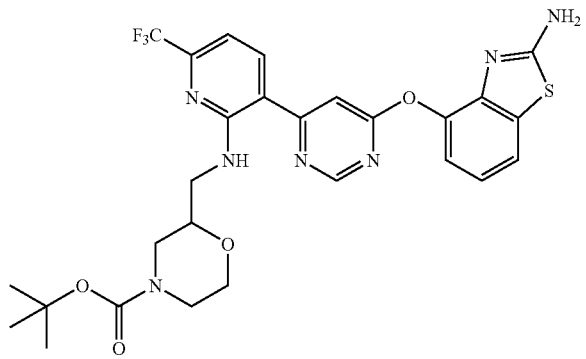

(a) tert-Butyl 2-((3-(6-(2-aminobenzo[d]thiazol-4-yloxy)pyrimidin-4-yl)-6-(trifluoromethyl)pyridin-2-ylamino)methyl)morpholine-4-carboxylate. 4-(6-(2-Chloro-6-(trifluoromethyl)pyridin-3-yl)pyrimidin-4-yloxy)benzo[d]thiazol-2-amine, Example 1(b), (380 mg, 0.90 mmol) was reacted with tert-butyl 2-(aminomethyl)morpholine-4-carboxylate (390 mg, 1.8 mmol, PharmaCore) under the conditions of Example 6(e) to give the title compound as an off-white solid. MS (ESI, pos. ion.) m/z: 604 (M+1).

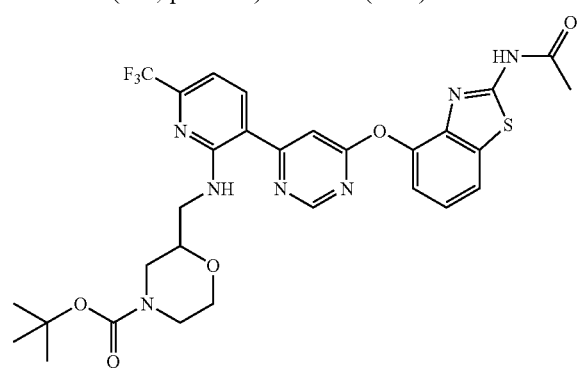

(b) tert-Butyl 2-((3-(6-(2-acetamidobenzo[d]thiazol-4-yloxy)pyrimidin-4-yl)-6-(trifluoromethyl)pyridin-2-ylamino)methyl)morpholine-4-carboxylate. tert-Butyl 2-((3-(6-(2-aminobenzo[d]thiazol-4-yloxy)pyrimidin-4-yl)-6-(trifluoromethyl)pyridin-2-ylamino)methyl)morpholine-4-carboxylate from step (a) above (234 mg, 0.39 mmol) was reacted with acetic anhydride (110 µL, 1.17 mmol, Aldrich) under the conditions of Example 2 to give the title compound as a light-yellow solid. MS (ESI, pos. ion.) m/z: 646 (M+1).

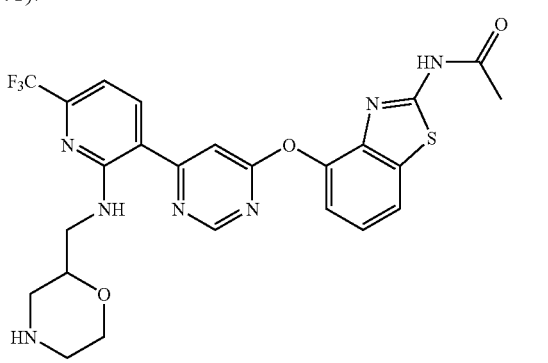

(c) N-(4-(6-(2-(Morpholin-2-ylmethylamino)-6-(trifluoromethyl)pyridin-3-yl)-pyrimidin-4-yloxy)benzo[d]thiazol-2-yl)acetamide. tert-Butyl 2-((3-(6-(2-acetamidobenzo[d]thiazol-4-yloxy)pyrimidin-4-yl)-6-(trifluoromethyl)pyridin-2-ylamino)methyl)morpholine-4-carboxylate from step (b) above (110 mg, 0.17 mmol) was reacted with 1:1 mixture of DCM/TFA (5 mL) under the conditions of Example 3(c) to give the title compound as a yellow solid. MS (ESI, pos. ion.) m/z: 546 (M+1).

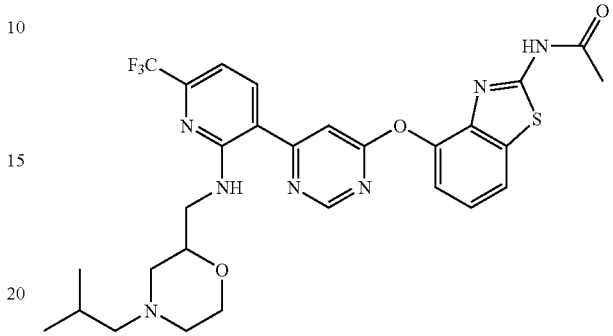

(d) N-(4-(6-(2-((4-Isobutylmorpholin-2-yl)methylamino)-6-(trifluoromethyl)-pyridin-3-yl)pyrimidin-4-yloxy)benzo[d]thiazol-2-yl)acetamide. N-(4-(6-(2-(Morpholin-2-ylmethylamino)-6-(trifluoromethyl)pyridin-3-yl)pyrimidin-4-yloxy)benzo[d]thiazol-2-yl)acetamide from step (c) above (78 mg, 0.14 mmol) was reacted with isobutyraldehyde (52 µL, 0.56 mmol, Aldrich) under the conditions of Example 3(d) to give the title compound as a yellow solid. MS (ESI, pos. ion.) m/z: 602 (M+1).

EXAMPLE 9

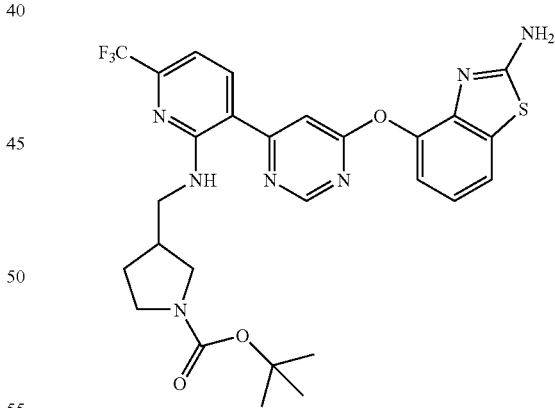

(a) tert-Butyl 3-((3-(6-(2-aminobenzo[d]thiazol-4-yloxy)pyrimidin-4-yl)-6-(trifluoromethyl)pyridin-2-ylamino)methyl)pyrrolidine-1-carboxylate. 4-(6-(2-Chloro-6-(trifluoromethyl)pyridin-3-yl)pyrimidin-4-yloxy)benzo[d]thiazol-2-amine, Example 1(b), (320 mg, 0.76 mmol) was reacted with tert-butyl 3-(aminomethyl)pyrrolidine-1-carboxylate (450 mg, 2.3 mmol, Astatech) under the conditions of Example 3(a) to give the title compound as a yellow solid. MS (ESI, pos ion) m/z: 588 (M+1).

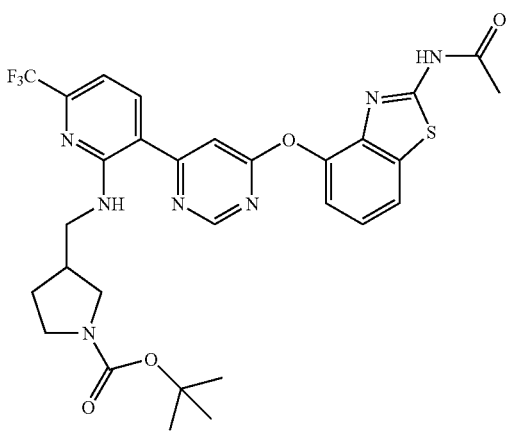

(b) tert-Butyl 3-((3-(6-(2-acetamidobenzo[d]thiazol-4-yloxy)pyrimidin-4-yl)-6-(trifluoromethyl)pyridin-2-ylamino)methyl)pyrrolidine-1-carboxylate. tert-Butyl 3-((3-(6-(2-aminobenzo[d]thiazol-4-yloxy)pyrimidin-4-yl)-6-(trifluoromethyl)pyridin-2-ylamino)methyl)pyrrolidine-1-carboxylate from step (a) above (110 mg, 0.19 mmol) was reacted with acetic anhydride (53 µL, 0.57 mmol, Aldrich) under the conditions of Example 2 to give the title compound as a yellow solid. MS (ESI, pos. ion.) m/z: 630 (M+1).

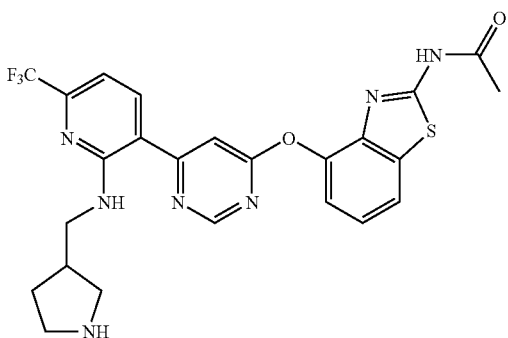

(c) N-(4-(6-(2-(Pyrrolidin-3-ylmethylamino)-6-(trifluoromethyl)pyridin-3-yl)-pyrimidin-4-yloxy)benzo[d]thiazol-2-yl)acetamide. tert-Butyl 3-((3-(6-(2-acetamidobenzo[d]thiazol-4-yloxy)pyrimidin-4-yl)-6-(trifluoromethyl)pyridin-2-ylamino)methyl)pyrrolidine-1-carboxylate from step (b) above (110 mg, 0.17 mmol) was reacted with 1:1 mixture of DCM/TFA (5 mL) under the conditions of Example 3(c) to give the title compound as a yellow solid. MS (ESI, pos. ion.) m/z: 530 (M+1).

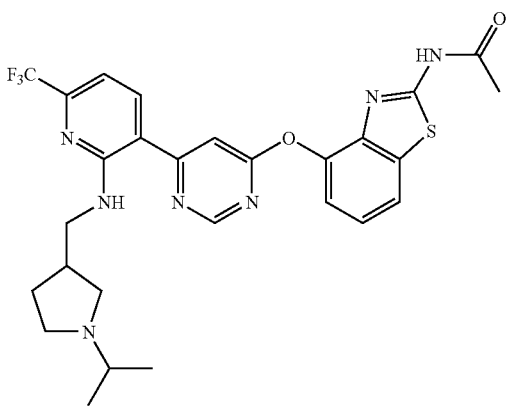

(d) N-(4-(6-(2-(((1-Isopropylpyrrolidin-3-yl)methylamino)-6-(trifluoromethyl)-pyridin-3-yl)pyrimidin-4-yloxy)benzo[d]thiazol-2-yl)acetamide. N-(4-(6-(2-(Pyrrolidin-3-ylmethylamino)-6-(trifluoromethyl)pyridin-3-yl)pyrimidin-4-yloxy)benzo[d]thiazol-2-yl)acetamide from step (c) above (55 mg, 0.10 mmol) was reacted with acetone (38 µL, 0.50 mmol, Aldrich) under the conditions of Example 3(d) to give the title compound as a yellow solid. MS (ESI, pos. ion.) m/z: 572 (M+1).

EXAMPLE 10

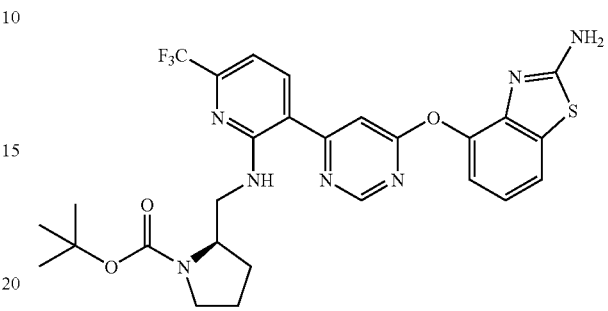

(a) (2R)-tert-Butyl 2-((3-(6-(2-aminobenzo[d]thiazol-4-yloxy)pyrimidin-4-yl)-6-(trifluoromethyl)pyridin-2-ylamino)methyl)pyrrolidine-1-carboxylate. 4-(6-(2-Chloro-6-(trifluoromethyl)pyridin-3-yl)pyrimidin-4-yloxy)benzo[d]thiazol-2-amine, Example 1(b), (260 mg, 0.61 mmol) was reacted with (2R)-tert-butyl 2-(aminomethyl)pyrrolidine-1-carboxylate (244 mg, 1.22 mmol, Astatech) under the conditions of Example 6(e) to give the title compound as a yellow solid. MS (ESI, pos. ion.) m/z: 588 (M+1).

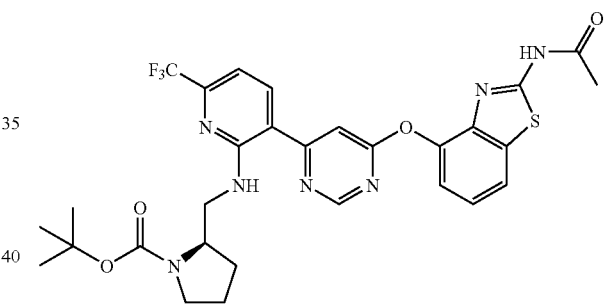

(b) (2R)-tert-Butyl 2-((3-(6-(2-acetamidobenzo[d]thiazol-4-yloxy)pyrimidin-4-yl)-6-(trifluoromethyl)pyridin-2-ylamino)methyl)pyrrolidine-1-carboxylate. (2R)-tert-Butyl 2-((3-(6-(2-aminobenzo[d]thiazol-4-yloxy)pyrimidin-4-yl)-6-(trifluoromethyl)pyridin-2-ylamino)methyl)pyrrolidine-1-carboxylate from step (a) above (190 mg, 0.32 mmol) was reacted with acetic anhydride (91 µL, 0.96 mmol, Aldrich) under the conditions of Example 2 to give the title compound as a yellow solid. MS (ESI, pos. ion.) m/z: 645 (M+1).

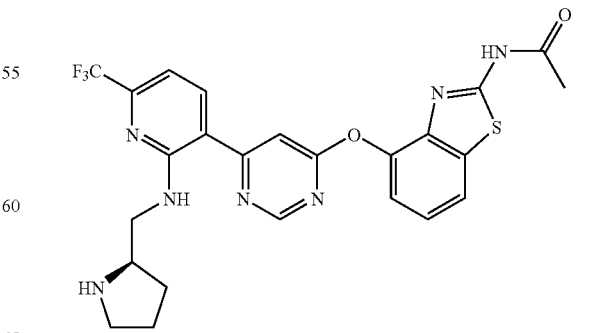

(c) N-(4-(6-(2-((R)-Pyrrolidin-2-ylmethylamino)-6-(trifluoromethyl)pyridin-3-yl)pyrimidin-4-yloxy)benzo[d]thiazol-2-yl)acetamide. (2R)-tert-Butyl 2-((3-(6-(2-acetamido-benzo[d]thiazol-4-yloxy)pyrimidin-4-yl)-6-(trifluoromethyl)pyridin-2-ylamino)methyl)pyrrolidine-1-carboxylate from step (b) above (110 mg, 0.17 mmol) was reacted with 1:1 mixture of DCM/TFA (5 mL) under the conditions of Example 3(c) to give the title compound as a yellow solid. MS (ESI, pos. ion.) m/z: 530 (M+1).

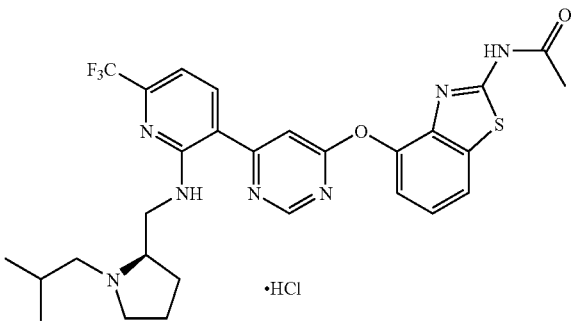

(d) N-(4-(6-(2-(((R)-1-Isobutylpyrrolidin-2-yl)methylamino)-6-(trifluoromethyl)pyridin-3-yl)pyrimidin-4-yloxy)benzo[d]thiazol-2-yl)acetamide hydrochloride. N-(4-(6-(2-((R)-Pyrrolidin-2-ylmethylamino)-6-(trifluoromethyl)-pyridin-3-yl)pyrimidin-4-yloxy)benzo[d]thiazol-2-yl) acetamide from step (c) above (39 mg, 0.07 mmol) was reacted with isobutyraldehyde (25 μL, 0.28 mmol, Aldrich) under the conditions of Example 3(d) to give the title compound as a free base. The free base was treated with 1 M solution of HCl in Et$_2$O (70 μL, 0.07 mmol, Aldrich) to give the desired hydrochloride salt as a light-yellow solid. MS (ESI, pos. ion.) m/z: 586 (M+1).

EXAMPLE 11

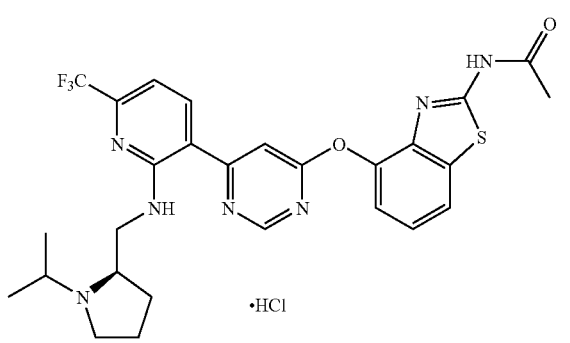

N-(4-(6-(2-(((R)-1-Isopropylpyrrolidin-2-yl)methylamino)-6-(trifluoromethyl)pyridin-3-yl)pyrimidin-4-yloxy)benzo[d]thiazol-2-yl)acetamide hydrochloride. N-(4-(6-(2-((R)-Pyrrolidin-2-ylmethylamino)-6-(trifluoromethyl)pyridin-3-yl)pyrimidin-4-yloxy)benzo[d]thiazol-2-yl) acetamide, Example 10(c), (40 mg, 0.07 mmol) was reacted with acetone (26 μL, 0.35 mmol, Aldrich) under the conditions of Example 10(d) to give the title compound as a yellow solid. MS (ESI, pos. ion.) m/z: 558 (M+1).

EXAMPLE 12

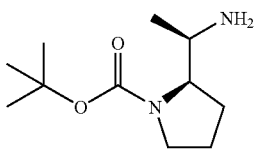

(a) (R)-tert-Butyl 2-((R)-1-aminoethyl)pyrrolidine-1-carboxylate. To a solution of (R)-tert-butyl 2-((R)-1-(benzylhydroxyamino)ethyl)pyrrolidine-1-carboxylate (910 mg, 2.84 mmol, prepared according to Merino, P.; Franco, S.; Gascon, J. M.; Merchan, F. L.; Tejero, T. *Tetrahedron: Asymmetry*, 1999, 10, 1867-1871) in MeOH (15 mL) was added 20% palladium hydroxide on activated charcoal (0.4 g, Aldrich). The reaction mixture was stirred under a hydrogen atmosphere at room temperature for 48 h. The catalyst was filtered off through a plug of Celite® and the filter cake was washed with MeOH. The combined filtrates were evaporated and the residue was dried in vacuuo to provide the title compound as a colorless oil. MS (ESI, pos. ion.) m/z: 215 (M+1).

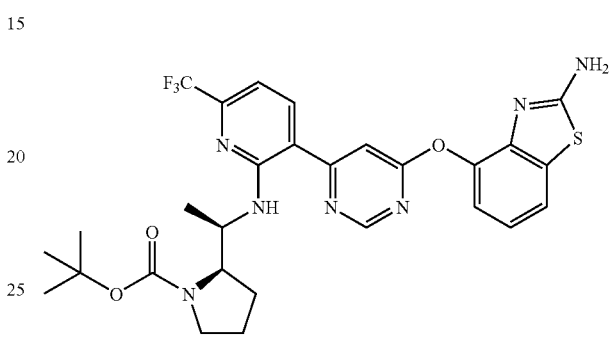

(b) (R)-tert-Butyl 2-((R)-1-(3-(6-(2-aminobenzo[d]thiazol-4-yloxy)pyrimidin-4-yl)-6-(trifluoromethyl)pyridin-2-ylamino)ethyl)pyrrolidine-1-carboxylate. 4-(6-(2-Chloro-6-(trifluoromethyl)pyridin-3-yl)pyrimidin-4-yloxy)benzo[d]thiazol-2-amine, Example 1(b), (300 mg, 0.71 mmol) was reacted with (R)-tert-butyl 2-((R)-1-aminoethyl)pyrrolidine-1-carboxylate from step (a) above (456 mg, 2.13 mmol) under the conditions of Example 3(a) to give the title compound as a light-yellow solid. MS (ESI, pos. ion.) m/z: 602 (M+1).

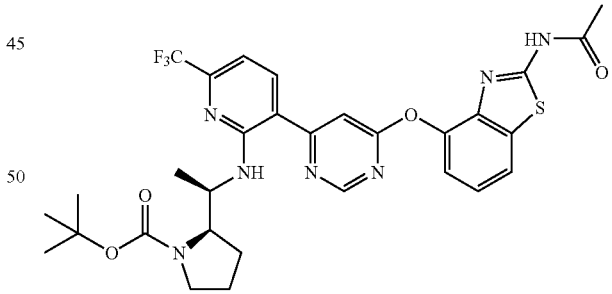

(c) (R)-tert-Butyl 2-((R)-1-(3-(6-(2-acetamidobenzo[d]thiazol-4-yloxy)pyrimidin-4-yl)-6-(trifluoromethyl)pyridin-2-ylamino)ethyl)pyrrolidine-1-carboxylate. (R)-tert-Butyl 2-((R)-1-(3-(6-(2-aminobenzo[d]thiazol-4-yloxy)pyrimidin-4-yl)-6-(trifluoromethyl)pyridin-2-ylamino)ethyl)pyrrolidine-1-carboxylate from step (b) above (130 mg, 0.21 mmol) was reacted with acetic anhydride (61 μL, 0.63 mmol, Aldrich) under the conditions of Example 2 to give the title compound as a yellow solid. MS (ESI, pos. ion.) m/z: 644 (M+1).

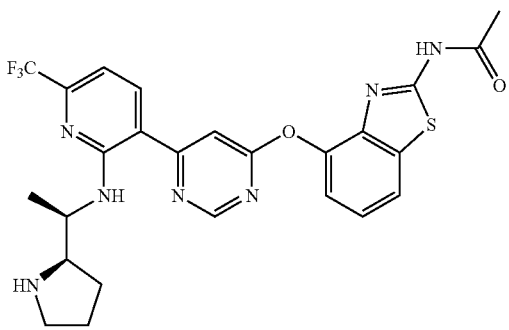

(d) N-(4-(6-(2-((R)-1-((R)-Pyrrolidin-2-yl)ethylamino)-6-(trifluoromethyl)-pyridin-3-yl)pyrimidin-4-yloxy)benzo[d]thiazol-2-yl)acetamide. (R)-tert-Butyl 2-((R)-1-(3-(6-(2-acetamidobenzo[d]thiazol-4-yloxy)pyrimidin-4-yl)-6-(trifluoromethyl)pyridin-2-ylamino)ethyl)pyrrolidine-1-carboxylate from step (c) above (112 mg, 0.17 mmol) was reacted with 1:1 mixture of DCM/TFA (2 mL) under the conditions of Example 3(c) to give the title compound as a yellow solid. MS (ESI, pos. ion.) m/z: 544 (M+1).

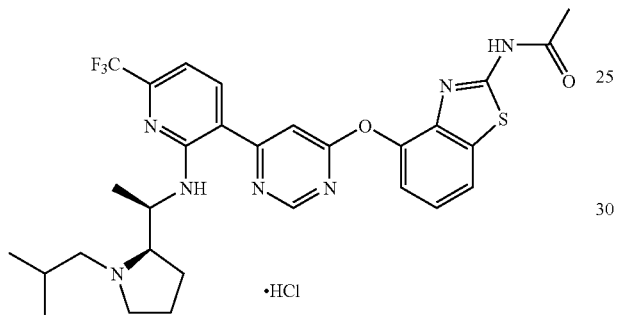

(e) N-(4-(6-(2-((R)-1-((R)-1-Isobutylpyrrolidin-2-yl)ethylamino)-6-(trifluoromethyl)pyridin-3-yl)pyrimidin-4-yloxy)benzo[d]thiazol-2-yl)acetamide hydrochloride. N-(4-(6-(2-((R)-1-((R)-Pyrrolidin-2-yl)ethylamino)-6-(trifluoromethyl)pyridin-3-yl)pyrimidin-4-yloxy)benzo[d]thiazol-2-yl)acetamide from step (d) above (58 mg, 0.1 mmol) was reacted with isobutyraldehyde (13 μL, 0.13 mmol, Aldrich) under the conditions of Example 10(d) to give the title compound as a light-yellow solid. MS (ESI, pos. ion.) m/z: 600 (M+1).

EXAMPLE 13

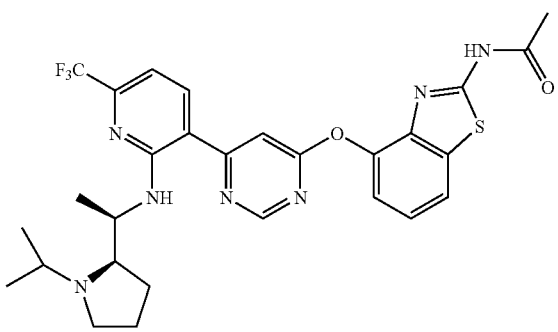

N-(4-(6-(2-((R)-1-((R)-1-Isopropylpyrrolidin-2-yl)ethylamino)-6-(trifluoromethyl)pyridin-3-yl)pyrimidin-4-yloxy)benzo[d]thiazol-2-yl)acetamide. N-(4-(6-(2-((R)-1-((R)-Pyrrolidin-2-yl)ethylamino)-6-(trifluoromethyl)pyridin-3-yl)-pyrimidin-4-yloxy)benzo[d]thiazol-2-yl)acetamide, Example 12(d), (135 mg, 0.25 mmol) was reacted with acetone (56 μL, 0.75 mmol, Aldrich) under the conditions of Example 3(d) to give the title compound as a yellow solid. MS (ESI, pos. ion.) m/z: 586 (M+1).

EXAMPLE 14

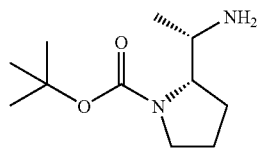

(a) (S)-tert-Butyl 2-((S)-1-aminoethyl)pyrrolidine-1-carboxylate. (S)-tert-Butyl 2-((S)-1-(benzylhydroxyamino)ethyl)pyrrolidine-1-carboxylate (950 mg, 3.0 mmol, prepared according to Merino, P.; Franco, S.; Gascon, J. M.; Merchan, F. L.; Tejero, T. Tetrahedron: Asymmetry, 1999, 10, 1867-1871) was hydrogenated under the conditions of Example 12(a) to provide the title compound as a colorless oil. MS (ESI, pos. ion.) m/z: 215 (M+1).

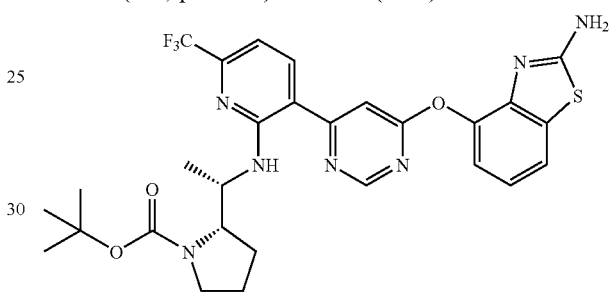

(b) (S)-tert-Butyl 2-((S)-1-(3-(6-(2-aminobenzo[d]thiazol-4-yloxy)pyrimidin-4-yl)-6-(trifluoromethyl)pyridin-2-ylamino)ethyl)pyrrolidine-1-carboxylate. 4-(6-(2-Chloro-6-(trifluoromethyl)pyridin-3-yl)pyrimidin-4-yloxy)-benzo[d]thiazol-2-amine, Example 1(b), (460 mg, 1.08 mmol) was reacted with (S)-tert-butyl 2-((S)-1-aminoethyl)pyrrolidine-1-carboxylate from step (a) above (460 mg, 2.16 mmol) under the conditions of Example 3(a) to give the title compound as a light-yellow solid. MS (ESI, pos. ion.) m/z: 602 (M+1).

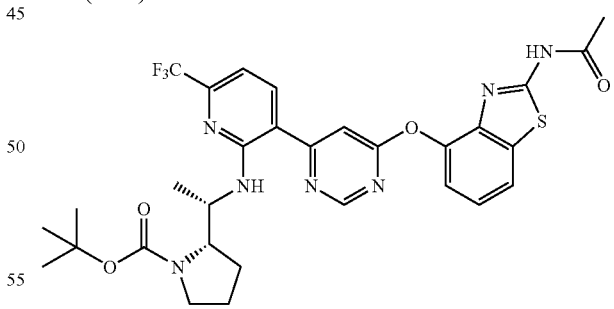

(c) (S)-tert-Butyl 2-((S)-1-(3-(6-(2-acetamidobenzo[d]thiazol-4-yloxy)pyrimidin-4-yl)-6-(trifluoromethyl)pyridin-2-ylamino)ethyl)pyrrolidine-1-carboxylate. (S)-tert-Butyl 2-((S)-1-(3-(6-(2-aminobenzo[d]thiazol-4-yloxy)pyrimidin-4-yl)-6-(trifluoromethyl)pyridin-2-ylamino)ethyl)pyrrolidine-1-carboxylate from step (b) above (110 mg, 0.18 mmol) was reacted with acetic anhydride (52 μL, 0.54 mmol, Aldrich) under the conditions of Example 2 to give the title compound as a yellow solid. MS (ESI, pos. ion.) m/z: 644 (M+1).

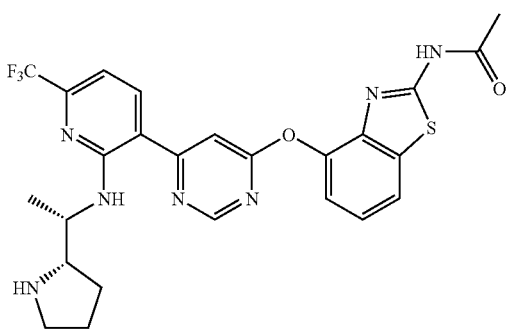

(d) N-(4-(6-(2-((S)-1-((S)-Pyrrolidin-2-yl)ethylamino)-6-(trifluoromethyl)-pyridin-3-yl)pyrimidin-4-yloxy)benzo[d]thiazol-2-yl)acetamide. (S)-tert-Butyl 2-((S)-1-(3-(6-(2-acetamidobenzo[d]thiazol-4-yloxy)pyrimidin-4-yl)-6-(trifluoromethyl)pyridin-2-ylamino)ethyl)pyrrolidine-1-carboxylate from step (c) above (105 mg, 0.16 mmol) was reacted with 1:1 mixture of DCM/TFA (4 mL) under the conditions of Example 3(c) to give the title compound as a light-yellow solid. MS (ESI, pos. ion.) m/z: 544 (M+1).

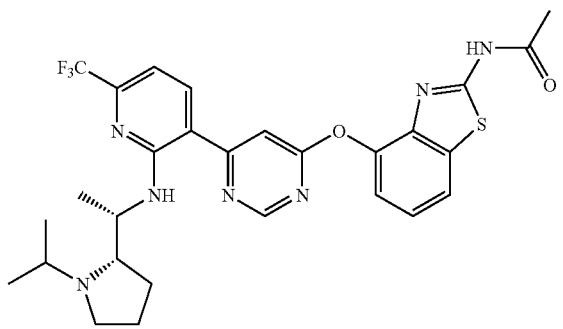

(e) N-(4-(6-(2-((S)-1-((S)-1-Isopropylpyrrolidin-2-yl)ethylamino)-6-(trifluoromethyl)pyridin-3-yl)pyrimidin-4-yloxy)benzo[d]thiazol-2-yl)acetamide. N-(4-(6-(2-((S)-1-((S)-Pyrrolidin-2-yl)ethylamino)-6-(trifluoromethyl)pyridin-3-yl)pyrimidin-4-yloxy)benzo[d]thiazol-2-yl)acetamide from step (d) above (52 mg, 0.09 mmol) was reacted with acetone (35 μL, 0.45 mmol, Aldrich) under the conditions of Example 3(d) to give the title compound as a yellow solid. MS (ESI, pos. ion.) m/z: 586 (M+1).

EXAMPLE 15

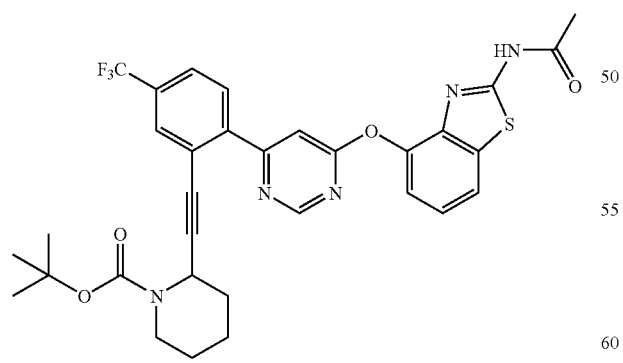

(a) tert-Butyl 2-(2-(2-(6-(2-acetamidobenzo[d]thiazol-4-yloxy)pyrimidin-4-yl)-5-(trifluoromethyl)phenyl)ethynyl)piperidine-1-carboxylate. To a solution of N-(4-(6-(2-iodo-4-(trifluoromethyl)phenyl)pyrimidin-4-yloxy)benzo[d]thiazol-2-yl)acetamide (480 mg, 0.86 mmol, prepared according to the procedure described in WO2004014871), tert-butyl 2-ethynylpiperidine-1-carboxylate (360 mg, 1.72 mmol, prepared according to the procedure described in WO200044728), palladium acetate (20 mg, 0.09 mmol, Aldrich) and triphenyl phosphine (45 mg, 0.17 mmol, Aldrich) in DMF (3 mL) was added triethylamine (6 mL, Aldrich) with stirring at room temperature under argon. The reaction mixture was heated at 80° C. with stirring for 18 h, a second portion of tert-butyl 2-ethynylpiperidine-1-carboxylate (300 mg, 1.42 mmol) was added, and the stirring was continued at 90° C. for an additional 18 h. The reaction mixture was allowed to reach room temperature and was partitioned between EtOAc and $H_2O$. The organic phase was separated, washed with $H_2O$ and brine, dried over $Na_2SO_4$, filtered, and evaporated in vacuo. Purification of the residue by silica gel column chromatography [gradient: 0-1% (2N $NH_3$ in MeOH)/DCM] afforded the title compound as a tan solid. MS (ESI, pos. ion.) m/z: 638 (M+1).

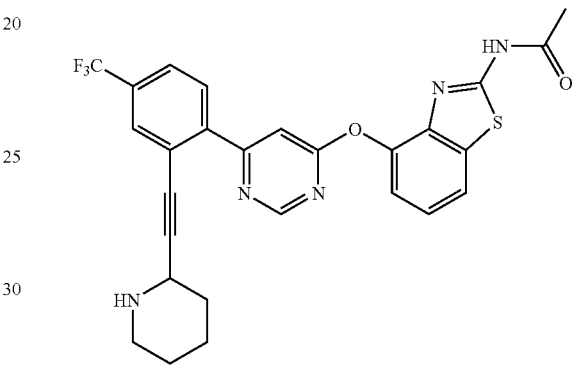

(b) N-(4-(6-(2-(2-(Piperidin-2-yl)ethynyl)-4-(trifluoromethyl)phenyl)pyrimidin-4-yloxy)benzo[d]thiazol-2-yl)acetamide. tert-Butyl 2-(2-(2-(6-(2-acetamidobenzo[d]thiazol-4-yloxy)pyrimidin-4-yl)-5-(trifluoromethyl)phenyl)-ethynyl)piperidine-1-carboxylate from step (a) above (280 mg, 0.44 mmol) was reacted with 1:1 mixture of DCM/TFA (5 mL) under the conditions of Example 3(c) to give the title compound as a tan solid. MS (ESI, pos. ion.) m/z: 538 (M+1).

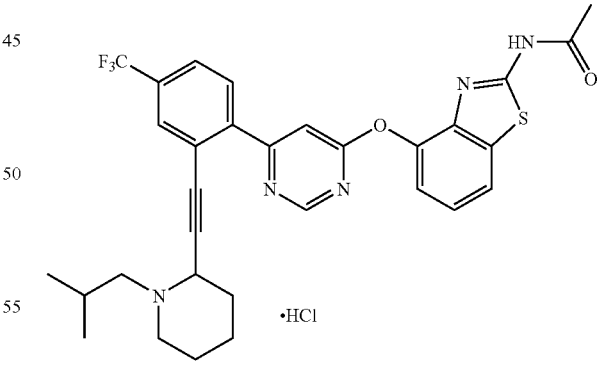

(c) N-(4-(6-(2-(2-(1-Isobutylpiperidin-2-yl)ethynyl)-4-(trifluoromethyl)phenyl)pyrimidin-4-yloxy)benzo[d]thiazol-2-yl)acetamide hydrochloride. N-(4-(6-(2-(2-(Piperidin-2-yl)ethynyl)-4-(trifluoromethyl)phenyl)pyrimidin-4-yloxy)benzo[d]thiazol-2-yl)acetamide from step (b) above (140 mg, 0.26 mmol) was reacted with isobutyraldehyde (33 μL, 0.36 mmol, Aldrich) under the conditions of Example 10(d) to give the title compound. MS (ESI, pos. ion) m/z: 594 (M+1).

EXAMPLE 16

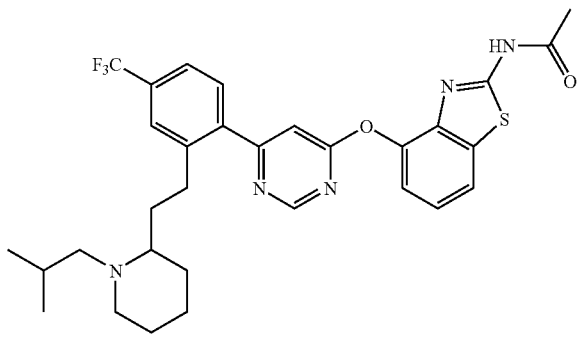

N-(4-(6-(2-(2-(1-Isobutylpiperidin-2-yl)ethyl)-4-(trifluoromethyl)phenyl)pyrimidin-4-yloxy)benzo[d]thiazol-2-yl)acetamide. A solution of N-(4-(6-(2-(2-(1-isobutylpiperidin-2-yl)ethynyl)-4-(trifluoromethyl)phenyl)pyrimidin-4-yloxy)benzo[d]thiazol-2-yl)acetamide hydrochloride, Example 15(c), (221 mg, 0.37 mmol) in dioxane (5 mL) was hydrogenated under the conditions of Example 12(a) to provide the title compound as a tan solid. MS (ESI, pos. ion) m/z: 598 (M+1).

EXAMPLE 17

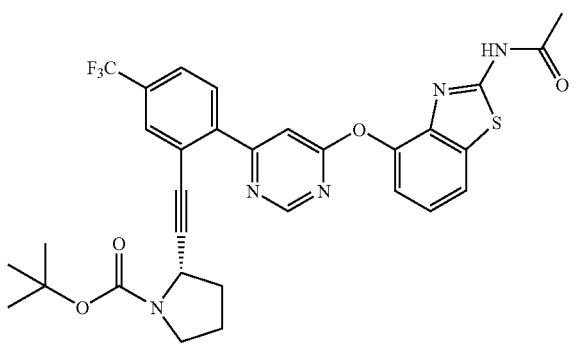

(a) (2S)-tert-Butyl 2-(2-(2-(6-(2-acetamidobenzo[d]thiazol-4-yloxy)pyrimidin-4-yl)-5-(trifluoromethyl)phenyl)ethynyl)pyrrolidine-1-carboxylate. N-(4-(6-(2-Iodo-4-(trifluoromethyl)phenyl)pyrimidin-4-yloxy)benzo[d]thiazol-2-yl)-acetamide (450 mg, 0.81 mmol, prepared according to the procedure described in WO2004014871) was reacted with (S)-tert-butyl 2-ethynylpyrrolidine-1-carboxylate (314 mg, 1.62 mmol, prepared according to the procedure described on WO200044728) under the conditions of Example 15(a) to give the title compound as a tan solid. MS (ESI, pos. ion.) m/z: 624 (M+1).

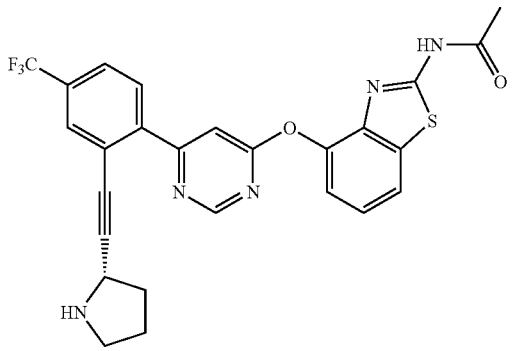

(b) N-(4-(6-(2-(2-((S)-Pyrrolidin-2-yl)ethynyl)-4-(trifluoromethyl)phenyl)pyrimidin-4-yloxy)benzo[d]thiazol-2-yl) acetamide. (2S)-tert-Butyl 2-(2-(2-(6-(2-acetamidobenzo[d]thiazol-4-yloxy)pyrimidin-4-yl)-5-(trifluoromethyl)phenyl)-ethynyl)pyrrolidine-1-carboxylate from step (a) above (250 mg, 0.40 mmol) was reacted with 1:1 mixture of DCM/TFA (6 mL) under the conditions of Example 3(c) to give the title compound as a brown solid. MS (ESI, pos. ion.) m/z: 524 (M+1).

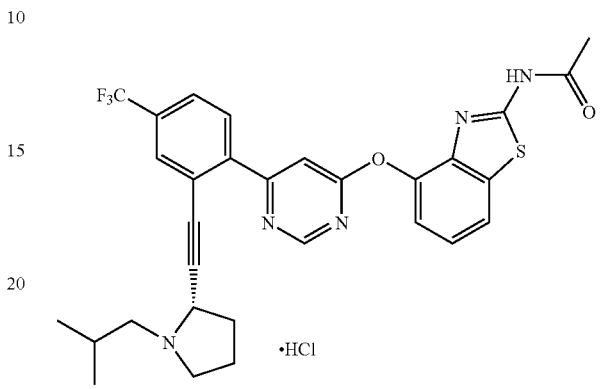

(c) N-(4-(6-(2-(2-((S)-1-Isobutylpyrrolidin-2-yl)ethynyl)-4-(trifluoromethyl)phenyl)pyrimidin-4-yloxy)benzo[d]thiazol-2-yl)acetamide hydrochloride. N-(4-(6-(2-(2-((S)-Pyrrolidin-2-yl)ethynyl)-4-(trifluoromethyl)phenyl)pyrimidin-4-yloxy)benzo[d]thiazol-2-yl)acetamide from step (b) (51 mg, 0.09 mmol) was reacted with isobutyraldehyde (11 μL, 0.12 mmol, Aldrich) under the conditions of Example 10(d) to give the title compound as a brown solid. MS (ESI, pos. ion.) m/z: 580 (M+1).

EXAMPLE 18

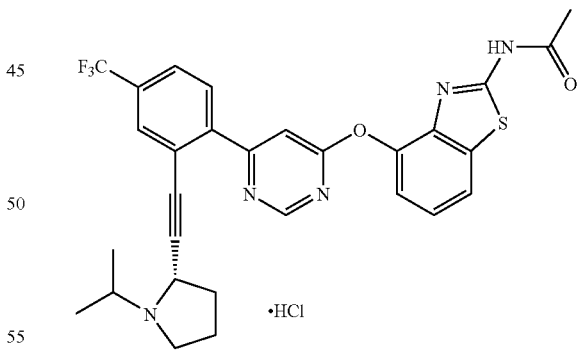

N-(4-(6-(2-(2-((S)-1-Isopropylpyrrolidin-2-yl)ethynyl)-4-(trifluoromethyl)phenyl)pyrimidin-4-yloxy)benzo[d]thiazol-2-yl)acetamide hydrochloride. N-(4-(6-(2-(2-((S)-Pyrrolidin-2-yl)ethynyl)-4-(trifluoromethyl)phenyl)pyrimidin-4-yloxy)benzo[d]thiazol-2-yl)acetamide, Example 17(b), (50 mg, 0.09 mmol), was reacted with acetone (20 μL, 0.27 mmol, Aldrich) under the conditions of Example 10(d) to give the title compound as a tan solid. MS (ESI, pos. ion.) m/z: 566 (M+1).

EXAMPLE 19

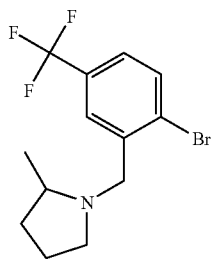

(a) 1-(2-Bromo-5-(trifluoromethyl)benzyl)-2-methylpyrrolidine. 2-Bromo-5-(trifluoromethyl)benzaldehyde (3.8 g, 15 mmol, prepared according to the procedure described in *J. Med. Chem.* 1986, 29, 1142-1452.) was reacted with 2-methylpyrrolidine (2.0 g, 23.5 mmol, Aldrich) under the conditions of Example 3(d) to give the title compound as a light-yellow oil. MS (ESI, pos. ion) m/z: 322 (M+1).

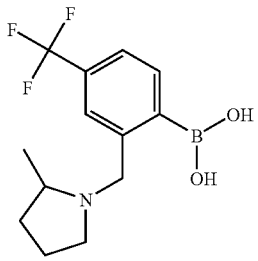

(b) 2-((2-Methylpyrrolidin-1-yl)methyl)-4-(trifluoromethyl)phenylboronic acid. A solution of 1-(2-bromo-5-(trifluoromethyl)benzyl)-2-methylpyrrolidine from step (a) above (0.97 g, 3 mmol) in anhydrous THF (4 mL) was added dropwise to a stirred suspension of Mg (highly reactive Rieke® metal) in THF (3.8 mL, 6 mmol, Rieke) at 0° C. under argon atmosphere. After the addition, the reaction mixture was heated to reflux for 3 h and then allowed to reach room temperature. The reaction mixture was cooled to −60° C. and trimethylborate (0.68 mL, 6 mmol, Aldrich) was added dropwise with stirring. The stirring was continued for 1 h at −60° C., and then for 16 h at room temperature. The reaction mixture was quenched with sat. aqueous solution of NH$_4$Cl (15 mL), extracted with Et$_2$O (100 mL), dried over Na$_2$SO$_4$, and filtered. The filtrate was evaporated under reduced pressure and the residue was dried in vacuo to give the title compound as an amorphous solid. MS (ESI, pos. ion.) m/z: 288 (M+1).

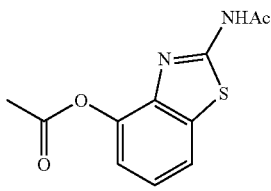

(c) Acetic acid 2-acetylamino-benzothiazol-4-yl ester. To the suspension of 2-amino-4-hydroxybenzothiazole (8.3 g, 50 mmol, Fluorochem Ltd.) in toluene (100 mL) was added acetic anhydride (47 mL, 500 mmol). The reaction mixture was heated at 110° C. for 16 h. The solvents were evaporated in vacuo to give the title compound as a tan solid. MS (ESI, pos. ion.) m/z: 251 (M+1).

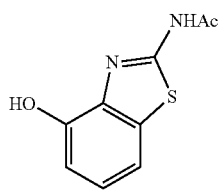

(d) N-(4-Hydroxy-benzothiazol-2-yl)-acetamide. To the suspension of acetic acid 2-acetylamino-benzothiazol-4-yl ester from step (c) above (9.7 g, 39 mmol) in MeOH (200 mL) was added potassium carbonate (11 g, 78 mmol). The reaction mixture was stirred at 25° C. for 6 h, most of the solvent was evaporated in vacuo, and the residue was acidified with 10% HCl to pH 5. The mixture was then extracted with EtOAc (3×), the combined EtOAc extracts were washed with brine, dried over Na$_2$SO$_4$, filtered, and concentrated in vacuo to give the title compound as a tan solid. MS (ESI, pos. ion.) m/z: 209 (M+1).

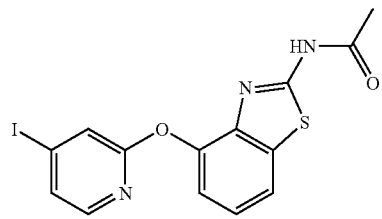

(e) N-(4-(4-Iodopyridin-2-yloxy)benzo[d]thiazol-2-yl)acetamide. To a solution of N-(4-hydroxy-benzothiazol-2-yl)-acetamide from step (d) above (4.68 g, 22 mmol) in DMF (30 mL) was added sodium hydride (60% in mineral oil, 0.96 g, 24 mmol) in small portions with stirring under nitrogen. The reaction mixture was stirred at room temperature for 10 min and 2-fluoro-4-iodopyridine (3.35 g, 15 mmol, Asymchem) was added in one portion. The reaction mixture was heated at 160° C. with stirring for 3 h. After cooling to room temperature, the mixture was diluted with water, and extracted with EtOAc (3×). The combined organic extracts were washed with brine, dried over Na$_2$SO$_4$, filtered, and evaporated in vacuo. The residue was purified by silica gel column chromatography (gradient 10-20% EtOAc/hexane) to give the title compound as a white solid. MS (ESI, pos. ion.) m/z: 412 (M+1).

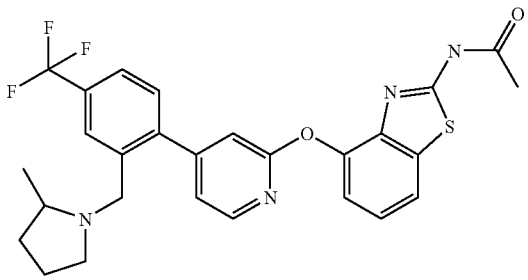

(f) N-(4-(6-(2-(2-(1-Methylpyrrolidin-2-yl)ethoxy)-4-(trifluoromethyl)phenyl)pyrimidin-4-yloxy)benzo[d]thiazol-2-yl)acetamide A mixture of 2-((2-methylpyrrolidin-1-yl)methyl)-4-(trifluoromethyl)phenylboronic acid from step (b) above (72 mg, 0.25 mmol), N-(4-(4-iodopyridin-2-yloxy)benzo[d]thiazol-2-yl)acetamide from step (e) above (103 mg, 0.25 mmol), PdCl$_2$(PPh$_3$)$_2$ (18 mg, 0.025 mmol, Aldrich), Na$_2$CO$_3$.H$_2$O (62 mg, 0.5 mmol), dimethoxyethane (0.7 mL), H$_2$O (0.3 mL) and EtOH (0.2 mL) was heated in a microwave synthesizer at 120° C. with stirring for 10 min. The reaction mixture was diluted with water (5 mL) and extracted with EtOAc (2×10 mL). The combined organic extracts were washed with brine, dried over Na$_2$SO$_4$ and filtered. The filtrate was evaporated in vacuo and the residue was purified by silica gel column chromatography (6% MeOH/hexane) to give the title compound. MS (ESI, pos. ion) m/z: 527 (M+1).

EXAMPLE 20

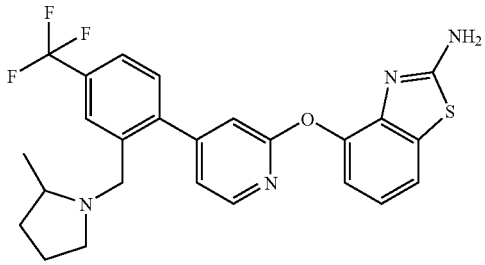

4-(6-(2-(2-(1-Methylpyrrolidin-2-yl)ethoxy)-4-(trifluoromethyl)phenyl)pyrimidin-4-yloxy)benzo[d]thiazol-2-amine. The title compound was formed as a side product of the reaction described in Example 19(f) and was isolated as an amorphous solid (12 mg, 10%). MS (ESI, pos. ion.) m/z: 485 (M+1).

EXAMPLE 21

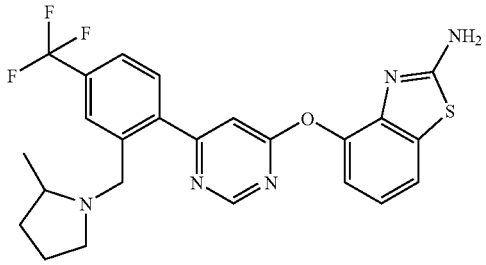

4-(6-(2-((2-Methylpyrrolidin-1-yl)methyl)-4-(trifluoromethyl)phenyl)pyrimidin-4-yloxy)benzo[d]thiazol-2-amine. 2-((2-Methylpyrrolidin-1-yl)-methyl)-4-(trifluoromethyl) phenylboronic acid, Example 19(b), (72 mg, 0.25 mmol) and 4-(6-iodopyrimidin-4-yloxy)benzo[d]thiazol-2-amine (93 mg, 0.25 mmol, prepared as described in WO04014871) was reacted under conditions of Example 19(f) to give the title compound. MS (ESI, pos. ion.) m/z: 486 (M+1).

EXAMPLE 22

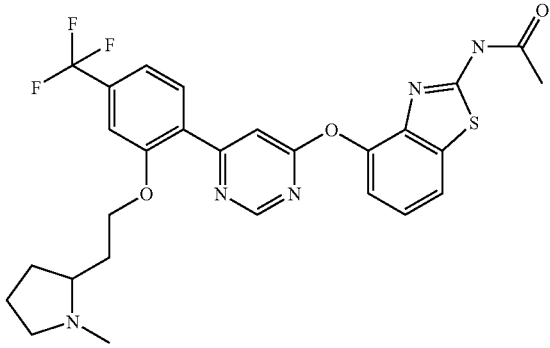

N-(4-(6-(2-(2-(1-Methylpyrrolidin-2-yl)ethoxy)-4-(trifluoromethyl)phenyl)pyrimidin-4-yloxy)benzo[d]thiazol-2-yl)acetamide. A mixture of N-(4-(6-(2-hydroxy-4-(trifluoromethyl)phenyl)pyrimidin-4-yloxy)benzo[d]thiazol-2-yl)-acetamide (89 mg, 0.2 mmol, prepared as described in WO04014871), 2-(2-chloroethyl)-1-methylpyrrolidine hydrochloride (56 mg, 0.3 mmol, Aldrich), sodium carbonate (62 mg, 0.6 mmol, Aldrich), sodium iodide (45 mg, 0.3 mmol) and acetone (1 mL) was heated in a microwave synthesizer at 150° C. for 40 min. The reaction mixture diluted with water (10 mL) and extracted with EtOAc (2×20 mL). The combined organic extracts were washed with brine, dried over Na$_2$SO$_4$, filtered, and evaporated in vacuo. The residue was purified by silica gel column chromatography (10% MeOH/CH$_2$Cl$_2$) to give the title compound as an amorphous solid. MS (ESI, pos. ion.) m/z: 558 (M+1).

EXAMPLE 23

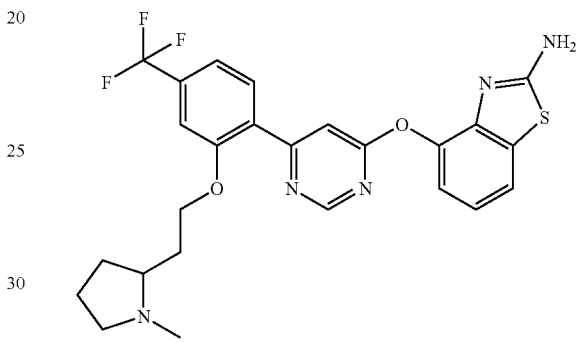

4-(6-(2-(2-(1-Methylpyrrolidin-2-yl)ethoxy)-4-(trifluoromethyl)phenyl)pyrimidin-4-yloxy)benzo[d]thiazol-2-amine. The title compound was formed as a side product of the reaction described in Example 22 and was isolated as an amorphous solid. MS (ESI, pos. ion) m/z: 516 (M+1).

EXAMPLE 24

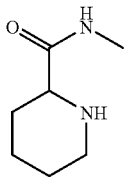

(a) N-Methylpiperidine-2-carboxamide. To methyl pipecolinate hydrochloride (5.0 g, 28 mmol, Aldrich) was added methylamine (20 mL, 40 wt. % solution in H$_2$O, Aldrich). The mixture was stirred at 25° C. for 18 h and then evaporated under reduced pressure. The residue was dried in vacuo to give the crude title compound, which was used in the next step without additional purification.

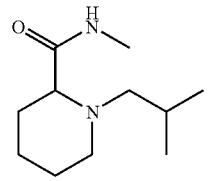

(b) 1-Isobutyl-N-methylpiperidine-2-carboxamide. The crude N-methylpiperidine-2-carboxamide from step (a)

above (2 g) was reacted with isobutyraldehyde (5.5 mL, 60 mmol, Aldrich) under the conditions of Example 3(d) to give the crude title compound, which was dried in vacuo and used in the next step without additional purification.

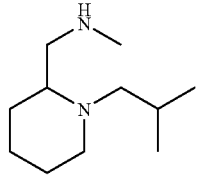

(c) (1-Isobutylpiperidin-2-yl)-N-methylmethanamine. The crude 1-isobutyl-N-methylpiperidine-2-carboxamide from step (b) above was reacted with LiAlH₄ (1 M in THF, 24 mL, 24 mmol, Aldrich) under the conditions of Example 6(d) to give the title compound. MS (ESI, pos. ion) m/z: 185 (M+1).

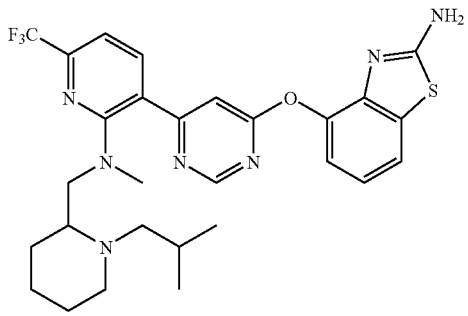

(d) 4-(6-(2-(((1-Isobutylpiperidin-2-yl)methyl)(methyl) amino)-6-(trifluoromethyl)pyridin-3-yl)pyrimidin-4-yloxy) benzo[d]thiazol-2-amine. A mixture of (1-isobutylpiperidin-2-yl)-N-methylmethanamine from step (c) above (0.39 g, 2.1 mmol), 2-methyl-2-pentene (0.61 mL, 5.0 mmol, Aldrich), and 4-(6-(2-chloro-6-(trifluoromethyl)pyridin-3-yl) pyrimidin-4-yloxy)benzo[d]thiazol-2-amine, Example 1(b), (0.30 g, 0.7.1 mmol) in DMSO (4 mL) was stirred at 35° C. for 20 h. The reaction mixture was allowed to reach 25° C. and was diluted with 2:1 mixture of EtOAc/hexane. The mixture was washed with aqueous solution of NaHCO₃, H₂O and brine, dried over Na₂SO₄, filtered, and evaporated under reduced pressure. Purification of the residue by silica gel chromatography (gradient: 0-1% NEt₃/EtOAc) afforded the title compound as a yellow solid. MS (ESI, pos. ion.) m/z: 572 (M+1). MP 98.9-101.9° C.

ADDITIONAL EXAMPLES

Following the procedures described above for Example 6(c,d) and Example 24, or with slight modifications thereof, and following procedures familiar to one of ordinary skill in the art, the following examples were prepared from 4-(6-(2-chloro-6-(trifluoromethyl)pyridin-3-yl)pyrimidin-4-yloxy)benzo[d]thiazol-2-amine [Example 1(b)]:

| No. | Structure | MS* | M.P. ° C. |
|---|---|---|---|
| 25 | 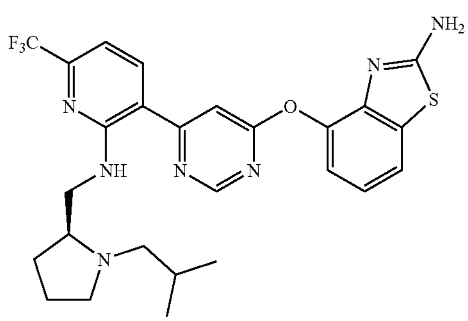 | 544 (M + 1) | 198 dec. |
| 26 | 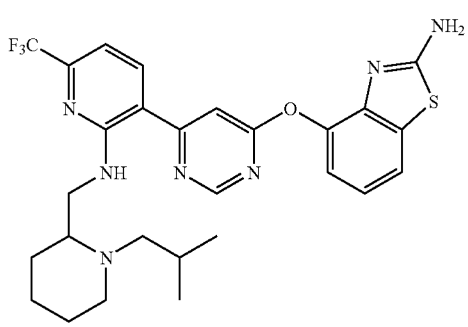 | 558 (M + 1) | 118.0-118.2 |

-continued

| No. | Structure | MS* | M.P. °C. |
|---|---|---|---|
| 27 | 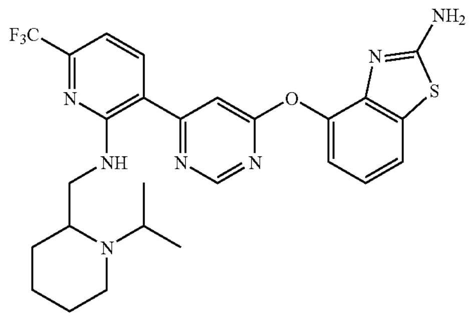 | 544 (M + 1) | 211.3-213.0 |
| 28 | 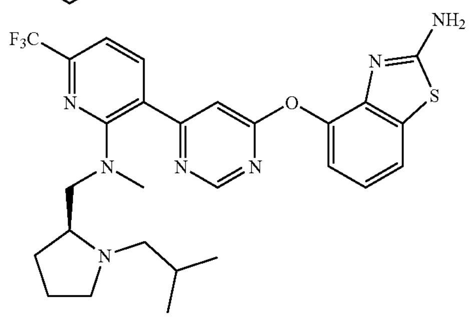 | 558 (M + 1) | 93.2-96.8 |

*(ESI, pos. ion) m/z

EXAMPLE 29

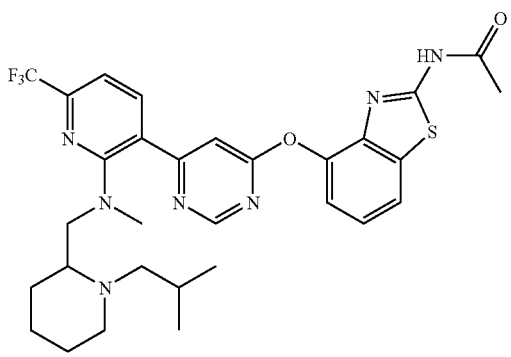

N-(4-(6-(2-(((1-isobutylpiperidin-2-yl)methyl)(methyl)amino)-6-(trifluoromethyl)pyridin-3-yl)pyrimidin-4-yloxy)benzo[d]thiazol-2-yl)acetamide. A mixture of 4-(6-(2-(((1-isobutylpiperidin-2-yl)methyl)(methyl)amino)-6-(trifluoromethyl)pyridin-3-yl)pyrimidin-4-yloxy)benzo[d]thiazol-2-amine, Example 24(d), (0.14 g, 0.24 mmol) and acetic anhydride (5 mL, Aldrich) in pyridine (20 mL) was stirred at 25° C. for 24 h. The reaction mixture was partitioned between aqueous solution of NaHCO₃ and EtOAc. The organic phase was separated, washed with brine, dried over Na₂SO₄, filtered and evaporated under reduced pressure. Purification of the residue by silica gel column chromotography (gradient: 50-100% EtOAc/hexane) afforded the title compound as a yellow solid. MS (ESI, pos. ion.) m/z: 614 (M+1). Mp: 123.2-125.4° C.

ADDITIONAL EXAMPLES

The following examples were prepared by treating the compounds of Example 25, Example 26 and Example 27 with acetic anhydride under the conditions described for Example 29:

| No. | Structure | MS | M.P. °C. |
|---|---|---|---|
| 30 | 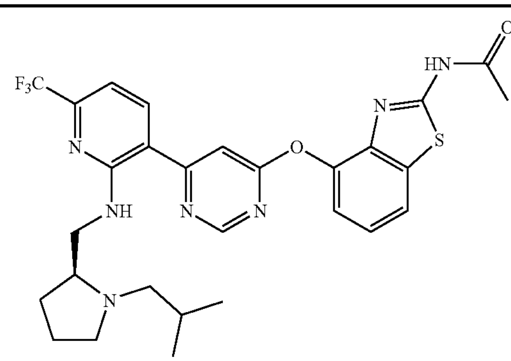 | 586 (M + 1) | 105.8-107.3 |

-continued

| No. | Structure | MS | M.P. ° C. |
|---|---|---|---|
| 31 | 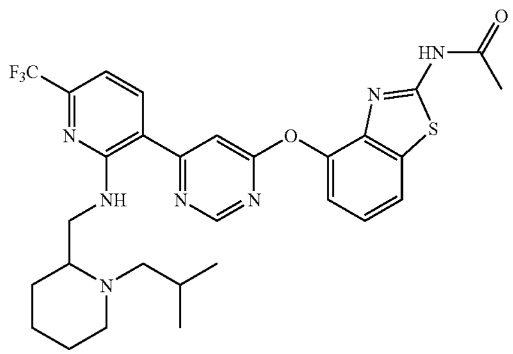 | 600 (M + 1) | 121.7–121.9 |
| 32 | 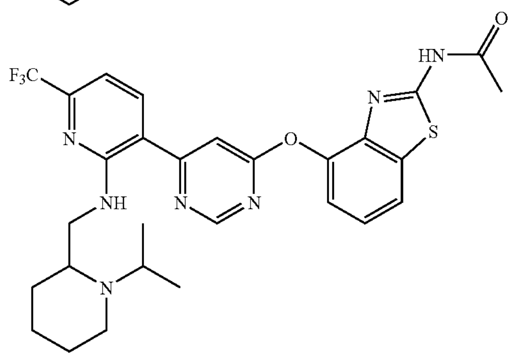 | 586 (M + 1) | 159.3–162.0 |

EXAMPLE 33

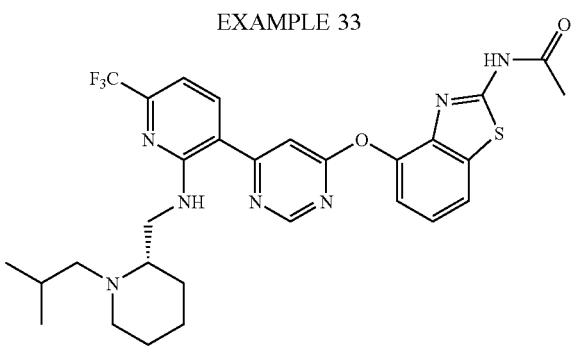

N-(4-(6-(2-(((S)-1-Isobutylpiperidin-2-yl)methylamino)-6-(trifluoromethyl)-pyridin-3-yl)pyrimidin-4-yloxy)benzo[d]thiazol-2-yl)acetamide. The title compound was prepared from (S)-2-aminomethyl-N-Boc-piperidine (AstaTech) and 4-(6-(2-chloro-6-(trifluoromethyl)pyridin-3-yl)pyrimidin-4-yloxy)-benzo[d]thiazol-2-amine, Example 1(b), analogous to the procedures described for Example 3(a-d). MS (ESI, pos. ion.) m/z: 600 (M+1).

EXAMPLE 34

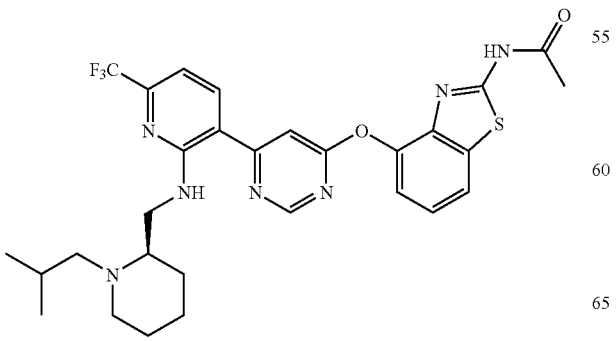

N-(4-(6-(2-(((R)-1-Isobutylpiperidin-2-yl)methylamino)-6-(trifluoromethyl)-pyridin-3-yl)pyrimidin-4-yloxy)benzo[d]thiazol-2-yl)acetamide. Chiral separation of N-(4-(6-(2-(((R,S)-1-isobutylpiperidin-2-yl)methylamino)-6-(trifluoromethyl)pyridin-3-yl)pyrimidin-4-yloxy)benzo[d]thiazol-2-yl)acetamide, Example 31, [Chiralcel OD-H (250× 21 mm, 5μ), A: hexane (0.2% diethylamine), B: ethanol (0.2% diethylamine), isocratic: 45:55 A:B, 20 mL/min] afforded the title compound as a pale-yellow solid. MS (ESI, pos. ion.) m/z: 600 (M+1). The assignment of (R) configuration was based on comparison of the product with an authentic sample of the corresponding (S) enantiomer described in Example 33.

EXAMPLE 35

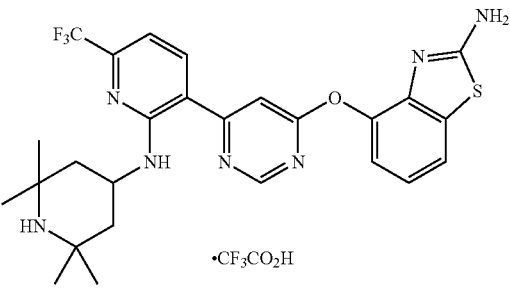

4-(6-(2-(2,2,6,6-Tetramethylpiperidin-4-ylamino)-6-(trifluoromethyl)pyridin-3-yl)pyrimidin-4-yloxy)benzo[d]thiazol-2-amine trifluoroacetic acid salt. 4-(6-(2-Chloro-6-(trifluoromethyl)pyridin-3-yl)pyrimidin-4-yloxy)benzo[d]thiazol-2-amine, Example 1(b), (0.20 g, 0.47 mmol) was reacted with 4-amino-2,2,6,6-tetramethylpiperidine (0.33 mL, 1.9 mmol, Aldrich) under the conditions of Example 24(d) to give the crude product. Purification of the product by reverse phase preparative HPLC (Phenomenex Prodigy 5μ ODS-3 100 Å column, gradient: 10-100% CH₃CN (0.1% TFA)/H₂O (0.1% TFA) over 15 min) afforded the title compound as a pale-yellow solid. MS (ESI, pos. ion.) m/z: 544 (M+1). Mp: 264.0-265.1° C.

EXAMPLE 36

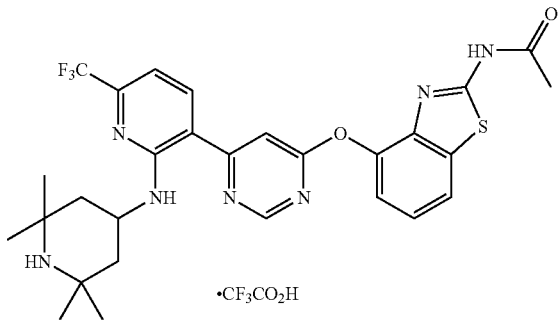

N-(4-(6-(2-(2,2,6,6-Tetramethylpiperidin-4-ylamino)-6-(trifluoromethyl)-pyridin-3-yl)pyrimidin-4-yloxy)benzo[d]thiazol-2-yl)acetamide trifluoroacetic acid salt. The title compound was prepared analogous to Example 29 using 4-(6-(2-(((1-isobutylpiperidin-2-yl)methyl)(methyl)amino)-6-(trifluoromethyl)pyridin-3-yl)pyrimidin-4-yloxy)benzo[d]thiazol-2-amine trifluoroacetic acid salt, Example 35, (0.020 g, 0.037 mmol) and acetic anhydride (0.5 mL, Aldrich) in pyridine (2 mL). Purification by reverse phase preparative HPLC (Phenomenex Prodigy 5μ ODS-3 100 Å column, gradient: 10-100% CH₃CN (0.1% TFA)/H₂O (0.1% TFA) over 15 min) afforded the title compound as a pale-yellow solid. MS (ESI, pos. ion.) m/z: 586 (M+1). Mp: 253.4-254.1° C.

EXAMPLE 37

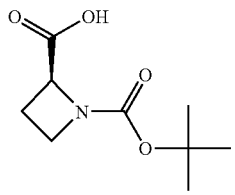

(a) (S)-1-(tert-Butyloxycarbonyl)azetidine-2-carboxylic acid. A mixture of L-azetidine-2-carboxylic acid (1.0 g, 9.9 mmol, Toronto Research), tetramethylammonium hydroxide pentahydrate (2.0 g, 11 mmol, Aldrich) and di-tert-butyl dicarbonate (3.2 g, 15 mmol, Aldrich) in acetonitrile (50 mL) was stirred for 3 d at 25° C. Additional amount of di-tert-butyl dicarbonate (1.0 g, 4.6 mmol) was added and the mixture was stirred for 5 h at 25° C. The reaction mixture was evaporated under reduced pressure and the residue was partitioned between aqueous solution of K₂CO₃ and 1:1 mixture of EtOAc/hexane. The aqueous phase was separated, acidified with aqueous solution of citric acid, and extracted with EtOAc (3×). The combined extracts were washed with brine, dried over Na₂SO₄, filtered and evaporated under reduced pressure. The residue was dried under vacuo to afford the title compound as a white solid. MS (ESI, neg. ion.) m/z: 200 (M−1).

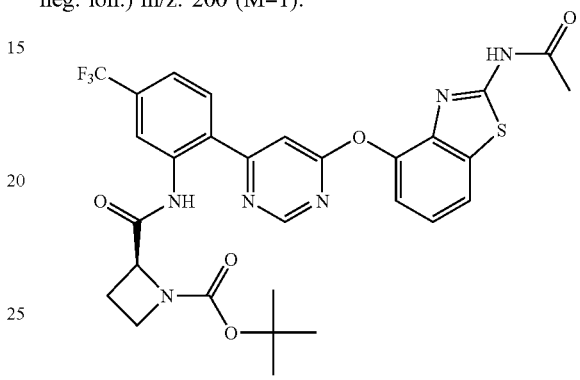

(b) (2S)-tert-Butyl 2-((2-(6-(2-acetamidobenzo[d]thiazol-4-yloxy)pyrimidin-4-yl)-5-(trifluoromethyl)phenyl)carbamoyl)azetidine-1-carboxylate. To a solution of N-(4-(6-(2-amino-4-(trifluoromethyl)phenyl)pyrimidin-4-yloxy)-benzo[d]thiazol-2-yl)acetamide (1.5 g, 3.3 mmol, prepared as described in WO04014871) and (S)-1-(tert-butyloxycarbonyl)azetidine-2-carboxylic acid from step (a) above (1.0 g, 5.0 mmol) in CH₂Cl₂ (10 mL) was added N,N-diisopropylethylamine (0.87 mL, 5.0 mmol, Aldrich) and chlorodipyrrolidinocarbenium hexafluorophosphate (1.7 g, 5.0 mmol, Fluka). The mixture was stirred for 4 d at 25° C. and diluted with EtOAc. The mixture was washed with aqueous solution of NaHCO₃, H₂O and brine, dried over Na₂SO₄, and filtered. The filtrate was evaporated under reduced pressure and the residue was purified by silica gel column chromatography (gradient: 5-55% EtOAc/hexane) to give the title compound as a yellow solid. MS (ESI, pos. ion.) m/z: 629 (M+1).

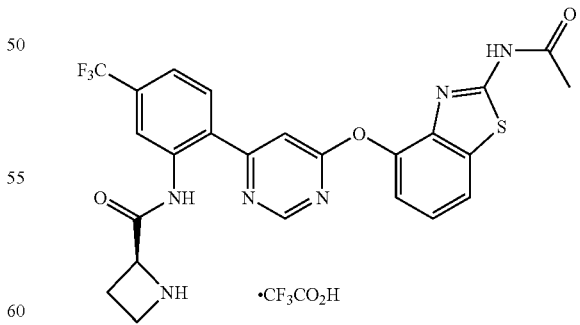

(c) (2S)-N-(2-(6-(2-Acetamidobenzo[d]thiazol-4-yloxy)pyrimidin-4-yl)-5-(trifluoromethyl)phenyl)azetidine-2-carboxamide trifluoracetic acid salt. (2S)-tert-Butyl 2-((2-(6-(2-acetamidobenzo[d]thiazol-4-yloxy)pyrimidin-4-yl)-5-(trifluoromethyl)phenyl)carbamoyl)azetidine-1-carboxylate from step (b) above (1.5 g, 2.4 mmol) was reacted with 1:1 mixture of CH₂Cl₂/trifluoroacetic acid (40 mL) under the conditions of Example 3(c) to afford the title compound as a yellow solid. MS (ESI, pos. ion.) m/z: 529 (M+1).

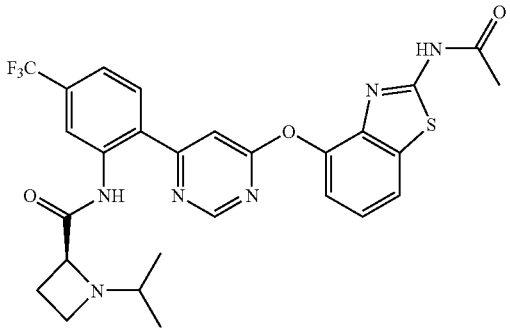

(d) (2S)-N-(2-(6-(2-Acetamidobenzo[d]thiazol-4-yloxy) pyrimidin-4-yl)-5-(trifluoromethyl)phenyl)-1-isopropylazetidine-2-carboxamide. (2S)-N-(2-(6-(2-Acetamidobenzo[d]thiazol-4-yloxy)pyrimidin-4-yl)-5-(trifluoromethyl)-phenyl)azetidine-2-carboxamide TFA salt from step (c) above (0.30 g, 0.47 mmol) was reacted with acetone (0.086 mL, 1.2 mmol) under the conditions of Example 3(d) to give the title compound as a white solid. MS (ESI, pos. ion.) m/z: 571 (M+1). Mp: 198.8-199.4° C.

EXAMPLE 38

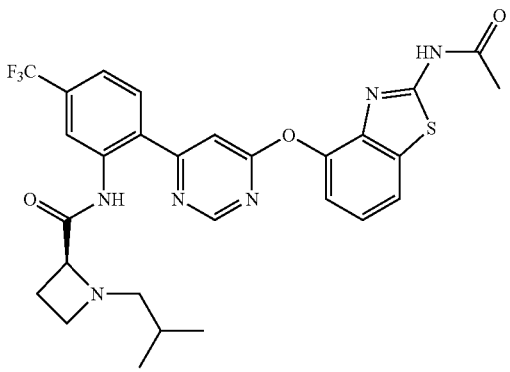

(2S)-N-(2-(6-(2-Acetamidobenzo[d]thiazol-4-yloxy)pyrimidin-4-yl)-5-(trifluoromethyl)phenyl)-1-isobutylazetidine-2-carboxamide. The title compound was prepared by reacting (2S)-N-(2-(6-(2-acetamidobenzo[d]thiazol-4-yloxy) pyrimidin-4-yl)-5-(trifluoromethyl)phenyl)azetidine-2-carboxamide trifluoroacetic acid salt [Example 37(c)] with isobutyraldehyde (Aldrich) under the conditions of Example 3(d). MS (ESI, pos. ion.) m/z: 585 (M+1). Mp: 174.4-174.9° C.

EXAMPLE 39

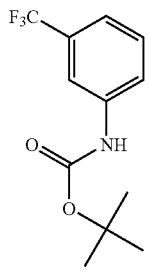

(a) (3-Trifluoromethylphenyl)carbamic acid tert-butyl ester. To a 250-mL, round-bottomed flask was added 3-(trifluoromethyl)aniline (5.0 g, 31 mmol, Aldrich), THF (100 mL), di-tert-butyl dicarbonate (20 g, 93 mmol, Aldrich) and 4-(dimethylamino)pyridine (0.38 g, 3.1 mmol, Aldrich). The mixture was heated at reflux for 3 h. K₂CO₃ (13 g, 93 mmol) and MeOH (50 mL) were added, and heating was continued for 18 h. After cooling to room temperature, the mixture was diluted with CH₂Cl₂, then filtered and washed with CH₂Cl₂. The filtrate was concentrated to afford a brown oil. The oil was dissolved in EtOAc (200 mL) and washed with H₂O (2×100 mL), brine (1×100 mL), dried over Na₂SO₄, filtered and concentrated in vacuum onto silica gel. Purification by silica gel chromatography with gradient from 0% to 15% solution of EtOAc in hexanes afforded the title compound as a colorless oil which solidified upon standing to a while solid. MS (ESI, neg. ion.) m/z: 260 (M−1).

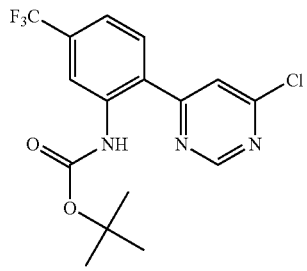

(b) [2-(6-Chloropyrimidin-4-yl)-5-trifluoromethylphenyl]carbamic acid tert-butyl ester. (Analogous to the procedures of Boisnard, S.; Carbonnelle, A. C.; Zhu, J. Org. Let. 2001, 3, 2061-2064 and Hewawasam, P.; Meanwell, N. A. Tetrahedron Lett. 1994, 35, 7303). To a 500-mL, round-bottomed flask containing (3-trifluoromethylphenyl)carbamic acid tert-butyl ester from step (a) above (2.5 g, 9.6 mmol) in THF (100 mL) stirred at −40° C. was added sec-BuLi (17 mL, 1.3 M in cyclohexane, Aldrich) over 10 min. The mixture was stirred for 1 h at −40° C. and then cooled to −78° C. Trimethyl borate (4.4 mL, 38 mmol, Aldrich) was added over 10 min. The reaction mixture was allowed to warm to room temperature and stirred for 10 min at that temperature. The mixture was quenched with aqueous solution of KH₂PO₄ and concentrated to remove the THF. The aqueous mixture was extracted with EtOAc (3×100 mL) and the combined extracts were washed with brine, dried over Na₂SO₄, filtered, and concentrated to afford a yellow foam. The foam was dissolved in CH₃CN (30 mL) and treated with 4,6-dichloropyrimidine (4.1 g, 28 mmol, Aldrich) followed by a solution of Na₂CO₃ (2.9 g, 28 mmol) in H₂O (30 mL). Tetrakis(triphenylphosphine)-palladium(0) (0.53 g, 0.46 mmol, Strem) was added and the mixture was stirred at 75° C. for 15 h. After allowing to cool to room temperature, the mixture was concentrated in vacuum to remove the CH₃CN and then extracted with EtOAc. The combined extracts were washed with H₂O and brine, dried over Na₂SO₄, and concentrated in vacuum. Purification of the residue by silica gel chromatography with gradient from 0% to 10% solution of EtOAc in hexanes afforded the title compound as a colorless oil. MS (ESI, pos. ion.) m/z: 374 (M+1).

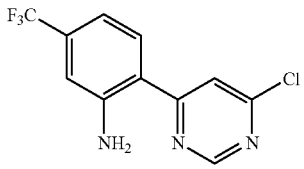

(c) 2-(6-Chloropyrimidin-4-yl)-5-(trifluoromethyl)benzenamine. [2-(6-Chloropyrimidin-4-yl)-5-trifluoromethylphenyl]carbamic acid tert-butyl ester from step (b) above was reacted with 1:1 mixture of DCM/TFA under the conditions of Example 3(c) to give the title compound.

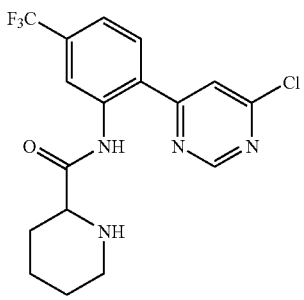

(d) N-(2-(6-Chloropyrimidin-4-yl)-5-(trifluoromethyl)phenyl)piperidine-2-carboxamide: To a mixture of 2-(6-chloropyrimidin-4-yl)-5-(trifluoromethyl)-benzenamine from step (c) above (2.0 g, 7.3 mmol) and 1-(tert-butoxycarbonyl)-2-piperidinecarboxylic acid (2.5 g, 11 mmol, Aldrich) in $CH_2Cl_2$ (20 mL) was added N,N-diisopropylethylamine (1.9 mL, 11 mmol, Aldrich) and chlorodipyrrolidinocarbenium hexafluorophosphate (3.6 g, 11 mmol, Fluka) with stirring at 0° C. The reaction mixture was allowed to reach 25° C. and was stirred for 20 h. The mixture was diluted with hexane (20 mL) and filtered. The filter cake was washed with 1:1 mixture of EtOAc/hexane and dried in vacuo to afford the title compound as a white solid. MS (ESI, pos. ion) m/z: 385 (M+1).

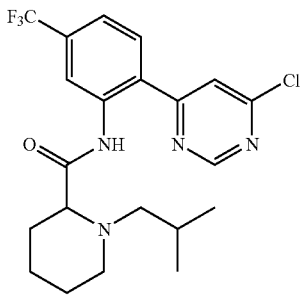

(e) N-(2-(6-Chloropyrimidin-4-yl)-5-(trifluoromethyl)phenyl)-1-isobutylpiperidine-2-carboxamide. N-(2-(6-Chloropyrimidin-4-yl)-5-(trifluoromethyl)phenyl)piperidine-2-carboxamide from step (d) above (0.40 g, 0.90 mmol) was reacted with isobutyraldehyde (0.28 mL, 3.1 mmol, Aldrich) under the conditions of Example 3(d) to give the title compound as a white solid. MS (ESI, pos. ion.) m/z: 441 (M+1).

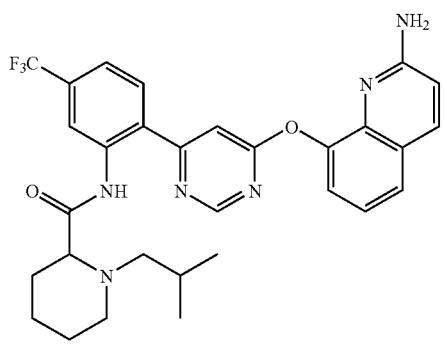

(f) N-(2-(6-(2-Aminoquinolin-8-yloxy)pyrimidin-4-yl)-5-(trifluoromethyl)-phenyl)-1-isobutylpiperidine-2-carboxamide. To a stirred solution of 2-amino-8-hydroxyquinoline (0.061 g, 0.38 mmol, Fluka) in DMF (2.0 mL) was added NaH (60% dispersion in mineral oil, 0.015 g, 0.38 mmol, Aldrich) at 25° C. The mixture was stirred for 10 min and a solution of N-(2-(6-chloropyrimidin-4-yl)-5-(trifluoromethyl)phenyl)-1-isobutylpiperidine-2-carboxamide from step (e) above (0.14 g, 0.32 mmol) in DMF (2.5 mL) was added. The reaction mixture was stirred for 24 h at 25° C., diluted with aqueous solution of $NaHCO_3$ (100 mL), and extracted with 1:1 mixture of EtOAc/hexane (2×75 mL). The combined extracts were washed with $H_2O$ (2×75 mL) and brine (1×75 mL), dried over $Na_2SO_4$, filtered and evaporated under reduced pressure. Purification of the residue by silica gel column chromatography (gradient: 20-50% EtOAc/hexane) afforded the title compound as a white solid. MS (ESI, pos. ion.) m/z: 565 (M+1). Mp: 111.1-113.9° C.

EXAMPLE 40 AND EXAMPLE 41

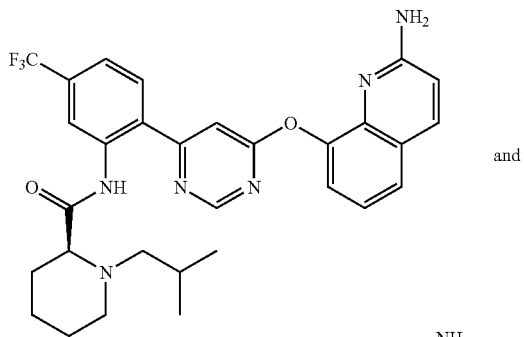

and

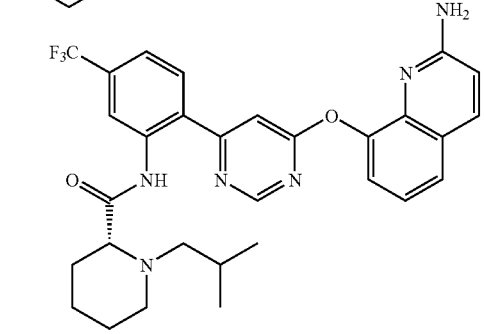

(2S)-N-(2-(6-(2-Aminoquinolin-8-yloxy)pyrimidin-4-yl)-5-(trifluoromethyl)-phenyl)-1-isobutylpiperidine-2-carboxamide and (2R)-N-(2-(6-(2-Aminoquinolin-8-yloxy)pyrimidin-4-yl)-5-(trifluoromethyl)phenyl)-1-isobutylpiperidine-2-carboxamide. Chiral separation (Chiralpak ADH (250×21 mm, 5μ), A: liquid $CO_2$, B: ethanol:acetonitrile:diethylamine (50:50:0.2), isocratic: 60:40 A:B, 60 mL/min, 24 mg/injection) of N-(2-(6-(2- aminoquinolin-8-yloxy)pyrimidin-4-yl)-5-(trifluoromethyl) phenyl)-1-isobutylpiperidine-2-carboxamide (Example 39) afforded the title compounds. MS (ESI, pos. ion.) m/z: 565 (M+1).

EXAMPLE 42

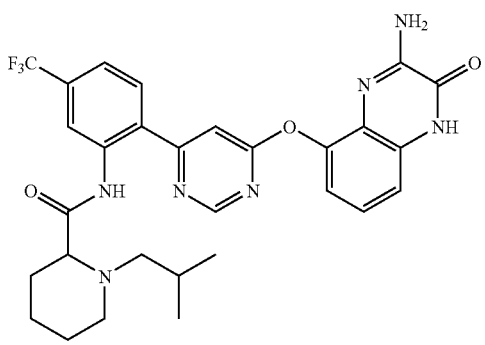

N-(2-(6-(3-Amino-2-oxo-1,2-dihydroquinoxalin-5-yloxy)pyrimidin-4-yl)-5-(trifluoromethyl)phenyl)-1-isobutylpiperidine-2-carboxamide. A mixture of 3-amino-5-hydroxyquinoxalin-2(1H)-one (0.067 g, 0.38 mmol, prepared as described in WO04014871), N-(2-(6-chloropyrimidin-4-yl)-5-(trifluoromethyl)-phenyl)-1-isobutylpiperidine-2-carboxamide, Example 39(e), (0.14 g, 0.32 mmol) and $Cs_2CO_3$ (0.12 g, 0.38 mmol, Strem) in DMF (2.5 mL) was stirred for 3 d at 25° C. The mixture was diluted with aqueous solution of $NaHCO_3$ (100 mL) and extracted with 1:1 mixture of EtOAc/hexane (2×75 mL). The combined extracts were washed with $H_2O$ (2×75 mL) and brine (75 mL), dried over $Na_2SO_4$, filtered, and evaporated under reduced pressure. Purification of the residue by silica gel column chromatography (gradient: 25-60% EtOAc/hexane) afforded the title compound as a white solid. MS (ESI, pos. ion.) m/z: 582 (M+1). Mp: >250° C.

EXAMPLE 43

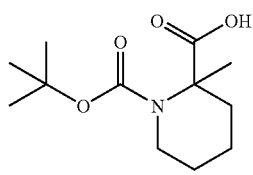

(a) 1-(tert-Butoxycarbonyl)-2-methylpiperidine-2-carboxylic acid. 2-Methyl-2-piperidinecarboxylic acid (1.0 g, 5.6 mmol, Tyger Scientific) was reacted with di-tert-butyl dicarbonate (2.8 g, 13 mmol, Aldrich) under the conditions of Example 37(a) to give the title compound as a white solid. MS (ESI, neg. ion) m/z: 242 (M−1).

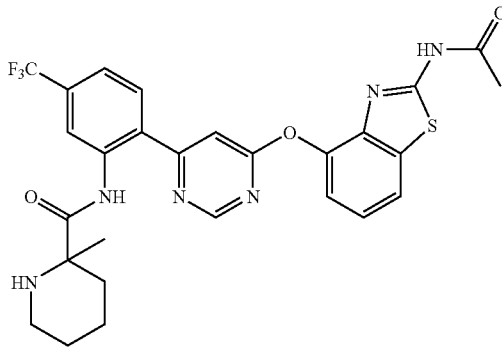

(b) N-(2-(6-(2-Acetamidobenzo[d]thiazol-4-yloxy)pyrimidin-4-yl)-5-(trifluoromethyl)phenyl)-2-methylpiperidine-2-carboxamide. 1-(tert-Butoxycarbonyl)-2-methylpiperidine-2-carboxylic acid from step (a) above (0.75 g, 3.1 mmol) was reacted with N-(4-(6-(2-amino-4-(trifluoromethyl)phenyl)pyrimidin-4-yloxy)-benzo[d]thiazol-2-yl)acetamide (0.46 g, 1.0 mmol, prepared as described in WO04014871) under the conditions of Example 39(d) to give the title compound as a yellow solid. MS (ESI, pos. ion) m/z: 571 (M+1). Mp: 146.4-148.8° C.

EXAMPLE 44

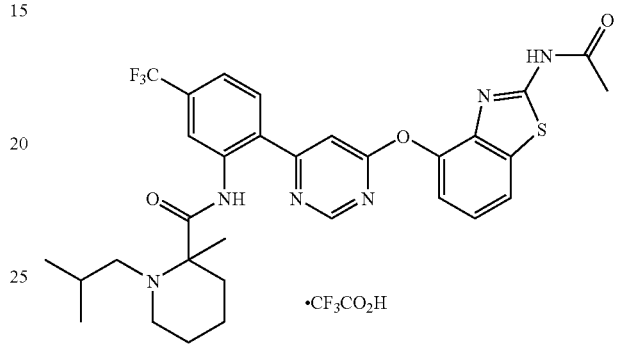

N-(2-(6-(2-Acetamidobenzo[d]thiazol-4-yloxy)pyrimidin-4-yl)-5-(trifluoromethyl)phenyl)-1-isobutyl-2-methylpiperidine-2-carboxamide trifluoroacetic acid salt. N-(2-(6-(2-Acetamidobenzo[d]thiazol-4-yloxy)pyrimidin-4-yl)-5-(trifluoromethyl)phenyl)-2-methylpiperidine-2-carboxamide, Example 43(b), (0.14 g, 0.24 mmol) was reacted with isobutyraldehyde (0.044 mL, 0.48 mmol) under the conditions of Example 3(d) to give the crude product. Purification by reverse phase preparative HPLC [Phenomenex Prodigy 5μ ODS-3 100 Å column, gradient: 3-100% $CH_3CN$ (0.1% TFA)/$H_2O$ (0.1% TFA) over 15 min] afforded the title compound as a pale-yellow solid. MS (ESI, pos. ion.) m/z: 627 (M+1). Mp: <80° C.

EXAMPLE 45

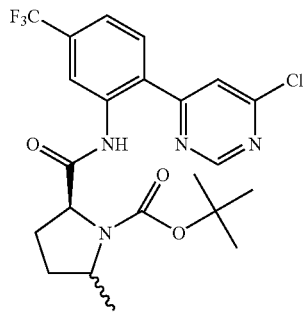

(a) (2S,5S,R)-tert-Butyl 2-((2-(6-chloropyrimidin-4-yl)-5-(trifluoromethyl)-phenyl)carbamoyl)-5-methylpyrrolidine-1-carboxylate. To a solution of 2-(6-chloropyrimidin-4-yl)-5-(trifluoromethyl)benzenamine, Example 39(c), (0.26 g, 0.96 mmol) and (2S,5R,S)-1-(tert-butoxycarbonyl)-5-methylpyrrolidine-2-carboxylic acid (0.20 g, 0.87 mmol, AnaSpec) in $CH_2Cl_2$ (5 mL) was added 1-[3-(dimethylamino)propyl]-3-ethylcarbodiimide hydrochloride (0.18 g, 0.96 mmol, Aldrich) at 25° C. The reaction mixture was stirred at 25° C. for 3 d and partitioned between 1:1 mixture of EtOAc/hexane (100 mL) and H₂O (100 mL). The organic phase was separated, washed with H₂O (100 mL) and brine (100 mL), dried over Na₂SO₄, filtered and evaporated under reduced pressure. Purification of the residue by silica gel column chromatography (gradient: 1-15% EtOAc/hexane) afforded the title compound as a mixture of diastereoisomers. MS (ESI, pos. ion.) m/z: 485 (M+1).

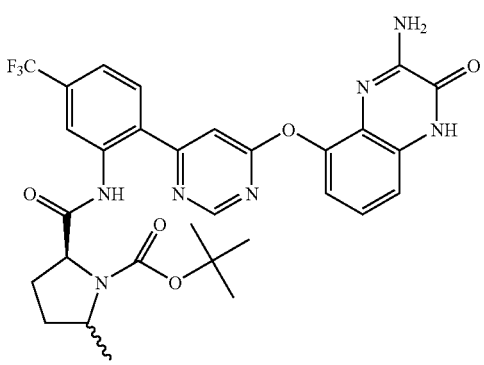

(b) (2S,5S,R)-tert-Butyl 2-((2-(6-(3-amino-2-oxo-1,2-dihydroquinoxalin-5-yloxy)pyrimidin-4-yl)-5-(trifluoromethyl)phenyl)carbamoyl)-5-methylpyrrolidine-1-carboxylate. (2S,5S,R)-tert-Butyl 2-((2-(6-chloropyrimidin-4-yl)-5-(trifluoromethyl)phenyl)carbamoyl)-5-methylpyrrolidine-1-carboxylate from step (a) above (0.22 g, 0.45 mmol) was reacted with 3-amino-5-hydroxyquinoxalin-2(1H)-one (0.096 g, 0.54 mmol, prepared as described in WO04014871) under the conditions of Example 42 to afford the title compound as mixture of diastereoisomers. MS (ESI, pos. ion) m/z: 626 (M+1).

EXAMPLE 46

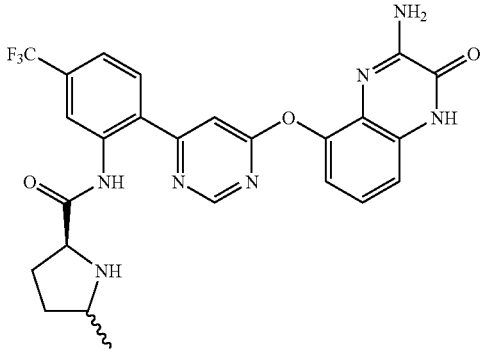

(2S,5R,S)-N-(2-(6-(3-Amino-2-oxo-1,2-dihydroquinoxalin-5-yloxy)pyrimidin-4-yl)-5-(trifluoromethyl)phenyl)-5-methylpyrrolidine-2-carboxamide. (2S,5S,R)-tert-Butyl 2-((2-(6-(3-amino-2-oxo-1,2-dihydroquinoxalin-5-yloxy)pyrimidin-4-yl)-5-(trifluoromethyl)phenyl)carbamoyl)-5-methylpyrrolidine-1-carboxylate, Example 45(b), (0.19 g, 0.30 mmol) was reacted with 1:1 mixture of DCM/TFA under the conditions of Example 3(c) to give the title compound as mixture of diastereoisomers. MS (ESI, pos. ion) m/z: 526 (M+1).

EXAMPLE 47

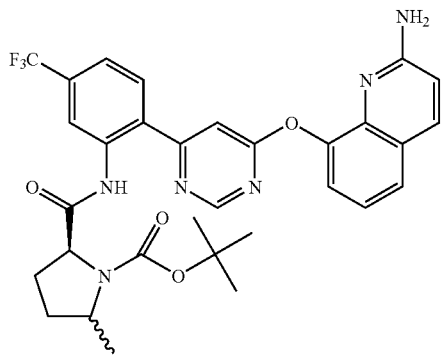

(2S,5R,S)-tert-Butyl 2-((2-(6-(2-aminoquinolin-8-yloxy)pyrimidin-4-yl)-5-(trifluoromethyl)phenyl)carbamoyl)-5-methylpyrrolidine-1-carboxylate. (2S,5R,S)-tert-Butyl 2-((2-(6-chloropyrimidin-4-yl)-5-(trifluoromethyl)phenyl)-carbamoyl)-5-methylpyrrolidine-1-carboxylate, Example 45(a), (0.11 g, 0.22 mmol) was reacted with 2-amino-8-hydroxyquinoline (0.042 g, 0.26 mmol, Fluka) under the conditions of Example 39(f) to afford the title compound as a mixture of diastereoisomers. MS (ESI, pos. ion.) m/z: 609 (M+1).

EXAMPLE 48

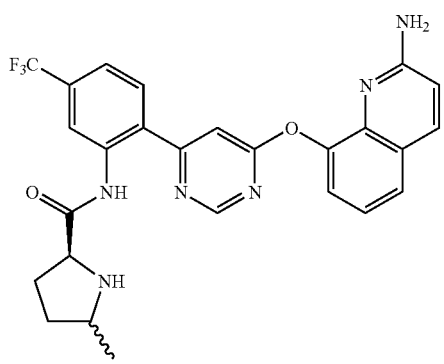

(2S,5R,S)-N-(2-(6-(2-Aminoquinolin-8-yloxy)pyrimidin-4-yl)-5-(trifluoromethyl)phenyl)-5-methylpyrrolidine-2-carboxamide (2S,5R,S)-tert-Butyl 2-((2-(6-(2-aminoquinolin-8-yloxy)pyrimidin-4-yl)-5-(trifluoromethyl)phenyl)carbamoyl)-5-methylpyrrolidine-1-carboxylate, Example 47, (0.10 g, 0.16 mmol), CH₂Cl₂ (15 mL) was reacted with 1:1 mixture of DCM/TFA under the conditions of Example 3(c) to give the title compound as a mixture of diastereoisomers. MS (ESI, pos. ion.) m/z: 509 (M+1). Mp: 162.9-164.0° C.

EXAMPLE 49

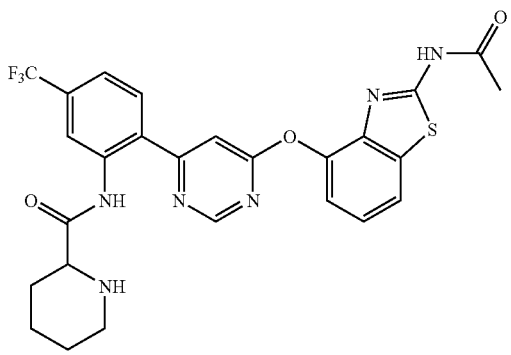

(a) N-(2-(6-(2-Acetamidobenzo[d]thiazol-4-yloxy)pyrimidin-4-yl)-5-(trifluoromethyl)phenyl)piperidine-2-carboxamide. A mixture of N-(4-(6-(2-amino-4-(trifluoromethyl)phenyl)pyrimidin-4-yloxy)benzo[d]thiazol-2-yl) acetamide (3.0 g, 6.7 mmol, prepared as described in WO04014871), 1-(tert-butoxycarbonyl)-2-piperidinecarboxylic acid (3.9 g, 17 mmol, Aldrich), N,N-diisopropylethylamine (7.0 mL, 40 mmol, Aldrich) and chloro-dipyrrolidinocarbenium hexafluorophosphate (5.6 g, 17 mmol, Fluka) in CH$_2$Cl$_2$ (30 mL) was divided into three equal portions and placed into three glass reaction vials. The reaction vials were stirred and heated by a microwave synthesizer at 100° C. for 30 min, at 110° C. for 30 min and at 115° C. for 45 min. The reaction vials were cooled to room temperature and additional amounts of 1-(tert-butoxycarbonyl)-2-piperidinecarboxylic acid (1.3 g, 5.6 mmol, Aldrich) and chloro-dipyrrolidinocarbenium hexafluorophosphate (1.86 g, 5.6 mmol, Fluka) were added into each vial. The vials were heated at 110° C. by a microwave synthesizer for 45 min and cooled to 25° C. The reaction mixtures of the three vials were combined and partitioned between EtOAc (200 mL) and aq. NaHCO$_3$ (100 mL). The organic phase was separated, washed with brine, dried over Na$_2$SO$_4$, filtered, and evaporated under reduced pressure. Purification of the residue by silica gel column chromatography [gradient: 0.5-5.0% MeOH (2 M in NH$_3$)/CH$_2$Cl$_2$] afforded the title compound as a pale-yellow solid. MS (ESI, pos. ion.) m/z: 557 (M+1).

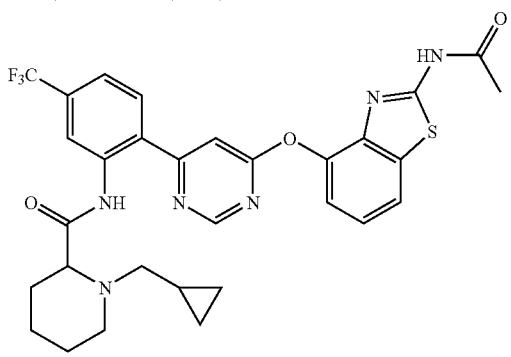

(b) N-(2-(6-(2-Acetamidobenzo[d]thiazol-4-yloxy) pyrimidin-4-yl)-5-(trifluoromethyl)phenyl)-1-(cyclopropylmethyl)piperidine-2-carboxamide N-(2-(6-(2-Acetamidobenzo[d]thiazol-4-yloxy)pyrimidin-4-yl)-5-(trifluoromethyl)phenyl)piperidine-2-carboxamide from step (a) above (0.40 g, 0.72 mmol) was reacted with cyclopropanecarboxaldehyde (0.16 mL, 2.2 mmol, Aldrich) under the conditions of Example 3(d) to give the title compound as an off-white solid. MS (ESI, pos. ion.) m/z: 611 (M+1). Mp: 212.3-213.5° C.

EXAMPLE 50

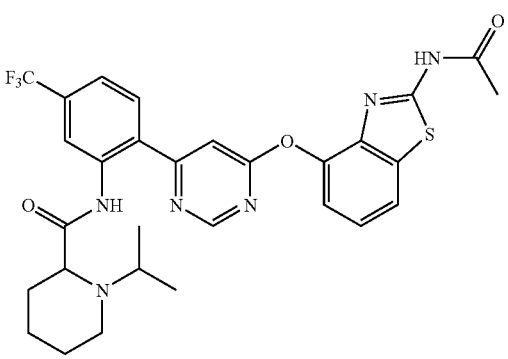

N-(2-(6-(2-Acetamidobenzo[d]thiazol-4-yloxy)pyrimidin-4-yl)-5-(trifluoromethyl)phenyl)-1-isopropylpiperidine-2-carboxamide. N-(2-(6-(2-Acetamidobenzo[d]thiazol-4-yloxy)pyrimidin-4-yl)-5-(trifluoromethyl)phenyl)-piperidine-2-carboxamide, Example 49(a), (0.40 g, 0.72 mmol) was reacted with acetone under the conditions of Example 3(d) to give the title compound. MS (ESI, pos. ion.) m/z: 599 (M+1). Mp: 260° C. (with dec.).

EXAMPLE 51

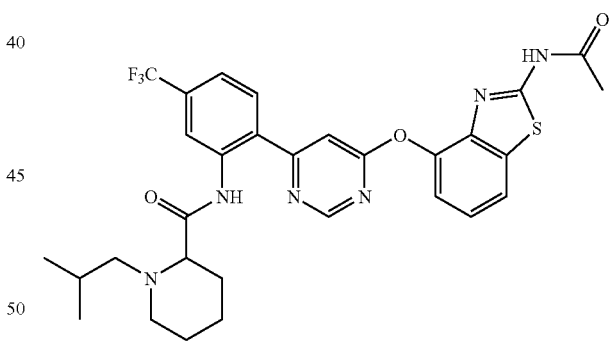

N-(2-(6-(2-Acetamidobenzo[d]thiazol-4-yloxy)pyrimidin-4-yl)-5-(trifluoromethyl)phenyl)-1-isobutylpiperidine-2-carboxamide N-(2-(6-(2-Acetamidobenzo[d]thiazol-4-yloxy)pyrimidin-4-yl)-5-(trifluoromethyl)phenyl)piperidine-2-carboxamide, Example 49(a), (0.50 g, 0.90 mmol) was reacted with isobutyraldehyde (0.16 mL, 1.8 mmol, Aldrich) under the conditions of Example 3(d) to give the title compound as a white solid. MS (ESI, pos. ion) m/z: 613 (M+1). Mp: 153.4-154.9° C.

EXAMPLE 52 AND EXAMPLE 53

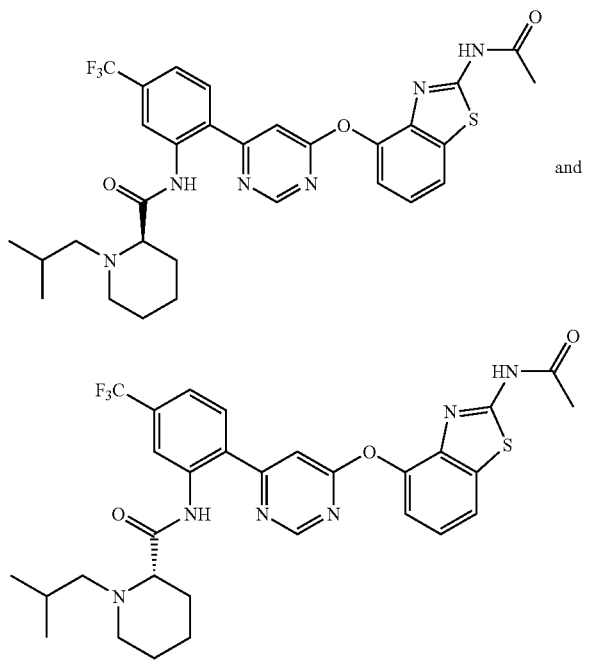

and (2R)-N-(2-(6-(2-Acetamidobenzo[d]thiazol-4-yloxy)pyrimidin-4-yl)-5-(trifluoromethyl)phenyl)-1-isobutylpiperidine-2-carboxamide and (2S)-N-(2-(6-(2-Acetamidobenzo[d]thiazol-4-yloxy)pyrimidin-4-yl)-5-(trifluoromethyl)phenyl)-1-isobutylpiperidine-2-carboxamide. Chiral separation [Chiralcel OD-H (250×21 mm, 5µ), A: hexane (0.2% diethylamine), B: ethanol (0.2% diethylamine), isocratic: 60:40 A:B, 20 mL/min] of N-(2-(6-(2-acetamido-benzo[d]-thiazole-4-yloxy)pyrimidin-4-yl)-5-(trifluoromethyl)phenyl)-1-isobutylpiperidine-2-carboxamide (Example 51) afforded the title compounds as amorphous solids. MS (ESI, pos. ion) m/z: 613 (M+1).

EXAMPLE 54

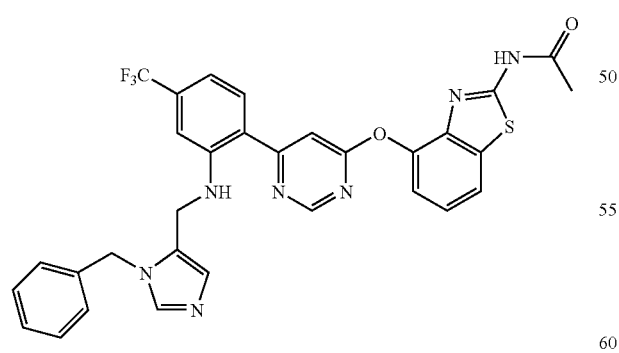

N-(4-(6-(2-((1-Benzyl-1H-imidazol-5-yl)methylamino)-4-(trifluoromethyl)-phenyl)pyrimidin-4-yloxy)benzo[d]thiazol-2-yl)acetamide. A mixture of N-(4-(6-(2-amino-4-(trifluoromethyl)phenyl)pyrimidin-4-yloxy)benzo[d]thiazol-2-yl)-acetamide (0.20 g, 0.45 mmol, prepared as described in WO04014871) and 1-benzyl-1H-imidazole-5-carbaldehyde (0.21 g, 1.1 mmol, Combi-Blocks) in 1,2-dichloroethane (4 mL) was stirred for 24 h at 25° C. Sodium triacetoxy-borohydride (0.24 g, 1.1 mmol) was added and the mixture was stirred for 4 d at 25° C. Additional amounts of 1-benzyl-1H-imidazole-5-carbaldehyde (0.21 g, 1.1 mmol, Combi-Blocks) and sodium triacetoxyborohydride (0.24 g, 1.1 mmol) were added, and the mixture was stirred for 24 h at 25° C. The mixture was partitioned between $H_2O$ and EtOAc, the organic phase was separated, washed with $H_2O$ and brine, dried over $Na_2SO_4$, and filtered. The filtrate was evaporated under reduced pressure and the residue was purified by silica gel column chromatography [gradient: 0.5-2.2% MeOH (2 M in $NH_3$)/$CH_2Cl_2$] to give the title compound as a yellow solid. MS (ESI, pos. ion) m/z: 616 (M+1). Mp: 264.0-264.1° C.

EXAMPLE 55

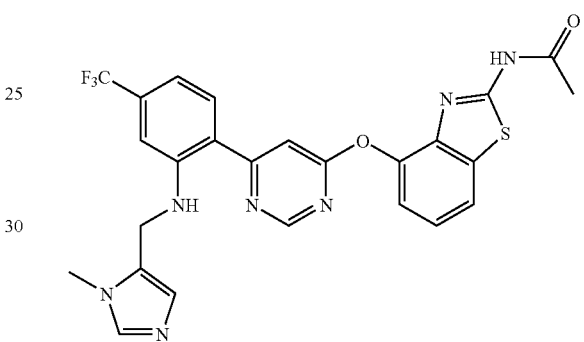

N-(4-(6-(2-((1-Methyl-1H-imidazol-5-yl)methylamino)-4-(trifluoromethyl)-phenyl)pyrimidin-4-yloxy)benzo[d]thiazol-2-yl)acetamide. N-(4-(6-(2-Amino-4-(trifluoromethyl)phenyl)pyrimidin-4-yloxy)benzo[d]thiazol-2-yl) acetamide (prepared as described in WO04014871) was reacted with 1-methyl-1H-imidazole-5-carbaldehyde (Acros) under the conditions of Example 54 to give the title compound. MS (ESI, pos. ion) m/z: 540 (M+1). Mp: 263.0-265.2° C.

EXAMPLE 56

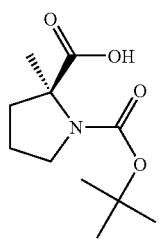

(a) (2S)-1-(tert-Butoxycarbonyl)-2-methylpyrrolidine-2-carboxylic acid. α-Methyl-L-proline (1.0 g, 7.7 mmol, Fluka) was reacted with di-tert-butyl dicarbonate (3.5 g, 16.2 mmol, Aldrich) under the conditions of Example 37(a) to give the title compound as a white solid. MS (ESI, neg. ion.) m/z: 228 (M−1).

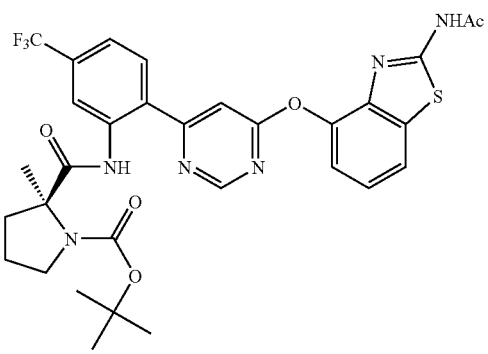

(b) tert-Butyl 2-((2-(6-(2-acetamidobenzo[d]thiazol-4-yloxy)pyrimidin-4-yl)-5-(trifluoromethyl)phenyl)carbamoyl)-2-methylpyrrolidine-1-carboxylate. (S)-1-(tert-Butoxycarbonyl)-2-methylpyrrolidine-2-carboxylic acid from step (a) above (458 mg, 2.0 mmol) was reacted with N-(4-(6-(2-amino-4-(trifluoromethyl)phenyl)pyrimidin-4-yloxy)benzo[d]thiazol-2-yl)acetamide (446 mg, 1.0 mmol, prepared as described in WO04/014871) under the conditions of Example 37(b) to give the title compound as a white solid. MS (ESI, neg. ion.) m/z: 657 (M−1).

EXAMPLE 57

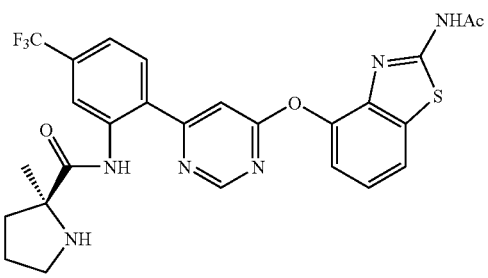

(2S)-N-(2-(6-(2-Acetamidobenzo[d]thiazol-4-yloxy)pyrimidin-4-yl)-5-(trifluoromethyl)phenyl)-2-methylpyrrolidine-2-carboxamide. The title product was obtained as a side product of the reaction described in Example 56. MS (ESI, pos. ion.) m/z: 557 (M+1).

EXAMPLE 58

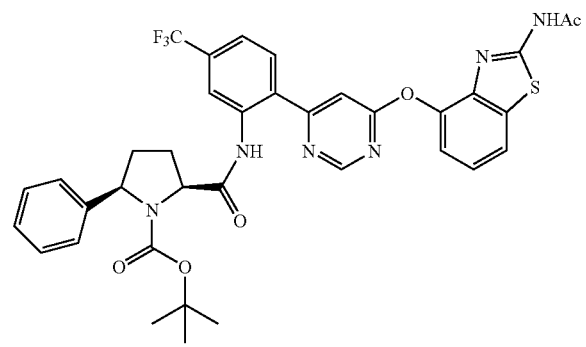

(2S,5R)-tert-Butyl 2-((2-(6-(2-acetamidobenzo[d]thiazol-4-yloxy)pyrimidin-4-yl)-5-(trifluoromethyl)phenyl)carbamoyl)-5-phenylpyrrolidine-1-carboxylate. (2S,5R)-1-(tert-Butoxycarbonyl)-5-phenylpyrrolidine-2-carboxylic acid (350 mg, 1.2 mmol, Neosystem-T) was reacted with N-(4-(6-(2-amino-4-(trifluoromethyl)-phenyl)pyrimidin-4-yloxy)benzo[d]thiazol-2-yl)acetamide (446 mg, 1.0 mmol, prepared as described in WO04014871) under the conditions of Example 45(a) to give the title compound as a white solid. MS (ESI, neg. ion.) m/z: 719 (M−1).

EXAMPLE 59

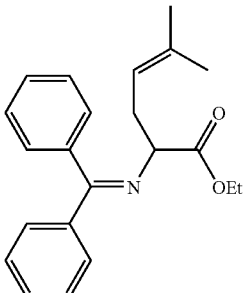

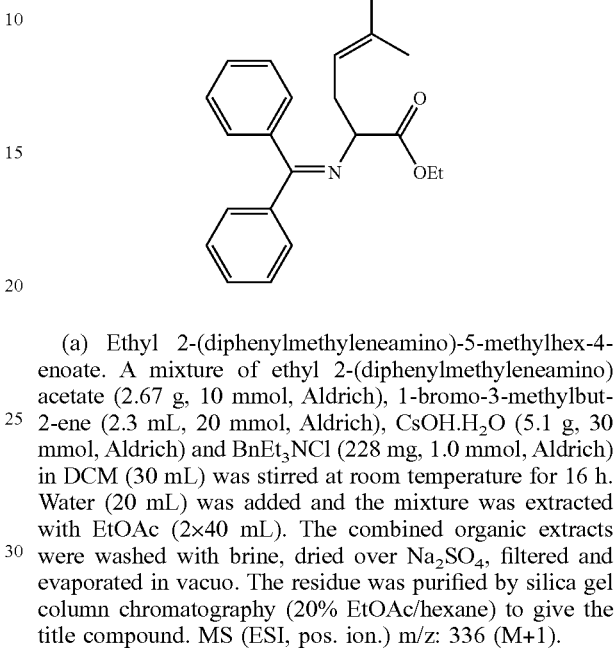

(a) Ethyl 2-(diphenylmethyleneamino)-5-methylhex-4-enoate. A mixture of ethyl 2-(diphenylmethyleneamino)acetate (2.67 g, 10 mmol, Aldrich), 1-bromo-3-methylbut-2-ene (2.3 mL, 20 mmol, Aldrich), CsOH.H$_2$O (5.1 g, 30 mmol, Aldrich) and BnEt$_3$NCl (228 mg, 1.0 mmol, Aldrich) in DCM (30 mL) was stirred at room temperature for 16 h. Water (20 mL) was added and the mixture was extracted with EtOAc (2×40 mL). The combined organic extracts were washed with brine, dried over Na$_2$SO$_4$, filtered and evaporated in vacuo. The residue was purified by silica gel column chromatography (20% EtOAc/hexane) to give the title compound. MS (ESI, pos. ion.) m/z: 336 (M+1).

(b) Ethyl 2-amino-5-methylhex-4-enoate. A solution of ethyl 2-(diphenylmethyleneamino)-5-methylhex-4-enoate from step (a) above (2.71 g, 8 mmol) in a 1:1:1 mixture of THF/H$_2$O/AcOH (30 mL) was stirred at room temperature for 2 h. The reaction mixture was evaporated in vacuo and the residue was dissolved in EtOAc (50 mL). The solution was washed with saturated aqueous solution of NaHCO$_3$ (30 mL) and brine (20 mL), dried over Na$_2$SO$_4$, and filtered. The solvent was removed in vacuo and the residue was purified by silica gel column chromatography (EtOAc) to give the title compound. MS (ESI, pos. ion.) m/z: 172 (M+1).

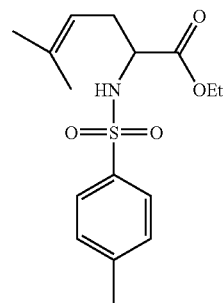

(c) Ethyl 5-methyl-2-(4-methylphenylsulfonamido)hex-4-enoate. A mixture of ethyl 2-amino-5-methylhex-4-enoate from step (b) above (1.2 g, 7.0 mmol), p-toluenesulfonyl chloride (2.0 g, 11 mmol, Aldrich) and pyridine (1.13 mL, 14 mmol, Aldrich) in DCM (20 mL, Aldrich) was stirred at room temperature for 2 h. Saturated aqueous solution of NaHCO$_3$ (20 mL) was added and the mixture was extracted with EtOAc (2×40 mL). The combined organic extracts were washed with brine (10 mL), dried over Na$_2$SO$_4$ and filtered. The filtrate was evaporated in vacuo and the residue was purified by silica gel column chromatography (20% EtOAc/hexane) to give the title compound. MS (ESI, pos. ion.) m/z: 326 (M+1).

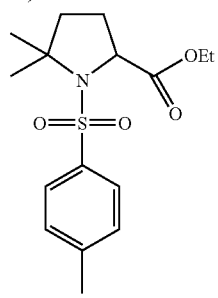

(d) Ethyl 5,5-dimethyl-1-tosylpyrrolidine-2-carboxylate. To a solution of ethyl 5-methyl-2-(4-methylphenylsulfonamido)hex-4-enoate from step (c) above (1.95 g, 6 mmol) in chloroform (20 mL) was added CF$_3$SO$_3$H (0.27 mL, 3.0 mmol, Aldrich) dropwise with stirring at 0° C. After the addition, the mixture was stirred at 0° C. for 2 h. The reaction mixture was allowed to reach room temperature and was diluted with EtOAc (50 mL). The mixture was washed with saturated aqueous solution of NaHCO$_3$ (30 mL) and brine (20 mL), dried over Na$_2$SO$_4$ and filtered. The filtrate was evaporated in vacuo and the residue was purified by silica gel column chromatography (20% EtOAc/hexanes) to give the title compound as a white solid. MS (ESI, pos. ion.) m/z: 326 (M+1).

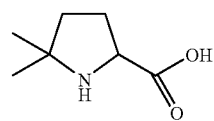

(e) 5,5-Dimethylpyrrolidine-2-carboxylic acid. A mixture of ethyl 5,5-dimethyl-1-tosylpyrrolidine-2-carboxylate from step (d) above (1.62 g, 5.0 mmol) and phenol (1.4 g, 15 mmol, Aldrich) in 50 mL of 48% HBr (Aldrich) was stirred at 70° C. for 5 h. The reaction mixture was allowed to reach room temperature and was extracted with 80% EtOAc/hexane (2×40 mL). The combined extracts were evaporated under reduced pressure and the residue was dried under vacuo to give the crude title compound, which was used in the next step without additional purification.

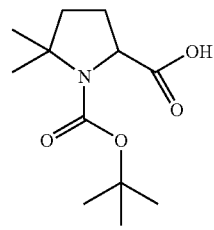

(f) 1-(tert-Butoxycarbonyl)-5,5-dimethylpyrrolidine-2-carboxylic acid. To a mixture of 5,5-dimethylpyrrolidine-2-carboxylic acid from step (e) above (5 mmol) and 5N NaOH (4 mL) in THF (30 mL) was added di-tert-butyl dicarbonate (1.64 g, 7.5 mmol, Aldrich) portionwise with stirring at 0° C. The reaction mixture was allowed to reach room temperature and the stirring was continued for 2 h. The reaction mixture was quenched with 1N HCl (30 mL) and extracted with EtOAc (2×50 mL). The combined organic extracts were washed with brine (10 mL), dried over Na$_2$SO$_4$ and filtered. The filtrate was evaporated in vacuo and the residue was purified by silica gel column chromatography (EtOAc) to give the title compound. MS (ESI, pos. ion) m/z: 244 (M+1).

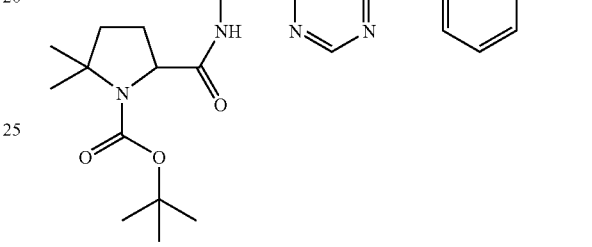

(g) tert-Butyl 5-((2-(6-(2-acetamidobenzo[d]thiazol-4-yloxy)pyrimidin-4-yl)-5-(trifluoromethyl)phenyl)carbamoyl)-2,2-dimethylpyrrolidine-1-carboxylate. 1-(tert-Butoxycarbonyl)-5,5-dimethylpyrrolidine-2-carboxylic acid from step (f) above (243 mg, 1.0 mmol) was reacted with N-(4-(6-(2-amino-4-(trifluoromethyl)phenyl)pyrimidin-4-yloxy)benzo[d]thiazol-2-yl)acetamide (446 mg, 1.0 mmol, prepared as described in WO04014871) under the conditions of Example 45(a) to give the title compound as a white solid. MS (ESI, neg. ion.) m/z: 671 (M−1).

EXAMPLE 60

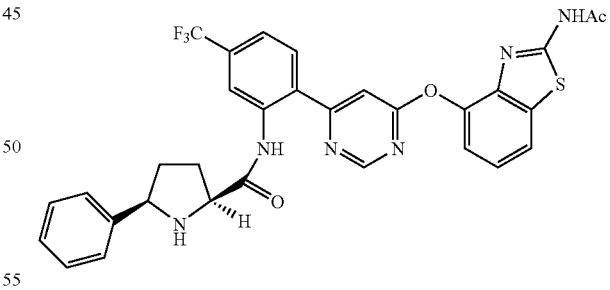

(2S,5R)-N-(2-(6-(2-Acetamidobenzo[d]thiazol-4-yloxy)pyrimidin-4-yl)-5-(trifluoromethyl)phenyl)-5-phenylpyrrolidine-2-carboxamide (2S,5R)-tert-Butyl 2-((2-(6-(2-acetamidobenzo[d]thiazol-4-yloxy)pyrimidin-4-yl)-5-(trifluoromethyl)phenyl)carbamoyl)-5-phenylpyrrolidine-1-carboxylate, Example 58, (575 mg, 0.8 mmol) was reacted with TFA under the condition of Example 3(c) to give the title compound as a white solid. MS (ESI, pos. ion.) m/z: 619 (M+1).

EXAMPLE 61

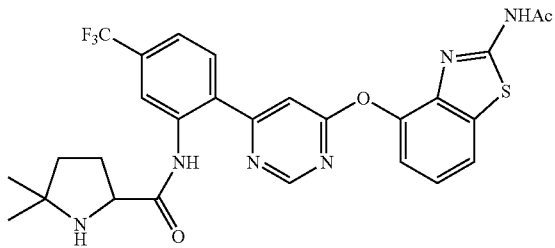

N-(2-(6-(2-Acetamidobenzo[d]thiazol-4-yloxy)pyrimidin-4-yl)-5-(trifluoromethyl)phenyl)-5,5-dimethylpyrrolidine-2-carboxamide. The title compound was prepared by reacting tert-butyl 5-((2-(6-(2-acetamidobenzo[d]thiazol-4-yloxy)pyrimidin-4-yl)-5-(trifluoromethyl)phenyl)carbamoyl)-2,2-dimethylpyrrolidine-1-carboxylate [Example 59 (g)] with TFA under the condition of Example 3(c). MS (ESI, pos. ion.) m/z: 619 (M+1).

EXAMPLE 62

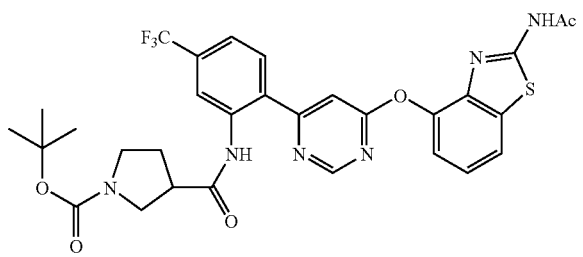

(a) tert-Butyl 3-((2-(6-(2-acetamidobenzo[d]thiazol-4-yloxy)pyrimidin-4-yl)-5-(trifluoromethyl)phenyl)carbamoyl)pyrrolidine-1-carboxylate. 1-(tert-Butoxycarbonyl)pyrrolidine-3-carboxylic acid (258 mg, 1.2 mmol, Astatech) was reacted with N-(4-(6-(2-amino-4-(trifluoromethyl)phenyl)pyriridin-4-yloxy)-benzo[d]thiazol-2-yl)acetamide (446 mg, 1.0 mmol, prepared as described in WO04014871) under the conditions of Example 45(a) to give the title compound as a white solid. MS (ESI, neg. ion.) m/z: 643 (M−1).

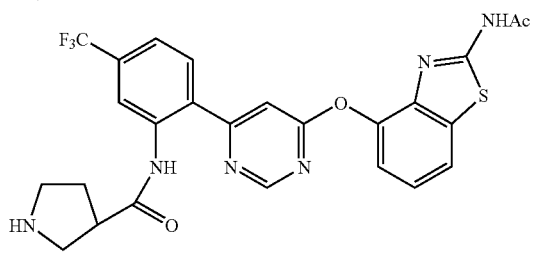

(b) N-(2-(6-(2-Acetamidobenzo[d]thiazol-4-yloxy)pyrimidin-4-yl)-5-(trifluoromethyl)phenyl)pyrrolidine-3-carboxamide. tert-Butyl 3-((2-(6-(2-acetamidobenzo[d]thiazol-4-yloxy)pyrimidin-4-yl)-5-(trifluoromethyl)phenyl)carbamoyl)pyrrolidine-1-carboxylate from step (a) above (516 mg, 0.8 mmol) was reacted with 1:1 mixture of TFA/DCM (4 mL) under the conditions of Example 3(d) to give the title compound as a white solid. MS (ESI, pos. ion) m/z: 543 (M+1).

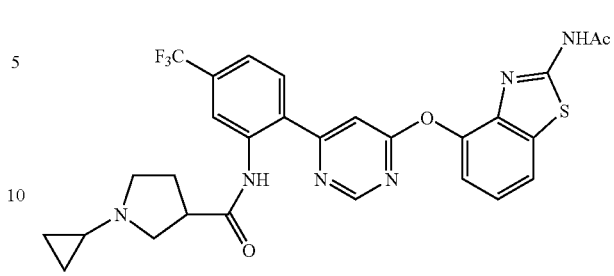

(c) N-(2-(6-(2-Acetamidobenzo[d]thiazol-4-yloxy)pyrimidin-4-yl)-5-(trifluoromethyl)phenyl)-1-cyclopropylpyrrolidine-3-carboxamide. A mixture of N-(2-(6-(2-acetamidobenzo[d]thiazol-4-yloxy)pyrimidin-4-yl)-5-(trifluoromethyl)-phenyl)pyrrolidine-3-carboxamide from step (b) above (54 mg, 0.1 mmol), (1-ethoxycyclopropoxy)trimethylsilane (0.10 mL, 0.5 mmol, Aldrich), sodium cyanoborohydride (25 mg, 0.4 mmol, Aldrich) and acetic acid (0.6 mL, Aldrich) in methanol (2 mL, Aldrich) was heated at reflux for 16 h. The reaction mixture was allowed to reach room temperature and was filtered. The filtrate was evaporated under reduced pressure and the residue was dissolved in EtOAc (20 mL). The EtOAc solution was washed with saturated aqueous solution of NaHCO$_3$ (10 mL) and brine (5 mL), dried over Na$_2$SO$_4$, and filtered. The filtrate was evaporated in vacuo and the residue was purified by silica gel column chromatography (50% EtOAc/hexane) to give the title compound as a white solid. MS (ESI, pos. ion.) m/z: 583 (M+1).

EXAMPLE 63

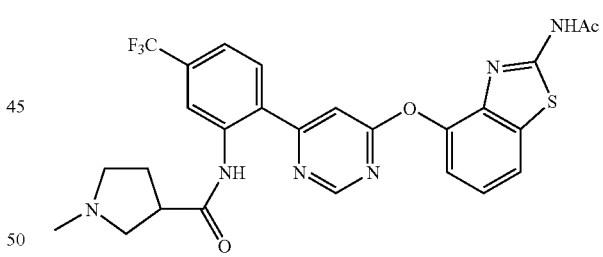

N-(2-(6-(2-Acetamidobenzo[d]thiazol-4-yloxy)pyrimidin-4-yl)-5-(trifluoromethyl)phenyl)-1-methylpyrrolidine-3-carboxamide. A mixture of N-(2-(6-(2-acetamidobenzo[d]thiazol-4-yloxy)pyrimidin-4-yl)-5-(trifluoromethyl)phenyl)-pyrrolidine-2-carboxamide, Example 62(b), (108 mg, 0.2 mmol), MeI (0.014 mL, 0.24 mmol, Aldrich) and NaHCO$_3$ (33 mg, 0.4 mmol) in DMF (2 mL) was stirred at room temperature for 18 h. The mixture was diluted with water (5 mL) and extracted with EtOAc (2×20 mL). The combined organic extracts were washed with brine (5 mL), dried over Na$_2$SO$_4$, filtered and evaporated under reduced pressure. The residue was purified by silica gel column chromatography (10% MeOH/EtOAc) to give the title compound as a white solid. MS (ESI, pos. ion.) m/z: 557 (M+1).

EXAMPLE 64

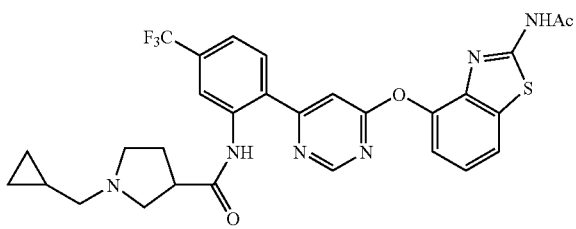

N-(2-(6-(2-Acetamidobenzo[d]thiazol-4-yloxy)pyrimidin-4-yl)-5-(trifluoromethyl)phenyl)-1-(cyclopropylmethyl)pyrrolidine-3-carboxamide. The title compound was prepared by reacting N-(2-(6-(2-acetamidobenzo[d]thiazol-4-yloxy)pyrimidin-4-yl)-5-(trifluoromethyl)phenyl)pyrrolidine-2-carboxamide [Example 62(b)] with cyclopropanecarboxaldehyde (Aldrich) under the conditions of Example 3(d). MS (ESI, pos. ion.) m/z: 597 (M+1).

EXAMPLE 65

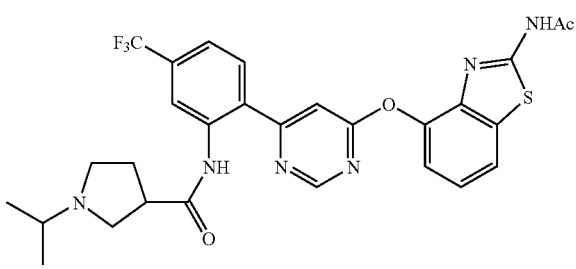

N-(2-(6-(2-Acetamidobenzo[d]thiazol-4-yloxy)pyrimidin-4-yl)-5-(trifluoromethyl)phenyl)-1-isopropylpyrrolidine-3-carboxamide. The title compound was prepared by reacting N-(2-(6-(2-acetamidobenzo[d]thiazol-4-yloxy)pyrimidin-4-yl)-5-(trifluoromethyl)phenyl)pyrrolidine-2-carboxamide [Example 62(b)] with acetone under the conditions of Example 3(d). MS (ESI, pos. ion.) m/z: 585 (M+1).

EXAMPLE 66

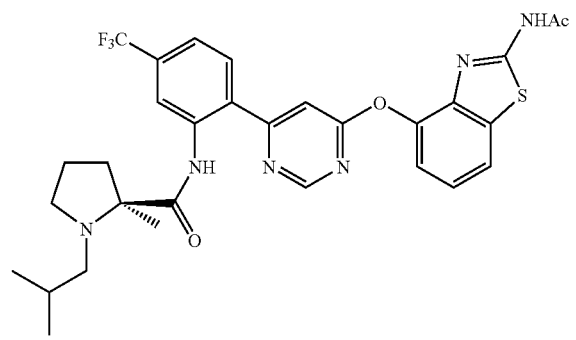

(2S)-N-(2-(6-(2-Acetamidobenzo[d]thiazol-4-yloxy)pyrimidin-4-yl)-5-(trifluoromethyl)phenyl)-1-isobutyl-2-methylpyrrolidine-2-carboxamide. (2S)-N-(2-(6-(2-Acetamidobenzo[d]thiazol-4-yloxy)pyrimidin-4-yl)-5-(trifluoromethyl)phenyl)-2-methylpyrrolidine-2-carboxamide, Example 57, (56 mg, 0.1 mmol) was reacted with 2-methyl-propionaldehyde (0.011 mL, 0.12 mmol, Aldrich) under the conditions of Example 3(d) to give the title compound as a white solid. MS (ESI, pos. ion.) m/z: 613 (M+1).

EXAMPLE 67

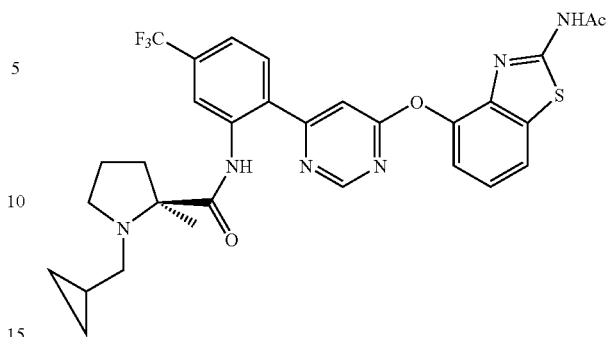

(2S)-N-(2-(6-(2-Acetamidobenzo[d]thiazol-4-yloxy)pyrimidin-4-yl)-5-(trifluoromethyl)phenyl)-1-(cyclopropylmethyl)-2-methylpyrrolidine-2-carboxamide. (2S)-N-(2-(6-(2-Acetamidobenzo[d]thiazol-4-yloxy)pyrimidin-4-yl)-5-(trifluoromethyl)phenyl)-2-methylpyrrolidine-2-carboxamide (Example 57) was reacted with cyclopropanecarboxaldehyde (Aldrich) under the conditions of Example 3(d) to give the title compound as a white solid. MS (ESI, pos. ion.) m/z: 611 (M+1).

EXAMPLE 68

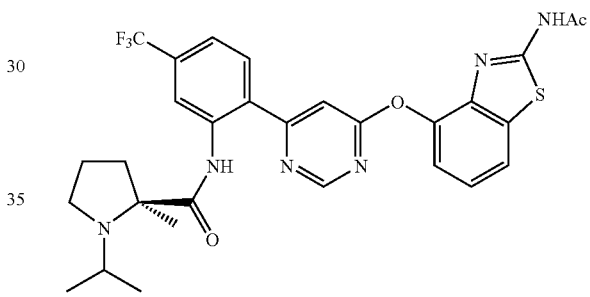

(2S)-N-(2-(6-(2-Acetamidobenzo[d]thiazol-4-yloxy)pyrimidin-4-yl)-5-(trifluoromethyl)phenyl)-1-isopropyl-2-methylpyrrolidine-2-carboxamide. (2S)-N-(2-(6-(2-Acetamidobenzo[d]thiazol-4-yloxy)pyrimidin-4-yl)-5-(trifluoromethyl)phenyl)-2-methylpyrrolidine-2-carboxamide (Example 57) was reacted with acetone under the conditions of Example 3(d) to give the title compound as a white solid. MS (ESI, pos. ion.) m/z: 599 (M+1).

EXAMPLE 69

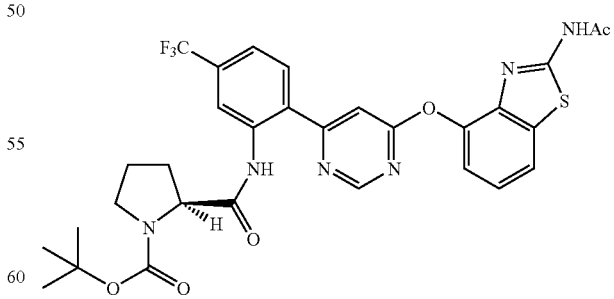

(a) (2S)-tert-Butyl 2-((2-(6-(2-acetamidobenzo[d]thiazol-4-yloxy)pyrimidin-4-yl)-5-(trifluoromethyl)phenyl)carbamoyl)pyrrolidine-1-carboxylate. N-(tert-Butoxycarbonyl)-L-proline (Aldrich) was reacted with N-(4-(6-(2-amino-4-(trifluoromethyl)phenyl)pyrimidin-4-yloxy)benzo[d]

thiazol-2-yl)acetamide (446 mg, 1.0 mmol, prepared as described in WO04/014871) under the conditions of Example 37(b) to give the title compound as a white solid. MS (ESI, pos. ion.) m/z: 643 (M+1).

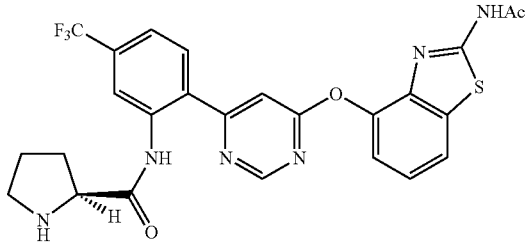

(b) (2S)-N-(2-(6-(2-Acetamidobenzo[d]thiazol-4-yloxy)pyrimidin-4-yl)-5-(trifluoromethyl)phenyl)pyrrolidine-2-carboxamide. (2S)-tert-Butyl 2-((2-(6-(2-acetamidobenzo[d]thiazol-4-yloxy)pyrimidin-4-yl)-5-(trifluoromethyl)phenyl)-carbamoyl)pyrrolidine-1-carboxylate from step (a) above was reacted with 1:1 mixture of TFA/DCM under the conditions of Example 3(c) to give the title compound. MS (ESI, pos. ion.) m/z: 543 (M+1).

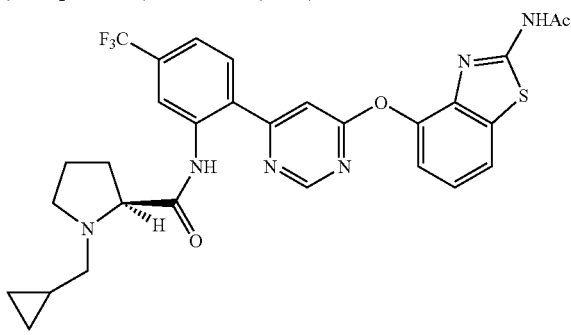

(c) (2S)-N-(2-(6-(2-Acetamidobenzo[d]thiazol-4-yloxy)pyrimidin-4-yl)-5-(trifluoromethyl)phenyl)-1-(cyclopropylmethyl)pyrrolidine-2-carboxamide. (2S)-N-(2-(6-(2-Acetamidobenzo[d]thiazol-4-yloxy)pyrimidin-4-yl)-5-(trifluoromethyl)phenyl)pyrrolidine-2-carboxamide from step (b) above was reacted with cyclopropanecarboxaldehyde (Aldrich) under the conditions of Example 3(d) to give the title compound as a white solid. MS (ESI, pos. ion.) m/z: 597 (M+1).

EXAMPLE 70

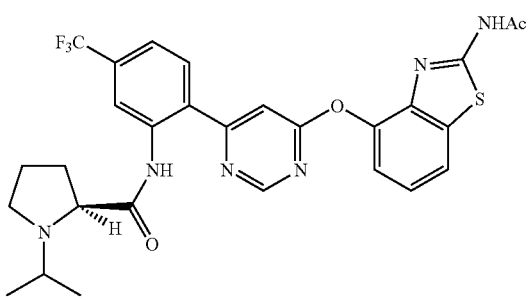

(2S)-N-(2-(6-(2-Acetamidobenzo[d]thiazol-4-yloxy)pyrimidin-4-yl)-5-(trifluoromethyl)phenyl)-1-isopropylpyrrolidine-2-carboxamide. (2S)-N-(2-(6-(2-Acetamidobenzo[d]thiazol-4-yloxy)pyrimidin-4-yl)-5-(trifluoromethyl)phenyl)pyrrolidine-2-carboxamide [Example 69(b)] was reacted with acetone under the conditions of Example 3(d) to give the title compound as a white solid. MS (ESI, pos. ion.) m/z: 585 (M+1).

EXAMPLE 71

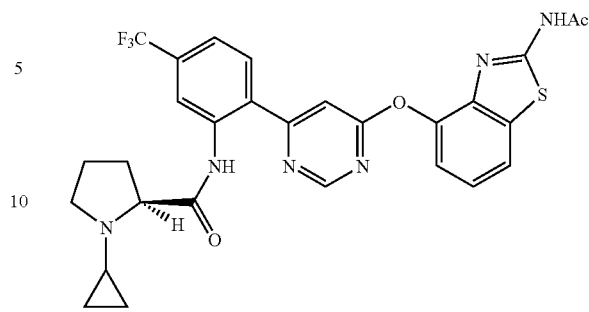

(2S)-N-(2-(6-(2-Acetamidobenzo[d]thiazol-4-yloxy)pyrimidin-4-yl)-5-(trifluoromethyl)phenyl)-1-cyclopropylpyrrolidine-2-carboxamide. (2S)-N-(2-(6-(2-Acetamidobenzo[d]thiazol-4-yloxy)pyrimidin-4-yl)-5-(trifluoromethyl)phenyl)pyrrolidine-2-carboxamide [Example 69(b)] was reacted with (1-ethoxycyclopropoxy)trimethylsilane (Aldrich) under the conditions of Example 62(c) to give the title compound as a white solid. MS (ESI, pos. ion.) m/z: 583 (M+1).

EXAMPLE 72

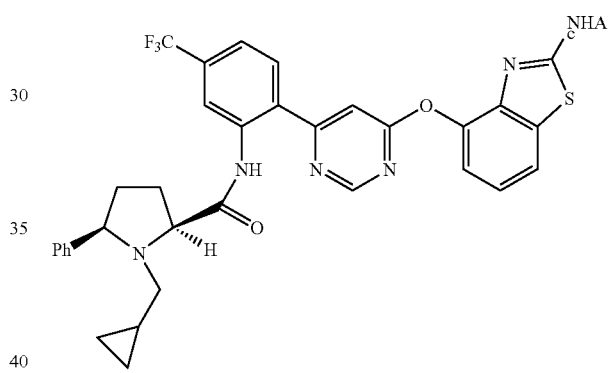

(2S,5R)-N-(2-(6-(2-Acetamidobenzo[d]thiazol-4-yloxy)pyrimidin-4-yl)-5-(trifluoromethyl)phenyl)-1-(cyclopropylmethyl)-5-phenylpyrrolidine-2-carboxamide. (2S,5R)-N-(2-(6-(2-Acetamidobenzo[d]thiazol-4-yloxy)pyrimidin-4-yl)-5-(trifluoromethyl)phenyl)-5-phenylpyrrolidine-2-carboxamide, Example 60, (62 mg, 0.1 mmol) was reacted with cyclopropanecarboxaldehyde (0.009 mL, 0.12 mmol, Aldrich) under the conditions of Example 3(d) to give the title compound as a white solid. MS (ESI, pos. ion.) m/z: 673 (M+1).

EXAMPLE 73

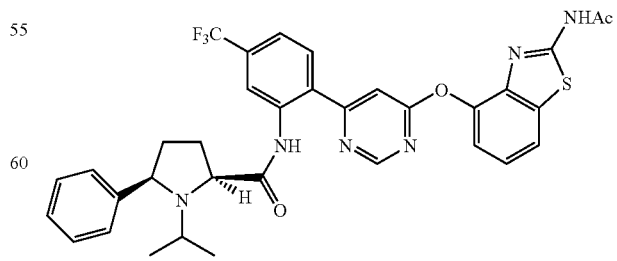

(2S,5R)-N-(2-(6-(2-Acetamidobenzo[d]thiazol-4-yloxy)pyrimidin-4-yl)-5-(trifluoromethyl)phenyl)-1-isopropyl-5-phenylpyrrolidine-2-carboxamide. (2S,5R)-N-(2-(6-(2-Acetamidobenzo[d]thiazol-4-yloxy)pyrimidin-4-yl)-5-(trifluoromethyl)phenyl)-5-phenylpyrrolidine-2-carboxamide, Example 60, (62 mg, 0.1 mmol) was reacted with acetone (0.009 mL, 0.12 mmol) under the conditions of Example 3(d) to give the title compound as a white solid (51 mg, 78%). MS (ESI, pos. ion.) m/z: 661 (M+1).

EXAMPLE 74

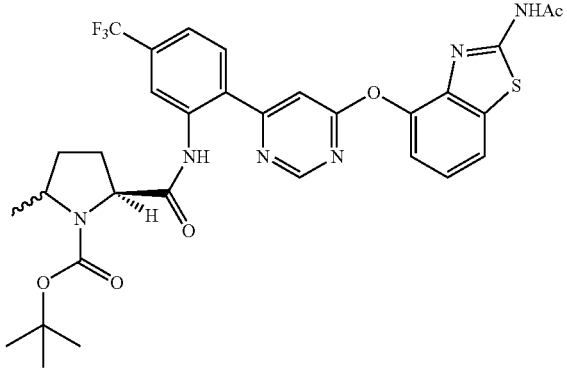

(2S,5R,S)-tert-Butyl 2-((2-(6-(2-acetamidobenzo[d]thiazol-4-yloxy)pyrimidin-4-yl)-5-(trifluoromethyl)phenyl)carbamoyl)-5-methylpyrrolidine-1-carboxylate. N-(4-Hydroxy-benzothiazol-2-yl)-acetamide [Example 19(d)] was reacted with (2S,5R,S)-tert-butyl 2-((2-(6-chloropyrimidin-4-yl)-5-(trifluoromethyl)phenyl)carbamoyl)-5-methylpyrrolidine-1-carboxylate [Example 45(a)] under the conditions of Example 39(f) to give the title compound as a mixture of diastereoisomers. MS (ESI, pos. ion.) m/z: 657 (M+1).

EXAMPLE 75

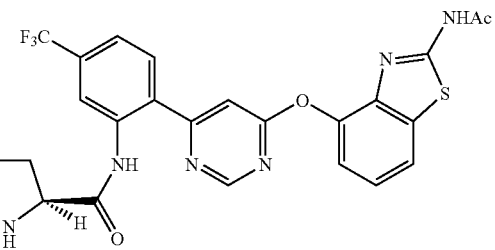

(2S,5R,S)-N-(2-(6-(2-Acetamidobenzo[d]thiazol-4-yloxy)pyrimidin-4-yl)-5-(trifluoromethyl)phenyl)-5-methylpyrrolidine-2-carboxamide. (2S,5R,S)-tert-Butyl 2-((2-(6-(2-acetamidobenzo[d]thiazol-4-yloxy)pyrimidin-4-yl)-5-(trifluoromethyl)phenyl)carbamoyl)-5-methylpyrrolidine-1-carboxylate (Example 74) was reacted with 1:1 mixture of TFA/DCM under the conditions of Example 3(d) to give the title compound as a mixture of diastereoisomers. MS (ESI, pos. ion) m/z: 557 (M+1).

ADDITIONAL EXAMPLES

The following examples were prepared by treating (2S,5R,S)-N-(2-(6-(2-acetamidobenzo[d]thiazol-4-yloxy)pyrimidin-4-yl)-5-(trifluoromethyl)phenyl)-5-methylpyrrolidine-2-carboxamide (Example 75) with acetone or 2-methyl-propionaldehyde under the conditions of Example 3(d). The products were isolated as mixtures of diastereoisomers.

| No. | Structure | MS | M.P. ° C. |
|---|---|---|---|
| 76 | ![structure] | 599 (M + 1) | Amorphous solid |
| 77 | ![structure] | 613 (M + 1) | Amorphous solid |

EXAMPLE 78

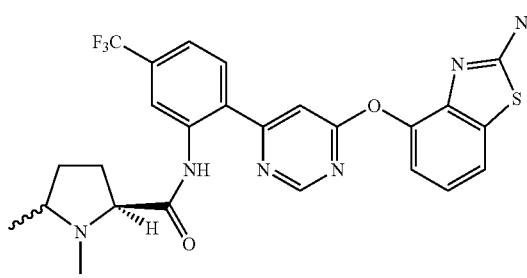

(2S,5R,S)-N-(2-(6-(2-Acetamidobenzo[d]thiazol-4-yloxy)pyrimidin-4-yl)-5-(trifluoromethyl)phenyl)-1,5-dimethylpyrrolidine-2-carboxamide. (2S,5R,S)-N-(2-(6-(2-Acetamidobenzo[d]thiazol-4-yloxy)pyrimidin-4-yl)-5-(trifluoromethyl)phenyl)-5-methylpyrrolidine-2-carboxamide (Example 75) reacted with iodomethane (Aldrich) under the conditions of Example 63 to give the title compound as a mixture of diastereoisomers. MS (ESI, pos. ion) m/z: 571 (M+1).

EXAMPLE 79

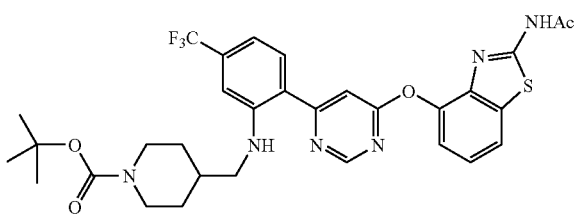

(a) tert-Butyl 4-((2-(6-(2-acetamidobenzo[d]thiazol-4-yloxy)pyrimidin-4-yl)-5-(trifluoromethyl)phenylamino)methyl)piperidine-1-carboxylate. N-(4-(6-(2-amino-4-(trifluoromethyl)phenyl)pyrimidin-4-yloxy)benzo[d]thiazol-2-yl)-acetamide (1.0 g, 2.2 mmol, prepared as described in WO04014871) was reacted with tert-butyl 4-formylpiperidine-1-carboxylate (1.2 g, 5.6 mmol, Aldrich) under the conditions of Example 3(d) to give the title compound as a yellow crystalline solid. (MS (ESI, pos. ion.) m/z: 644 (M+1).

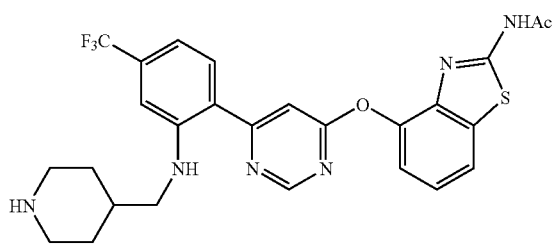

(b) N-(4-(6-(2-(Piperidin-4-ylmethylamino)-4-(trifluoromethyl)phenyl)pyrimidin-4-yloxy)benzo[d]thiazol-2-yl)acetamide. tert-Butyl 4-((2-(6-(2-acetamidobenzo[d]thiazol-4-yloxy)pyrimidin-4-yl)-5-(trifluoromethyl)-phenylamino)methyl)piperidine-1-carboxylate from step (a) above (0.20 g, 0.30 mmol) was reacted with TFA under the conditions of Example 3(c) to give the title compound as a yellow crystalline solid. MS (ESI, pos. ion.) m/z: 543 (M+1).

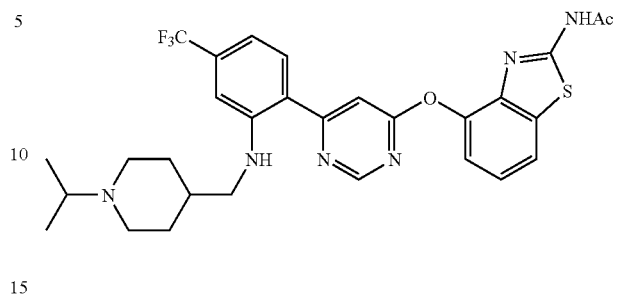

(c) N-(4-(6-(2-((1-Isopropylpiperidin-4-yl)methylamino)-4-(trifluoromethyl)-phenyl)pyrimidin-4-yloxy)benzo[d]thiazol-2-yl)acetamide To a solution of N-(4-(6-(2-(piperidin-4-ylmethylamino)-4-(trifluoromethyl)-phenyl)pyrimidin-4-yloxy)benzo[d]thiazol-2-yl)acetamide from step (b) above (0.20 g, 0.36 mmol) in acetone (20 mL) were added two drops of glacial acetic acid. The reaction mixture was stirred under reflux for 53 h and was allowed to reach room temperature. Sodium triacetoxy borohydride (0.16 g, 0.73 mmol, Aldrich) was added and the mixture was stirred under reflux for 5 h. The reaction mixture was allowed to reach room temperature, quenched with water (2 mL), and evaporated in vacuo. The residue was dissolved in EtOAc (10 mL) and the solution was washed with water (2×20 mL), dried over $Na_2SO_4$ and filtered. The filtrate was evaporated in vacuo and the residue was dissolved in MeOH (2 mL), and purified by reverse phase HPLC (Phenomenex Prodigy 5μ ODS-3 100 Å column, gradient: 20-100% $CH_3CN$ (0.1% TFA)/$H_2O$ (0.1% TFA) over 15 min) to give the title compound as TFA salt. To the salt was added sat. aqueous solution of $NaHCO_3$ and the mixture was extracted with ethyl acetate (2×25 mL). The combined organic extracts were washed with water (2×20 mL), dried over $Na_2SO_4$ and filtered. The filtrate was evaporated in vacuo to afford title compound as yellow film. MS (ESI, pos. ion.) m/z: 585 (M+1).

EXAMPLE 80

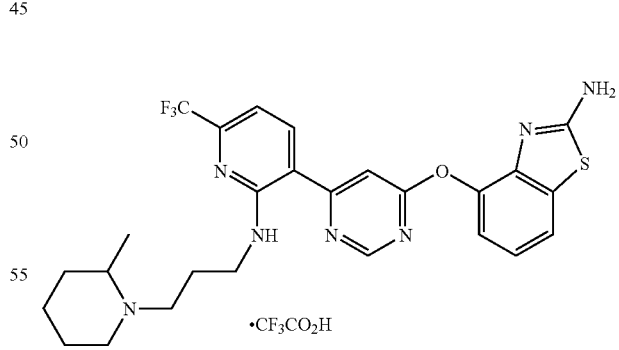

4-(6-(2-(3-(2-Methylpiperidin-1-yl)propylamino)-6-(trifluoromethyl)pyridin-3-yl)pyrimidin-4-yloxy)benzo[d]thiazol-2-amine trifluoroacetic acid salt. A mixture of 4-(6-2-chloro-6-(triflouromethyl)pyridine-3-yl)pyrimidin-4-yloxy)-benzo[d]thiazole-2-amine, Example 1(b), (100 mg, 0.236 mmol), 3-(2-methylpiperidin-1-yl)propan-1-amine (184 mg, 1.179 mmol, Aldrich) and potassium carbonate (59 mg, 0.424 mmol) was heated in a microwave synthesizer at 60° C. for 10 min. The reaction mixture was dissolved in DCM (10 mL), filtered, and concentrated in vacuo. The residue was purified by reverse phase HPLC (Phenomenex Prodigy 5μ ODS-3 100 Å column, gradient: 20-100% CH₃CN (0.1% TFA)/H₂O (0.1% TFA) over 15 min) to give the title compound as a bright-yellow amorphous solid. MS (ESI, pos. ion.) m/z: (M+1).

EXAMPLE 81

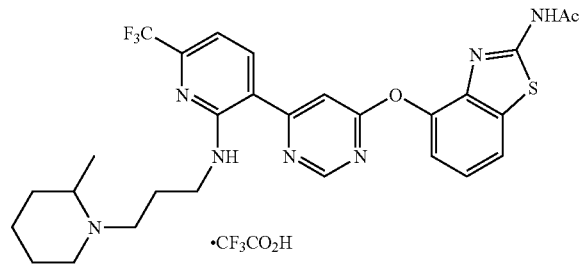

N-(4-(6-(2-(3-(2-Methylpiperidin-1-yl)propylamino)-6-(trifluoromethyl)-pyridin-3-yl)pyrimidin-4-yloxy)benzo[d]thiazol-2-yl)acetamide trifluoroacetic acid salt. A mixture of 4-(6-(2-(3-(2-methylpiperidin-1-yl)propylamino)-6-(trifluoromethyl)pyridin-3-yl)pyrimidin-4-yloxy)benzo [d]thiazol-2-amine trifluoroacetic acid salt, Example 80, (29 mg, 0.052 mmol), potassium carbonate (35 mg, 0.253 mmol) and acetic anhydride (2 mL) was heated at 90° C. in a microwave synthesizer for 10 min. to give MS (ESI, pos. ion.) m/z: 658 (M+1). The reaction mixture was dissolved in DCM (10 mL), filtered, and concentrated in vacuo. The residue was purified by reverse phase HPLC (Phenomenex Prodigy 5μ ODS-3 100 Å column, gradient: 20-100% CH₃CN (0.1% TFA)/H₂O (0.1% TFA) over 15 min) to give the title compound as a light-yellow amorphous solid. MS (ESI, pos. ion.) m/z: 700 (M+1).

EXAMPLE 82

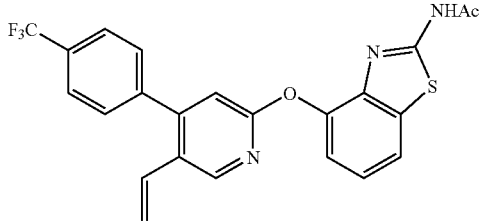

(a) N-(4-(4-(4-(Trifluoromethyl)phenyl)-5-vinylpyridin-2-yloxy)-benzo[d]thiazol-2-yl)acetamide. A mixture of N-(4-(5-bromo-4-(4-(trifluoromethyl)phenyl)pyridin-2-yloxy)benzo[d]thiazol-2-yl)acetamide (1.51 g, 3 mmol, prepared as described in WO 04/014871), tributyl(vinyl)tin (1.0 mL, 3 mmol, Aldrich), tetrakis(triphenylphosphine)palladium(0) (0.17 g, 0.1 mmol, Aldrich), lithium chloride (0.4 g, 9 mmol, Aldrich) and 2,6-di-tert-butyl-4-methylphenol (0.01 g, 0.05 mmol, Aldrich) in dioxane (10 mL) was heated at 95° C. for 5 h under nitrogen atmosphere. After cooling to room temperature, the reaction mixture was partitioned between EtOAc (50 mL) and water (40 mL). The organic layer was separated, washed with brine (50 mL), dried over Na₂SO₄, and filtered. The filtrate was evaporated under reduced pressure, and the residue purified by silica gel column chromatography (30% EtOAc/hexane) to give the title compound as an off-white amorphous solid. MS (ESI, pos. ion) m/z: 456 (M+1).

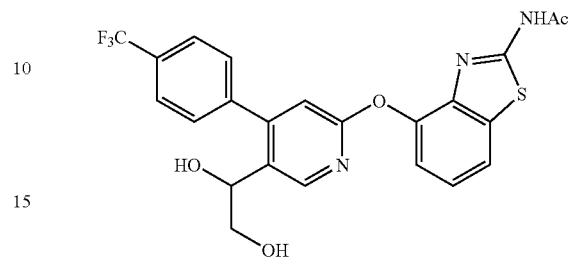

(b) N-(4-(5-(1,2-Dihydroxyethyl)-4-(4-(trifluoromethyl)phenyl)pyridin-2-yloxy)benzo[d]thiazol-2-yl)acetamide. A mixture of N-(4-(4-(4-(trifluoromethyl)phenyl)-5-vinylpyridin-2-yloxy)benzo[d]thiazol-2-yl)acetamide from step (a) above (0.93 g, 2.0 mmol), 4-methylmorpholine N-oxide (0.29 g, 2.5 mmol, Aldrich) and osmium tetroxide (0.026 g, 0.10 mmol) in acetone (12 mL) and water (1.2 mL) was stirred at room temperature for 3 h. The reaction mixture was diluted with sat. aqueous solution of NaHSO₃ (15 mL) and extracted with a 3:1 mixture of EtOAc/MeOH (3×15 mL). The combined organic extracts were washed with brine (30 mL), dried over Na₂SO₄, and filtered. The filtrate was evaporated under reduced pressure, and the solid residue was suspended in 1:1 mixture of EtOAc/hexanes (40 mL). The suspension was filtered, and the filter cake was separated and dried in vacuo to give the title compound as an off-white amorphous solid. MS (ESI, pos. ion) m/z: 490 (M+1).

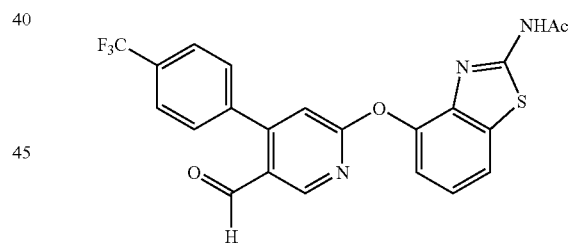

(c) N-(4-(5-Formyl-4-(4-(trifluoromethyl)phenyl)pyridin-2-yloxy)-benzo[d]thiazol-2-yl)acetamide. To a suspension of N-(4-(5-(1,2-dihydroxyethyl)-4-(4-(trifluoromethyl)phenyl)pyridin-2-yloxy)benzo[d]thiazol-2-yl)acetamide from step (b) above (0.78 g, 1.6 mmol) in DCM (12 mL) was added lead (IV) acetate (0.85 g, 1.9 mmol) with stirring at 0° C. The reaction mixture was stirred at 0° C. for 1.5 h and filtered through a pad of Celite®. The filter cake was washed with DCM and the combined filtrates were partitioned between DCM (20 mL) and sat. aqueous solution of NaHCO₃ (15 mL). The organic layer was separated, and the aqueous layer was extracted with DCM (10 mL). The combined organic extracts were washed with brine, dried over Na₂SO₄, and filtered. The filtrate was evaporated under reduced pressure, and the residue was dried in vacuo to give the title compound as a tan amorphous solid. MS (ESI, pos. ion) m/z: 458 (M+1).

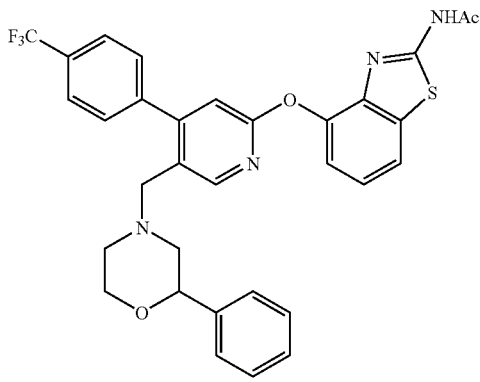

(d) N-(4-(5-((2-Phenylmorpholino)methyl)-4-(4-(trifluoromethyl)phenyl)-pyridin-2-yloxy)benzo[d]thiazol-2-yl)acetamide. To a solution of N-(4-(5-formyl-4-(4-(trifluoromethyl)phenyl)pyridin-2-yloxy)benzo[d]thiazol-2-yl)-acetamide from step (c) above (92 mg, 0.20 mmol) and 2-phenylmorpholine (98 mg, 0.60 mmol, Aldrich) in DCM (2 mL) was added sodium triacetoxyborohydride (213 mg, 1 mmol, Aldrich), and the mixture was heated at 40° C. for 3 h under nitrogen atmosphere. The reaction mixture was partitioned between DCM (10 mL) and sat. aqueous solution of NaHCO$_3$ (10 mL), and the organic layer was separated. The aqueous layer was extracted with DCM (2×5 mL), and the combined organic extracts were washed with brine, dried over Na$_2$SO$_4$, and filtered. The filtrate was evaporated under reduced pressure, and the residue was purified by silica gel column chromatography (gradient: 10-50% EtOAc/hexane) to give the title compound as an off-white amorphous solid. MS (ESI, pos. ion) m/z: 605 (M+1).

EXAMPLE 83

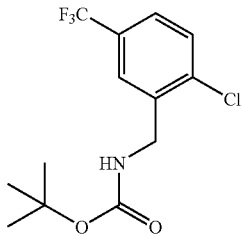

(a) tert-Butyl 2-chloro-5-(trifluoromethyl)benzylcarbamate. To a 100-mL, round-bottomed flask was added THF (20 mL), (2-chloro-5-(trifluoromethyl)-phenyl)methanamine (1.045 g, 5 mmol, Lancaster), 1 N NaOH (0.3 mL, 8 mmol) and di-tert-butyl carbonate (1.0 g, 6 mmol) with stirring at 0° C. The reaction mixture was stirred at 0° C. for 1 h, diluted with water (20 mL), and extracted with EtOAc (2×20 mL). The combined organic extracts were washed with water (20 mL) and brine (20 mL), dried over Na$_2$SO$_4$, and filtered. The filtrate was evaporated under reduced pressure, and the residue was purified by silica gel column chromatography (20% EtOAc/hexane) to give the title compound as an amorphous solid. MS (ESI, pos. ion.) m/z: 310 (M+1).

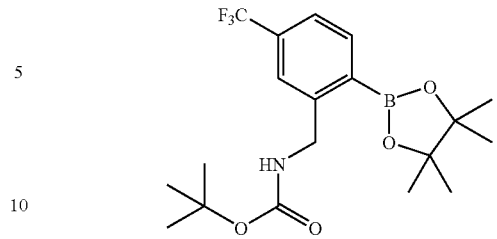

(b) tert-Butyl 2-(4,4,5,5-tetramethyl-1,3,2-dioxaborolan-2-yl)-5-(trifluoromethyl)benzylcarbamate. To a 100-mL, round-bottomed flask were added dioxane (18 mL), bis(dibenzylideneacetone)palladium (52 mg, 0.09 mmol, Acros) and tricyclohexylphosphine (61 mg, 0.2 mmol, Aldrich) under nitrogen atmosphere, and the mixture was stirred for 30 min at room temperature. Bis(pinacolato)diboron (838 mg, 3 mmol, Aldrich), potassium acetate (281 µL, 5 mmol) and tert-butyl 2-chloro-5-(trifluoromethyl)benzylcarbamate from step (a) above (309 mg, 3 mmol) were then added, and the reaction mixture was heated at 80° C. for 18 h with stirring under nitrogen atmosphere. The reaction mixture was left to reach room temperature, diluted with water (40 mL), and extracted with EtOAc (2×40 mL). The combined organic extracts were washed with water (20 mL) and brine (20 mL), dried over Na$_2$SO$_4$, and filtered. The filtrate was evaporated under reduced pressure, and the residue was purified by silica gel column chromatography (15% EtOAc/hexane) to give the title compound as an amorphous solid. MS (ESI, pos. ion.) m/z: 400 (M+1).

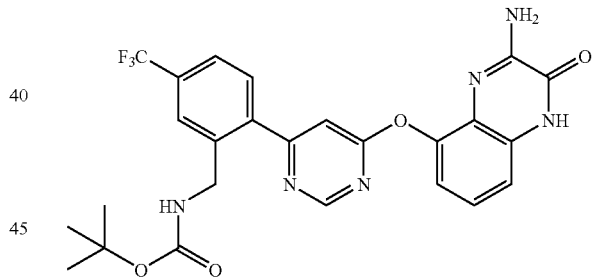

(c) tert-Butyl (2-(6-(3-amino-2-oxo-1,2-dihydroquinoxalin-5-yloxy)pyrimidin-4-yl)-5-(trifluoromethyl)phenyl)methylcarbamate. A mixture of sodium carbonate (106 mg, 1 mmol), tetrakis(triphenylphosphine)palladium (29 mg, 0.03 mmol, Aldrich), tert-butyl 2-(4,4,5,5-tetramethyl-1,3,2-dioxaborolan-2-yl)-5-(trifluoromethyl)benzylcarbamate from step (b) above (201 mg, 0.5 mmol) and 3-amino-5-(6-iodopyrimidin-4-yloxy)quinoxalin-2(1H)-one, Example 6(a), (191 mg, 0.5 mmol) in dioxane (4 mL) was heated in a microwave synthesizer at 150° C. for 10 min. The reaction mixture was diluted with water (20 mL), and extracted with EtOAc (2×30 mL). The combined organic extracts were washed with water (10 mL) and brine (10 mL), dried over Na$_2$SO$_4$, and filtered. The filtrate was evaporated under reduced pressure, and the residue was purified by silica gel column chromatography (70% EtOAc/hexane) to give the title compound as an amorphous solid. MS (ESI, pos. ion.) m/z: 529 (M+1).

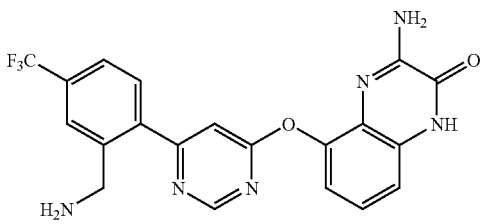

(d) 3-Amino-5-(6-(2-(aminomethyl)-4-(trifluoromethyl)phenyl)pyrimidin-4-yloxy)quinoxalin-2(1H)-one. tert-Butyl (2-(6-(3-amino-2-oxo-1,2-dihydroquinoxalin-5-yloxy)pyrimidin-4-yl)-5-(trifluoromethyl)phenyl)-methylcarbamate from step(c) above (105 mg, 0.2 mmol) was treated with 1:1 mixture of DCM/TFA (2 mL) under the conditions of Example 3(c). The crude reaction product was purified by silica gel column chromatography, eluting with 10% [MeOH containing 1% NH$_4$OH (28% NH$_3$ in H$_2$O)] in DCM to give the title compound as an amorphous solid. MS (ESI, pos. ion.) m/z: 429 (M+1).

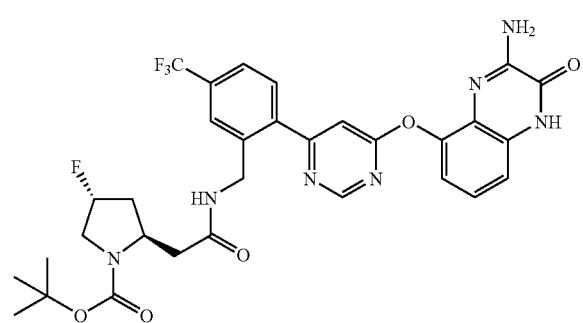

(e) (2S,4R)-tert-Butyl 2-(((2-(6-(3-amino-2-oxo-1,2-dihydroquinoxalin-5-yloxy)pyrimidin-4-yl)-5-(trifluoromethyl)phenyl)methyl)carbamoyl)-4-fluoropyrrolidine-1-carboxylate. (2S,4R)-1-(tert-Butoxycarbonyl)-4-fluoropyrrolidine-2-carboxylic acid (117 mg, 500 μmol, Bachem) was reacted with 3-amino-5-(6-(2-(aminomethyl)-4-(trifluoromethyl)phenyl)pyrimidin-4-yloxy)quinoxalin-2(1H)-one from step (d) above (214 mg, 500 μmol) under the conditions of Example 45(a). The crude reaction product was purified by silica gel column chromatography (5% MeOH/DCM) to give the title compound as a white solid. MS (ESI, pos. ion.) m/z: 644 (M+1).

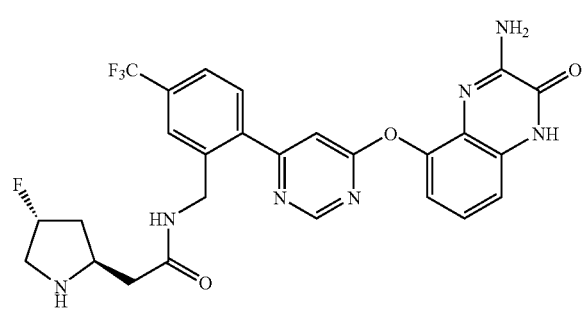

(f) (2S,4R)-N-((2-(6-(3-Amino-2-oxo-1,2-dihydroquinoxalin-5-yloxy)pyrimidin-4-yl)-5-(trifluoromethyl)phenyl)methyl)-4-fluoropyrrolidine-2-carboxamide. (2S,4R)-tert-Butyl 2-(((2-(6-(3-amino-2-oxo-1,2-dihydroquinoxalin-5-yloxy)pyrimidin-4-yl)-5-(trifluoromethyl)phenyl)methyl)-carbamoyl)-4-fluoropyrrolidine-1-carboxylate from step (e) above (128 mg, 199 μmol) was treated with 1:1 mixture of DCM/TFA (2 mL) under the conditions of Example 3(c). The crude reaction product was purified by silica gel column chromatography, eluting with 10% [MeOH containing 1% NH$_4$OH (28% NH$_3$ in H$_2$O)] in DCM to give the title compound as an amorphous solid. MS (ESI, pos. ion.) m/z: 544 (M+1).

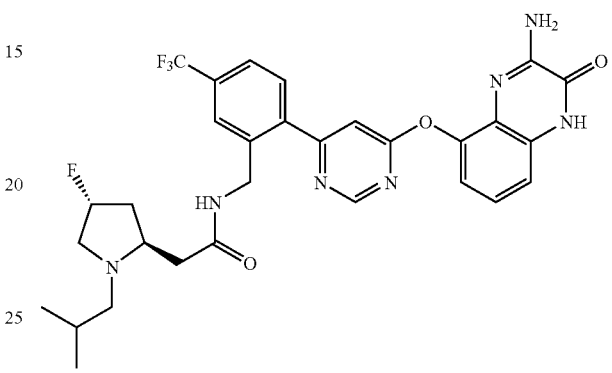

(g) (2S,4R)-N-((2-(6-(3-Amino-2-oxo-1,2-dihydroquinoxalin-5-yloxy)pyrimidin-4-yl)-5-(trifluoromethyl)phenyl)methyl)-4-fluoro-1-isobutyl-pyrrolidine-2-carboxamide. (2S,4R)-N-((2-(6-(3-Amino-2-oxo-1,2-dihydro-quinoxalin-5-yloxy)pyrimidin-4-yl)-5-(trifluoromethyl)phenyl)methyl)-4-fluoropyrrolidine-2-carboxamide from step (f) above was reacted with isobutyraldehyde (1.2 g, 16.5 mmol, Aldrich) under the conditions of Example 3(d) to give the title compound as an amorphous solid. MS (ESI, pos. ion.) m/z: 600 (M+1).

Capsaicin-induced Ca$^{2+}$ influx in primary dorsal root ganglion neurons. Embryonic 19 day old (E19) dorsal root ganglia (DRG) were dissected from timed-pregnant, terminally anesthetized Sprague-Dawley rats (Charles River, Wilmington, Mass.) and collected in ice-cold L-15 media (Life Technologies, Grand Island, N.Y.) containing 5% heat inactivated horse serum (Life Technologies). The DRG were then dissociated into single cell suspension using a papain dissociation system (Worthington Biochemical Corp., Freehold, N.J.). The dissociated cells were pelleted at 200×g for 5 min and re-suspended in EBSS containing 1 mg/mL ovomucoid inhibitor, 1 mg/mL ovalbumin and 0.005% DNase. Cell suspension was centrifuged through a gradient solution containing 10 mg/mL ovomucoid inhibitor, 10 mg/mL ovalbumin at 200×g for 6 min to remove cell debris; and filtered through a 88-μm nylon mesh (Fisher Scientific, Pittsburgh, Pa.) to remove any clumps. Cell number was determined with a hemocytometer and cells were seeded into poly-ornithine 100 μg/mL (Sigma) and mouse laminin 1 μg/mL (Life Technologies)-coated 96-well plates at 10×10$^3$ cells/well in complete medium. The complete medium consists of minimal essential medium (MEM) and Ham's F12, 1:1, penicillin (100 U/mL), and streptomycin (100 μg/mL), and nerve growth factor (10 ng/mL), 10% heat inactivated horse serum (Life Technologies). The cultures were kept at 37° C., 5% CO$_2$ and 100% humidity. For controlling the growth of non-neuronal cells, 5-fluoro-2'-deoxyuridine (75 μM) and uridine (180 μM) were included in the medium. Activation of VR1 was achieved in these cellular assays using either a capsaicin stimulus (ranging from 0.01-10 μM) or by an acid stimulus (addition of 30 mM Hepes/Mes buffered at pH 4.1). Compounds were also tested in an assay format to evaluate their agonist properties at VR1. The activation of VR1 is followed as a function of cellular uptake of radioactive calcium ($^{45}Ca^{2+}$:Amersham CES3-2mCi).

Capsaicin Antagonist Assay: E-19 DRG cells at 3 days in culture are incubated with serial concentrations of VR1 antagonists, in HBSS (Hanks buffered saline solution supplemented with BSA 0.1 mg/mL and 1 mM Hepes at pH 7.4) for 15 min, room temperature. Cells are then challenged with a VR1 agonist, capsaicin (500 nM), in activation buffer containing 0.1 mg/mL BSA, 15 mM Hepes, pH 7.4, and 10 μCi/mL $^{45}Ca^{2+}$ (Amersham CES3-2mCi) in Ham's F12 for 2 min at room temperature.

The following compounds exhibit IC50 values of less than 10 mM in the Human VR1 Capsaicin Antagonist Assay:

(2R)-N-(2-(6-((2-(acetylamino)-1,3-benzothiazol-4-yl)oxy)-4-pyrimidinyl)-5-(trifluoromethyl)phenyl)-1-(cyclopropylmethyl)-2-piperidinecarboxamide;

(2R)-N-(2-(6-((2-(acetylamino)-1,3-benzothiazol-4-yl)oxy)-4-pyrimidinyl)-5-(trifluoromethyl)phenyl)-1-(1-methylethyl)-2-piperidinecarboxamide;

(2R)-N-(2-(6-((2-(acetylamino)-1,3-benzothiazol-4-yl)oxy)-4-pyrimidinyl)-5-(trifluoromethyl)phenyl)-1-(2-methylpropyl)-2-piperidinecarboxamide;

(2R)-N-(2-(6-((2-(acetylamino)-1,3-benzothiazol-4-yl)oxy)-4-pyrimidinyl)-5-(trifluoromethyl)phenyl)-2-methyl-2-piperidinecarboxamide;

(2R)-N-(2-(6-((2-amino-8-quinolinyl)oxy)-4-pyrimidinyl)-5-(trifluoromethyl)phenyl)-1-(2-methylpropyl)-2-piperidinecarboxamide;

(2R)-N-(2-(6-((3-amino-2-oxo-1,2-dihydro-5-quinoxalinyl)oxy)-4-pyrimidinyl)-5-(trifluoromethyl)phenyl)-1-(2-methylpropyl)-2-piperidinecarboxamide;

(2S)-N-(2-(6-((2-(acetylamino)-1,3-benzothiazol-4-yl)oxy)-4-pyrimidinyl)-5-(trifluoromethyl)phenyl)-1-(1-methylethyl)-2-azetidinecarboxamide;

(2S)-N-(2-(6-((2-(acetylamino)-1,3-benzothiazol-4-yl)oxy)-4-pyrimidinyl)-5-(trifluoromethyl)phenyl)-1-(2-methylpropyl)-2-azetidinecarboxamide;

(2S)-N-(2-(6-((2-(acetylamino)-1,3-benzothiazol-4-yl)oxy)-4-pyrimidinyl)-5-(trifluoromethyl)phenyl)-1-(cyclopropylmethyl)-2-piperidinecarboxamide;

(2S)-N-(2-(6-((2-(acetylamino)-1,3-benzothiazol-4-yl)oxy)-4-pyrimidinyl)-5-(trifluoromethyl)phenyl)-1-(1-methylethyl)-2-piperidinecarboxamide;

(2S)-N-(2-(6-((2-(acetylamino)-1,3-benzothiazol-4-yl)oxy)-4-pyrimidinyl)-5-(trifluoromethyl)phenyl)-1-(2-methylpropyl)-2-piperidinecarboxamide;

(2S)-N-(2-(6-((2-(acetylamino)-1,3-benzothiazol-4-yl)oxy)-4-pyrimidinyl)-5-(trifluoromethyl)phenyl)-2-methyl-2-piperidinecarboxamide;

(2S)-N-(2-(6-((2-amino-8-quinolinyl)oxy)-4-pyrimidinyl)-5-(trifluoromethyl)phenyl)-1-(2-methylpropyl)-2-piperidinecarboxamide;

(2S)-N-(2-(6-((2-amino-8-quinolinyl)oxy)-4-pyrimidinyl)-5-(trifluoromethyl)phenyl)-1-(2-methylpropyl)-2-piperidinecarboxamide;

(2S)-N-(2-(6-((3-amino-2-oxo-1,2-dihydro-5-quinoxalinyl)oxy)-4-pyrimidinyl)-5-(trifluoromethyl)phenyl)-1-(2-methylpropyl)-2-piperidinecarboxamide;

(5R)-N-(2-(6-((2-(acetylamino)-1,3-benzothiazol-4-yl)oxy)-4-pyrimidinyl)-5-(trifluoromethyl)phenyl)-1-(cyclopropylmethyl)-5-phenyl-L-prolinamide;

(5R)-N-(2-(6-((2-(acetylamino)-1,3-benzothiazol-4-yl)oxy)-4-pyrimidinyl)-5-(trifluoromethyl)phenyl)-1-(1-methylethyl)-5-phenyl-L-prolinamide;

(5R)-N-(2-(6-((2-(acetylamino)-1,3-benzothiazol-4-yl)oxy)-4-pyrimidinyl)-5-(trifluoromethyl)phenyl)-5-phenyl-L-prolinamide;

(5R)-N-(2-(6-((2-(acetylamino)-1,3-benzothiazol-4-yl)oxy)-4-pyrimidinyl)-5-(trifluoromethyl)phenyl)-5-methyl-1-(1-methylethyl)-L-prolinamide;

(5R)-N-(2-(6-((2-amino-8-quinolinyl)oxy)-4-pyrimidinyl)-5-(trifluoromethyl)phenyl)-5-methyl-L-prolinamide;

(5R)-N-(2-(6-((3-amino-2-oxo-1,2-dihydro-5-quinoxalinyl)oxy)-4-pyrimidinyl)-5-(trifluoromethyl)phenyl)-5-methyl-L-prolinamide;

(5R)-N-(2-(6-((3-amino-2-oxo-1,2-dihydro-5-quinoxalinyl)oxy)-4-pyrimidinyl)-5-(trifluoromethyl)phenyl)-5-methyl-L-prolinamide;

(5S)-N-(2-(6-((2-(acetylamino)-1,3-benzothiazol-4-yl)oxy)-4-pyrimidinyl)-5-(trifluoromethyl)phenyl)-5-methyl-1-(1-methylethyl)-L-prolinamide;

(5S)-N-(2-(6-((2-amino-8-quinolinyl)oxy)-4-pyrimidinyl)-5-(trifluoromethyl)phenyl)-5-methyl-L-prolinamide;

(5S)-N-(2-(6-((3-amino-2-oxo-1,2-dihydro-5-quinoxalinyl)oxy)-4-pyrimidinyl)-5-(trifluoromethyl)phenyl)-5-methyl-L-prolinamide;

(5S)-N-(2-(6-((3-amino-2-oxo-1,2-dihydro-5-quinoxalinyl)oxy)-4-pyrimidinyl)-5-(trifluoromethyl)phenyl)-5-methyl-L-prolinamide;

2-{2-[6-(2-acetylamino-benzothiazol-4-yloxy)pyrimidin-4-yl]-5-trifluoromethyl-phenylcarbamoyl}-5-phenyl-pyrrolidine-1-carboxylic acid tert-butyl ester;

2-{2-[6-(2-acetylamino-benzothiazol-4-yloxy)pyrimidin-4-yl]-5-trifluoromethyl-phenylcarbamoyl}-2-methyl-pyrrolidine-1-carboxylic acid tert-butyl ester;

2-{2-[6-(2-amino-quinolin-8-yloxy)pyrimidin-4-yl]-5-trifluoromethyl-phenylcarbamoyl}-5-methyl-pyrrolidine-1-carboxylic acid tert-butyl ester;

2-{2-[6-(3-amino-2-oxo-1,2-dihydro-quinoxalin-5-yloxy)pyrimidin-4-yl]-5-trifluoromethyl-phenylcarbamoyl}-5-methyl-pyrrolidine-1-carboxylic acid tert-butyl ester;

3-amino-5-(6-{2-[(1-isobutyl-piperidin-2-ylmethyl)-amino]-6-trifluoromethyl-pyridin-3-yl}-pyrimidin-4-yloxy)-1H-quinoxalin-2-one;

4-((4-(2-(((2R)-2-methyl-1-pyrrolidinyl)methyl)-4-(trifluoromethyl)phenyl)-2-pyridinyl)oxy)-1,3-benzothiazol-2-amine;

4-((4-(2-(((2S)-2-methyl-1-pyrrolidinyl)methyl)-4-(trifluoromethyl)phenyl)-2-pyridinyl)oxy)-1,3-benzothiazol-2-amine;

4-((6-(2-((((2R)-1-(1-methylethyl)-2-piperidinyl)methyl)amino)-6-(trifluoromethyl)-3-pyridinyl)-4-pyrimidinyl)oxy)-1,3-benzothiazol-2-amine;

4-((6-(2-((((2R)-1-(2-methylpropyl)-2-piperidinyl)methyl)amino)-6-(trifluoromethyl)-3-pyridinyl)-4-pyrimidinyl)oxy)-1,3-benzothiazol-2-amine;

4-((6-(2-((((2S)-1-(1-methylethyl)-2-piperidinyl)methyl)amino)-6-(trifluoromethyl)-3-pyridinyl)-4-pyrimidinyl)oxy)-1,3-benzothiazol-2-amine;

4-((6-(2-((((2S)-1-(2-methylpropyl)-2-pyrrolidinyl)methyl)amino)-6-(trifluoromethyl)-3-pyridinyl)-4-pyrimidinyl)oxy)-1,3-benzothiazol-2-amine;

4-((6-(2-(((2R)-2-methyl-1-pyrrolidinyl)methyl)-4-(trifluoromethyl)phenyl)-4-pyrimidinyl)oxy)-1,3-benzothiazol-2-amine;

4-((6-(2-(((2S)-2-methyl-1-pyrrolidinyl)methyl)-4-(trifluoromethyl)phenyl)-4-pyrimidinyl)oxy)-1,3-benzothiazol-2-amine;

4-((6-(2-(((4-(phenylmethyl)-2-morpholinyl)methyl) amino)-6-(trifluoromethyl)-3-pyridinyl)-4-pyrimidinyl) oxy)-1,3-benzothiazol-2-amine;

4-((6-(2-(((1-methyl-1-((2R)-1-(2-methylpropyl)-2-piperidinyl)ethyl)amino)-6-(trifluoromethyl)-3-pyridinyl)-4-pyrimidinyl)oxy)-1,3-benzothiazol-2-amine;

4-((6-(2-((2-(1-methyl-2-pyrrolidinyl)ethyl)oxy)-4-(trifluoromethyl)phenyl)-4-pyrimidinyl)oxy)-1,3-benzothiazol-2-amine;

4-((6-(2-((2,2,6,6-tetramethyl-4-piperidinyl)amino)-6-(trifluoromethyl)-3-pyridinyl)-4-pyrimidinyl)oxy)-1,3-benzothiazol-2-amine;

4-((6-(2-((3-(2-methyl-1-piperidinyl)propyl)amino)-6-(trifluoromethyl)-3-pyridinyl)-4-pyrimidinyl)oxy)-1,3-benzothiazol-2-amine;

4-((6-(2-(methyl(((2R)-1-(2-methylpropyl)-2-piperidinyl) methyl)amino)-6-(trifluoromethyl)-3-pyridinyl)-4-pyrimidinyl)oxy)-1,3-benzothiazol-2-amine;

4-((6-(2-(methyl(((2S)-1-(2-methylpropyl)-2-piperidinyl) methyl)amino)-6-(trifluoromethyl)-3-pyridinyl)-4-pyrimidinyl)oxy)-1,3-benzothiazol-2-amine;

4-((6-(2-(methyl(((2S)-1-(2-methylpropyl)-2-pyrrolidinyl) methyl)amino)-6-(trifluoromethyl)-3-pyridinyl)-4-pyrimidinyl)oxy)-1,3-benzothiazol-2-amine;

5-{2-[6-(2-acetylamino-benzothiazol-4-yloxy)pyrimidin-4-yl]-5-trifluoromethyl-phenylcarbamoyl}-2,2-dimethyl-pyrrolidine-1-carboxylic acid tert-butyl ester;

8-(6-{2-[(1-isobutyl-piperidin-2-ylmethyl)-amino]-6-trifluoromethyl-pyridin-3-yl}-pyrimidin-4-yloxy)-quinolin-2-ylamine;

N-(2-(6-((2-(acetylamino)-1,3-benzothiazol-4-yl)oxy)-4-pyrimidinyl)-5-(trifluoromethyl)phenyl)-1-cyclopropyl-L-prolinamide;

N-(2-(6-((2-(acetylamino)-1,3-benzothiazol-4-yl)oxy)-4-pyrimidinyl)-5-(trifluoromethyl)phenyl)-2-methyl-1-(2-methylpropyl)prolinamide;

N-(2-(6-((2-(acetylamino)-1,3-benzothiazol-4-yl)oxy)-4-pyrimidinyl)-5-(trifluoromethyl)phenyl)-2-methyl-1-(1-methylethyl)prolinamide;

N-(2-(6-((2-(acetylamino)-1,3-benzothiazol-4-yl)oxy)-4-pyrimidinyl)-5-(trifluoromethyl)phenyl)-1-(cyclopropylmethyl)-L-prolinamide;

N-(2-(6-((2-(acetylamino)-1,3-benzothiazol-4-yl)oxy)-4-pyrimidinyl)-5-(trifluoromethyl)phenyl)-1-(cyclopropylmethyl)-2-methylprolinamide;

N-(2-(6-((2-(acetylamino)-1,3-benzothiazol-4-yl)oxy)-4-pyrimidinyl)-5-(trifluoromethyl)phenyl)-1-(cyclopropylmethyl)-2-methyl-L-prolinamide;

N-(2-(6-((2-(acetylamino)-1,3-benzothiazol-4-yl)oxy)-4-pyrimidinyl)-5-(trifluoromethyl)phenyl)-2-methyl-1-(2-methylpropyl)-L-prolinamide;

N-(2-(6-((2-(acetylamino)-1,3-benzothiazol-4-yl)oxy)-4-pyrimidinyl)-5-(trifluoromethyl)phenyl)-1-(1-methylethyl)-L-prolinamide;

N-(2-(6-((2-(acetylamino)-1,3-benzothiazol-4-yl)oxy)-4-pyrimidinyl)-5-(trifluoromethyl)phenyl)-5,5-dimethylprolinamide;

N-(2-(6-((2-(acetylamino)-1,3-benzothiazol-4-yl)oxy)-4-pyrimidinyl)-5-(trifluoromethyl)phenyl)-2-methylprolinamide;

N-(2-(6-((2-(acetylamino)-1,3-benzothiazol-4-yl)oxy)-4-pyrimidinyl)-5-(trifluoromethyl)phenyl)-2-methyl-1-(1-methylethyl)-L-prolinamide;

N-(2-(6-((2-(acetylamino)-1,3-benzothiazol-4-yl)oxy)-4-pyrimidinyl)-5-(trifluoromethyl)phenyl)-2-methyl-L-prolinamide;

N-(2-(6-((2-(acetylamino)-1,3-benzothiazol-4-yl)oxy)-4-pyrimidinyl)-5-(trifluoromethyl)phenyl)-1-cyclopropyl-3-pyrrolidinecarboxamide;

N-(2-(6-((2-(acetylamino)-1,3-benzothiazol-4-yl)oxy)-4-pyrimidinyl)-5-(trifluoromethyl)phenyl)-1-(cyclopropylmethyl)-3-pyrrolidinecarboxamide;

N-(2-(6-((2-(acetylamino)-1,3-benzothiazol-4-yl)oxy)-4-pyrimidinyl)-5-(trifluoromethyl)phenyl)-1-(1-methylethyl)-3-pyrrolidinecarboxamide;

N-(2-(6-((2-(acetylamino)-1,3-benzothiazol-4-yl)oxy)-4-pyrimidinyl)-5-(trifluoromethyl)phenyl)-1-methyl-3-pyrrolidinecarboxamide;

N-(4-((4-(2-(((2R)-2-methyl-1-pyrrolidinyl)methyl)-4-(trifluoromethyl)phenyl)-2-pyridinyl)oxy)-1,3-benzothiazol-2-yl)acetamide;

N-(4-((4-(2-(((2S)-2-methyl-1-pyrrolidinyl)methyl)-4-(trifluoromethyl)phenyl)-2-pyridinyl)oxy)-1,3-benzothiazol-2-yl)acetamide;

N-(4-((6-(2-((((2R)-1-(1-methylethyl)-2-piperidinyl)methyl)amino)-6-(trifluoromethyl)-3-pyridinyl)-4-pyrimidinyl)oxy)-1,3-benzothiazol-2-yl)acetamide;

N-(4-((6-(2-((((2R)-1-(1-methylethyl)-2-pyrrolidinyl)methyl)amino)-6-(trifluoromethyl)-3-pyridinyl)-4-pyrimidinyl)oxy)-1,3-benzothiazol-2-yl)acetamide;

N-(4-((6-(2-((((2R)-1-(2-methylpropyl)-2-piperidinyl)methyl)amino)-6-(trifluoromethyl)-3-pyridinyl)-4-pyrimidinyl)oxy)-1,3-benzothiazol-2-yl)acetamide;

N-(4-((6-(2-((((2R)-1-(2-methylpropyl)-2-piperidinyl)methyl)amino)-6-(trifluoromethyl)-3-pyridinyl)-4-pyrimidinyl)oxy)-1,3-benzothiazol-2-yl)acetamide;

N-(4-((6-(2-((((2R)-1-(2-methylpropyl)-2-pyrrolidinyl)methyl)amino)-6-(trifluoromethyl)-3-pyridinyl)-4-pyrimidinyl)oxy)-1,3-benzothiazol-2-yl)-acetamide;

N-(4-((6-(2-((((2R)-4-(2-methylpropyl)-2-morpholinyl)methyl)amino)-6-(trifluoromethyl)-3-pyridinyl)-4-pyrimidinyl)oxy)-1,3-benzothiazol-2-yl)-acetamide;

N-(4-((6-(2-((((2S)-1-(1-methylethyl)-2-piperidinyl)methyl)amino)-6-(trifluoromethyl)-3-pyridinyl)-4-pyrimidinyl)oxy)-1,3-benzothiazol-2-yl)acetamide;

N-(4-((6-(2-((((2S)-1-(2-methylpropyl)-2-piperidinyl)methyl)amino)-6-(trifluoromethyl)-3-pyridinyl)-4-pyrimidinyl)oxy)-1,3-benzothiazol-2-yl)acetamide;

N-(4-((6-(2-((((2S)-1-(2-methylpropyl)-2-piperidinyl)methyl)amino)-6-(trifluoromethyl)-3-pyridinyl)-4-pyrimidinyl)oxy)-1,3-benzothiazol-2-yl)acetamide;

N-(4-((6-(2-((((2S)-1-(2-methylpropyl)-2-pyrrolidinyl)methyl)amino)-6-(trifluoromethyl)-3-pyridinyl)-4-pyrimidinyl)oxy)-1,3-benzothiazol-2-yl)acetamide;

N-(4-((6-(2-((((2S)-4-(2-methylpropyl)-2-morpholinyl)methyl)amino)-6-(trifluoromethyl)-3-pyridinyl)-4-pyrimidinyl)oxy)-1,3-benzothiazol-2-yl)-acetamide;

N-(4-((6-(2-((((3R)-1-(1-methylethyl)-3-pyrrolidinyl)methyl)amino)-6-(trifluoromethyl)-3-pyridinyl)-4-pyrimidinyl)oxy)-1,3-benzothiazol-2-yl)acetamide;

N-(4-((6-(2-((((3S)-1-(1-methylethyl)-3-pyrrolidinyl)methyl)amino)-6-(trifluoromethyl)-3-pyridinyl)-4-pyrimidinyl)oxy)-1,3-benzothiazol-2-yl)acetamide;

N-(4-((6-(2-(((1-(1-methylethyl)-4-piperidinyl)methyl) amino)-4-(trifluoromethyl)phenyl)-4-pyrimidinyl)oxy)-1,3-benzothiazol-2-yl)acetamide;

N-(4-((6-(2-(((1-(phenylmethyl)-1H-imidazol-5-yl)methyl) amino)-4-(trifluoromethyl)phenyl)-4-pyrimidinyl)oxy)-1,3-benzothiazol-2-yl)acetamide;

N-(4-((6-(2-(((1-methyl-1H-imidazol-5-yl)methyl)amino)-4-(trifluoromethyl)phenyl)-4-pyrimidinyl)oxy)-1,3-benzothiazol-2-yl)acetamide;

N-(4-((6-(2-(((1R)-1-((2R)-1-(1-methylethyl)-2-pyrrolidinyl)ethyl)amino)-6-(trifluoromethyl)-3-pyridinyl)-4-pyrimidinyl)oxy)-1,3-benzothiazol-2-yl)-acetamide;

N-(4-((6-(2-(((1R)-1-((2R)-1-(2-methylpropyl)-2-pyrrolidinyl)ethyl)amino)-6-(trifluoromethyl)-3-pyridinyl)-4-pyrimidinyl)oxy)-1,3-benzothiazol-2-yl)-acetamide;

N-(4-((6-(2-(((1S)-1-((2S)-1-(1-methylethyl)-2-pyrrolidinyl)ethyl)amino)-6-(trifluoromethyl)-3-pyridinyl)-4-pyrimidinyl)oxy)-1,3-benzothiazol-2-yl)-acetamide;

N-(4-((6-(2-(((2R)-1-(2-methylpropyl)-2-piperidinyl)ethynyl)-4-(trifluoromethyl)phenyl)-4-pyrimidinyl)oxy)-1,3-benzothiazol-2-yl)acetamide;

N-(4-((6-(2-(((2S)-1-(1-methylethyl)-2-pyrrolidinyl)ethynyl)-4-(trifluoromethyl)phenyl)-4-pyrimidinyl)oxy)-1,3-benzothiazol-2-yl)acetamide;

N-(4-((6-(2-(((2S)-1-(2-methylpropyl)-2-piperidinyl)ethynyl)-4-(trifluoromethyl)phenyl)-4-pyrimidinyl)oxy)-1,3-benzothiazol-2-yl)acetamide;

N-(4-((6-(2-(((2S)-1-(2-methylpropyl)-2-pyrrolidinyl)ethynyl)-4-(trifluoromethyl)phenyl)-4-pyrimidinyl)oxy)-1,3-benzothiazol-2-yl)acetamide;

N-(4-((6-(2-(((3R)-1-(1-methylethyl)-3-pyrrolidinyl)amino)-6-(trifluoromethyl)-3-pyridinyl)-4-pyrimidinyl)oxy)-1,3-benzothiazol-2-yl)acetamide;

N-(4-((6-(2-(((3R)-1-(2-methylpropyl)-3-pyrrolidinyl)amino)-6-(trifluoromethyl)-3-pyridinyl)-4-pyrimidinyl)oxy)-1,3-benzothiazol-2-yl)acetamide;

N-(4-((6-(2-(((4-(phenylmethyl)-2-morpholinyl)methyl)amino)-6-(trifluoromethyl)-3-pyridinyl)-4-pyrimidinyl)oxy)-1,3-benzothiazol-2-yl)acetamide;

N-(4-((6-(2-((2-(1-methyl-2-pyrrolidinyl)ethyl)oxy)-4-(trifluoromethyl)phenyl)-4-pyrimidinyl)oxy)-1,3-benzothiazol-2-yl)acetamide;

N-(4-((6-(2-((2,2,6,6-tetramethyl-4-piperidinyl)amino)-6-(trifluoromethyl)-3-pyridinyl)-4-pyrimidinyl)oxy)-1,3-benzothiazol-2-yl)acetamide;

N-(4-((6-(2-((3-((2R)-2-methyl-1-piperidinyl)propyl)amino)-6-(trifluoromethyl)-3-pyridinyl)-4-pyrimidinyl)oxy)-1,3-benzothiazol-2-yl)acetamide;

N-(4-((6-(2-(2-((2R)-1-(2-methylpropyl)-2-piperidinyl)ethyl)-4-(trifluoromethyl)phenyl)-4-pyrimidinyl)oxy)-1,3-benzothiazol-2-yl)acetamide;

N-(4-((6-(2-(2-((2S)-1-(2-methylpropyl)-2-piperidinyl)ethyl)-4-(trifluoromethyl)phenyl)-4-pyrimidinyl)oxy)-1,3-benzothiazol-2-yl)acetamide;

N-(4-((6-(2-(methyl(((2R)-1-(2-methylpropyl)-2-piperidinyl)methyl)amino)-6-(trifluoromethyl)-3-pyridinyl)-4-pyrimidinyl)oxy)-1,3-benzothiazol-2-yl)-acetamide; and N-(4-((6-(2-(methyl(((2S)-1-(2-methylpropyl)-2-piperidinyl)methyl)amino)-6-(trifluoromethyl)-3-pyridinyl)-4-pyrimidinyl)oxy)-1,3-benzothiazol-2-yl)-acetamide.

Acid Antagonist Assay: Compounds are pre-incubated with E-19 DRG cells at room temperature for 2 minutes prior to addition of $^{45}Ca^{2+}$ in 30 mM Hepes/Mes buffer (Final Assay pH 5) and then left for an additional 2 minutes prior to compound washout. Final concentration of $^{45}Ca^{2+}$ (Amersham CES3-2mCi) is 10 µCi/mL.

Agonist Assay: Compounds are incubated with E-19 DRG cells at room temperature for 2 minutes in the presence of $^{45}Ca^{2+}$ prior to compound washout. Final $^{45}Ca^{2+}$ (Amersham CES3-2mCi) at 10 µCi/mL.

Compound Washout and Analysis: Assay plates are washed using an ELX405 plate washer (Bio-Tek Instruments Inc.) immediately after functional assay. Wash 3× with PBS, 0.1 mg/mL BSA. Aspirate between washes. Read plates using a MicroBeta Jet (Wallac Inc.). Compound activity is then calculated using appropriate computational algorithms.

$^{45}$Calcium$^{2+}$ Assay Protocol

Compounds may be assayed using Chinese Hamster Ovary cell lines stably expressing either human VR1 or rat VR1 under a CMV promoter. Cells could be cultured in a Growth Medium, routinely passaged at 70% confluency using trypsin and plated in an assay plate 24 hours prior to compound evaluation.

Possible Growth Medium:
DMEM, high glucose (Gibco 11965-084).
10% Dialyzed serum (Hyclone SH30079.03).
1× Non-Essential Amino Acids (Gibco 11140-050).
1× Glutamine-Pen-Strep (Gibco 10378-016).
Geneticin, 450 µg/mL (Gibco 10131-035).

Compounds could be diluted in 100% DMSO and tested for activity over several log units of concentration [40 µM-2 pM]. Compounds may be further diluted in HBSS buffer (pH 7.4) 0.1 mg/mL BSA, prior to evaluation. Final DMSO concentration in assay would be 0.5-1%. Each assay plate could be controlled with a buffer only and a known antagonist compound (either capsazepine or one of the described VR1 antagonists).

Activation of VR1 could be achieved in these cellular assays using either a capsaicin stimulus (ranging from 0.1-1 µM) or by an acid stimulus (addition of 30 mM Hepes/Mes buffered at pH 4.1). Compounds could also be tested in an assay format to evaluate their agonist properties at VR1.

Capsaicin Antagonist Assay: Compounds may be pre-incubated with cells (expressing either human or rat VR1) at room temperature for 2 minutes prior to addition of $^{45}Ca^{2+}$ and Capsaicin and then left for an additional 2 minutes prior to compound washout. Capsaicin (200 nM) can be added in HAM's F12, 0.1 mg/mL BSA, 15 mM Hepes at pH 7.4. Final $^{45}Ca^{2+}$ (Amersham CES3-2mCi) added could be 10 µCi/mL.

Acid Antagonist Assay: Compounds can be pre-incubated with cells (expressing either human or rat VR1) for 2 minutes prior to addition of $^{45}Ca^{2+}$ in 30 mM Hepes/Mes buffer (Final Assay pH 5) and then left for an additional 2 minutes prior to compound washout. Final $^{45}Ca^{2+}$ (Amersham CES3-2mCi) added could be 10 µCi/mL.

Agonist Assay: Compounds can be incubated with cells (expressing either human or rat VR1) for 2 minutes in the presence of $^{45}Ca^{2+}$ prior to compound washout. Final $^{45}Ca^{2+}$ (Amersham CES3-2mCi) added could be 10 µCi/mL.

Compound Washout and Analysis: Assay plates would be washed using an ELX405 plate washer (Bio-Tek Instruments Inc.) immediately after the functional assay. One could wash 3× with PBS, 0.1 mg/mL BSA, aspirating between washes. Plates could then be read using a MicroBeta Jet (Wallac Inc.) and compound activity calculated using appropriate computational algorithms.

Useful nucleic acid sequences and proteins may be found in U.S. Pat. Nos. 6,335,180, 6,406,908 and 6,239,267, herein incorporated by reference in their entirety.

For the treatment of vanilloid-receptor-diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating vanilloid-receptor-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$)-alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3, dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:

1. A compound having the structure:

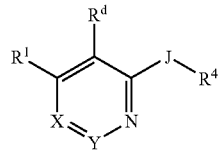

or any pharmaceutically-acceptable salt thereof, wherein:

J is O or S;
X is N or C($R^2$);
Y is N or C($R^3$), wherein at least one of X and Y is not N;
n is independently, at each instance, 0, 1 or 2;
$R^1$ is

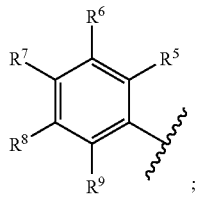

or $R^1$ is $R^b$ substituted by 1, 2 or 3 substituents selected from $R^e$, $R^h$, —O$R^e$, —O$R^h$, —O$C_{2-6}$alkylN$R^a R^e$, —O$C_{2-6}$alkylO$R^e$, —N$R^a R^e$, —N$R^a R^h$, —N$R^a C_{2-6}$alkylN$R^a R^e$, —N$R^a C_{2-6}$alkylO$R^e$, —CO$_2 R^e$, —OC(=O)$R^e$, —C(=O)$R^e$, —C(=O)N$R^a R^e$, —C(=O)N$R^a R^h$, —N$R^a$C(=O)$R^e$, —N$R^a$C(=O)$R^h$, —N$R^a$C(=O)N$R^a R^e$, —N$R^a$CO$_2 R^e$, —$C_{1-8}$alkylO$R^e$, —$C_{1-6}$alkylN$R^a R^e$, —S(=O)$_n R^e$, —S(=O)$_2$N$R^a R^e$, —N$R^a$S(=O)$_2 R^e$, —OS(=O)$_2 R^e$, —OC(=O)N$R^a R^e$, —OC$_{2-6}$alkylN$R^a R^h$, —OC$_{2-6}$alkylO$R^h$, —N$R^a C_{2-6}$alkylN$R^a R^h$, —N$R^h C_{2-6}$alkylN$R^a R^a$, —N$R^h C_{2-6}$alkylO$R^a$, —N$R^a C_{2-6}$alkylO$R^h$, —CO$_2 R^h$, —OC(=O)$R^h$, —C(=O)$R^h$, —N$R^e$C(=O)$R^a$, —N$R^h$C(=O)$R^a$, —N$R^h$C(=O)N$R^a R^a$, —N$R^e$C(=O)N$R^a R^a$, —N$R^h$CO$_2 R^a$, —N$R^e$CO$_2 R^a$, —$C_{1-8}$alkylO$R^h$, —$C_{1-6}$alkylN$R^a R^h$, —S(=O)$_n R^h$, —S(=O)$_2$N$R^a R^h$, —N$R^a$S(=O)$_2 R^h$, —N$R^h$S(=O)$_2 R^a$, —OS(=O)$_2 R^h$ and OC(=O)N$R^a R^h$, and additionally substituted by 0, 1, 2 or 3 substituents independently selected from halo, cyano, nitro, $C_{1-8}$alkyl, $C_{1-4}$haloalkyl, $R^i$, $R^k$, —O$R^a$, —N$R^a R^a$, —O$C_{2-6}$alkylN$R^a R^a$, —O$C_{2-6}$alkylO$R^a$, —N$R^a C_{2-6}$alkylN$R^a R^a$, —N$R^a C_{2-6}$alkylO$R^a$, —CO$_2 R^a$, —OC(=O)$R^a$, —C(=O)($C_{1-6}$alkyl), —C(=O)N$R^a R^a$, —N$R^a$C(=O)$R^a$, —N$R^a$C(=O)N$R^a R^a$, —N$R^a$CO$_2 R^a$, —$C_{1-8}$alkylO$R^a$, —$C_{1-6}$alkylN$R^a R^a$, —S(=O)$_n R^a$, —S(=O)$_2$N$R^a R^a$, —N$R^a$S(=O)$_2 R^a$, —OS(=O)$_2 R^a$ and —OC(=O)N$R^a R^e$;

$R^2$ is selected from H, halo, cyano, nitro, $R^i$, $R^k$, —OH, —O$R^i$, —O$R^k$, —C(=O)O$R^i$, —C(=O)O$R^k$, —OC(=O)$R^i$, —OC(=O)$R^k$, —S(O)$_n R^i$, —S(O)$_n R^k$, —N($R^a$)S(O)$_n R^i$, —N($R^a$)S(O)$_n R^k$, —S(O)$_n$N($R^a$)$R^i$, —S(O)$_n$N($R^a$)$R^k$, —NH$_2$, —C(=O)N$R^a R^i$, —C(=O)N$R^a R^k$, —N$R^a$C(=O)$R^i$ and —N$R^a$C(=O)$R^k$, —N$R^a R^i$ and —N$R^a R^k$;

$R^3$ is selected from H, halo, cyano, nitro, $R^i$, $R^k$, —OH, —O$R^i$, —O$R^k$, —C(=O)O$R^i$, —C(=O)O$R^k$, —OC(=O)$R^i$, —OC(=O)$R^k$, —S(O)$_n R^i$, —S(O)$_n R^k$, —N($R^a$)S(O)$_n R^i$, —N($R^a$)S(O)$_n R^k$, —S(O)N($R^a$)$R^i$, —S(O)N($R^a$)$R^k$, —NH$_2$, —C(=O)N$R^a R^i$, —C(=O)N$R^a R^k$, —N$R^a$C(=O)$R^i$ and —N$R^a$C(=O)$R^k$, —N$R^a R^i$ and —N$R^a R^k$;

$R^4$ is independently at each instance

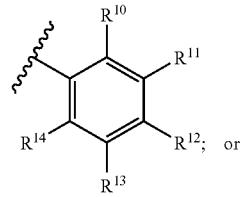

$R^4$ is independently at each instance a saturated, partially-saturated or unsaturated 5- or 6-membered ring heterocycle containing 1, 2 or 3 atoms selected from O, N and S that is optionally vicinally fused with a saturated, partially-saturated or unsaturated 3-, 4- or 5-atom bridge containing 0, 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from oxo, thioxo, $R^k$, $C_{1-4}$haloalkyl, cyano, nitro, —C(=O)$R^a$, —C(=O)O$R^a$, —C(=O)N$R^a R^a$, —C(=NR$^a$)N$R^a R^a$, —O$R^a$, —OC(=O)$R^a$, —OC(=O)N$R^a R^a$, —OC(=O)N($R^a$)S(=O)$_2 R^a$, —O$C_{2-6}$alkylN$R^a R^a$, —O$C_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=NR$^a$)N$R^a R^a$, —N($R^a$)S(=O)$_2 R^a$, —N($R^a$)S(=O)$_2$N$R^a R^a$, —N$R^a C_{2-6}$alkylN$R^a R^a$ and —N$R^a C_{2-6}$alkylO$R^a$; and wherein the heterocycle is additionally substituted by 0 or 1 groups independently selected from $R^i$ and additionally substituted by 0, 1, 2, 3, 4 or 5 substituents independently selected from Br, Cl, F and I; or $R^4$ is independently at each instance naphthyl substituted by 1, 2 or 3 substituents independently selected from $R^k$, $C_{1-4}$haloalkyl, cyano, nitro, —C(=O)$R^a$, —C(=O)O$R^a$, —C(=O)N$R^a R^a$, —C(=NR$^a$)N$R^a R^a$, —O$R^a$, —OC(=O)$R^a$, —OC(=O)N$R^a R^a$, —OC(=O)N($R^a$)S(=O)$_2 R^a$, —O$C_{2-6}$alkylN$R^a R^a$, —O$C_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=NR$^a$)N$R^a R^a$, —N($R^a$)S(=O)$_2 R^a$, —N($R^a$)S(=O)$_2$N$R^a R^a$, —N$R^a C_{2-6}$alkylN$R^a R^a$ and —N$R^a C_{2-6}$alkylO$R^a$; and wherein the naphthyl is additionally substituted by 0 or 1 groups independently selected from $R^i$ and additionally substituted by 0, 1, 2, 3, 4 or 5 substituents independently selected from Br, Cl, F and I;

$R^5$ is independently, at each instance, H, $R^k$, $C_{1-4}$haloalkyl, halo, cyano, nitro, —C(=O)$R^a$, —C(=O)O$R^a$, —C(=O)N$R^a R^a$, —C(=NR$^a$)N$R^a R^a$, —O$R^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^6$ is independently, at each instance, H, R$^k$, C$_{1-4}$haloalkyl, halo, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^7$ is independently, at each instance, H, R$^k$, C$_{1-4}$haloalkyl, halo, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and A)
- R$^8$ is independently, at each instance, H, R$^k$, C$_{1-4}$haloalkyl, halo, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and
- R$^9$ is independently, at each instance, R$^e$, R$^h$, —OR$^e$, —OR$^h$, —OC$_{2-6}$alkylNR$^a$R$^e$, —OC$_{2-6}$alkylOR$^e$, —NR$^a$R$^e$, —NR$^a$R$^h$, —NR$^a$C$_{2-6}$alkylNR$^a$R$^e$, —NR$^a$C$_{2-6}$alkylOR$^e$, —CO$_2$R$^e$, —OC(=O)R$^e$, —C(=O)R$^e$, —C(=O)NR$^a$R$^e$, —C(=O)NR$^a$R$^h$, —NR$^a$C(=O)R$^e$, —NR$^a$C(=O)R$^h$, —NR$^a$C(=O)NR$^a$R$^e$, —NR$^a$CO$_2$R$^e$, —C$_{1-8}$alkylOR$^e$, —C$_{1-6}$alkylNR$^a$R$^e$, —S(=O)$_n$R$^e$, —S(=O)$_2$NR$^a$R$^e$, —NR$^a$S(=O)$_2$R$^e$, —OS(=O)$_2$R$^e$, —OC(=O)NR$^a$R$^e$, —OR$^h$, —OC$_{2-6}$alkylNR$^a$R$^h$, —OC$_{2-6}$alkylOR$^h$, —NR$^a$C$_{2-6}$alkylNR$^a$R$^h$, —NR$^h$C$_{2-6}$alkylNR$^a$R$^a$, —NR$^h$C$_{2-6}$alkylOR$^a$, —NR$^a$C$_{2-6}$alkylOR$^h$, —CO$_2$R$^h$, —OC(=O)R$^h$, —C(=O)R$^h$, —C(=O)NR$^a$R$^h$, —NR$^e$C(=O)R$^a$, —NR$^h$C(=O)R$^a$, —NR$^h$C(=O)NR$^a$R$^a$, —NR$^e$C(=O)NR$^a$R$^a$, —NR$^h$CO$_2$R$^a$, —NR$^e$CO$_2$R$^a$, —C$_{1-8}$alkylOR$^h$, —C$_{1-6}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^a$, —OS(=O)$_2$R$^h$ or —OC(=O)NR$^a$R$^h$; or B)
- R$^8$ is independently, at each instance, R$^e$, R$^h$, —OR$^e$, —OC$_{2-6}$alkylNR$^a$R$^e$, —OC$_{2-6}$alkylOR$^e$, —NR$^a$R$^e$, —NR$^a$R$^h$, —NR$^a$C$_{2-6}$alkylNR$^a$R$^e$, —NR$^a$C$_{2-6}$alkylOR$^e$, —CO$_2$R$^e$, —OC(=O)R$^e$, —C(=O)R$^e$, —C(=O)NR$^a$R$^e$, —C(=O)NR$^a$R$^h$, —NR$^a$C(=O)R$^e$, —NR$^a$C(=O)R$^h$, —NR$^a$C(=O)NR$^a$R$^e$, —NR$^a$CO$_2$R$^e$, —C$_{1-8}$alkylOR$^e$, —C$_{1-6}$alkylNR$^a$R$^e$, —S(=O)$_n$R$^e$, —S(=O)$_2$NR$^a$R$^e$, —NR$^a$S(=O)$_2$R$^e$, —OS(=O)$_2$R$^e$, —OC(=O)NR$^a$R$^e$, —OR$^h$, —OC$_{2-6}$alkylNR$^a$R$^h$, —OC$_{2-6}$alkylOR$^h$, —NR$^a$C$_{2-6}$alkylNR$^a$R$^h$, —NR$^h$C$_{2-6}$alkylNR$^a$R$^a$, —NR$^h$C$_{2-6}$alkylOR$^a$, —NR$^a$C$_{2-6}$alkylOR$^h$, —CO$_2$R$^h$, —OC(=O)R$^h$, —C(=O)NR$^a$R$^h$, —NR$^e$C(=O)R$^a$, —NR$^h$C(=O)R$^a$, —NR$^h$C(=O)NR$^a$R$^a$, —NR$^e$C(=O)NR$^a$R$^a$, —NR$^h$CO$_2$R$^a$, —NR$^e$CO$_2$R$^a$, —C$_{1-8}$alkylOR$^h$, —C$_{1-6}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^a$, —OS(=O)$_2$R$^h$ or —OC(=O)NR$^a$R$^h$; and
- R$^9$ is independently, at each instance, H, R$^k$, C$_{1-4}$haloalkyl, halo, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^{10}$ is independently, at each instance, selected from H, halo, C$_{1-8}$alkyl, C$_{1-4}$haloalkyl, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OH, —NH$_2$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{10}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, wherein the ring is substituted by 0, 1 or 2 oxo or thioxo groups, wherein the ring is substituted by 0, 1, 2 or 3 groups selected from $R^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^k$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or $R^{10}$ is $C_{1-4}$alkyl substituted by 0, 1, 2 or 3 groups selected from $C_{1-4}$haloalkyl, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$;

$R^{11}$ is independently, at each instance, selected from H, cyano, nitro, —OH, —NH$_2$, —SH, $C_{1-8}$alkyl, $C_{1-4}$haloalkyl, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or $R^{11}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from $R^k$, halo, cyano, nitro, —C(=O)R$^k$, —C(=O)OR$^k$, —C(=O)NR$^a$R$^k$, —C(=NR$^a$)NR$^a$R$^k$, —OH, —NH$_2$, —SH, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or $R^{11}$ is $C_{1-4}$alkyl substituted by 0, 1, 2 or 3 groups selected from $C_{1-4}$haloalkyl, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^a$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^a$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$;

or R$^{10}$ and R$^{11}$ together are a saturated, partially-saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^i$, R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$;

or R$^{10}$ and R$^{11}$ together are a saturated or partially unsaturated 3-, 4- or 5-carbon bridge, wherein the bridge is substituted by 0, 1 or 2 substituents selected from oxo, thioxo, R$^i$, R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —C(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$;

R$^{12}$ is independently, at each instance, selected from H, C$_{1-8}$alkyl, C$_{1-4}$haloalkyl, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —C(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$;

or R$^{12}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^i$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{12}$ is C$_{1-4}$alkyl substituted by 0, 1, 2 or 3 groups selected from C$_{1-4}$haloalkyl, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$, and additionally substituted by 0, 1 or 2 halo groups; or R$^{11}$ and R$^{12}$ together are a saturated, partially-saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^i$, R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^i$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{11}$ and R$^{12}$ together are a saturated or partially unsaturated 3-, 4- or 5-carbon bridge, wherein the bridge is substituted by 0, 1 or 2 substituents selected from oxo, thioxo, R$^i$, R$^k$, halo, cyano, nitro, —OH, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —O(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$;

R$^{13}$ is independently, at each instance, selected from H, halo, cyano, nitro, C$_{1-4}$haloalkyl, —OH, —NH$_2$, —SH, C$_{1-8}$alkyl, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —(NR$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N (R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{13}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from R$^k$, halo, cyano, nitro, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{13}$ is C$_{1-4}$alkyl substituted by 0, 1 or 2 groups selected from C$_{1-4}$haloalkyl, cyano, nitro, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)

OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$;

R$^{14}$ is independently, at each instance, selected from H, C$_{1-8}$alkyl, C$_{1-4}$haloalkyl, halo, cyano, nitro, —OH, —NH$_2$, —NH$_2$, —SH, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; or R$^{14}$ is a saturated, partially-saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, wherein the ring is substituted by 0, 1 or 2 oxo or thioxo groups, wherein the ring is substituted by 0, 1, 2 or 3 groups selected from R$^k$, halo, cyano, nitro, —C(=O)R$^k$, —C(=O)OR$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C (=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$;
or R$^{14}$ is C$_{1-4}$alkyl substituted by 0, 1, 2 or 3 groups selected from C$_{1-4}$haloalkyl, halo, cyano, nitro, —C(=O)R$^k$, —C(=O)NR$^a$R$^k$, —C(=NR$^a$)NR$^a$R$^k$, —OR$^k$, —OC(=O)R$^k$, —OC(=O)NR$^a$R$^k$, —OC(=O)N(R$^a$)S(=O)$_2$R$^k$, —OC$_{2-6}$alkylNR$^a$R$^k$, —OC$_{2-6}$alkylOR$^k$, —SR$^k$, —S(=O)R$^k$, —S(=O)$_2$R$^k$, —S(=O)$_2$NR$^a$R$^k$, —S(=O)$_2$N(R$^a$)C(=O)R$^k$, —S(=O)$_2$N(R$^a$)C(=O)OR$^k$, —S(=O)$_2$N(R$^a$)C(=O)NR$^a$R$^k$, —NR$^a$R$^k$, —N(R$^a$)C(=O)R$^k$, —N(R$^a$)C(=O)OR$^k$, —N(R$^a$)C(=O)NR$^a$R$^k$, —N(R$^a$)C(=NR$^a$)NR$^a$R$^k$, —N(R$^a$)S(=O)$_2$R$^k$, —N(R$^a$)S(=O)$_2$NR$^a$R$^k$, —NR$^a$C$_{2-6}$alkylNR$^a$R$^k$, —NR$^a$C$_{2-6}$alkylOR$^k$, —C(=O)R$^i$, —C(=O)OR$^i$, —C(=O)NR$^a$R$^i$, —C(=NR$^a$)NR$^a$R$^i$, —OR$^i$, —OC(=O)R$^i$, —OC(=O)NR$^a$R$^i$, —OC(=O)N(R$^a$)S(=O)$_2$R$^i$, —OC(=O)N(R$^i$)S(=O)$_2$R$^k$, —OC$_{2-6}$alkylNR$^a$R$^i$, —OC$_{2-6}$alkylOR$^i$, —SR$^i$, —S(=O)R$^i$, —S(=O)$_2$R$^i$, —S(=O)$_2$NR$^a$R$^i$, —S(=O)$_2$N(R$^i$)C(=O)R$^k$, —S(=O)$_2$N(R$^a$)C(=O)R$^i$, —S(=O)$_2$N(R$^i$)C(=O)OR$^k$, —S(=O)$_2$N(R$^a$)C(=O)OR$^i$, —S(=O)$_2$N(R$^i$)C(=O)NR$^a$R$^k$, —S(=O)$_2$N(R$^a$)C(=O)NR$^a$R$^i$, —NR$^a$R$^i$, —N(R$^i$)C(=O)R$^k$, —N(R$^a$)C(=O)R$^i$, —N(R$^i$)C(=O)OR$^k$, —N(R$^a$)C(=O)OR$^i$, —N(R$^i$)C(=O)NR$^a$R$^k$, —N(R$^a$)C(=O)NR$^a$R$^i$, —N(R$^i$)C(=NR$^a$)NR$^a$R$^k$, —N(R$^a$)C(=NR$^a$)NR$^a$R$^i$, —N(R$^i$)S(=O)$_2$R$^k$, —N(R$^a$)S(=O)$_2$R$^i$, —N(R$^i$)S(=O)$_2$NR$^a$R$^k$, —N(R$^a$)S(=O)$_2$NR$^a$R$^i$, —NR$^i$C$_{2-6}$alkylNR$^a$R$^k$, —NR$^a$C$_{2-6}$alkylNR$^a$R$^i$, —NR$^i$C$_{2-6}$alkylOR$^k$ and —NR$^a$C$_{2-6}$alkylOR$^i$; wherein at least one of R$^{10}$, R$^{11}$, R$^{12}$, R$^{13}$ and R$^{14}$ is other than H;

R$^a$ is independently, at each instance, H, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl;

R$^b$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups;

R$^d$ is independently in each instance hydrogen or —CH$_3$;

R$^e$ is, independently, in each instance, C$_{1-9}$alkyl substituted by a group independently selected from R$^h$; and wherein the C$_{1-9}$alkyl is additionally substituted by 0, 1, 2 or 3 substituents selected from halo, C$_{1-4}$haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —C(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^h$ is, independently, in each instance, phenyl or a saturated, partially saturated or unsaturated 5-, 6- or 7-membered monocyclic or 6-, 7-, 8-, 9-, 10- or 11-membered bicyclic ring containing 1, 2 or 3 atoms selected from N, O and S, so long as the combination of O and S atoms is not greater than 2, wherein the ring is substituted by 0 or 1 oxo or thioxo groups, wherein the phenyl and monocycle are substituted by 1, 2 or 3 groups independently selected from C$_{1-9}$alkyl substituted by 0, 1, 2 or 3 substituents selected from halo, cyano, nitro, C$_{1-4}$haloalkyl, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and wherein the phenyl and monocycle are additionally substituted by 0, 1 or 2 substituents selected from C$_{1-9}$alkyl, halo, cyano, nitro, C$_{1-4}$haloalkyl, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^i$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the available carbon atoms of the ring are substituted by 0, 1 or 2 oxo or thioxo groups, wherein the ring is substituted by 0, 1, 2 or 3 substituents independently selected from C$_{1-9}$alkyl, halo, cyano, nitro, C$_{1-4}$haloalkyl, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$, —NR$^a$C$_{2-6}$alkylOR$^a$, and C$_{1-9}$alkyl substituted by 1, 2 or 3 substituents selected from halo, cyano, nitro, C$_{1-4}$haloalkyl, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and R$^k$ is, independently, in each instance, C$_{1-9}$alkyl or C$_{1-4}$alkyl(phenyl) wherein either is substituted by 0, 1, 2, 3 or 4 substituents selected from halo, C$_{1-4}$haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and wherein the C$_{1-9}$alkyl is additionally substituted by 0 or 1 groups independently selected from R$^i$ and additionally substituted by 0, 1, 2, 3, 4 or 5 substituents independently selected from Br, Cl, F and I.

2. A compound according to claim 1 that is selected from the group of:

(2S)-N-(2-(6-(7R)-7-hydroxy-5,6,7,8-tetrahydronaphthalen-1-ylamino)pyrimidin-4-yl)-5-(trifluoromethyl)phenyl)-1-isopropylpyrrolidine-2-carboxamide hydrochloride;

(2S)-N-(2-(6-(7S)-7-hydroxy-5,6,7,8-tetrahydronaphthalen-1-ylamino)pyrimidin-4-yl)-5-(trifluoromethyl)phenyl)-1-isopropylpyrrolidine-2-carboxamide hydrochloride;

(2S)-tert-butyl 2-((2-(6-((7S)-7-hydroxy-5,6,7,8-tetrahydro-naphthalen-1-ylamino)pyrimidin-4-yl)-5-(trifluoromethyl)phenyl)-carbamoyl)-pyrrolidine-1-carboxylate;

(2S)-tert-butyl 2-((2-(6-((7S)-7-hydroxy-5,6,7,8-tetrahydro-naphthalen-1-ylamino)pyrimidin-4-yl)-5-(trifluoromethyl)phenyl)-carbamoyl)-pyrrolidine-1-carboxylate (2S,5R,S,7R,S)-N-(2-(6-(7-hydroxy-5,6,7,8-tetrahydronaphthalen-1-ylamino)pyrimidin-4-yl)-5-(trifluoromethyl)phenyl)-5-methylpyrrolidine-2-carboxamide hydrochloride;

(2S,5R,S,7R,S)-N-(2-(6-(7-hydroxy-5,6,7,8-tetrahydronaphthalen-1-ylamino)pyrimidin-4-yl)-5-(trifluoromethyl)phenyl)-1-isopropyl-5-methylpyrrolidine-2-carboxamide hydrochloride;

(2S,5R,S,7R,S)-N-(2-(6-(7-hydroxy-5,6,7,8-tetrahydronaphthalen-1-ylamino)-pyrimidin-4-yl)-5-(trifluoromethyl)phenyl)-1-isobutyl-5-methylpyrrolidine-2-carboxamide hydrochloride; and (2S,R)-8-({6-[2-({[(2S,R)-1-isobutylpiperidin-2-yl]methyl}amino)-6-(trifluoromethyl)pyridin-3-yl]pyrimidin-4-yl}amino)-1,2,3,4-tetrahydronaphthalen-2-ol;

or any pharmaceutically-acceptable salts thereof.

3. A pharmaceutical composition comprising a compound according to claim 1 and a pharmaceutically-acceptable diluent or carrier.

4. A compound to claim 1, or a pharmaceutically acceptable salt thereof, wherein:

R$^1$ is

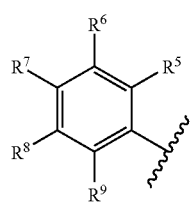

5. A compound to claim 1, or a pharmaceutically acceptable salt thereof, wherein:

R$^1$ is R$^b$ substituted by 1, 2 or 3 substituents selected from R$^e$, R$^h$, —OR$^e$, —OR$^h$, —OC$_{2-6}$alkylNR$^a$R$^e$, —OC$_{2-6}$alkylOR$^e$, —NR$^a$R$^e$, —NR$^a$R$^h$, —NR$^a$C$_{2-6}$alkylNR$^a$R$^e$, —NR$^a$C$_{2-6}$alkylOR$^e$, —CO$_2$R$^e$, —OC(=O)R$^e$, —C(=O)R$^e$, —C(=O)NR$^a$R$^e$, —C(=O)NR$^a$R$^h$, —NR$^a$C(=O)R$^e$, —NR$^a$C(=O)R$^h$, —NR$^a$C(=O)NR$^a$R$^e$, —NR$^a$CO$_2$R$^e$, —C$_{1-8}$alkylOR$^e$, —C$_{1-6}$alkylNR$^a$R$^e$, —S(=O)$_n$R$^e$, —S(=O)$_2$NR$^a$R$^e$, —NR$^a$S(=O)$_2$R$^e$, —OS(=O)$_2$R$^e$, —OC(=O)NR$^a$R$^e$, —OC$_{2-6}$alkylNR$^a$R$^h$, —OC$_{2-6}$alkylOR$^h$, —NR$^a$C$_{2-6}$alkylNR$^a$R$^h$, —NR$^h$C$_{2-6}$alkylNR$^a$R$^a$, —NR$^h$C$_{2-6}$alkylOR$^a$, —NR$^a$C$_{2-6}$alkylOR$^h$, —CO$_2$R$^h$, —OC(=O)R$^h$, —C(=O)R$^h$, —NR$^e$C(=O)R$^a$, —NR$^h$C(=O)R$^a$, —NR$^h$C(=O)NR$^a$R$^a$, —NR$^e$C(=O)NR$^a$R$^a$, —NR$^h$CO$_2$R$^a$, —NR$^e$CO$_2$R$^a$, —C$_{1-8}$alkylOR$^h$, —C$_{1-6}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^a$, —OS(=O)$_2$R$^h$ and —OC(=O)NR$^a$R$^h$, and additionally substituted by 0, 1, 2 or 3 substituents independently selected from halo, cyano, nitro, C$_{1-8}$alkyl, C$_{1-4}$haloalkyl, R$^i$, R$^k$, —OR$^a$, —NR$^a$R$^a$, —OC$_{2-6}$alkylNR$^a$R$^a$, —OC$_{2-6}$alkylOR$^a$, —NR$^a$C$_{2-6}$alkylNR$^a$R$^a$, —NR$^a$C$_{2-6}$alkylOR$^a$, —CO$_2$R$^a$, —OC(=O)R$^a$, —C(=O)(C$_{1-6}$alkyl), —C(=O)NR$^a$R$^a$, —NR$^a$C(=O)R$^a$, —NR$^a$C(=O)NR$^a$R$^a$, —NR$^a$CO$_2$R$^a$, —C$_{1-8}$alkylOR$^a$, —C$_{1-6}$alkylNR$^a$R$^a$, —S(=O)$_n$R$^a$, —S(=O)$_2$NR$^a$R$^a$, —NR$^a$S(=O)$_2$R$^a$, —OS(=O)$_2$R$^a$ and —OC(=O)NR$^a$R$^e$.

6. A compound according to claim 1, or a pharmaceutically acceptable salt thereof, wherein:

R$^1$ is

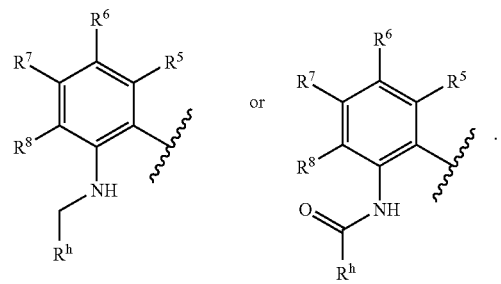

In another embodiment, in conjunction with any one of the above and below embodiments, R$^2$ is selected from H, halo, cyano, nitro, R$^i$, R$^k$, —OH, —OR$^i$, —OR$^k$, —C(=O)OR$^i$, —C(=O)OR$^k$, —OC(=O)R$^i$, —OC(=O)R$^k$, —S(O)$_n$R$^i$, —S(O)$_n$R$^k$, —N(R$^a$)S(O)$_n$R$^i$, —N(R$^a$)S(O)$_n$R$^k$, —S(O)$_n$N(R$^a$)R$^i$, —S(O)$_n$N(R$^a$)R$^k$, —NH$_2$, —C(=O)NR$^a$R$^i$, —C(=O)NR$^a$R$^k$, —NR$^a$C(=O)R$^i$ and —NR$^a$C(=O)R$^k$, —NR$^a$R$^i$ and —NR$^a$R$^k$.

7. A compound according to claim 1, or a pharmaceutically acceptable salt thereof, wherein:

R$^4$ independently at each instance

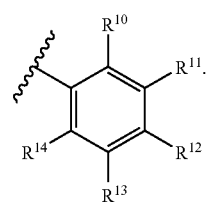

8. A compound according to claim 1, or a pharmaceutically acceptable salt thereof, wherein:

$R^4$ is independently at each instance a saturated, partially-saturated or unsaturated 5- or 6-membered ring heterocycle containing 1, 2 or 3 atoms selected from O, N and S that is optionally vicinally fused with a saturated, partially-saturated or unsaturated 3-, 4- or 5-atom bridge containing 0, 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from oxo, thioxo, $R^k$, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$; and wherein the heterocycle is additionally substituted by 0 or 1 groups independently selected from $R^i$ and additionally substituted by 0, 1, 2, 3, 4 or 5 substituents independently selected from Br, Cl, F and I; or $R^4$ is independently at each instance naphthyl substituted by 1, 2 or 3 substituents independently selected from $R^k$, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$; and wherein the naphthyl is additionally substituted by 0 or 1 groups independently selected from $R^i$ and additionally substituted by 0, 1, 2, 3, 4 or 5 substituents independently selected from Br, Cl, F and I;

9. A compound according to claim 1, or a pharmaceutically acceptable salt thereof, wherein:

$R^4$ is independently at each instance a saturated, partially-saturated or unsaturated 5- or 6-membered ring heterocycle containing 1, 2 or 3 atoms selected from O, N and S that is vicinally fused with a saturated, partially-saturated or unsaturated 3-, 4- or 5-atom bridge containing 0, 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from oxo, thioxo, $R^k$, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$; and wherein the heterocycle is additionally substituted by 0 or 1 groups independently selected from $R^i$ and additionally substituted by 0, 1, 2, 3, 4 or 5 substituents independently selected from Br, Cl, F and I.

10. A compound according to claim 4, or a pharmaceutically acceptable salt thereof, wherein:

$R^7$ is $C_{3-5}$alkyl or $C_{1-2}$haloalkyl.

11. A compound according to claim 1, or a pharmaceutically acceptable salt thereof, wherein:

$R^8$ is independently, at each instance, $R^e$, $R^h$, —O$R^e$, —O$C_{2-6}$alkylN$R^aR^e$, —O$C_{2-6}$alkylO$R^e$, —N$R^aR^e$, —N$R^aR^h$, —N$R^aC_{2-6}$alkylN$R^aR^e$, —N$R^aC_{2-6}$alkylO$R^e$, —CO$_2R^e$, —OC(=O)$R^e$, —C(=O)$R^e$, —C(=O)N$R^aR^h$, —N$R^a$C(=O)$R^e$, —N$R^a$C(=O)$R^h$, —N$R^a$C(=O)N$R^aR^e$, —N$R^a$CO$_2R^e$, —$C_{1-8}$alkylO$R^e$, —$C_{1-6}$alkylN$R^aR^e$, —S(=O)$_nR^e$, —S(=O)$_2$N$R^aR^e$, —N$R^a$S(=O)$_2R^e$, —OS(=O)$_2R^e$, —OC(=O)N$R^aR^e$, —O$R^h$, —O$C_{2-6}$alkylN$R^aR^h$, —O$C_{2-6}$alkylO$R^h$, —N$R^aC_{2-6}$alkylN$R^aR^h$, —N$R^hC_{2-6}$alkylN$R^aR^a$, —N$R^hC_{2-6}$alkylO$R^a$, —N$R^aC_{2-6}$alkylO$R^h$, —CO$_2R^h$, —OC(=O)$R^h$, —C(=O)N$R^aR^h$, —N$R^e$C(=O)$R^a$, —N$R^h$C(=O)$R^a$, —N$R^h$C(=O)N$R^aR^a$, —N$R^e$C(=O)N$R^aR^a$, —N$R^h$CO$_2R^a$, —N$R^e$CO$_2R^a$, —$C_{1-8}$alkylO$R^h$, —$C_{1-6}$alkylN$R^aR^h$, —S(=O)$_nR^h$, —S(=O)$_2$N$R^aR^h$, —N$R^a$S(=O)$_2R^h$, —N$R^h$S(=O)$_2R^a$, —OS(=O)$_2R^h$ or —OC(=O)N$R^aR^h$; and $R^9$ is $R^k$, $C_{1-4}$haloalkyl, halo, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$.

* * * * *